(12) United States Patent
Koike et al.

(10) Patent No.: US 9,296,746 B2
(45) Date of Patent: Mar. 29, 2016

(54) HETEROCYCLIC COMPOUND

(71) Applicant: TAKEDA PHARMACEUTICAL COMPANY LIMITED, Osaka (JP)

(72) Inventors: Tatsuki Koike, Kanagawa (JP); Masato Yoshikawa, Kanagawa (JP); Izumi Nomura, Kanagawa (JP); Yoshiteru Ito, Kanagawa (JP); Eiji Kimura, Kanagawa (JP); Tomoaki Hasui, Kanagawa (JP); Haruhi Ando, Kanagawa (JP); Hiromi Fukuda, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/435,899

(22) PCT Filed: Oct. 15, 2013

(86) PCT No.: PCT/JP2013/078008
§ 371 (c)(1),
(2) Date: Apr. 15, 2015

(87) PCT Pub. No.: WO2014/061676
PCT Pub. Date: Apr. 24, 2014

(65) Prior Publication Data
US 2015/0266872 A1 Sep. 24, 2015

(30) Foreign Application Priority Data

Oct. 16, 2012 (JP) ................................. 2012-229227

(51) Int. Cl.
| | | |
|---|---|---|
| *C07D 413/02* | (2006.01) | |
| *C07D 403/02* | (2006.01) | |
| *A61K 31/4245* | (2006.01) | |
| *A61K 31/416* | (2006.01) | |
| *C07D 471/04* | (2006.01) | |
| *C07D 519/00* | (2006.01) | |
| *C07D 413/04* | (2006.01) | |

(52) U.S. Cl.
CPC ............ *C07D 471/04* (2013.01); *C07D 413/04* (2013.01); *C07D 519/00* (2013.01)

(58) Field of Classification Search
CPC ............... C07D 413/02; C07D 403/02; A61K 31/4245; A61K 31/4196; A61K 31/422; A61K 31/4192; A61K 31/416
USPC .......... 514/359, 365, 381; 548/131, 215, 254, 548/255, 312.4, 362.5
See application file for complete search history.

(56) References Cited

U.S. PATENT DOCUMENTS

| | | | | |
|---|---|---|---|---|
| 5,134,155 | A | * | 7/1992 | Connolly ............. C07D 231/56 514/403 |
| 2005/0101614 | A1 | | 5/2005 | Lin et al. |
| 2007/0078147 | A1 | | 4/2007 | Schumacher et al. |
| 2009/0076070 | A1 | | 3/2009 | Harada et al. |
| 2010/0010053 | A1 | | 1/2010 | Castro Pineiro et al. |
| 2010/0029729 | A1 | | 2/2010 | Castro Pineiro et al. |
| 2010/0137288 | A1 | | 6/2010 | Schumacher et al. |
| 2010/0168159 | A1 | | 7/2010 | Harada et al. |
| 2010/0280032 | A1 | | 11/2010 | Zhou et al. |
| 2010/0298314 | A1 | | 11/2010 | Reddy et al. |
| 2011/0077243 | A1 | | 3/2011 | Hynes |
| 2011/0086839 | A1 | | 4/2011 | Castro Pineiro et al. |
| 2012/0115811 | A1 | | 5/2012 | Du et al. |
| 2013/0090341 | A1 | | 4/2013 | Koike et al. |
| 2014/0088118 | A1 | | 3/2014 | Koike et al. |
| 2014/0088146 | A1 | | 3/2014 | Koike et al. |
| 2014/0141511 | A1 | | 5/2014 | Zhou et al. |
| 2014/0228373 | A1 | | 8/2014 | Koike et al. |

FOREIGN PATENT DOCUMENTS

| | | |
|---|---|---|
| JP | 2007-502257 | 2/2007 |
| JP | 2009-509964 | 3/2009 |
| JP | 2010-513495 | 4/2010 |
| JP | 2010-248183 | 11/2010 |
| JP | 2011-524880 | 9/2011 |
| JP | 2011-525184 | 9/2011 |
| WO | 2007/116866 | 10/2007 |
| WO | 2008/057246 | 5/2008 |

(Continued)

OTHER PUBLICATIONS

International Search Report issued Nov. 12, 2013 in International (PCT) Application No. PCT/JP2013/078008.
Hiraoka et al., "Syntheses of 5,5'-Methylenebisisoxazole Derivative and Its Reactions with Electrophiles", Chem. Pharm. Bull., vol. 20, No. 1, 1972, pp. 122-132.

(Continued)

*Primary Examiner* — Niloofar Rahmani
(74) *Attorney, Agent, or Firm* — Winderoth, Lind & Ponack, L.L.P.

(57) ABSTRACT

The present invention provides a compound or a salt thereof useful for an agent for the prophylaxis or treatment of neurodegenerative disease and the like. The present invention relates to a compound represented by the formula

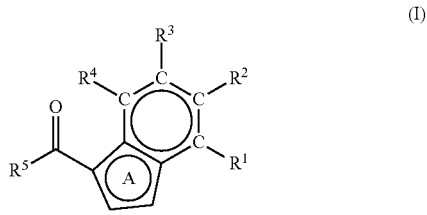

wherein each symbol is as defined in the present specification, or a salt thereof.

13 Claims, No Drawings

(56) References Cited

FOREIGN PATENT DOCUMENTS

| WO | 2010/093849 | 8/2010 |
| WO | 2010/110400 | 9/2010 |
| WO | 2013/054822 | 4/2013 |

OTHER PUBLICATIONS

Wang et al., "Tandem [5+1] annulation-isocyanide cyclization: efficient synthesis of hydroindolones", Chem. Commun., vol. 47, 2011, pp. 12316-12318.

* cited by examiner

```
                            SEQUENCE LISTING

<160> NUMBER OF SEQ ID NOS: 2

<210> SEQ ID NO 1
<211> LENGTH: 26
<212> TYPE: DNA
<213> ORGANISM: Artificial
<220> FEATURE:
<223> OTHER INFORMATION: PCR primer

<400> SEQUENCE: 1
gccccggagc catgagcccc gggctg                                        26

<210> SEQ ID NO 2
<211> LENGTH: 26
<212> TYPE: DNA
<213> ORGANISM: Artificial
<220> FEATURE:
<223> OTHER INFORMATION: PCR primer

<400> SEQUENCE: 2
gtcctgcctg gaggccccct cagcag                                        26
```

HETEROCYCLIC COMPOUND

TECHNICAL FIELD

The present invention relates to a heterocyclic compound having a cholesterol 24-hydroxylase (in the present specification, sometimes to be abbreviated as "CH24H") inhibitory action, a pharmaceutical composition comprising same, and the like.

BACKGROUND OF THE INVENTION

Alzheimer's disease is a progressive neurodegenerative disease characterized by the deposition of amyloid β protein (Aβ), accumulation of phosphorylated tau in a nerve cell (neurofibrillary tangle), and nerve cell death. In recent years, the number of patients with Alzheimer's disease is increasing because of aging, but an effective treatment method has not been developed as yet. The therapeutic drugs for Alzheimer's disease which are currently used in the medical practice are mainly acetylcholinesterase (AchE) inhibitors. While AchE inhibitors is confirmed to provide a certain level of usefulness, since they are used with the aim of supplementing decreased acetylcholine, the treatment with AchE inhibitor is merely a symptomatic therapy. Thus, the prompt development of a basic remedy and prophylactic drug has been strongly desired.

It has been clarified that the presence of allele ε4 of apolipoprotein E (ApoE) controlling the cholesterol metabolism is a strong risk factor of Alzheimer's disease [non-patent document 1: Science, vol. 261, 921-923, 1993]. After this finding, the correlation between plural gene polymorphisms playing a role in the expression of protein controlling the cholesterol metabolism and the onset frequency of Alzheimer's disease has been shown, suggesting the correlation between the cholesterol metabolism and Alzheimer's disease [non-patent document 2: Neurobiol. Aging, vol. 24, 421-426, 2003, non-patent document 3: Mol. Psychiatry, vol. 8, 635-638, 2003]. Moreover, it has been reported that Cyp46 (same as "cholesterol 24-hydroxylase (CH24H)"), which is cholesterol oxidase specifically expressed in the brain, is a risk factor of Alzheimer's disease [non-patent document 4: Neurosci. Lett., vol. 328, pages 9-12, 2002]. Furthermore, it has also been to reported that Cyp46 (CH24H) is expressed in periphery of deposited amyloid in Alzheimer's disease patients [non-patent document 5: J. Biol. Chem., vol. 279, pages 34674-34681, 2004], 24S-hydroxycholesterol (24-HC), which is a metabolite thereof, increases in the brain spinal cord fluid (CSF) of Alzheimer's disease patients [non-patent document 6: Neurosci. Lett., vol. 324, pages 83-85, 2002, non-patent document 7: Neurosci. Lett., vol. 397, pages 83-87, 2006], 24-HC induces cell death of SH-SY5Y cell, which is a human neuroblast line [non-patent document 8: Brain Res., vol. 818, pages 171-175, 1999], and rats in which 24-HC was injected into the lateral cerebral ventricle showed impaired short-term memory, which is commonly observed in Alzheimer's disease, suggesting that hippocampal neurons were damaged by 24-HC [non-patent document 9: Neuroscience, vol. 164, pages 398-403, 2009]. These findings suggest that Cyp46 (CH24H) is deeply involved in the pathology of Alzheimer's disease. Therefore, a compound that inhibits the Cyp46 (CH24H) activity (i.e., Cyp46 (CH24H) inhibitor) suppresses neuronal cell death, increase in Aβ, intracerebral inflammation and the like observed in Alzheimer's disease, by decreasing intracerebral 24-HC, and is promising as a therapeutic or prophylactic drug showing not only an improvement of symptoms but also a suppression of progression. Moreover, it has been reported that an AchE inhibitor clinically used as a therapeutic drug for Alzheimer's disease shows an improvement effect on memory disorders induced by Aβ in mouse [non-patent document 10: British Journal of Pharmacology, vol. 149, pages 998-1012, 2006]. Thus, a Cyp46 (CH24H) inhibitor showing an improvement effect for memory disorders in Aβ overexpression animal model (APP transgenic mouse, APP/PS1 double transgenic mouse, etc.) is promising as a therapeutic drug for Alzheimer's disease.

As a concept of the preclinical stage of Alzheimer's disease, a mild cognitive impairment has been proposed, and about half of those having this disorder is said to progress into the Alzheimer's disease in the future. In recent years, it has been reported that 24-HC increases not only in patients with Alzheimer's disease but also in CSF of patients with mild cognitive impairment [non-patent document 7: Neurosci. Lett., vol. 397, pages 83-87, 2006]. This finding suggests that Cyp46 (CH24H) is involved in the pathology of mild cognitive impairment, and therefore, a Cyp46 (CH24H) inhibitor is promising as a new therapeutic drug for Alzheimer's disease or a prophylactic drug for the progression into the Alzheimer's disease.

In recent years, moreover, it has been reported that 24-HC in the blood increases before expression of the symptom in an autoimmune encephalomyelitis model, which is an animal model of multiple sclerosis which is one of the demyelination diseases in the central nervous system [non-patent document 11: J. Neurosci. Res., vol. 85, pages 1499-1505, 2007]. Multiple sclerosis is often developed in younger people of about 30 years old, and scarcely developed in the elderly of 60 years or older. It has also been reported that 24-HC in the blood increases in multiple sclerosis patients aged from 21 to 50 [non-patent document 12: Neurosci. Lett., vol. 331, pages 163-166, 2002]. These findings suggest that Cyp46 (CH24H) is involved in the pathology of multiple sclerosis, and therefore, a Cyp46 (CH24H) inhibitor is promising as a new therapeutic or prophylactic drug for multiple sclerosis.

Traumatic brain injury (also referred to as TBI in the present specification) is a condition having an extremely harmful influence on the personal health, for which no effective cure has been established. In the repair process following tissue damage by TBI, reconstruction of neuronal cell membrane and distribution of intracerebral cholesterol along with the growth of glial cell are suggested to be activated [non-patent document 13: Proc. Natl. Acad. Sci. USA, vol. 102, pages 8333-8338, 2005]. In a rat TBI model, an enhanced expression of Cyp46 (CH24H) after trauma has been reported [non-patent document 14: J. Neurotrauma, vol. 25, pages 1087-1098, 2008]. Moreover, it has also been reported that 24-HC is injurious to neuronal cells [non-patent document 8: Brain Res., vol. 818, pages 171-175, 1999]. Therefore, a Cyp46 (CH24H) inhibitor is promising as a new therapeutic or prophylactic drug for TBI.

As a pathological significance of 24-HC in neurodegenerative diseases, an inflammatory gene expression-enhancing action in neuronal cells has been reported [non-patent document 15: Mol. Neurosci., vol. 16, pages 909-913, 2005]. In addition, it is suggested that an intracerebral inflammation reaction accompanied by activation of glial cell is a pathological change characteristic of neurodegenerative diseases [non-patent document 16: Glia, vol. 50, pages 427-434, 2005]. In recent years, an effectiveness of therapy by suppression of intracerebral inflammation has also been reported for neurodegenerative diseases such as Huntington's disease, Parkinson's disease and amyotrophic lateral sclerosis and the like [non-patent document 17: Mol. Neurodegeneration, vol. 4, pages 47-59, 2009]. Therefore, suppression of intracerebral inflammation via decreasing 24-HC by the inhibition of Cyp46 (CH24H) is promising as a new therapeutic or prophylactic drug for neurodegenerative diseases such as Huntington's disease, Parkinson's disease, cerebral infarction, glaucoma, amyotrophic lateral sclerosis and the like.

Glaucoma is the main cause of blindness, and is considered to be a serious social problem. However, there is no effective cure of a normal intraocular pressure type-visual field constriction, which is the major symptom of the disease. In recent years, it has been reported that gene polymorphisms of Cyp46 (CH24H) associated with high value of 24-HC in blood is related to the risk of the onset of glaucoma [non-patent document 18: Invest. Ophthalmol. Vis. Sci., vol. 50, pages 5712-5717, 2009]. Thus, a Cyp46 (CH24H) inhibitor is promising as a therapeutic or prophylactic drug for glaucoma.

Spasm is a disease that occurs convulsively along with abnormal electric excitement of intracerebral neuronal cells. Spasm is also one of the characteristic clinical findings in epilepsia or Alzheimer's disease [non-patent document 19: Epilepsia, vol. 47, pages 867-872, 2006], and it has been reported that spasm occurs with high frequency in APP/PS1 double transgenic mouse which is one of the Alzheimer's disease models due to Aβ overexpression [non-patent document 20: J. Neurosci., vol. 29, pages 3453-3462, 2012]. It has been reported that carbamazepine, which is a therapeutic drug for spasm, shows a short term memory-improvement effect in a Y-maze test using mouse spasm model [non-patent document 21: J. Neurol. Neurosurg. Psychiatry, vol. 48, pages 459-468, 1985]. Thus, a Cyp46 (CH24H) inhibitor showing a short term memory-improvement effect in animal model showing spasm symptoms is promising as a new therapeutic or prophylactic drug for disease such as Alzheimer's disease, epilepsia, spasm and the like.

Since schizophrenia shows a variety of psychological symptoms such as hallucination, delusion, excitation, manic-depressive state and the like, therapeutic drugs therefor have been developed with various approaches. In recent years, it has been pointed out that changes in the cholesterol metabolism are involved in the abnormality of neural activity seen in schizophrenia [non-patent document 22: J. Psychiatry Neurosci., vol. 36, pages 47-55, 2011]. Since cytotoxic factors such as oxidative stress also contribute to the pathology of schizophrenia, neuronal cell toxicity of 24-HC may aggravate the symptoms [non-patent document 23: Psychoneuroendocrinology, vol. 28, pages 83-96, 2003]. Therefore, a Cyp46 (CH24H) inhibitor that inhibits metabolizing cholesterol to 24-HC in the brain is promising as a therapeutic or prophylactic drug for schizophrenia.

Examples of the compound having a structure similar to the compound described in the present specification include the following compounds [non-patent Document 24, 25].

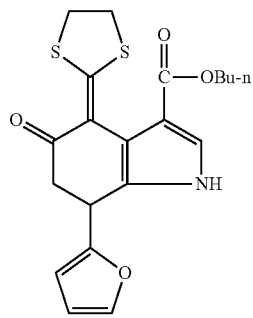

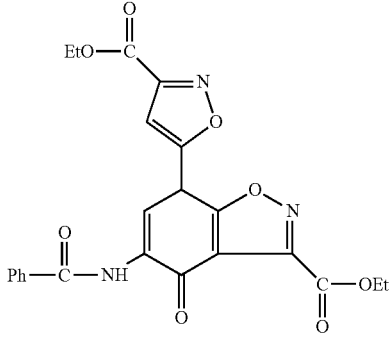

Patent Document 1 discloses the following compound as an agent for the treatment of neurodegenerative diseases (Alzheimer's disease, mild cognitive impairment, multiple sclerosis etc.).

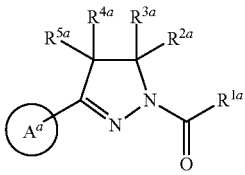

(Ia)

wherein
Ring $A^a$ is an optionally substituted ring;
$R^{1a}$ is an optionally substituted heterocyclic group or the like;
$R^{2a}$ is a hydrogen atom, an optionally substituted $C_{1-6}$ alkyl group, an optionally substituted $C_{3-6}$ cycloalkyl group, or an optionally substituted hydroxy group;
$R^{3a}$ is an optionally substituted $C_{1-6}$ alkyl group, an optionally substituted $C_{3-6}$ cycloalkyl group, or an optionally substituted hydroxy group; or,
$R^{2a}$ and $R^{3a}$ in combination optionally form an oxo group, a $C_{1-3}$ alkylidene group, or an optionally substituted ring; and
$R^{4a}$ and $R^{5a}$ are the same or different and each is a hydrogen atom, a halogen atom, an optionally substituted $C_{1-6}$ alkyl group, an optionally substituted $C_{3-6}$ cycloalkyl group, or an optionally substituted hydroxy group; or,
$R^{4a}$ and $R^{5a}$ in combination optionally form an oxo group, a $C_{1-3}$ alkylidene group, or an optionally substituted ring.

Patent Document 2 discloses the following compound as an agent for the treatment of bone diseases (osteoporosis, bone fracture etc.).

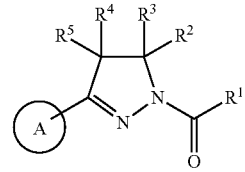

(I)

wherein
Ring A is an optionally substituted $C_{6-14}$ aromatic hydrocarbon, or an optionally substituted heterocycle;
$R^1$ is an optionally substituted bicyclic fused furyl group, an optionally substituted bicyclic fused imidazolyl group, or an optionally substituted bicyclic fused triazolyl group or the like;

$R^2$ is a hydrogen atom, an optionally substituted $C_{1-6}$ alkyl group, an optionally substituted $C_{3-6}$ cycloalkyl group, or an optionally substituted hydroxy group;
$R^3$ is an optionally substituted $C_{1-6}$ alkyl group, an optionally substituted $C_{3-6}$ cycloalkyl group, or an optionally substituted hydroxy group; or,
$R^2$ and $R^3$ in combination optionally form a $C_{1-3}$ alkylidene group, or an optionally substituted ring; and
$R^4$ and $R^5$ are the same or different and each is a hydrogen atom, a halogen atom, an optionally substituted $C_{1-6}$ alkyl group, an optionally substituted $C_{3-6}$ cycloalkyl group, or an optionally substituted hydroxy; or,
$R^4$ and $R^5$ in combination optionally form an oxo group, a $C_{1-3}$ alkylidene group, or an optionally substituted ring.

DOCUMENT LIST

Patent Document

Patent Document 1: WO 2010/110400
Patent Document 2: JP 2010-248183

Non-Patent Document

Non-Patent Document 1: Science, vol. 261, pages 921-923, 1993
Non-Patent Document 2: Neurobiology of Aging (Neurobiol. Aging), vol. 24, pages 421-426, 2003
Non-Patent Document 3: Molecular Psychiatry (Mol. Psychiatry), vol. 8, pages 635-638, 2003

Non-Patent Document 4: Neuroscience Letters (Neurosci. Lett.), vol. 328, pages 9-12, 2002

Non-Patent Document 5: Journal of the Biological Chemistry (J. Biol. Chem.), vol. 279, pages 34674-34681, 2004
Non-Patent Document 6: Neuroscience Letters (Neurosci. Lett.), vol. 324, pages 83-85, 2002
Non-Patent Document 7: Neuroscience Letters (Neurosci. Lett.), vol. 397, pages 83-87, 2006
Non-Patent Document 8: Brain Research (Brain Res.), vol. 818, pages 171-175, 1999
Non-Patent Document 9: Neuroscience, vol. 164, pages 398-403, 2009
Non-Patent Document 10: British Journal of Pharmacology, vol. 149, pages 998-1012, 2006
Non-Patent Document 11: Journal of Neuroscience Research (J. Neurosci. Res.), vol. 85, pages 1499-1505, 2007
Non-Patent Document 12: Neuroscience Letters (Neurosci. Lett.), vol. 331, pages 163-166, 2002
Non-Patent Document 13: Proceedings of the National Academy of Sciences USA (Proc. Natl. Acad. Sci. USA), vol. 102, pages 8333-8338, 2005
Non-Patent Document 14: Journal of Neurotrauma (J. Neurotrauma), vol. 25, pages 1087-1098, 2008
Non-Patent Document 15: Molecular Neuroscience (Mol. Neurosci.), vol. 16, pages 909-913, 2005
Non-Patent Document 16: Glia, vol. 50, pages 427-434, 2005
Non-Patent Document 17: Molecular Neurodegeneration (Mol. Neurodegeneration), vol. 4, pages 47-59, 2009
Non-Patent Document 18: Investigative Ophthalmology & Visual Science (Invest. Opthalmol. Vis. Sci.), vol. 50, pages 5712-5717, 2009
Non-Patent Document 19: Epilepsia, vol. 47, pages 867-872, 2006
Non-Patent Document 20: Journal of Neuroscience (J. Neurosci.), vol. 29, pages 3453-3462, 2012
Non-Patent Document 21: Journal of Neurology Neurosurgery Psychiatry (J. Neurol. Neurosurg. Psychiatry), vol. 48, pages 459-468, 1985
Non-Patent Document 22: Journal of Psychiatry Neuroscience (J. Psychiatry Neurosci.), vol. 36, pages 47-55, 2011
Non-Patent Document 23: Psychoneuroendocrinology, vol. 28, pages 83-96, 2003
Non-Patent Document 24: Chemical Communications (Cambridge, United Kingdom), 47(45), pages 12316-12318, 2011
Non-Patent Document 25: Chemical & Pharmaceutical Bulletin, 20(1), pages 122-32, 1972

SUMMARY OF THE INVENTION

Problems to be Solved by the Invention

An object of the present invention is to provide a compound having a superior CH24H inhibitory action, which is useful as an agent for the prophylaxis or treatment of neurodegenerative diseases (e.g., Alzheimer's disease, mild cognitive impairment, Huntington's disease, Parkinson's disease, amyotrophic lateral sclerosis, traumatic brain injury, cerebral infarction, glaucoma, multiple sclerosis etc.), epilepsy, schizophrenia or the like.

Means of Solving the Problems

The present inventors have conducted intensive studies in an attempt to solve the above-mentioned problem and found that a compound represented by the following formula has a superior CH24H inhibitory action, which resulted in the completion of the present invention.
Accordingly, the present invention provides the following.
[1] A compound represented by the formula (I):

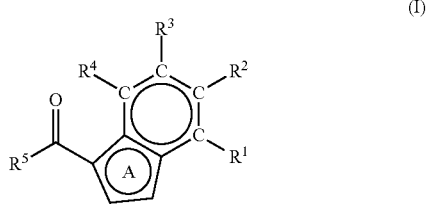

wherein
$R^1$ is a 5-membered nitrogen-containing aromatic heterocyclic group optionally substituted by 1 to 3 substituents selected from (1) an optionally substituted $C_{1-6}$ alkyl group, (2) a halogen atom, (3) an optionally substituted hydroxy group, (4) an optionally substituted sulfanyl group, and (5) an optionally substituted amino group;
$R^2$ is a hydrogen atom or a substituent;
$R^3$ is an optionally substituted $C_{1-6}$ alkyl group, a halogen atom, a cyano group, an acyl group, an optionally substituted hydroxy group, an optionally substituted sulfanyl group, an optionally substituted amino group, an optionally substituted carbocyclic group, or an optionally substituted heterocyclic group;
$R^4$ is a hydrogen atom or a substituent;
$R^5$ is an optionally substituted $C_{1-6}$ alkyl group, an optionally substituted hydroxy group, an optionally substituted amino group, an optionally substituted carbocyclic group, or an optionally substituted heterocyclic group; and Ring A is an optionally further substituted 5-membered aromatic heterocycle, or a salt thereof (in the present specification, to be referred as "compound (I)").

[2] The compound or salt of the above-mentioned [1], wherein $R^1$ is a 5-membered nitrogen-containing aromatic heterocyclic group optionally substituted by 1 to 3 optionally substituted $C_{1-6}$ alkyl group(s).

[3] The compound or salt of the above-mentioned [1] or [2], wherein $R^2$ is a hydrogen atom.

[4] The compound or salt of any one of the above-mentioned [1] to [3], wherein $R^3$ is an optionally substituted $C_{1-6}$ alkyl group, a halogen atom, a cyano group, an acyl group, an optionally substituted carbocyclic group, or an optionally substituted heterocyclic group.

[5] The compound or salt of any one of the above-mentioned [1] to [4], wherein $R^3$ is an optionally substituted $C_{1-6}$ alkyl group, a halogen atom, a cyano group, an acyl group, an optionally substituted $C_{3-8}$ cycloalkyl group, or an optionally substituted 5- or 6-membered aromatic heterocyclic group.

[6] The compound or salt of any one of the above-mentioned [1] to [5], wherein $R^4$ is a hydrogen atom.

[7] The compound or salt of any one of the above-mentioned [1] to [6], wherein $R^5$ is an optionally substituted $C_{1-6}$ alkyl group, an optionally substituted hydroxy group, an optionally substituted amino group, an optionally substituted $C_{3-8}$ cycloalkyl group, or an optionally substituted 3- to 12-membered non-aromatic heterocyclic group.

[8] The compound or salt of any one of the above-mentioned [1] to [7], wherein Ring A is an optionally further substituted 5-membered nitrogen-containing aromatic heterocycle.

[9] The compound or salt of any one of the above-mentioned [1] to [8], wherein the partial structure formula:

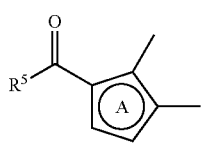

in the formula (I) is

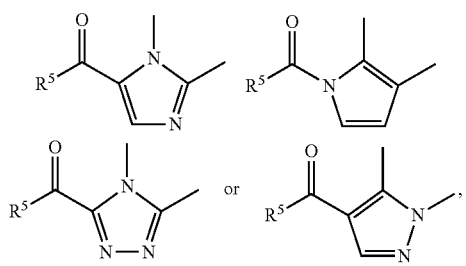

each of which is a optionally substituted.

[10] The compound or salt of any one of the above-mentioned [1] to [8], wherein the partial structure formula:

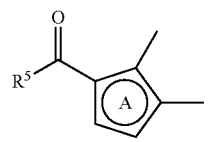

in the formula (I) is

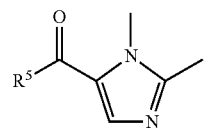

which is a optionally substituted.

[11] The compound or salt of the above-mentioned [1], wherein $R^1$ is a 5-membered nitrogen-containing aromatic heterocyclic group optionally substituted by one $C_{1-6}$ alkyl group;

$R^2$ is a hydrogen atom;

$R^3$ is (1) a $C_{1-8}$ alkyl group optionally substituted by 1 to 3 substituents selected from
    (a) a halogen atom, and
    (b) a $C_{1-8}$ alkoxy group,
(2) a halogen atom,
(3) a cyano group,
(4) a $C_{1-8}$ alkyl-carbonyl group,
(5) a $C_{3-8}$ cycloalkyl group, or
(6) a 5- or 6-membered aromatic heterocyclic group;

$R^4$ is a hydrogen atom;

$R^5$ is (1) a hydroxy group,
(2) a $C_{1-6}$ alkoxy group,
(3) an amino group optionally mono- or di-substituted by substituent(s) selected from
    (a) a $C_{1-6}$ alkyl group optionally substituted by 1 to 3 substituents selected from
        (i) a $C_{1-6}$ alkoxy group,
        (ii) a $C_{3-8}$ cycloalkyl group,
        (iii) a halogen atom,
        (iv) a 3- to 8-membered monocyclic non-aromatic heterocyclic group optionally substituted by one $C_{1-6}$ alkyl group, and
        (v) a $C_{6-14}$ aryl group,
    (b) a $C_{3-8}$ cycloalkyl group,
    (c) a 3- to 8-membered monocyclic non-aromatic heterocyclic group, and
    (d) a $C_{6-14}$ aryl group,
(4) a $C_{3-8}$ cycloalkyl group, or
(5) a 3- to 12-membered nitrogen-containing non-aromatic heterocyclic group optionally substituted by 1 to 4 substituents selected from
    (a) a $C_{1-6}$ alkoxy group optionally substituted by 1 to 3 halogen atoms,
    (b) a halogen atom,
    (c) a hydroxy group,
    (d) a $C_{1-6}$ alkyl group,
    (e) an oxo group, and
    (f) a cyano group; and Ring A is a 5-membered nitrogen-containing aromatic heterocycle optionally further substituted by one $C_{1-6}$ alkyl group.

[12] The compound or salt of the above-mentioned [1], wherein
$R^1$ is
(1) an oxazolyl group,
(2) an imidazolyl group,
(3) a triazolyl group, or
(4) a pyrazolyl group,
each of which is optionally substituted by one $C_{1-6}$ alkyl group;
$R^2$ is a hydrogen atom;
$R^3$ is
(1) a $C_{1-6}$ alkyl group optionally substituted by 1 to 3 substituents selected from
    (a) a halogen atom, and
    (b) a $C_{1-6}$ alkoxy group,
(2) a halogen atom,
(3) a cyano group,
(4) a $C_{1-6}$ alkyl-carbonyl group,
(5) a $C_{3-8}$ cycloalkyl group, or
(6) an oxazolyl group;
$R^4$ is a hydrogen atom;
$R^5$ is
(1) a hydroxy group,
(2) a $C_{1-6}$ alkoxy group,
(3) an amino group optionally mono- or di-substituted by substituent(s) selected from
    (a) a $C_{1-6}$ alkyl group optionally substituted by 1 to 3 substituents selected from
        (i) a $C_{1-6}$ alkoxy group,
        (ii) a $C_{3-8}$ cycloalkyl group,
        (iii) a halogen atom,
        (iv) an oxetanyl group and a tetrahydrofuranyl group, each of which is optionally substituted by one $C_{1-6}$ alkyl group, and
        (v) a $C_{6-14}$ aryl group,
    (b) a $C_{3-8}$ cycloalkyl group,
    (c) an oxetanyl group, a tetrahydropyranyl group and a tetrahydrofuranyl group, and
    (d) a $C_{6-14}$ aryl group,
(4) a $C_{3-8}$ cycloalkyl group, or
(5) an azetidinyl group, a pyrrolidinyl group, a morpholinyl group, a piperazinyl group, a piperidyl group, an oxazepanyl group, an 8-oxa-3-azabicyclo[3.2.1]octyl group, a 3-azabicyclo[3.1.0]hexyl group, a 2-oxa-5-azabicyclo[2.2.1]heptyl group, a 3-oxa-8-azabicyclo[3.2.1]octyl group, a 3-oxa-6-azabicyclo[3.1.1]heptyl group, a 6-oxa-3-azabicyclo[3.1.1]heptyl group, a 2-oxa-6-azaspiro[3.3]heptyl group, a 2-oxa-6-azaspiro[3.5]nonyl group, a 1-oxa-7-azaspiro[4.4]nonyl group, a 2-oxa-7-azaspiro[4.4]nonyl group, a 2-oxa-6-azaspiro[3.4]octyl group, a dioxidothiomorpholinyl group or a 3,7-dioxa-9-azabicyclo[3.3.1]nonyl group, each of which is optionally substituted by 1 to 4 substituents selected from
    (a) a $C_{1-6}$ alkoxy group optionally substituted by 1 to 3 halogen atoms,
    (b) a halogen atom,
    (c) a hydroxy group,
    (d) a $C_{1-6}$ alkyl group,
    (e) an oxo group, and
    (f) a cyano group; and
Ring A is
(1) imidazole,
(2) pyrrole,
(3) triazole, or
(4) pyrazole,
each of which is optionally further substituted by one $C_{1-6}$ alkyl group.

[13] The compound or salt of the above-mentioned [1], wherein.
$R^1$ is
(1) an oxazolyl group,
(2) an imidazolyl group,
(3) a triazolyl group, or
(4) a pyrazolyl group optionally substituted by one $C_{1-6}$ alkyl group;
$R^2$ is a hydrogen atom;
$R^3$ is
(1) a $C_{1-6}$ alkyl group optionally substituted by 1 to 3 substituents selected from
    (a) a halogen atom, and
    (b) a $C_{1-6}$ alkoxy group,
(2) a halogen atom,
(3) a cyano group,
(4) a $C_{1-6}$ alkyl-carbonyl group,
(5) a cyclopropyl group, or
(6) an oxazolyl group;
$R^4$ is a hydrogen atom;
$R^5$ is
(1) a hydroxy group,
(2) a $C_{1-6}$ alkoxy group,
(3) an amino group optionally mono- or di-substituted by substituent(s) selected from
    (a) a $C_{1-6}$ alkyl group optionally substituted by 1 to 3 substituents selected from
        (i) a $C_{1-6}$ alkoxy group,
        (ii) a cyclopropyl group,
        (iii) a halogen atom,
        (iv) an oxetanyl group optionally substituted by one $C_{1-6}$ alkyl group, and a tetrahydrofuranyl group, and
        (v) a phenyl group,
    (b) a cyclopropyl group,
    (c) an oxetanyl group, a tetrahydropyranyl group and a tetrahydrofuranyl group, and
    (d) a phenyl group,
(4) a cyclopropyl group, or
(5) an azetidinyl group, a pyrrolidinyl group, a morpholinyl group, a piperazinyl group, a piperidyl group, an oxazepanyl group, an 8-oxa-3-azabicyclo[3.2.1]octyl group, a 3-azabicyclo[3.1.0]hexyl group, a 2-oxa-5-azabicyclo[2.2.1]heptyl group, a 3-oxa-8-azabicyclo[3.2.1]octyl group, a 3-oxa-6-azabicyclo[3.1.1]heptyl group, a 6-oxa-3-azabicyclo[3.1.1]heptyl group, a 2-oxa-6-azaspiro[3.3]heptyl group, a 2-oxa-6-azaspiro[3.5]nonyl group, a 1-oxa-7-azaspiro[4.4]nonyl group, a 2-oxa-7-azaspiro[4.4]nonyl group, a 2-oxa-6-azaspiro[3.4]octyl group, a dioxidothiomorpholinyl group or a 3,7-dioxa-9-azabicyclo[3.3.1]nonyl group, each of which is optionally substituted by 1 to 4 substituents selected from
    (a) a $C_{1-6}$ alkoxy group optionally substituted by 1 to 3 halogen atoms,
    (b) a halogen atom,
    (c) a hydroxy group,
    (d) a $C_{1-6}$ alkyl group,
    (e) an oxo group, and
    (f) a cyano group; and
Ring A is
(1) imidazole,
(2) pyrrole,
(3) triazole, or
(4) pyrazole,
each of which is optionally further substituted by one $C_{1-6}$ alkyl group.
[14] The compound or salt of any one of the above-mentioned [1] to [13], wherein R[1] is
(1) 1,3-oxazol-5-yl,
(2) 1H-imidazol-1-yl,
(3) 1H-1,2,4-triazol-1-yl, or
(4) 1H-pyrazol-5-yl or 1H-pyrazol-4-yl, each of which is optionally substituted by one $C_{1-6}$ alkyl group.
[15] The compound or salt of the above-mentioned [1], wherein
R[1] is
(1) an oxazolyl group, or
(2) a triazolyl group;
R[2] is a hydrogen atom;
R[3] is a $C_{1-6}$ alkyl group optionally substituted by 1 to 3 halogen atoms;
R[4] is a hydrogen atom;
R[5] is
(1) an amino group optionally di-substituted by substituents selected from
    (a) a $C_{1-6}$ alkyl group, and
    (b) a tetrahydropyranyl group, or
(2) an azetidinyl group, a pyrrolidinyl group, a 2-oxa-5-azabicyclo[2.2.1]heptyl group, a 3-oxa-8-azabicyclo[3.2.1]octyl group or a 3-oxa-6-azabicyclo[3.1.1]heptyl group, each of which is optionally substituted by 1 to 4 substituents selected from
    (a) a $C_{1-6}$ alkoxy group optionally substituted by 1 to 3 halogen atoms, and
    (b) a halogen atom; and
Ring A is imidazole.
[16] The compound or salt of the above-mentioned [1], wherein
R[1] is an oxazolyl group;
R[2] is a hydrogen atom;
R[3] is a $C_{1-6}$ alkyl group optionally substituted by 1 to 3 halogen atoms;
R[4] is a hydrogen atom;
R[5] is
(1) an amino group optionally di-substituted by substituents selected from
    (a) a $C_{1-6}$ alkyl group, and
    (b) a tetrahydropyranyl group, or
(2) an azetidinyl group optionally substituted by one halogen atom, a 3-oxa-8-azabicyclo[3.2.1]octyl group or a 3-oxa-6-azabicyclo[3.1.1]heptyl group; and
Ring A is imidazole.
[17] The compound or salt of the above-mentioned [1], which is selected from
3-oxa-8-azabicyclo[3.2.1]oct-8-yl(8-(1,3-oxazol-5-yl)-6-(trifluoromethyl)imidazo[1,2-a]pyridin-3-yl)methanone or a salt thereof;
3-oxa-6-azabicyclo[3.1.1]hept-6-yl(8-(1,3-oxazol-5-yl)-6-(trifluoromethyl)imidazo[1,2-a]pyridin-3-yl)methanone or a salt thereof; and
N-methyl-8-(1,3-oxazol-5-yl)-N-(tetrahydro-2H-pyran-4-yl)-6-(trifluoromethyl)imidazo[1,2-a]pyridine-3-carboxamide or a salt thereof.
[18] 3-Oxa-8-azabicyclo[3.2.1]oct-8-yl(8-(1,3-oxazol-5-yl)-6-(trifluoromethyl)imidazo[1,2-a]pyridin-3-yl)methanone or a salt thereof.
[19] 3-Oxa-6-azabicyclo[3.1.1]hept-6-yl(8-(1,3-oxazol-5-yl)-6-(trifluoromethyl)imidazo[1,2-a]pyridin-3-yl)methanone or a salt thereof.
[20] N-Methyl-8-(1,3-oxazol-5-yl)-N-(tetrahydro-2H-pyran-4-yl)-6-(trifluoromethyl)imidazo[1,2-a]pyridine-3-carboxamide or a salt thereof.
[21] A medicament comprising the compound or salt of the above-mentioned [1].
[22] The medicament of the above-mentioned [21], which is a cholesterol 24-hydroxylase inhibitor.
[23] The medicament of the above-mentioned [21], which is an agent for the prophylaxis or treatment of neurodegenerative disease or epilepsy.
[24] The medicament of the above-mentioned [23], wherein the neurodegenerative disease is Alzheimer's disease, mild cognitive impairment, Huntington's disease, Parkinson's disease or multiple sclerosis.
[25] The compound or salt of the above-mentioned [1] for use in the prophylaxis or treatment of neurodegenerative disease or epilepsy.
[26] The compound or salt of the above-mentioned [25], wherein the neurodegenerative disease is Alzheimer's disease, mild cognitive impairment, Huntington's disease, Parkinson's disease or multiple sclerosis.
[27] A method of inhibiting cholesterol 24-hydroxylase in a mammal, which comprises administering an effective amount of the compound or salt of the above-mentioned [1] to the mammal.
[28] A method for the prophylaxis or treatment of neurodegenerative disease or epilepsy, which comprises administering an effective amount of the compound or salt of the above-mentioned [1] to the mammal.
[29] The method of the above-mentioned [28], wherein the neurodegenerative disease is Alzheimer's disease, mild cognitive impairment, Huntington's disease, Parkinson's disease or multiple sclerosis.
[30] Use of the compound or salt of the above-mentioned [1] for the production of an agent for the prophylaxis or treatment of neurodegenerative disease or epilepsy.
[31] The use of the above-mentioned [30], wherein the neurodegenerative disease is Alzheimer's disease, mild cognitive impairment, Huntington's disease, Parkinson's disease or multiple sclerosis.

Effect of the Invention

Compound (I) has a superior CH24H inhibitory action, which is useful as an agent for the prophylaxis or treatment of neurodegenerative diseases (e.g., Alzheimer's disease, mild cognitive impairment, Huntington's disease, Parkinson's disease, amyotrophic lateral sclerosis, traumatic brain injury, cerebral infarction, glaucoma, multiple sclerosis etc.), so epilepsy, schizophrenia or the like.

DETAILED DESCRIPTION OF THE INVENTION

In the present specification, the "halogen atom" means a fluorine atom, a chlorine atom, a bromine atom or an iodine atom.

In the present specification, examples of the "hydrocarbon (group)" include a "$C_{1-6}$ alkyl", a "$C_{2-6}$ alkenyl", a "$C_{2-6}$ alkynyl", a "$C_{3-8}$ cycloalkyl", a "$C_{3-8}$ cycloalkenyl", a "$C_{4-10}$ cycloalkadienyl", a "$C_{6-14}$ aryl", a "$C_{7-14}$ aralkyl", a "$C_{8-13}$ arylalkenyl" and the like.

In the present specification, the "$C_{1-6}$ alkyl (group)" means, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

In the present specification, the "$C_{2-6}$ alkenyl (group)" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl or the like.

In the present specification, the "C$_{2-6}$ alkynyl (group)" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl or the like.

In the present specification, the "C$_{3-8}$ cycloalkyl (group)" means, for example, cyclopropyl, cyclobutyl, cyclopentyl, cyclohexyl, cycloheptyl, cyclooctyl or the like.

In the present specification, the "C$_{3-8}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl) or the like.

In the present specification, the "C$_{4-10}$ cycloalkadienyl (group)" means, for example, 2,4-cyclopentadien-1-yl, 2,4-cyclohexadien-1-yl, 2,5-cyclohexadien-1-yl or the like.

In the present specification, the "C$_{6-14}$ aryl (group)" means, for example, phenyl, 1-naphthyl, 2-naphthyl or the like.

In the present specification, the "C$_{7-14}$ aralkyl (group)" means, for example, benzyl, phenethyl or the like.

In the present specification, the "C$_{8-13}$ arylalkenyl (group)" means, for example, styryl or the like.

In the present specification, the "heterocyclic group" means an aromatic heterocyclic group or a non-aromatic heterocyclic group.

In the present specification, the "aromatic heterocyclic group" means, for example, a 5- to 12-membered aromatic heterocyclic group, more specifically, the following monocyclic aromatic heterocyclic group or fused aromatic heterocyclic group.

In the present specification, examples of the "monocyclic aromatic heterocyclic group" include a 5- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized). Examples thereof include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like.

In the present specification, examples of the "fused aromatic heterocyclic group" include an 8- to 12-membered fused aromatic heterocyclic group, specifically, a group derived from a fused ring wherein a ring corresponding to the above-mentioned 5- to 7-membered monocyclic aromatic heterocyclic group is fused with a C$_{6-14}$ aromatic hydrocarbon; and a group derived from a fused ring wherein rings corresponding to the above-mentioned 5- to 7-membered monocyclic aromatic heterocyclic groups are fused. Examples thereof include quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl, 2H-imidazo[1,2-a]pyridin-3-yl), thienopyridyl (e.g., thieno[2,3-b]pyridin-3-yl), imidazopyrazinyl (e.g., 1H-imidazo[4,5-b]pyrazin-2-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

In the present specification, the "non-aromatic heterocyclic group" means, for example, a 3- to 12-membered non-aromatic heterocyclic group, more specifically, the following monocyclic non-aromatic heterocyclic group, fused non-aromatic heterocyclic group, bridged non-aromatic heterocyclic group or spiro non-aromatic heterocyclic group.

In the present specification, examples of the "monocyclic non-aromatic heterocyclic group" include a 3- to 8-membered (preferably 5- or 6-membered) monocyclic non-aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized). Examples thereof include aziridinyl (e.g., 1-aziridinyl, aziridin-2-yl), azetidinyl (e.g., 1-azetidinyl, 2-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), oxetanyl (e.g., oxetan-2-yl, oxetan-3-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), azepanyl (e.g., 1-azepanyl, 2-azepanyl, 3-azepanyl, 4-azepanyl), dihydropyridyl (e.g., dihydropyridin-1-yl, dihydropyridin-2-yl, dihydropyridin-3-yl, dihydropyridin-4-yl), tetrahydropyridyl (e.g., 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl), oxazepanyl (e.g., 1,4-oxazepanyl) and the like.

In the present specification, examples of the "fused non-aromatic heterocyclic group" include an 8- to 12-membered fused non-aromatic heterocyclic group, specifically, a group derived from a fused ring wherein a ring corresponding to the above-mentioned 3- to 8-membered monocyclic non-aromatic heterocyclic group is fused with a $C_{6-14}$ aromatic hydrocarbon; a group derived from a fused ring wherein rings corresponding to the above-mentioned 3- to 8-membered monocyclic non-aromatic heterocyclic groups are fused; a group derived from a fused ring wherein a ring corresponding to the above-mentioned 3- to 8-membered monocyclic non-aromatic heterocyclic group is fused with a ring corresponding to the above-mentioned 5- to 7-membered monocyclic aromatic heterocyclic group; and a group wherein the above-mentioned group is partially saturated. Examples thereof include dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), dihydrobenzodioxinyl (e.g., 2,3-dihydro-1,4-benzodioxin-2-yl), dihydrobenzodioxepinyl (e.g., 3,4-dihydro-2H-1,5-benzodioxepin-2-yl), chromenyl (e.g., 4H-chromen-2-yl, 2H-chromen-3-yl), dihydrochromenyl (e.g., 3,4-dihydro-2H-chromen-2-yl), dihydroquinolyl (e.g., 1,2-dihydroquinolin-4-yl), tetrahydroquinolyl (e.g., 1,2,3,4-tetrahydroquinolin-4-yl), dihydroisoquinolyl (e.g., 1,2-dihydroisoquinolin-4-yl), tetrahydroisoquinolyl (e.g., 1,2,3,4-tetrahydroisoquinolin-4-yl), dihydrophthalazinyl (e.g., 1,4-dihydrophthalazin-4-yl) and the like.

In the present specification, examples of the "bridged non-aromatic heterocyclic group" include a group derived from a ring wherein a ring corresponding to the above-mentioned 3- to 8-membered monocyclic non-aromatic heterocyclic group is bridged by a $C_{1-4}$ alkyl chain (e.g., methylene, ethylene, trimethylene, tetramethylene), for example, 8-oxa-3-azabicyclo[3.2.1]octyl, 3-azabicyclo[3.1.0]hexyl, 2-oxa-5-azabicyclo[2.2.1]heptyl, 3-oxa-8-azabicyclo[3.2.1]octyl, 3-oxa-6-azabicyclo[3.1.1]heptyl, 6-oxa-3-azabicyclo[3.1.1]heptyl and the like.

In the present specification, examples of the "spiro non-aromatic heterocyclic group" include a group derived from a ring wherein a ring corresponding to the above-mentioned 3- to 8-membered monocyclic non-aromatic heterocyclic group is spiro-bonded to a non-aromatic ring, for example, 2-oxa-6-azaspiro[3.3]heptyl, 2-oxa-6-azaspiro[3.5]nonyl, 1-oxa-7-azaspiro[4.4]nonyl, 2-oxa-7-azaspiro[4.4]nonyl, 2-oxa-6-azaspiro[3.4]octyl, 6-azaspiro[3.4]octyl, 2-azaspiro[4.4]nonyl and the like.

In the present specification, examples of the "5- or 6-membered aromatic heterocyclic group" include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like.

In the present specification, examples of the "5- or 6-membered nitrogen-containing aromatic heterocyclic group" include a 5- or 6-membered nitrogen-containing aromatic heterocyclic group containing, as a ring-constituting atom besides carbon atoms, at least one nitrogen atom (optionally oxidized), and optionally containing 1 or 2 hetero atoms selected from an oxygen atom, a sulfur atom (optionally oxidized) and a nitrogen atom (optionally oxidized). Examples thereof include pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like.

In the present specification, examples of the "5-membered nitrogen-containing aromatic heterocyclic group" include a 5-membered group, from among the above-mentioned 5- or 6-membered nitrogen-containing aromatic heterocyclic group.

In the present specification, examples of the "carbocyclic group" include the above-mentioned "$C_{3-8}$ cycloalkyl (group)", "$C_{3-8}$ cycloalkenyl (group)", "$C_{4-10}$ cycloalkadienyl (group)" and "$C_{6-14}$ aryl (group)".

In the present specification, examples of the "non-aromatic ring" include a $C_{3-8}$ cycloalkane, a $C_{3-8}$ cycloalkene, a $C_{4-10}$ cycloalkadiene, a monocyclic non-aromatic heterocycle and a fused non-aromatic heterocycle.

In the present specification, the "$C_{3-8}$ cycloalkane" means, for example, cyclopropane, cyclobutane, cyclopentane, cyclohexane, cycloheptane, cyclooctane or the like.

In the present specification, the "$C_{3-8}$ cycloalkene" means, for example, cyclopropene, cyclobutene, cyclopentene, cyclohexene or the like.

In the present specification, the "$C_{4-10}$ cycloalkadiene" means, for example, 2,4-cyclopentadiene, 2,4-cyclohexadiene, 2,5-cyclohexadiene or the like.

In the present specification, the "monocyclic non-aromatic heterocycle" means, for example, a ring corresponding to the above-mentioned "monocyclic non-aromatic heterocyclic group".

In the present specification, the "fused non-aromatic heterocycle" means, for example, a ring corresponding to the above-mentioned "fused non-aromatic heterocyclic group".

In the present specification, examples of the "$C_{6-14}$ aromatic hydrocarbon" include benzene and naphthalene.

In the present specification, the "5- or 6-membered aromatic ring" means, for example, benzene, a 5- or 6-membered aromatic heterocycle or the like.

In the present specification, examples of the "5- or 6-membered aromatic heterocycle" include a 5- or 6-membered monocyclic aromatic heterocycle containing, as a ring-constituting atom besides carbon atoms, 1 to 4 hetero atoms selected from an oxygen atom, a sulfur atom (optionally oxidized) and a nitrogen atom (optionally oxidized). Examples thereof include furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazine and the like.

In the present specification, examples of the "5-membered aromatic heterocycle (group)" include a 5-membered one, from among the above-mentioned 5- or 6-membered aromatic heterocycle.

In the present specification, examples of the "5- or 6-membered nitrogen-containing aromatic heterocycle" include a 5- or 6-membered nitrogen-containing aromatic heterocycle containing, as a ring-constituting atom besides carbon atoms, at least one nitrogen atom (optionally oxidized), and optionally containing 1 or 2 hetero atoms selected from an oxygen atom, a sulfur atom (optionally oxidized) and a nitrogen atom (optionally oxidized). Examples thereof include pyridine, pyrimidine, pyridazine, pyrazine, pyrrole, imidazole, pyrazole, thiazole, isothiazole, oxazole, isoxazole, oxadiazole, thiadiazole, triazole, tetrazole, triazine and the like.

In the present specification, the "nitrogen-containing non-aromatic heterocycle (group)" means, for example, a 3- to 12-membered nitrogen-containing non-aromatic heterocycle (group), more specifically, the following monocyclic nitrogen-containing non-aromatic heterocycle (group), fused nitrogen-containing non-aromatic heterocycle (group), nitrogen-containing bridged non-aromatic heterocycle (group) or nitrogen-containing Spiro non-aromatic heterocycle (group).

In the present specification, examples of the "monocyclic nitrogen-containing non-aromatic heterocycle (group)" include a 3- to 8-membered nitrogen-containing non-aromatic heterocycle (group) containing, as a ring-constituting atom besides carbon atoms, at least one nitrogen atom, and optionally containing 1 or 2 hetero atoms selected from an oxygen atom, a sulfur atom and a nitrogen atom. Examples thereof include aziridinyl, azetidinyl, pyrrolidinyl, morpholinyl, piperazinyl, piperidyl, azepanyl, oxazepanyl, thiomorpholinyl, oxazolidinyl, thiazolidinyl, imidazolidinyl, oxazolinyl, thiazolinyl, imidazolinyl, dihydrooxadiazolyl, pyrazolidinyl, pyrazolinyl, tetrahydropyrimidinyl, dihydrotriazolyl, tetrahydrotriazolyl, dihydropyridyl, tetrahydropyridyl and the like.

In the present specification, examples of the "fused nitrogen-containing non-aromatic heterocycle (group)" include an 8- to 12-membered fused nitrogen-containing non-aromatic heterocyclic group, specifically, a group derived from a ring wherein a ring corresponding to the above-mentioned 3- to 8-membered monocyclic nitrogen-containing non-aromatic heterocyclic group is fused with a $C_{6-14}$ aromatic hydrocarbon; a group derived from a ring wherein rings corresponding to the above-mentioned 3- to 8-membered monocyclic nitrogen-containing non-aromatic heterocyclic group are fused; a group derived from a ring wherein a ring corresponding to the above-mentioned 3- to 8-membered monocyclic nitrogen-containing non-aromatic heterocycle is fused with a ring corresponding to the above-mentioned 5- to 7-membered monocyclic aromatic heterocyclic group; and a group wherein the above-mentioned group is partially saturated. Examples thereof include dihydroindolyl, dihydroisoindolyl, dihydroquinolyl, tetrahydroquinolyl, dihydroisoquinolyl, tetrahydroisoquinolyl, dihydrophthalazinyl and the like.

In the present specification, examples of the "bridged nitrogen-containing non-aromatic heterocycle (group)" include a group derived from a heterocycle wherein a group corresponding to the above-mentioned 3- to 8-membered monocyclic nitrogen-containing non-aromatic heterocyclic group is bridged by a $C_{1-4}$ alkyl chain (e.g., methylene, ethylene, trimethylene, tetramethylene). Examples thereof include 8-oxa-3-azabicyclo[3.2.1]octyl, 3-azabicyclo[3.1.0]hexyl, 2-oxa-5-azabicyclo[2.2.1]heptyl, 3-oxa-8-azabicyclo[3.2.1]octyl, 3-oxa-6-azabicyclo[3.1.1]heptyl and the like.

In the present specification, examples of the "spiro nitrogen-containing non-aromatic heterocycle (group)" include a group derived from a ring wherein a group corresponding to the above-mentioned 3- to 8-membered monocyclic nitrogen-containing non-aromatic heterocyclic group is spiro-bonded to a non-aromatic ring. Examples thereof include 2-oxa-6-azaspiro[3.3]heptyl, 2-oxa-6-azaspiro[3.5]nonyl, 1-oxa-7-azaspiro[4.4]nonyl, 2-oxa-7-azaspiro[4.4]nonyl, 2-oxa-6-azaspiro[3.4]octyl and the like.

In the present specification, examples of the "optionally substituted hydroxy group" include, unless otherwise specified, a "hydroxy group", an "optionally substituted $C_{1-6}$ alkoxy group", an "optionally substituted $C_{2-6}$ alkenyloxy group", an "optionally substituted $C_{2-6}$ alkynyloxy group", an "optionally substituted $C_{3-8}$ cycloalkyloxy group", an "optionally substituted $C_{3-8}$ cycloalkenyloxy group", an "optionally substituted $C_{4-10}$ cycloalkadienyloxy group", an "optionally substituted $C_{6-14}$ aryloxy group", an "optionally substituted $C_{7-14}$ aralkyloxy group", an "optionally substituted $C_{8-13}$ arylalkenyloxy group", an "optionally substituted heterocyclyl-oxy group" and the like.

In the present specification, the "$C_{1-6}$ alkoxy (group)" means, for example, methoxy, ethoxy, propoxy, isopropoxy, butoxy, isobutoxy, sec-butoxy, tert-butoxy, pentyloxy, isopentyloxy, hexyloxy or the like.

In the present specification, the "$C_{2-6}$ alkenyloxy (group)" means, for example, vinyloxy, 1-propenyloxy, 2-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyloxy, 3-hexenyloxy, 5-hexenyloxy or the like.

In the present specification, the "$C_{2-6}$ alkynyloxy (group)" means, for example, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1,1-dimethylprop-2-yn-1-yloxy, 1-hexynyloxy, 2-hexynyloxy, 3-hexynyloxy, 4-hexynyloxy, 5-hexynyloxy or the like.

In the present specification, the "$C_{3-8}$ cycloalkyloxy (group)" means, for example, cyclopropyloxy, cyclobutyloxy, cyclopentyloxy, cyclohexyloxy, cycloheptyloxy, cyclooctyloxy or the like.

In the present specification, the "$C_{3-8}$ cycloalkenyloxy (group)" means, for example, cyclopropenyloxy (e.g., 2-cyclopropen-1-yloxy), cyclobutenyloxy (e.g., 2-cyclobuten-1-yloxy), cyclopentenyloxy (e.g., 2-cyclopenten-1-yloxy, 3-cyclopenten-1-yloxy), cyclohexenyloxy (e.g., 2-cyclohexen-1-yloxy, 3-cyclohexen-1-yloxy) or the like.

In the present specification, the "$C_{4-10}$ cycloalkadienyloxy (group)" means, for example, 2,4-cyclopentadien-1-yloxy, 2,4-cyclohexadien-1-yloxy, 2,5-cyclohexadien-1-yloxy or the like.

In the present specification, the "$C_{6-14}$ aryloxy (group)" means, unless otherwise specified, for example, phenoxy, 1-naphthyloxy, 2-naphthyloxy or the like.

In the present specification, the "$C_{7-14}$ aralkyloxy (group)" means, unless otherwise specified, for example, benzyloxy, phenethyloxy or the like.

In the present specification, the "$C_{8-13}$ arylalkenyloxy (group)" means, for example, styryloxy or the like.

In the present specification, examples of the "heterocyclyl-oxy (group)" include hydroxy substituted by a heterocyclic group. Preferable examples of the heterocyclyl-oxy include tetrahydropyranyloxy, thiazolyloxy, pyridyloxy, pyrazolyloxy, oxazolyloxy, thienyloxy, furyloxy and the like.

In the present specification, examples of the "optionally substituted sulfanyl group" include, unless otherwise specified, a "sulfanyl group", an "optionally substituted $C_{1-6}$ alkylsulfanyl group", an "optionally substituted $C_{2-6}$ alkenylsulfanyl group", an "optionally substituted $C_{2-6}$ alkynylsulfanyl group", an "optionally substituted $C_{3-8}$ cycloalkylsulfanyl group", an "optionally substituted $C_{3-8}$ cycloalkenylsulfanyl group", an "optionally substituted $C_{4-10}$ cycloalkadienylsulfanyl group", an "optionally substituted $C_{6-14}$ arylsulfanyl group", an "optionally substituted $C_{7-14}$ aralkylsulfanyl group", an "optionally substituted $C_{8-13}$ arylalkenylsulfanyl group", an "optionally substituted heterocyclyl-sulfanyl group" and the like.

In the present specification, examples of the "$C_{1-6}$ alkylsulfanyl (group)" include, unless otherwise specified, methylsulfanyl, ethylsulfanyl, propylsulfanyl, isopropylsulfanyl, butylsulfanyl, sec-butylsulfanyl, tert-butylsulfanyl and the like.

In the present specification, examples of the "$C_{2-6}$ alkenylsulfanyl (group)" include, unless otherwise specified, vinyl sulfanyl, propenylsulfanyl, isopropenylsulfanyl and the like.

In the present specification, examples of the "$C_{2-6}$ alkynylsulfanyl (group)" include, unless otherwise specified, 2-butynyl sulfanyl, 2-pentynylsulfanyl, 5-hexynylsulfanyl and the like.

In the present specification, examples of the "$C_{3-8}$ cycloalkylsulfanyl (group)" include, unless otherwise specified, cyclopropylsulfanyl, cyclobutylsulfanyl, cyclopentylsulfanyl, cyclohexylsulfanyl, cycloheptylsulfanyl, cyclooctylsulfanyl and the like.

In the present specification, examples of the "$C_{3-8}$ cycloalkenylsulfanyl (group)" include, unless otherwise specified, for example, cyclopropenylsulfanyl (e.g., 2-cyclopropenylsulfanyl), cyclobutenylsulfanyl (e.g., 2-cyclobutenylsulfanyl), cyclopentenylsulfanyl (e.g., 1-cyclopentenylsulfanyl, 2-cyclopentenylsulfanyl, 3-cyclopentenylsulfanyl), cyclohexenylsulfanyl (e.g., 1-cyclohexenylsulfanyl, 2-cyclohexenylsulfanyl, 3-cyclohexenylsulfanyl) and the like.

In the present specification, the "$C_{4-10}$ cycloalkadienylsulfanyl (group)" means, for example, 2,4-cyclopentadien-1-ylsulfanyl, 2,4-cyclohexadien-1-ylsulfanyl, 2,5-cyclohexadien-1-ylsulfanyl or the like.

In the present specification, examples of the "$C_{6-14}$ arylsulfanyl (group)" include, unless otherwise specified, phenylsulfanyl, 1-naphthylsulfanyl, 2-naphthylsulfanyl and the like.

In the present specification, examples of the "$C_{7-14}$ aralkylsulfanyl (group)" include, unless otherwise specified, benzylsulfanyl, phenethylsulfanyl and the like.

In the present specification, "$C_{8-13}$ arylalkenylsulfanyl (group)" include styrylsulfanyl and the like.

In the present specification, examples of the "heterocyclylsulfanyl (group)" include sulfanyl substituted by the above-mentioned "heterocyclic group". Preferable examples of the heterocyclyl-sulfanyl include tetrahydropyranylsulfanyl, thiazolylsulfanyl, pyridylsulfanyl, pyrazolylsulfanyl, oxazolylsulfanyl, thienylsulfanyl, furylsulfanyl and the like.

In the present specification, examples of the "optionally substituted amino" include, unless otherwise specified, amino optionally mono- or di-substituted by substituent(s) selected from (1) an optionally substituted $C_{1-6}$ alkyl;
(2) an optionally substituted $C_{2-6}$ alkenyl;
(3) an optionally substituted $C_{2-6}$ alkynyl;
(4) an optionally substituted $C_{3-8}$ cycloalkyl;
(5) an optionally substituted $C_{3-8}$ cycloalkenyl;
(6) an optionally substituted $C_{4-10}$ cycloalkadienyl;
(7) an optionally substituted $C_{6-14}$ aryl;
(8) an optionally substituted $C_{7-14}$ aralkyl;
(9) an optionally substituted $C_{8-13}$ arylalkenyl;
(10) an optionally substituted heterocyclic group (preferably furyl, pyridyl, thienyl, pyrazolyl, thiazolyl, oxazolyl); and
(11) acyl.

When the "optionally substituted amino" is amino substituted by two substituents, these substituents are may be the same or different, and may form a nitrogen-containing heterocycle together with the adjacent nitrogen atom. Examples of the "nitrogen-containing heterocycle" include a 5- to 7-membered nitrogen-containing heterocycle containing, as a ring-constituting atom besides carbon atoms, at least one nitrogen atom, and optionally containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine, oxazepane and the like.

In the present specification, examples of the "acyl group" include, unless otherwise specified, a group represented by the formula: —$COR^A$, —CO—$OR^A$, —$SO_2R^A$, —$SOR^A$, —$PO(OR^A)(OR^B)$, —CO—$NR^{Aa}R^{Ba}$, —CS—$NR^{Aa}R^{Ba}$ or —$SO_2$—$NR^{Aa}R^{Ba}$ wherein $R^A$ and $R^B$ are the same or different and each is a hydrogen atom, an optionally substituted hydrocarbon group or an optionally substituted heterocyclic group, and $R^{Aa}$ and $R^{Ba}$ are the same or different and each is a hydrogen atom, an optionally substituted hydrocarbon group or an optionally substituted heterocyclic group, or $R^{Aa}$ and $R^{Ba}$ optionally form, together with the adjacent nitrogen atom, an optionally substituted nitrogen-containing heterocycle, and the like.

Examples of the "nitrogen-containing heterocycle" of the "optionally substituted nitrogen-containing heterocycle" formed by $R^{Aa}$ and $R^{Ba}$ together with the adjacent nitrogen atom include a 5- to 7-membered nitrogen-containing heterocycle containing, as a ring-constituting atom besides carbon atoms, at least one nitrogen atom and optionally containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

The nitrogen-containing heterocycle optionally has 1 to 2 substituents at substitutable positions. Examples of the substituent include hydroxy, optionally halogenated $C_{1-6}$ alkyl, $C_{6-14}$ aryl, $C_{7-14}$ aralkyl and the like. When the number of the substituents is 2, the respective substituents may be the same or different.

Preferable examples of the "acyl group" include formyl; carboxyl;
carbamoyl;
$C_{1-6}$ alkyl-carbonyl;
$C_1$-6 alkoxy-carbonyl;
$C_{3-8}$ cycloalkyl-carbonyl;
$C_{6-14}$ aryl-carbonyl;
$C_{7-14}$ aralkyl-carbonyl;
$C_{6-14}$ aryloxy-carbonyl;
$C_{7-14}$ aralkyloxy-carbonyl;
mono- or di-$C_{1-6}$ alkyl-carbamoyl;
mono- or di-$C_{6-14}$ aryl-carbamoyl;
mono- or di-$C_{3-8}$ cycloalkyl-carbamoyl;
mono- or di-$C_{7-14}$ aralkyl-carbamoyl;
$C_{1-6}$ alkylsulfonyl;
$C_{6-14}$ arylsulfonyl optionally substituted by nitro;
nitrogen-containing heterocyclyl-carbonyl;
$C_{1-6}$ alkylsulfinyl;
$C_{6-14}$ arylsulfinyl;
thiocarbamoyl;
sulfamoyl;

mono- or di-$C_{1-6}$ alkylsulfamoyl;
mono- or di-$C_{6-14}$ arylsulfamoyl;
mono- or di-$C_{7-14}$ aralkylsulfamoyl;
and the like.

In the present specification, examples of the "$C_{1-6}$ alkylenedioxy (group)" include methylenedioxy, ethylenedioxy and the like.

Each symbol of the formula (I) is explained below.

In the formula (I), $R^1$ is a 5-membered nitrogen-containing aromatic heterocyclic group optionally substituted by 1 to 3 substituents selected from (1) an optionally substituted $C_{1-6}$ alkyl group, (2) a halogen atom, (3) an optionally substituted hydroxy group, (4) an optionally substituted sulfanyl group and (5) an optionally substituted amino group.

The "5-membered nitrogen-containing aromatic heterocyclic group" of the "5-membered nitrogen-containing aromatic heterocyclic group optionally substituted by 1 to 3 substituents selected from (1) an optionally substituted $C_{1-6}$ alkyl group, (2) a halogen atom, (3) an optionally substituted hydroxy group, (4) an optionally substituted sulfanyl group and (5) an optionally substituted amino group" for $R^1$ is preferably oxazolyl, imidazolyl, triazolyl or pyrazolyl.

The "$C_{1-6}$ alkyl group" of the "optionally substituted $C_{1-6}$ alkyl group" in $R^1$ optionally has 1 to 5 (preferably 1 to 3) substituents at substitutable position(s). Examples of the substituent include substituents selected from the following Substituent Group A. When the number of the substituents is plural, the respective substituents may be the same or different.

Substituent Group A:
(1) a halogen atom;
(2) a cyano group;
(3) a nitro group;
(4) a hydroxy group;
(5) a $C_{3-8}$ cycloalkyl group optionally substituted by 1 to 3 substituents selected from
  (a) a halogen atom,
  (b) a cyano group, and
  (c) a $C_{1-6}$ alkyl group optionally substituted by 1 to 3 halogen atoms, and
  (d) a $C_{1-6}$ alkoxy group optionally substituted by 1 to 3 halogen atoms;
(6) a $C_{6-14}$ aryl group optionally substituted by 1 to 3 substituents selected from
  (a) a halogen atom,
  (b) a cyano group,
  (c) a $C_{1-6}$ alkyl group optionally substituted by 1 to 3 halogen atoms, and
  (d) a $C_{1-6}$ alkoxy group optionally substituted by 1 to 3 halogen atoms;
(7) a $C_{1-6}$ alkoxy group optionally substituted by 1 to 3 substituents selected from
  (a) a halogen atom,
  (b) a cyano group,
  (c) a $C_{3-8}$ cycloalkyl group optionally having 1 to 3 halogen atoms,
  (d) a $C_{3-8}$ cycloalkenyl group optionally having 1 to 3 halogen atoms,
  (e) a $C_{6-14}$ aryl group optionally having 1 to 3 halogen atoms, and
  (f) a 5- or 6-membered monocyclic aromatic heterocyclic group;
(8) a $C_{2-6}$ alkenyloxy group (e.g., vinyloxy, propenyloxy, butenyloxy, pentenyloxy, hexenyloxy) optionally having 1 to 3 halogen atoms;
(9) a $C_{2-6}$ alkynyloxy group (e.g., ethynyloxy, propynyloxy, butynyloxy, pentynyloxy, hexynyloxy) optionally having 1 to 3 halogen atoms;
(10) a $C_{3-8}$ cycloalkyloxy group (e.g., cyclopropyloxy, cyclobutyloxy, cyclopentyloxy, cyclohexyloxy) optionally having 1 to 3 halogen atoms;
(11) a $C_{3-8}$ cycloalkenyloxy group (e.g., cyclopropenyloxy, cyclobutenyloxy, cyclopentenyloxy, cyclohexenyloxy) optionally having 1 to 3 halogen atoms;
(12) a $C_{6-14}$ aryloxy group optionally having 1 to 3 halogen atoms;
(13) a $C_{7-14}$ aralkyloxy group optionally having 1 to 3 halogen atoms;
(14) a carbamoyl group optionally mono- or di-substituted by substituent(s) selected from
  (a) a $C_{1-6}$ alkyl group,
  (b) a $C_{3-6}$ cycloalkyl group,
  (c) a $C_{6-14}$ aryl group,
  (d) a $C_{1-6}$ alkoxy group,
  (e) a 5- or 6-membered monocyclic aromatic heterocyclic group,
  (f) an 8- to 12-membered fused aromatic heterocyclic group,
  (g) a 3- to 8-membered monocyclic non-aromatic heterocyclic group, and
  (h) an 8- to 12-membered fused non-aromatic heterocyclic group;
(15) a sulfamoyl group optionally mono- or di-substituted by substituent(s) selected from
  (a) a $C_{1-6}$ alkyl group,
  (b) a $C_{3-6}$ cycloalkyl group,
  (c) a $C_{6-14}$ aryl group,
  (d) a $C_{1-6}$ alkoxy group,
  (e) a 5- or 6-membered monocyclic aromatic heterocyclic group,
  (f) an 8- to 12-membered fused aromatic heterocyclic group,
  (g) a 3- to 8-membered monocyclic non-aromatic heterocyclic group, and
  (h) an 8- to 12-membered fused non-aromatic heterocyclic group;
(16) a formyl group;
(17) a $C_{1-6}$ alkyl-carbonyl group;
(18) a $C_{2-6}$ alkenyl-carbonyl group (e.g., acryloyl, butenoyl, pentenoyl, hexenoyl, heptenoyl);
(19) a $C_{2-6}$ alkynyl-carbonyl group (e.g., propioloyl, propynylcarbonyl, butynylcarbonyl, pentynylcarbonyl, hexynylcarbonyl);
(20) a $C_{3-8}$ cycloalkyl-carbonyl group (e.g., cyclopropylcarbonyl, cyclobutylcarbonyl, cyclopentylcarbonyl, cyclohexylcarbonyl);
(21) a $C_{3-8}$ cycloalkenyl-carbonyl group (e.g., cyclopropenylcarbonyl, cyclobutenylcarbonyl, cyclopentenylcarbonyl, cyclohexenylcarbonyl);
(22) a $C_{6-14}$ aryl-carbonyl group (e.g., benzoyl, 1-naphthylcarbonyl, 2-naphthylcarbonyl);
(23) a $C_{3-8}$ cycloalkyl-$C_{1-6}$ alkyl-carbonyl group (e.g., cyclopropylacetyl, 3-cyclopropylpropionyl, cyclobutylacetyl, cyclopentylacetyl, cyclohexylacetyl, cyclohexylpropionyl);
(24) a $C_{3-8}$ cycloalkenyl-$C_{1-6}$ alkyl-carbonyl group (e.g., cyclopentenylacetyl, cyclohexenylacetyl, 3-cyclohexenylpropionyl, 3-cyclohexenylpropionyl);
(25) a $C_{7-14}$ aralkyl-carbonyl group (e.g., phenylacetyl, 3-phenylpropionyl);
(26) a 5- or 6-membered monocyclic aromatic heterocyclylcarbonyl group (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl);
(27) an 8- to 12-membered fused aromatic heterocyclylcarbonyl group (e.g., benzofuranylcarbonyl, isobenzofuranylcarbonyl, benzothienylcarbonyl, isobenzothienylcarbonyl, indolylcarbonyl, isoindolylcarbonyl, indazolylcarbonyl, benzimidazolylcarbonyl, benzoxazolylcarbonyl);
(28) a 3- to 8-membered monocyclic non-aromatic heterocyclylcarbonyl group (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidylcarbonyl);
(29) an 8- to 12-membered fused non-aromatic heterocyclylcarbonyl group (e.g., dihydrobenzofuranyl);
(30) an amino group optionally mono- or di-substituted by substituent(s) selected from
    (a) a $C_{1-6}$ alkyl group optionally having 1 to 3 halogen atoms,
    (b) a $C_{1-6}$ alkyl-carbonyl group optionally having 1 to 3 halogen atoms,
    (c) a $C_{3-8}$ cycloalkyl-carbonyl group,
    (d) a $C_{6-14}$ aryl-carbonyl group optionally having 1 to 3 halogen atoms,
    (e) a 5- or 6-membered monocyclic aromatic heterocyclylcarbonyl group,
    (f) an 8- to 12-membered fused aromatic heterocyclylcarbonyl group,
    (g) a 3- to 8-membered monocyclic non-aromatic heterocyclylcarbonyl group, and
    (h) an 8- to 12-membered fused non-aromatic heterocyclylcarbonyl group;
(31) a sulfanyl group;
(32) a $C_{1-6}$ alkylsulfanyl group (e.g., methylsulfanyl, ethylsulfanyl);
(33) a $C_{2-6}$ alkenylsulfanyl group (e.g., vinylsulfanyl, propenylsulfanyl);
(34) a $C_{2-6}$ alkynylsulfanyl group (e.g., ethynylsulfanyl, propynylsulfanyl);
(35) a $C_{3-8}$ cycloalkylsulfanyl group (e.g., cyclopropylsulfanyl, cyclobutylsulfanyl);
(36) a $C_{3-8}$ cycloalkenylsulfanyl group (e.g., cyclopropenylsulfanyl, cyclobutenylsulfanyl);
(37) a $C_{6-14}$ arylsulfanyl group (e.g., phenylsulfanyl);
(38) a $C_{3-8}$ cycloalkyl-$C_{1-6}$ alkylsulfanyl group (e.g., cyclopropylmethylsulfanyl);
(39) a $C_{3-8}$ cycloalkenyl-$C_{1-6}$ alkylsulfanyl group (e.g., cyclopentenylmethylsulfanyl);
(40) a $C_{1-6}$ alkylsulfinyl group (e.g., methylsulfinyl, ethylsulfinyl);
(41) a $C_{2-6}$ alkenylsulfinyl group (e.g., vinylsulfinyl, propenylsulfinyl);
(42) a $C_{2-6}$ alkynylsulfinyl group (e.g., ethynylsulfinyl, propynylsulfinyl);
(43) a $C_{3-8}$ cycloalkylsulfinyl group (e.g., cyclopropylsulfinyl, cyclobutylsulfinyl);
(44) a $C_{3-8}$ cycloalkenylsulfinyl group (e.g., cyclopropenylsulfinyl, cyclobutenylsulfinyl);
(45) a $C_{6-14}$ arylsulfinyl group (e.g., phenylsulfinyl);
(46) a $C_{3-8}$ cycloalkyl-$C_{1-6}$ alkylsulfinyl group (e.g., cyclopropylmethylsulfinyl);
(47) a $C_{3-8}$ cycloalkenyl-$C_{1-6}$ alkylsulfinyl group (e.g., cyclopentenylmethylsulfinyl);
(48) a $C_{1-6}$ alkylsulfonyl group (e.g., methylsulfonyl, ethylsulfonyl);
(49) a $C_{2-6}$ alkenylsulfonyl group (e.g., vinylsulfonyl, propenylsulfonyl);
(50) a $C_{2-6}$ alkynylsulfonyl group (e.g., ethynylsulfonyl, propynylsulfonyl);
(51) a $C_{3-8}$ cycloalkylsulfonyl group (e.g., cyclopropylsulfonyl, cyclobutylsulfonyl);
(52) a $C_{3-8}$ cycloalkenylsulfonyl group (e.g., cyclopropenylsulfonyl, cyclobutenylsulfonyl);
(53) a $C_{6-14}$ arylsulfonyl group (e.g., phenylsulfonyl);
(54) a $C_{3-8}$ cycloalkyl-$C_{1-6}$ alkylsulfonyl group (e.g., cyclopropylmethylsulfonyl);
(55) a $C_{3-8}$ cycloalkenyl-$C_{1-6}$ alkylsulfonyl group (e.g., cyclopentenylmethylsulfonyl);
(56) a $C_{6-14}$ aryl-$C_{1-6}$ alkylsulfonyl group (e.g., benzylsulfonyl);
(57) a 5- or 6-membered monocyclic aromatic heterocyclylsulfonyl group (e.g., furylsulfonyl, thienylsulfonyl, pyridylsulfonyl);
(58) an 8- to 12-membered fused aromatic heterocyclylsulfonyl group (e.g., benzofuranylsulfonyl, isobenzofuranylsulfonyl);
(59) a 3- to 8-membered monocyclic non-aromatic heterocyclylsulfonyl group (e.g., oxiranylsulfonyl, azetidinylsulfonyl);
(60) an 8- to 12-membered fused non-aromatic heterocyclylsulfonyl group (e.g., dihydrobenzofuranylsulfonyl);
(61) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl, morpholinyl) optionally substituted by 1 to 3 substituents selected from
    (a) a halogen atom,
    (b) a $C_{1-6}$ alkyl group optionally substituted by 1 to 3 halogen atoms, and
    (c) a $C_{1-6}$ alkoxy group optionally substituted by 1 to 3 halogen atoms;
(62) an 8- to 12-membered fused aromatic heterocyclic group (e.g., benzofuranyl, isobenzofuranyl, benzothienyl, isobenzothienyl, indolyl, isoindolyl, indazolyl, benzimidazolyl, benzoxazolyl) optionally substituted by 1 to 3 substituents selected from
    (a) a halogen atom,
    (b) a $C_{1-6}$ alkyl group optionally substituted by 1 to 3 halogen atoms, and
    (c) a $C_{1-6}$ alkoxy group optionally substituted by 1 to 3 halogen atoms;
(63) a 3- to 8-membered monocyclic non-aromatic heterocyclic group (e.g., oxiranyl, azetidinyl, oxetanyl, thietanyl, pyrrolidinyl, tetrahydrofuryl, thiolanyl, piperidyl, piperazinyl, dihydrooxadiazolyl, thiazolinyl) optionally substituted by 1 to 3 substituents selected from
    (a) a halogen atom,
    (b) a $C_{1-6}$ alkyl group optionally substituted by 1 to 3 halogen atoms,
    (c) a $C_{1-6}$ alkoxy group optionally substituted by 1 to 3 halogen atoms, and
    (d) an oxo group;
(64) an 8- to 12-membered fused non-aromatic heterocyclic group (e.g., dihydrobenzofuranyl) optionally substituted by 1 to 3 substituents selected from
    (a) a halogen atom,
    (b) a $C_{1-6}$ alkyl group optionally substituted by 1 to 3 halogen atoms,
    (c) a $C_{1-6}$ alkoxy group optionally substituted by 1 to 3 halogen atoms, and
    (d) an oxo group;
(65) a 5- or 6-membered monocyclic aromatic heterocyclyloxy group (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy);

(66) an 8- to 12-membered fused aromatic heterocyclyloxy group (e.g., benzofuranyloxy, isobenzofuranyloxy, benzothienyloxy, isobenzothienyloxy, indolyloxy, isoindolyloxy, indazolyloxy, benzimidazolyloxy, benzoxazolyloxy);

(67) a 3- to 8-membered monocyclic non-aromatic heterocyclyloxy group (e.g., oxiranyloxy, azetidinyloxy, oxetanyloxy, thietanyloxy, pyrrolidinyloxy, tetrahydrofuryloxy, thiolanyloxy, piperidyloxy);

(68) an 8- to 12-membered fused non-aromatic heterocyclyloxy group (e.g., dihydrobenzofuranyloxy);

(69) a carboxy group;

(70) a $C_{1-6}$ alkoxy-carbonyl group;

(71) a $C_{2-6}$ alkenyloxy-carbonyl group (e.g., vinyloxycarbonyl, propenyloxycarbonyl, butenyloxycarbonyl, pentenyloxycarbonyl, hexenyloxycarbonyl);

(72) a $C_{2-6}$ alkynyloxy-carbonyl group (e.g., ethynyloxycarbonyl, propynyloxycarbonyl, butynyloxycarbonyl, pentynyloxycarbonyl, hexynyloxycarbonyl);

(73) a $C_{3-6}$ cycloalkyloxy-carbonyl group (e.g., cyclopropyloxycarbonyl, cyclobutyloxycarbonyl, cyclopentyloxycarbonyl, cyclohexyloxycarbonyl);

(74) a $C_{3-8}$ cycloalkenyloxy-carbonyl group (e.g., cyclopropenyloxycarbonyl, cyclobutenyloxycarbonyl, cyclopentenyloxycarbonyl, cyclohexenyloxycarbonyl);

(75) a $C_{6-14}$ aryloxy-carbonyl group (e.g., phenoxycarbonyl, 1-naphthyloxycarbonyl, 2-naphthyloxycarbonyl);

(76) a $C_{3-8}$ cycloalkyl-$C_{1-6}$ alkoxy-carbonyl group (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl);

(77) a $C_{3-8}$ cycloalkenyl-$C_{1-6}$ alkoxy-carbonyl group (e.g., cyclopentenylmethyloxycarbonyl, cyclohexenylmethyloxycarbonyl, cyclohexenylethyloxycarbonyl, cyclohexenylpropyloxycarbonyl);

(78) a $C_{7-14}$ aralkyloxy-carbonyl group (e.g., benzyloxycarbonyl, phenethyloxycarbonyl);

(79) a mono-$C_{1-6}$ alkylthio-carbamoyl group (e.g., methylthiocarbamoyl, ethylthiocarbamoyl, propylthiocarbamoyl);

(80) a di-$C_{1-6}$ alkylthio-carbamoyl group (e.g., dimethylthiocarbamoyl, diethylthiocarbamoyl, dipropylthiocarbamoyl);

(81) a $C_{1-6}$ alkyl-carbonyloxy group (e.g., acetyloxy, propanoyloxy, butanoyloxy, 2-methylpropanoyloxy);

(82) an imino group optionally substituted by a hydroxy group; and

(83) a $C_{1-6}$ alkylenedioxy group (e.g., methylenedioxy, ethylenedioxy).

$R^1$ is preferably a 5-membered nitrogen-containing aromatic heterocyclic group (preferably oxazolyl, imidazolyl, triazolyl or pyrazolyl) optionally substituted by 1 to 3 optionally substituted $C_{1-6}$ alkyl groups (e.g., methyl), particularly preferably a 5-membered nitrogen-containing aromatic heterocyclic group (preferably oxazolyl, imidazolyl, triazolyl or pyrazolyl) optionally substituted by one $C_{1-6}$ alkyl group (e.g., methyl).

In another embodiment, $R^1$ is more preferably a 5-membered nitrogen-containing aromatic heterocyclic group (preferably oxazolyl or triazolyl, more preferably 1,3-oxazol-5-yl or 1H-1,2,4-triazol-1-yl), particularly preferably an oxazolyl group (preferably 1,3-oxazol-5-yl).

In yet another embodiment, $R^1$ is more preferably a 5-membered nitrogen-containing aromatic heterocyclic group (preferably oxazolyl, triazolyl or pyrazolyl, more preferably 1,3-oxazol-5-yl, 1H-1,2,4-triazol-1-yl or 1H-pyrazol-4-yl).

In another embodiment, $R^1$ is more preferably
(1) an oxazolyl group (e.g., 1,3-oxazol-5-yl),
(2) an imidazolyl group (e.g., 1H-imidazol-1-yl),
(3) a triazolyl group (e.g., 1H-1,2,4-triazol-1-yl), or
(4) a pyrazolyl group (e.g., 1H-pyrazol-5-yl, 1H-pyrazol-4-yl), each of which is optionally substituted by one $C_{1-6}$ alkyl group (e.g., methyl),
further more preferably
(1) an oxazolyl group (e.g., 1,3-oxazol-5-yl),
(2) an imidazolyl group (e.g., 1H-imidazol-1-yl),
(3) a triazolyl group (e.g., 1H-1,2,4-triazol-1-yl), or
(4) a pyrazolyl group (e.g., 1H-pyrazol-5-yl, 1H-pyrazol-4-yl) optionally substituted by one $C_{1-6}$ alkyl group (e.g., methyl), still more preferably
(1) 1,3-oxazol-5-yl,
(2) 1H-imidazol-1-yl,
(3) 1H-1,2,4-triazol-1-yl, or
(4) 1H-pyrazol-5-yl or 1H-pyrazol-4-yl, each of which is optionally substituted by one $C_{1-6}$ alkyl group (e.g., methyl), still more preferably
(1) an oxazolyl group (e.g., 1,3-oxazol-5-yl), or
(2) a triazolyl group (e.g., 1H-1,2,4-triazol-1-yl), particularly preferably an oxazolyl group (e.g., 1,3-oxazol-5-yl).

In the formula (I), $R^2$ is a hydrogen atom or a substituent.

Examples of the "substituent" for $R^2$ include a "halogen atom", a "nitro group", a "cyano group", an "optionally substituted hydrocarbon group", an "optionally substituted heterocyclic group", an "optionally substituted hydroxy group", an "optionally substituted amino group", an "optionally substituted sulfanyl group", an "acyl group" and the like.

The $C_{1-6}$ alkyl group, $C_{2-6}$ alkenyl group and $C_{2-6}$ alkynyl group which are exemplified as the above-mentioned "hydrocarbon group" optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-8}$ cycloalkyl group, $C_{3-8}$ cycloalkenyl group, $C_{4-10}$ cycloalkadienyl group, $C_{5-14}$ aryl group, $C_{7-14}$ aralkyl group and $C_{8-13}$ arylalkenyl group which are exemplified as the above-mentioned "hydrocarbon group" optionally have 1 to 5 (preferably 1 to 3) substituents at substitutable position(s). Examples of the substituent include substituents selected from the following Substituent Group B. When the number of the substituents is plural, the respective substituents may be the same or different.

Substituent Group B:
(1) the above-mentioned Substituent Group A;
(2) a $C_{1-6}$ alkyl group optionally substituted by 1 to 3 substituents selected from
 (a) a halogen atom,
 (b) a cyano group,
 (c) a hydroxy group,
 (d) a $C_{3-8}$ cycloalkyl group optionally substituted by 1 to 3 substituents selected from
  (i) a halogen atom,
  (ii) a cyano group, and
  (iii) a $C_{1-6}$ alkyl group optionally substituted by 1 to 3 halogen atoms;
 (e) a $C_{6-14}$ aryl group optionally substituted by 1 to 3 substituents selected from
  (i) a halogen atom,
  (ii) a cyano group, and
  (iii) a $C_{1-6}$ alkyl group optionally substituted by 1 to 3 halogen atoms,
 (f) a $C_{1-6}$ alkoxy group optionally substituted by 1 to 3 halogen atoms, (g) an amino group optionally mono- or di-substituted by $C_{1-6}$ alkyl,
(h) a 5- or 6-membered monocyclic aromatic heterocyclic group,
(i) an 8- to 12-membered fused aromatic heterocyclic group,
(j) a 3- to 8-membered monocyclic non-aromatic heterocyclic group,
(k) an 8- to 12-membered fused non-aromatic heterocyclic group,
(l) a carboxy group, and
(m) a $C_{1-6}$ alkoxy-carbonyl group optionally substituted by 1 to 3 halogen atoms;
(3) a $C_{2-6}$ alkenyl group optionally substituted by 1 to 3 substituents selected from
  (a) a halogen atom,
  (b) a hydroxy group,
  (c) a $C_{1-6}$ alkoxy group,
  (d) an amino group optionally mono- or di-substituted by $C_{1-6}$ alkyl,
  (e) a carboxy group, and
  (f) a $C_{1-6}$ alkoxy-carbonyl group;
(4) a $C_{7-14}$ aralkyl group optionally substituted by 1 to 3 substituents selected from
  (a) a halogen atom,
  (b) a hydroxy group,
  (c) a $C_{1-6}$ alkoxy group, and
  (d) a $C_{1-6}$ alkyl group optionally substituted by 1 to 3 halogen atoms; and
(5) an oxo group.

The "heterocyclic group" of the above-mentioned "optionally substituted heterocyclic group" optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

$R^2$ is preferably a hydrogen atom.

In the formula (I), $R^3$ is an optionally substituted $C_{1-6}$ alkyl group, a halogen atom, a cyano group, an acyl group, an optionally substituted hydroxy group, an optionally substituted sulfanyl group, an optionally substituted amino group, an optionally substituted carbocyclic group, or an optionally substituted heterocyclic group.

Examples of the "optionally substituted $C_{1-6}$ alkyl group" for $R^3$ include those similar to the "optionally substituted $C_{1-6}$ alkyl group" for $R^1$.

Examples of the "optionally substituted carbocyclic group" for $R^3$ include those similar to the groups wherein the "hydrocarbon group" is a "carbocyclic group", from among the "optionally substituted hydrocarbon group" for $R^2$.

Examples of the "optionally substituted heterocyclic group" for $R^3$ include those similar to the "optionally substituted heterocyclic group" for $R^2$.

$R^3$ is preferably an optionally substituted $C_{1-6}$ alkyl group, a halogen atom, a cyano group, an acyl group, an optionally substituted carbocyclic group, or an optionally substituted heterocyclic group, more preferably an optionally substituted $C_{1-6}$ alkyl group, a halogen atom, a cyano group, an acyl group, an optionally substituted $C_{3-8}$ cycloalkyl group, or an optionally substituted 5- or 6-membered aromatic heterocyclic group.

$R^3$ is still more preferably
(1) a $C_{1-6}$ alkyl group (e.g., methyl, ethyl) optionally substituted by 1 to 3 substituents selected from
  (a) a halogen atom (e.g., a fluorine atom), and
  (b) a $C_{1-6}$ alkoxy group (e.g., ethoxy),
(2) a halogen atom (e.g., a fluorine atom, a chlorine atom),
(3) a cyano group,
(4) a $C_{1-6}$ alkyl-carbonyl group (e.g., acetyl),
(5) a $C_{3-8}$ cycloalkyl group (e.g., cyclopropyl), or
(6) a 5- or 6-membered aromatic heterocyclic group (e.g., oxazolyl),
particularly preferably a trifluoromethyl group.

In another embodiment, $R^3$ is still more preferably
(1) a $C_{1-6}$ alkyl group (e.g., methyl, ethyl) optionally substituted by 1 to 3 halogen atoms (e.g., a fluorine atom),
(2) a halogen atom (e.g., a fluorine atom, a chlorine atom),
(3) a $C_{1-6}$ alkyl-carbonyl group (e.g., acetyl),
(4) a $C_{3-8}$ cycloalkyl group (e.g., cyclopropyl), or
(5) a 5- or 6-membered aromatic heterocyclic group (e.g., oxazolyl),
particularly preferably a $C_{1-6}$ alkyl group (preferably methyl or ethyl, more preferably methyl) optionally substituted by 1 to 3 halogen atoms (preferably a fluorine atom).

In yet another embodiment, $R^3$ is more preferably
(1) a $C_{1-6}$ alkyl group (e.g., methyl, ethyl) optionally substituted by 1 to 3 substituents selected from
  (a) a halogen atom (e.g., a fluorine atom), and
  (b) a $C_{1-6}$ alkoxy group (e.g., ethoxy),
(2) a halogen atom (e.g., a fluorine atom, a chlorine atom),
(3) a cyano group,
(4) a $C_{1-6}$ alkyl-carbonyl group (e.g., acetyl),
(5) a $C_{3-8}$ cycloalkyl group (e.g., cyclopropyl), or
(6) an oxazolyl group (e.g., 1,3-oxazol-5-yl), still more preferably
(1) a $C_{1-6}$ alkyl group (e.g., methyl, ethyl) optionally substituted by 1 to 3 substituents selected from
  (a) a halogen atom (e.g., a fluorine atom), and
  (b) a $C_{1-6}$ alkoxy group (e.g., ethoxy),
(2) a halogen atom (e.g., a fluorine atom, a chlorine atom),
(3) a cyano group,
(4) a $C_{1-6}$ alkyl-carbonyl group (e.g., acetyl),
(5) a cyclopropyl group, or
(6) an oxazolyl group (e.g., 1,3-oxazol-5-yl),
particularly preferably a $C_{1-6}$ alkyl group (e.g., methyl) optionally substituted by 1 to 3 (preferably 3) halogen atoms (e.g., a fluorine atom).

In the formula (I), $R^4$ is a hydrogen atom or a substituent.
Examples of the "substituent" for $R^4$ include those similar to the "substituent" for $R^2$.

$R^4$ is preferably a hydrogen atom.

In the formula (I), $R^5$ is an optionally substituted $C_{1-6}$ alkyl group, an optionally substituted hydroxy group, an optionally substituted amino group, an optionally substituted carbocyclic group, or an optionally substituted heterocyclic group.

Examples of the "optionally substituted $C_{1-6}$ alkyl group" for $R^5$ include those similar to the "optionally substituted $C_{1-6}$ alkyl group" for $R^1$.

Examples of the "optionally substituted carbocyclic group" for $R^5$ include those similar to the "optionally substituted carbocyclic group" for $R^3$.

Examples of the "optionally substituted heterocyclic group" for $R^5$ include those similar to the "optionally substituted heterocyclic group" for $R^2$.

$R^5$ is preferably an optionally substituted $C_{1-6}$ alkyl group, an optionally substituted hydroxy group, an optionally substituted amino group, an optionally substituted $C_{3-8}$ cycloalkyl group, or an optionally substituted 3- to 12-membered non-aromatic heterocyclic group, more preferably
(1) a hydroxy group,
(2) a $C_{1-6}$ alkoxy group (e.g., ethoxy),
(3) an amino group optionally mono- or di-substituted by substituent(s) selected from (a) a C$_{1-6}$ alkyl group (e.g., methyl, ethyl, isopropyl) optionally substituted by 1 to 3 substituents selected from
  (i) a C$_{1-6}$ alkoxy group (e.g., methoxy),
  (ii) a C$_{3-8}$ cycloalkyl group (e.g., cyclopropyl),
  (iii) a halogen atom (e.g., a fluorine atom),
  (iv) a 3- to 8-membered monocyclic non-aromatic heterocyclic group (e.g., oxetanyl, tetrahydrofuranyl) optionally substituted by one C$_{1-6}$ alkyl group (e.g., methyl), and
  (v) a C$_{6-14}$ aryl group (e.g., phenyl),
(b) a C$_{3-8}$ cycloalkyl group (e.g., cyclopropyl),
(c) a 3- to 8-membered monocyclic non-aromatic heterocyclic group (e.g., oxetanyl, tetrahydropyranyl, tetrahydrofuranyl), and
(d) a C$_{6-14}$ aryl group (e.g., phenyl),
(4) a C$_{3-8}$ cycloalkyl group (e.g., cyclopropyl), or
(5) a 3- to 12-membered nitrogen-containing non-aromatic heterocyclic group (e.g., azetidinyl, pyrrolidinyl, morpholinyl, piperazinyl, piperidyl, oxazepanyl, 8-oxa-3-azabicyclo[3.2.1]octyl, 3-azabicyclo[3.1.0]hexyl, 2-oxa-5-azabicyclo[2.2.1]heptyl, 3-oxa-8-azabicyclo[3.2.1]octyl, 3-oxa-6-azabicyclo[3.1.1]heptyl, 6-oxa-3-azabicyclo[3.1.1]heptyl, 2-oxa-6-azaspiro[3.3]heptyl, 2-oxa-6-azaspiro[3.5]nonyl, 1-oxa-7-azaspiro[4.4]nonyl, 2-oxa-7-azaspiro[4.4]nonyl, 2-oxa-6-azaspiro[3.4]octyl) optionally substituted by 1 to 4 substituents selected from
  (a) a C$_{1-6}$ alkoxy group (e.g., methoxy, ethoxy) optionally substituted by 1 to 3 halogen atoms (e.g., a fluorine atom),
  (b) a halogen atom (e.g., a fluorine atom),
  (c) a hydroxy group,
  (d) a C$_{1-6}$ alkyl group (e.g., methyl), and
  (e) an oxo group.

In another embodiment, R$^5$ is more preferably
(1) a hydroxy group,
(2) a C$_{1-6}$ alkoxy group (e.g., ethoxy),
(3) an amino group optionally mono- or di-substituted by substituent(s) selected from
  (a) a C$_{1-6}$ alkyl group (e.g., methyl, ethyl, isopropyl) optionally substituted by 1 to 3 substituents selected from
    (i) a C$_{1-6}$ alkoxy group (e.g., methoxy),
    (ii) a C$_{3-8}$ cycloalkyl group (e.g., cyclopropyl),
    (iii) a halogen atom (e.g., a fluorine atom),
    (iv) a 3- to 8-membered monocyclic non-aromatic heterocyclic group (e.g., oxetanyl, tetrahydrofuranyl) optionally substituted by one C$_{1-6}$ alkyl group (e.g., methyl), and
    (v) a C$_{6-14}$ aryl group (e.g., phenyl),
  (b) a C$_{3-8}$ cycloalkyl group (e.g., cyclopropyl),
  (c) a 3- to 8-membered monocyclic non-aromatic heterocyclic group (e.g., oxetanyl, tetrahydropyranyl, tetrahydrofuranyl), and
  (d) a C$_{6-14}$ aryl group (e.g., phenyl),
(4) a C$_{3-8}$ cycloalkyl group (e.g., cyclopropyl), or
(5) a 3- to 12-membered nitrogen-containing non-aromatic heterocyclic group (e.g., azetidinyl, pyrrolidinyl, morpholinyl, piperazinyl, piperidyl, oxazepanyl, 8-oxa-3-azabicyclo[3.2.1]octyl, 3-azabicyclo[3.1.0]hexyl, 2-oxa-5-azabicyclo[2.2.1]heptyl, 3-oxa-8-azabicyclo[3.2.1]octyl, 3-oxa-6-azabicyclo[3.1.1]heptyl, 6-oxa-3-azabicyclo[3.1.1]heptyl, 2-oxa-6-azaspiro[3.3]heptyl, 2-oxa-6-azaspiro[3.5]nonyl, 1-oxa-7-azaspiro[4.4]nonyl, 2-oxa-7-azaspiro[4.4]nonyl, 2-oxa-6-azaspiro[3.4]octyl, 1,1-dioxidothiomorpholinyl, 3,7-dioxa-9-azabicyclo[3.3.1]nonyl) optionally substituted by 1 to 4 substituents selected from
  (a) a C$_{1-6}$ alkoxy group (e.g., methoxy, ethoxy) optionally substituted by 1 to 3 halogen atoms (e.g., a fluorine atom),
  (b) a halogen atom (e.g., a fluorine atom),
  (c) a hydroxy group,
  (d) a C$_{1-6}$ alkyl group (e.g., methyl),
  (e) an oxo group, and
  (f) a cyano group.

R$^5$ is still more preferably
(1) an amino group optionally mono- or di-substituted by substituent(s) selected from
  (a) a C$_{1-6}$ alkyl group (e.g., methyl), and
  (b) a 5- or 6-membered monocyclic non-aromatic heterocyclic group (e.g., tetrahydropyranyl), or
(2) a 3- to 12-membered nitrogen-containing non-aromatic heterocyclic group (e.g., azetidinyl, pyrrolidinyl, 2-oxa-5-azabicyclo[2.2.1]heptyl, 3-oxa-8-azabicyclo[3.2.1]octyl, 3-oxa-6-azabicyclo[3.1.1]heptyl) optionally substituted by 1 to 4 substituents selected from
  (a) a C$_{1-6}$ alkoxy group (e.g., ethoxy) optionally substituted by 1 to 3 halogen atoms (e.g., a fluorine atom), and
  (b) a halogen atom (e.g., a fluorine atom).

R$^5$ is particularly preferably
(1) an amino group optionally mono- or di-substituted by substituent(s) selected from
  (a) a C$_{1-6}$ alkyl group (e.g., methyl), and
  (b) a 5- or 6-membered monocyclic non-aromatic heterocyclic group (e.g., tetrahydropyranyl), or
(2) a 3- to 12-membered nitrogen-containing non-aromatic heterocyclic group (e.g., azetidinyl, 3-oxa-8-azabicyclo[3.2.1]octyl, 3-oxa-6-azabicyclo[3.1.1]heptyl) optionally substituted by 1 to 4 halogen atoms (e.g., a fluorine atom).

In another embodiment, R$^5$ is still more preferably
(1) a C$_{1-6}$ alkoxy group (e.g., ethoxy),
(2) an amino group optionally mono- or di-substituted by substituent(s) selected from
  (a) a C$_{1-6}$ alkyl group (e.g., methyl, ethyl) optionally substituted by C$_{6-14}$ aryl groups (e.g., phenyl),
  (b) a C$_{3-8}$ cycloalkyl group (e.g., cyclopropyl),
  (c) a 3- to 8-membered monocyclic non-aromatic heterocyclic group (e.g., tetrahydropyranyl), and
  (d) a C$_{6-14}$ aryl group (e.g., phenyl),
(3) a C$_{3-8}$ cycloalkyl group (e.g., cyclopropyl), or
(4) a 3- to 12-membered nitrogen-containing non-aromatic heterocyclic group (e.g., azetidinyl, pyrrolidinyl, morpholinyl, 2-oxa-5-azabicyclo[2.2.1]heptyl, 3-oxa-8-azabicyclo[3.2.1]octyl, 3-oxa-6-azabicyclo[3.1.1]heptyl, 2-oxa-6-azaspiro[3.3]heptyl, 3,7-dioxa-9-azabicyclo[3.3.1]nonyl) optionally substituted by 1 to 4 substituents selected from
  (a) a C$_{1-6}$ alkoxy group (e.g., methoxy, ethoxy) optionally substituted by 1 to 3 halogen atoms (e.g., a fluorine atom),
  (b) a halogen atom (e.g., a fluorine atom),
  (c) a hydroxy group, and
  (d) a cyano group.

R$^5$ is particularly preferably
(1) an amino group optionally mono- or di-substituted by substituent(s) selected from
  (a) a C$_{1-6}$ alkyl group (e.g., methyl),
  (b) a C$_{3-8}$ cycloalkyl group (e.g., cyclopropyl), and
  (c) a 3- to 8-membered monocyclic non-aromatic heterocyclic group (e.g., tetrahydropyranyl), or
(2) a 3- to 12-membered nitrogen-containing non-aromatic heterocyclic group (e.g., azetidinyl, pyrrolidinyl, 2-oxa-5-azabicyclo[2.2.1]heptyl, 3-oxa-8-azabicyclo[3.2.1]octyl, 3-oxa-6-azabicyclo[3.1.1]heptyl) optionally substituted by 1 to 4 substituents selected from (a) a $C_{1-6}$ alkoxy group (e.g., methoxy, ethoxy) optionally substituted by 1 to 3 halogen atoms (e.g., a fluorine atom), and
(b) a halogen atom (e.g., a fluorine atom).
In yet another embodiment, $R^5$ is more preferably
(1) a hydroxy group,
(2) a $C_{1-6}$ alkoxy group (e.g., ethoxy),
(3) an amino group optionally mono- or di-substituted by substituent(s) selected from
  (a) a $C_{1-6}$ alkyl group (e.g., methyl, ethyl, isopropyl) optionally substituted by 1 to 3 substituents selected from
    (i) a $C_{1-6}$ alkoxy group (e.g., methoxy),
    (ii) a $C_{3-8}$ cycloalkyl group (e.g., cyclopropyl),
    (iii) a halogen atom (e.g., a fluorine atom),
    (iv) an oxetanyl group (e.g., oxetan-3-yl) and a tetrahydrofuranyl group (e.g., tetrahydrofuran-2-yl), each of which is optionally substituted by one $C_{1-6}$ alkyl group (e.g., methyl), and
    (v) a $C_{6-14}$ aryl group (e.g., phenyl),
  (b) a $C_{3-8}$ cycloalkyl group, (e.g., cyclopropyl)
  (c) an oxetanyl group (e.g., oxetan-3-yl), a tetrahydropyranyl group (e.g., tetrahydro-2H-pyran-3-yl, tetrahydro-2H-pyran-4-yl) and a tetrahydrofuranyl group (e.g., tetrahydrofuran-2-yl, tetrahydrofuran-3-yl), and
  (d) a $C_{6-14}$ aryl group (e.g., phenyl),
(4) a $C_{3-8}$ cycloalkyl group (e.g., cyclopropyl), or
(5) an azetidinyl group (e.g., azetidin-1-yl), a pyrrolidinyl group (e.g., pyrrolidin-1-yl), a morpholinyl group (e.g., morpholin-4-yl), a piperazinyl group (e.g., piperazin-1-yl), a piperidyl group (e.g., piperidin-1-yl), an oxazepanyl group (e.g., 1,4-oxazepan-4-yl), an 8-oxa-3-azabicyclo[3.2.1]octyl group (e.g., 8-oxa-3-azabicyclo[3.2.1]oct-3-yl), a 3-azabicyclo[3.1.0]hexyl group (e.g., 3-azabicyclo[3.1.0]hex-3-yl), a 2-oxa-5-azabicyclo[2.2.1]heptyl group (e.g., 2-oxa-5-azabicyclo[2.2.1]hept-5-yl), a 3-oxa-8-azabicyclo[3.2.1]octyl group (e.g., 3-oxa-8-azabicyclo[3.2.1]oct-8-yl), a 3-oxa-6-azabicyclo[3.1.1]heptyl group (e.g., 3-oxa-6-azabicyclo[3.1.1]hept-6-yl), a 6-oxa-3-azabicyclo[3.1.1]heptyl group (e.g., 6-oxa-3-azabicyclo[3.1.1]hept-3-yl), a 2-oxa-6-azaspiro[3.3]heptyl group (e.g., 2-oxa-6-azaspiro[3.3]hept-6-yl), a 2-oxa-6-azaspiro[3.5]nonyl group (e.g., 2-oxa-6-azaspiro[3.5]non-6-yl), a 1-oxa-7-azaspiro[4.4]nonyl group (e.g., 1-oxa-7-azaspiro[4.4]non-7-yl), a 2-oxa-7-azaspiro[4.4]nonyl group (e.g., 2-oxa-7-azaspiro[4.4]non-7-yl), a 2-oxa-6-azaspiro[3.4]octyl group (e.g., 2-oxa-6-azaspiro[3.4]oct-6-yl), a dioxidothiomorpholinyl group (e.g., 1,1-dioxidothiomorpholin-4-yl) or a 3,7-dioxa-9-azabicyclo[3.3.1]nonyl group (e.g., 3,7-dioxa-9-azabicyclo[3.3.1]non-9-yl), each of which is optionally substituted by 1 to 4 substituents selected from
  (a) a $C_{1-6}$ alkoxy group (e.g., methoxy, ethoxy) optionally substituted by 1 to 3 halogen atoms (e.g., a fluorine atom),
  (b) a halogen atom (e.g., a fluorine atom),
  (c) a hydroxy group,
  (d) a $C_{1-6}$ alkyl group (e.g., methyl),
  (e) an oxo group, and
  (f) a cyano group,
further more preferably
(1) a hydroxy group,
(2) a $C_{1-6}$ alkoxy group (e.g., ethoxy),
(3) an amino group optionally mono- or di-substituted by substituent(s) selected from
  (a) a $C_{1-6}$ alkyl group (e.g., methyl, ethyl, isopropyl) optionally substituted by 1 to 3 substituents selected from
    (i) a $C_{1-6}$ alkoxy group (e.g., methoxy).
    (ii) a cyclopropyl group,
    (iii) a halogen atom (e.g., a fluorine atom),
    (iv) an oxetanyl group (e.g., oxetan-3-yl) optionally substituted by one $C_{1-6}$ alkyl group (e.g., methyl), and a tetrahydrofuranyl group (e.g., tetrahydrofuran-2-yl), and
    (v) a phenyl group,
  (b) a cyclopropyl group,
  (c) an oxetanyl group (e.g., oxetan-3-yl), a tetrahydropyranyl group (e.g., tetrahydro-2H-pyran-3-yl, tetrahydro-2H-pyran-4-yl) and a tetrahydrofuranyl group (e.g., tetrahydrofuran-2-yl, tetrahydrofuran-3-yl), and
  (d) a phenyl group,
(4) a cyclopropyl group, or
(5) an azetidinyl group (e.g., azetidin-1-yl), a pyrrolidinyl group (e.g., pyrrolidin-1-yl), a morpholinyl group (e.g., morpholin-4-yl), a piperazinyl group (e.g., piperazin-1-yl), a piperidyl group (e.g., piperidin-1-yl), an oxazepanyl group (e.g., 1,4-oxazepan-4-yl), an 8-oxa-3-azabicyclo[3.2.1]octyl group (e.g., 8-oxa-3-azabicyclo[3.2.1]oct-3-yl), a 3-azabicyclo[3.1.0]hexyl group (e.g., 3-azabicyclo[3.1.0]hex-3-yl), a 2-oxa-5-azabicyclo[2.2.1]heptyl group (e.g., 2-oxa-5-azabicyclo[2.2.1]hept-5-yl), a 3-oxa-8-azabicyclo[3.2.1]octyl group (e.g., 3-oxa-8-azabicyclo[3.2.1]oct-8-yl), a 3-oxa-6-azabicyclo[3.1.1]heptyl group (e.g., 3-oxa-6-azabicyclo[3.1.1]hept-6-yl), a 6-oxa-3-azabicyclo[3.1.1]heptyl group (e.g., 6-oxa-3-azabicyclo[3.1.1]hept-3-yl), a 2-oxa-6-azaspiro[3.3]heptyl group (e.g., 2-oxa-6-azaspiro[3.3]hept-6-yl), a 2-oxa-6-azaspiro[3.5]nonyl group (e.g., 2-oxa-6-azaspiro[3.5]non-6-yl), a 1-oxa-7-azaspiro[4.4]nonyl group (e.g., 1-oxa-7-azaspiro[4.4]non-7-yl), a 2-oxa-7-azaspiro[4.4]nonyl group (e.g., 2-oxa-7-azaspiro[4.4]non-7-yl), a 2-oxa-6-azaspiro[3.4]octyl group (e.g., 2-oxa-6-azaspiro[3.4]oct-6-yl), a dioxidothiomorpholinyl group (e.g., 1,1-dioxidothiomorpholin-4-yl) or a 3,7-dioxa-9-azabicyclo[3.3.1]nonyl group (e.g., 3,7-dioxa-9-azabicyclo[3.3.1]non-9-yl), each of which is optionally substituted by 1 to 4 substituents selected from
  (a) a $C_{1-6}$ alkoxy group (e.g., methoxy, ethoxy) optionally substituted by 1 to 3 halogen atoms (e.g., a fluorine atom),
  (b) a halogen atom (e.g., a fluorine atom),
  (c) a hydroxy group,
  (d) a $C_{1-6}$ alkyl group (e.g., methyl),
  (e) an oxo group, and
  (f) a cyano group,
still more preferably
(1) an amino group optionally di-substituted by substituents selected from
  (a) a $C_{1-6}$ alkyl group (e.g., methyl), and
  (b) a tetrahydropyranyl group (e.g., tetrahydro-2H-pyran-4-yl), or
(2) an azetidinyl group (e.g., azetidin-1-yl), a pyrrolidinyl group (e.g., pyrrolidin-1-yl), a 2-oxa-5-azabicyclo[2.2.1]heptyl group (e.g., 2-oxa-5-azabicyclo[2.2.1]hept-5-yl), a 3-oxa-8-azabicyclo[3.2.1]octyl group (e.g., 3-oxa-8-azabicyclo[3.2.1]oct-8-yl) or a 3-oxa-6-azabicyclo[3.1.1]heptyl group (e.g., 3-oxa-6-azabicyclo[3.1.1]hept-6-yl), each of which is optionally substituted by 1 to 4 substituents selected from
  (a) a $C_{1-6}$ alkoxy group (e.g., ethoxy) optionally substituted by 1 to 3 halogen atoms (e.g., a fluorine atom), and
  (b) a halogen atom (e.g., a fluorine atom),
particularly preferably
(1) an amino group optionally di-substituted by substituents selected from (a) a $C_{1-6}$ alkyl group (e.g., methyl), and
(b) a tetrahydropyranyl group (e.g., tetrahydro-2H-pyran-4-yl), or (2) an azetidinyl group (e.g., azetidin-1-yl) optionally substituted by one halogen atom (e.g., a fluorine atom), a 3-oxa-8-azabicyclo[3.2.1]octyl group (e.g., 3-oxa-8-azabicyclo[3.2.1]oct-8-yl) or a 3-oxa-6-azabicyclo[3.1.1]heptyl group (e.g., 3-oxa-6-azabicyclo[3.1.1]hept-6-yl).

In the formula (I), Ring A is an optionally further substituted 5-membered aromatic heterocycle.

The "5-membered aromatic heterocycle" of the "optionally further substituted 5-membered aromatic heterocycle" for Ring A optionally has 1 or 2 (preferably 1) substituents, in addition to —CO—$R^5$, at substitutable position(s). Examples of the substituent include substituents selected from the above-mentioned Substituent Group B.

Ring A is preferably an optionally further substituted 5-membered nitrogen-containing aromatic heterocycle (preferably imidazole, pyrrole, triazole or pyrazole), more preferably a 5-membered nitrogen-containing aromatic heterocycle (preferably imidazole, pyrrole, triazole or pyrazole) optionally further substituted by one $C_{1-6}$ alkyl group (e.g., methyl).

Ring A is still more preferably a 5-membered nitrogen-containing aromatic heterocycle (preferably imidazole or triazole), particularly preferably imidazole.

As preferable embodiment of Ring A, the "5-membered aromatic heterocycle" of the "optionally further substituted 5-membered aromatic heterocycle" for Ring A is preferably imidazole, pyrrole, triazole or pyrazole. More preferably it is the partial structure formula:

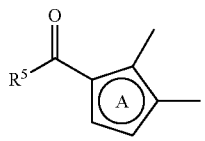

in the formula (I) is

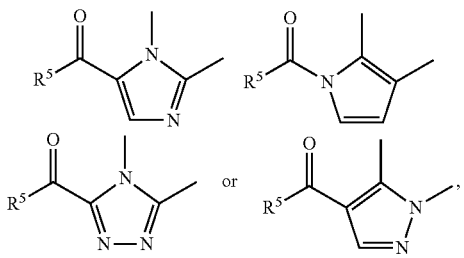

particularly preferably

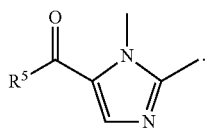

In another embodiment, Ring A is more preferably
(1) imidazole,
(2) pyrrole,
(3) triazole, or
(4) pyrazole, each of which is optionally further substituted by one $C_{1-6}$ alkyl group,
still more preferably imidazole.

Preferable specific examples of compound (I) include the following compounds:
[Compound A]
Compound (I) wherein
$R^1$ is a 5-membered nitrogen-containing aromatic heterocyclic group (preferably oxazolyl, imidazolyl, triazolyl or pyrazolyl) optionally substituted by 1 to 3 optionally substituted $C_{1-6}$ alkyl groups (e.g., methyl);
$R^2$ is a hydrogen atom;
$R^3$ is an optionally substituted $C_{1-6}$ alkyl group, a halogen atom, a cyano group, an acyl group, an optionally substituted carbocyclic group, or an optionally substituted heterocyclic group;
$R^4$ is a hydrogen atom;
$R^5$ is an optionally substituted $C_{1-6}$ alkyl group, an optionally substituted hydroxy group, an optionally substituted amino group, an optionally substituted $C_{3-8}$ cycloalkyl group, or an optionally substituted 3- to 12-membered non-aromatic heterocyclic group; and
Ring A is an optionally further substituted 5-membered nitrogen-containing aromatic heterocycle (preferably imidazole, pyrrole, triazole or pyrazole),
or a salt thereof.
[Compound B]
Compound (I) wherein
$R^1$ is a 5-membered nitrogen-containing aromatic heterocyclic group (preferably oxazolyl, imidazolyl, triazolyl or pyrazolyl) optionally substituted by one $C_{1-6}$ alkyl group (e.g., methyl);
$R^2$ is a hydrogen atom;
$R^3$ is
(1) a $C_{1-6}$ alkyl group (e.g., methyl, ethyl) optionally substituted by 1 to 3 substituents selected from
(a) a halogen atom (e.g., a fluorine atom), and
(b) a $C_{1-6}$ alkoxy group (e.g., ethoxy),
(2) a halogen atom (e.g., a fluorine atom, a chlorine atom),
(3) a cyano group,
(4) a $C_{1-6}$ alkyl-carbonyl group (e.g., acetyl),
(5) a $C_{3-8}$ cycloalkyl group (e.g., cyclopropyl), or
(6) a 5- or 6-membered aromatic heterocyclic group (e.g., oxazolyl);
$R^4$ is a hydrogen atom;
$R^5$ is
(1) a hydroxy group,
(2) a $C_{1-6}$ alkoxy group (e.g., ethoxy),
(3) an amino group optionally mono- or di-substituted by substituent(s) selected from
(a) a $C_{1-6}$ alkyl group (e.g., methyl, ethyl, isopropyl) optionally substituted by 1 to 3 substituents selected from
(i) a $C_{1-6}$ alkoxy group (e.g., methoxy),
(ii) a $C_{3-8}$ cycloalkyl group (e.g., cyclopropyl),
(iii) a halogen atom (e.g., a fluorine atom),
(iv) a 3- to 8-membered monocyclic non-aromatic heterocyclic group (e.g., oxetanyl, tetrahydrofuranyl) optionally substituted by one $C_{1-6}$ alkyl group (e.g., methyl), and
(v) a $C_{6-14}$ aryl group (e.g., phenyl),
(b) a $C_{3-8}$ cycloalkyl group (e.g., cyclopropyl),
(c) a 3- to 8-membered monocyclic non-aromatic heterocyclic group (e.g., oxetanyl, tetrahydropyranyl, tetrahydrofuranyl), and
(d) a $C_{6-14}$ aryl group (e.g., phenyl), (4) a $C_{3-8}$ cycloalkyl group (e.g., cyclopropyl), or
(5) a 3- to 12-membered nitrogen-containing non-aromatic heterocyclic group (e.g., azetidinyl, pyrrolidinyl, morpholinyl, piperazinyl, piperidyl, oxazepanyl, 8-oxa-3-azabicyclo[3.2.1]octyl, 3-azabicyclo[3.1.0]hexyl, 2-oxa-5-azabicyclo[2.2.1]heptyl, 3-oxa-8-azabicyclo[3.2.1]octyl, 3-oxa-6-azabicyclo[3.1.1]heptyl, 6-oxa-3-azabicyclo[3.1.1]heptyl, 2-oxa-6-azaspiro[3.3]heptyl, 2-oxa-6-azaspiro[3.5]nonyl, 1-oxa-7-azaspiro[4.4]nonyl, 2-oxa-7-azaspiro[4.4]nonyl, 2-oxa-6-azaspiro[3.4]octyl) optionally substituted by 1 to 4 substituents selected from
  (a) a $C_{1-6}$ alkoxy group (e.g., methoxy, ethoxy) optionally substituted by 1 to 3 halogen atoms (e.g., a fluorine atom),
  (b) a halogen atom (e.g., a fluorine atom),
  (c) a hydroxy group,
  (d) a $C_{1-6}$ alkyl group (e.g., methyl), and
  (e) an oxo group; and
Ring A is a 5-membered aromatic heterocycle (preferably imidazole, pyrrole, triazole or pyrazole) optionally further substituted by one $C_{1-6}$ alkyl group (e.g., methyl), or a salt thereof.

[Compound B-1]
Compound (I) wherein
$R^1$ is a 5-membered nitrogen-containing aromatic heterocyclic group (preferably oxazolyl, imidazolyl, triazolyl or pyrazolyl) optionally substituted by one $C_{1-6}$ alkyl group (e.g., methyl);
$R^2$ is a hydrogen atom;
$R^3$ is
(1) a $C_{1-6}$ alkyl group (e.g., methyl, ethyl) optionally substituted by 1 to 3 substituents selected from
  (a) a halogen atom (e.g., a fluorine atom), and
  (b) a $C_{1-6}$ alkoxy group (e.g., ethoxy),
(2) a halogen atom (e.g., a fluorine atom, a chlorine atom),
(3) a cyano group,
(4) a $C_{1-6}$ alkyl-carbonyl group (e.g., acetyl),
(5) a $C_{3-8}$ cycloalkyl group (e.g., cyclopropyl), or
(6) a 5- or 6-membered aromatic heterocyclic group (e.g., oxazolyl);
$R^4$ is a hydrogen atom;
$R^5$ is
(1) a hydroxy group,
(2) a $C_{1-6}$ alkoxy group (e.g., ethoxy),
(3) an amino group optionally mono- or di-substituted by substituent(s) selected from
  (a) a $C_{1-6}$ alkyl group (e.g., methyl, ethyl, isopropyl) optionally substituted by 1 to 3 substituents selected from
    (i) a $C_{1-6}$ alkoxy group (e.g., methoxy),
    (ii) a $C_{3-8}$ cycloalkyl group (e.g., cyclopropyl),
    (iii) a halogen atom (e.g., a fluorine atom),
    (iv) a 3- to 8-membered monocyclic non-aromatic heterocyclic group (e.g., oxetanyl, tetrahydrofuranyl) optionally substituted by one $C_{1-6}$ alkyl group (e.g., methyl), and
    (v) a $C_{6-14}$ aryl group (e.g., phenyl),
  (b) a $C_{3-8}$ cycloalkyl group (e.g., cyclopropyl),
  (c) a 3- to 8-membered monocyclic non-aromatic heterocyclic group (e.g., oxetanyl, tetrahydropyranyl, tetrahydrofuranyl), and
  (d) a $C_{6-14}$ aryl group (e.g., phenyl),
(4) a $C_{3-8}$ cycloalkyl group (e.g., cyclopropyl), or
(5) a 3- to 12-membered nitrogen-containing non-aromatic heterocyclic group (e.g., azetidinyl, pyrrolidinyl, morpholinyl, piperazinyl, piperidyl, oxazepanyl, 8-oxa-3-azabicyclo[3.2.1]octyl, 3-azabicyclo[3.1.0]hexyl, 2-oxa-5-azabicyclo[2.2.1]heptyl, 3-oxa-8-azabicyclo[3.2.1]octyl, 3-oxa-6-azabicyclo[3.1.1]heptyl, 6-oxa-3-azabicyclo[3.1.1]heptyl, 2-oxa-6-azaspiro[3.3]heptyl, 2-oxa-6-azaspiro[3.5]nonyl, 1-oxa-7-azaspiro[4.4]nonyl, 2-oxa-7-azaspiro[4.4]nonyl, 2-oxa-6-azaspiro[3.4]octyl, 1,1-dioxidothiomorpholinyl, 3,7-dioxa-9-azabicyclo[3.3.1]nonyl) optionally substituted by 1 to 4 substituents selected from
  (a) a $C_{1-6}$ alkoxy group (e.g., methoxy, ethoxy) optionally substituted by 1 to 3 halogen atoms (e.g., a fluorine atom),
  (b) a halogen atom (e.g., a fluorine atom),
  (c) a hydroxy group,
  (d) a $C_{1-6}$ alkyl group (e.g., methyl).
  (e) an oxo group, and
  (f) a cyano group; and
Ring A is a 5-membered aromatic heterocycle (preferably imidazole, pyrrole, triazole or pyrazole) optionally further substituted by one $C_{1-6}$ alkyl group (e.g., methyl), or a salt thereof.

[Compound B-2]
Compound (I) wherein
$R^1$ is
(1) an oxazolyl group (e.g., 1,3-oxazol-5-yl),
(2) an imidazolyl group (e.g., 1H-imidazol-1-yl),
(3) a triazolyl group (e.g., 1H-1,2,4-triazol-1-yl), or
(4) a pyrazolyl group (e.g., 1H-pyrazol-5-yl, 1H-pyrazol-4-yl), each of which is optionally substituted by one $C_{1-6}$ alkyl group (e.g., methyl);
$R^2$ is a hydrogen atom;
$R^3$ is
(1) a $C_{1-6}$ alkyl group (e.g., methyl, ethyl) optionally substituted by 1 to 3 substituents selected from
  (a) a halogen atom (e.g., a fluorine atom), and
  (b) a $C_{1-6}$ alkoxy group (e.g., ethoxy),
(2) a halogen atom (e.g., a fluorine atom, a chlorine atom),
(3) a cyano group,
(4) a $C_{1-6}$ alkyl-carbonyl group (e.g., acetyl),
(5) a $C_{3-8}$ cycloalkyl group (e.g., cyclopropyl), or
(6) an oxazolyl group (e.g., 1,3-oxazol-5-yl);
$R^4$ is a hydrogen atom;
$R^5$ is
(1) a hydroxy group,
(2) a $C_{1-6}$ alkoxy group (e.g., ethoxy),
(3) an amino group optionally mono- or di-substituted by substituent(s) selected from
  (a) a $C_{1-6}$ alkyl group (e.g., methyl, ethyl, isopropyl) optionally substituted by 1 to 3 substituents selected from
    (i) a $C_{1-6}$ alkoxy group (e.g., methoxy),
    (ii) a $C_{3-8}$ cycloalkyl group (e.g., cyclopropyl),
    (iii) a halogen atom (e.g., a fluorine atom),
    (iv) an oxetanyl group (e.g., oxetan-3-yl) and a tetrahydrofuranyl group (e.g., tetrahydrofuran-2-yl), each of which is optionally substituted by one $C_{1-6}$ alkyl group (e.g., methyl), and
    (v) a $C_{6-14}$ aryl group (e.g., phenyl),
  (b) a $C_{3-8}$ cycloalkyl group, (e.g., cyclopropyl)
  (c) an oxetanyl group (e.g., oxetan-3-yl), a tetrahydropyranyl group (e.g., tetrahydro-2H-pyran-3-yl, tetrahydro-2H-pyran-4-yl) and a tetrahydrofuranyl group (e.g., tetrahydrofuran-2-yl, tetrahydrofuran-3-yl), and
  (d) a $C_{6-14}$ aryl group (e.g., phenyl),
(4) a $C_{3-8}$ cycloalkyl group (e.g., cyclopropyl), or
(5) an azetidinyl group (e.g., azetidin-1-yl), a pyrrolidinyl group (e.g., pyrrolidin-1-yl), a morpholinyl group (e.g., morpholin-4-yl), a piperazinyl group (e.g., piperazin-1-yl), a piperidyl group (e.g., piperidin-1-yl), an oxazepanyl group (e.g., 1,4-oxazepan-4-yl), an 8-oxa-3-azabicyclo[3.2.1]octyl group (e.g., 8-oxa-3-azabicyclo[3.2.1]oct-3-yl), a 3-azabicyclo[3.1.0]hexyl group (e.g., 3-azabicyclo[3.1.0]hex-3-yl), a 2-oxa-5-azabicyclo[2.2.1]heptyl group (e.g., 2-oxa-5-azabicyclo[2.2.1]hept-5-yl), a 3-oxa-8-azabicyclo[3.2.1]octyl group (e.g., 3-oxa-8-azabicyclo[3.2.1]oct-8-yl), a 3-oxa-6-azabicyclo[3.1.1]heptyl group (e.g., 3-oxa-6-azabicyclo[3.1.1]hept-6-yl), a 6-oxa-3-azabicyclo[3.1.1]heptyl group (e.g., 6-oxa-3-azabicyclo[3.1.1]hept-3-yl), a 2-oxa-6-azaspiro[3.3]heptyl group (e.g., 2-oxa-6-azaspiro[3.3]hept-6-yl), a 2-oxa-6-azaspiro[3.5]nonyl group (e.g., 2-oxa-6-azaspiro[3.5]non-6-yl), a 1-oxa-7-azaspiro[4.4]nonyl group (e.g., 1-oxa-7-azaspiro[4.4]non-7-yl), a 2-oxa-7-azaspiro[4.4]nonyl group (e.g., 2-oxa-7-azaspiro[4.4]non-7-yl), a 2-oxa-6-azaspiro[3.4]octyl group (e.g., 2-oxa-6-azaspiro[3.4]oct-6-yl), a dioxidothiomorpholinyl group (e.g., 1,1-dioxidothiomorpholin-4-yl) or a 3,7-dioxa-9-azabicyclo[3.3.1]nonyl group (e.g., 3,7-dioxa-9-azabicyclo[3.3.1]non-9-yl), each of which is optionally substituted by 1 to 4 substituents selected from
- (a) a $C_{1-6}$ alkoxy group (e.g., methoxy, ethoxy) optionally substituted by 1 to 3 halogen atoms (e.g., a fluorine atom),
- (b) a halogen atom (e.g., a fluorine atom),
- (c) a hydroxy group,
- (d) a $C_{1-6}$ alkyl group (e.g., methyl),
- (e) an oxo group, and
- (f) a cyano group; and Ring A is
(1) imidazole,
(2) pyrrole,
(3) triazole, or
(4) pyrazole,
each of which is optionally further substituted by one $C_{1-6}$ alkyl group (e.g., methyl),
or a salt thereof.

[Compound B-3]
Compound (I) wherein
$R^1$ is
(1) an oxazolyl group (e.g., 1,3-oxazol-5-yl),
(2) an imidazolyl group (e.g., 1H-imidazol-1-yl),
(3) a triazolyl group (e.g., 1H-1,2,4-triazol-1-yl), or
(4) a pyrazolyl group (e.g., 1H-pyrazol-5-yl, 1H-pyrazol-4-yl) optionally substituted by one $C_{1-6}$ alkyl group (e.g., methyl);
$R^2$ is a hydrogen atom;
$R^3$ is
(1) a $C_{1-6}$ alkyl group (e.g., methyl, ethyl) optionally substituted by 1 to 3 substituents selected from
- (a) a halogen atom (e.g., a fluorine atom), and
- (b) a $C_{1-6}$ alkoxy group (e.g., ethoxy), (2) a halogen atom (e.g., a fluorine atom, a chlorine atom),
(3) a cyano group,
(4) a $C_{1-6}$ alkyl-carbonyl group (e.g., acetyl),
(5) a cyclopropyl group (e.g., cyclopropyl), or
(6) an oxazolyl group (e.g., 1,3-oxazol-5-yl);
$R^4$ is a hydrogen atom;
$R^5$ is
(1) a hydroxy group,
(2) a $C_{1-6}$ alkoxy group (e.g., ethoxy),
(3) an amino group optionally mono- or di-substituted by substituent(s) selected from
- (a) a $C_{1-6}$ alkyl group (e.g., methyl, ethyl, isopropyl) optionally substituted by 1 to 3 substituents selected from
  - (i) a $C_{1-6}$ alkoxy group (e.g., methoxy),
  - (ii) a cyclopropyl group,
  - (iii) a halogen atom (e.g., a fluorine atom),
  - (iv) an oxetanyl group (e.g., oxetan-3-yl) optionally substituted by one $C_{1-6}$ alkyl group (e.g., methyl), and a tetrahydrofuranyl group (e.g., tetrahydrofuran-2-yl), and
  - (v) a phenyl group,
- (b) a cyclopropyl group,
- (c) an oxetanyl group (e.g., oxetan-3-yl), a tetrahydropyranyl group (e.g., tetrahydro-2H-pyran-3-yl, tetrahydro-2H-pyran-4-yl) and a tetrahydrofuranyl group (e.g., tetrahydrofuran-2-yl, tetrahydrofuran-3-yl), and
- (d) a phenyl group, (4) a cyclopropyl group, or
(5) an azetidinyl group (e.g., azetidin-1-yl), a pyrrolidinyl group (e.g., pyrrolidin-1-yl), a morpholinyl group (e.g., morpholin-4-yl), a piperazinyl group (e.g., piperazin-1-yl), a piperidyl group (e.g., piperidin-1-yl), an oxazepanyl group (e.g., 1,4-oxazepan-4-yl), an 8-oxa-3-azabicyclo[3.2.1]octyl group (e.g., 8-oxa-3-azabicyclo[3.2.1]oct-3-yl), a 3-azabicyclo[3.1.0]hexyl group (e.g., 3-azabicyclo[3.1.0]hex-3-yl), a 2-oxa-5-azabicyclo[2.2.1]heptyl group (e.g., 2-oxa-5-azabicyclo[2.2.1]hept-5-yl), a 3-oxa-8-azabicyclo[3.2.1]octyl group (e.g., 3-oxa-8-azabicyclo[3.2.1]oct-8-yl), a 3-oxa-6-azabicyclo[3.1.1]heptyl group (e.g., 3-oxa-6-azabicyclo[3.1.1]hept-6-yl), a 6-oxa-3-azabicyclo[3.1.1]heptyl group (e.g., 6-oxa-3-azabicyclo[3.1.1]hept-3-yl), a 2-oxa-6-azaspiro[3.3]heptyl group (e.g., 2-oxa-6-azaspiro[3.3]hept-6-yl), a 2-oxa-6-azaspiro[3.5]nonyl group (e.g., 2-oxa-6-azaspiro[3.5]non-6-yl), a 1-oxa-7-azaspiro[4.4]nonyl group (e.g., 1-oxa-7-azaspiro[4.4]non-7-yl), a 2-oxa-7-azaspiro[4.4]nonyl group (e.g., 2-oxa-7-azaspiro[4.4]non-7-yl), a 2-oxa-6-azaspiro[3.4]octyl group (e.g., 2-oxa-6-azaspiro[3.4]oct-6-yl), a dioxidothiomorpholinyl group (e.g., 1,1-dioxidothiomorpholin-4-yl) or a 3,7-dioxa-9-azabicyclo[3.3.1]nonyl group (e.g., 3,7-dioxa-9-azabicyclo[3.3.1]non-9-yl), each of which is optionally substituted by 1 to 4 substituents selected from
- (a) a $C_{1-6}$ alkoxy group (e.g., methoxy, ethoxy) optionally substituted by 1 to 3 halogen atoms (e.g., a fluorine atom),
- (b) a halogen atom (e.g., a fluorine atom),
- (c) a hydroxy group,
- (d) a alkyl group (e.g., methyl),
- (e) an oxo group, and
- (f) a cyano group; and Ring A is
(1) imidazole,
(2) pyrrole,
(3) triazole, or
(4) pyrazole,
each of which is optionally further substituted by one $C_{1-6}$ alkyl group (e.g., methyl),
or a salt thereof.

[Compound C]
Compound (I) wherein
$R^1$ is a 5-membered nitrogen-containing aromatic heterocyclic group (e.g., oxazolyl, or triazolyl);
$R^2$ is a hydrogen atom;
$R^3$ is a $C_{1-6}$ alkyl group (e.g., methyl) optionally substituted by 1 to 3 halogen atoms (e.g., a fluorine atom);
$R^4$ is a hydrogen atom;
$R^5$ is
(1) an amino group optionally mono- or di-substituted by substituent(s) selected from
- (a) a $C_{1-6}$ alkyl group (e.g., methyl), and
- (b) a 5- or 6-membered monocyclic non-aromatic heterocyclic group (e.g., tetrahydropyranyl), or (2) a 3- to 12-membered nitrogen-containing non-aromatic heterocyclic group (e.g., azetidinyl, pyrrolidinyl, 2-oxa-5-azabicyclo[2.2.1]heptyl, 3-oxa-8-azabicyclo[3.2.1]octyl, 3-oxa-6-azabicyclo[3.1.1]heptyl) optionally substituted by 1 to 4 substituents selected from
(a) a $C_{1-6}$ alkoxy group (e.g., ethoxy) optionally substituted by 1 to 3 halogen atoms (e.g., a fluorine atom), and
(b) a halogen atom (e.g., a fluorine atom); and
Ring A is imidazole,
or a salt thereof.
[Compound C-1]
Compound (I) wherein
$R^1$ is
(1) an oxazolyl group (e.g., 1,3-oxazol-5-yl), or
(2) a triazolyl group (e.g., 1H-1,2,4-triazol-1-yl);
$R^2$ is a hydrogen atom;
$R^3$ is a $C_{1-6}$ alkyl group (e.g., methyl) optionally substituted by 1 to 3 (preferably 3) halogen atoms (e.g., a fluorine atom);
$R^4$ is a hydrogen atom;
$R^5$ is
(1) an amino group optionally di-substituted by substituents selected from
(a) a $C_{1-6}$ alkyl group (e.g., methyl), and
(b) a tetrahydropyranyl group (e.g., tetrahydro-2H-pyran-4-yl), or
(2) an azetidinyl group (e.g., azetidin-1-yl), a pyrrolidinyl group (e.g., pyrrolidin-1-yl), a 2-oxa-5-azabicyclo[2.2.1]heptyl group (e.g., 2-oxa-5-azabicyclo[2.2.1]hept-5-yl), a 3-oxa-8-azabicyclo[3.2.1]octyl group (e.g., 3-oxa-8-azabicyclo[3.2.1]oct-8-yl) or a 3-oxa-6-azabicyclo[3.1.1]heptyl group (e.g., 3-oxa-6-azabicyclo[3.1.1]hept-6-yl), each of which is optionally substituted by 1 to 4 substituents selected from
(a) a $C_{1-6}$ alkoxy group (e.g., ethoxy) optionally substituted by 1 to 3 halogen atoms (e.g., a fluorine atom), and
(b) a halogen atom (e.g., a fluorine atom); and
Ring A is imidazole,
or a salt thereof.
[Compound D]
Compound (I) wherein
$R^1$ is an oxazolyl group (e.g., 1,3-oxazol-5-yl);
$R^2$ is a hydrogen atom;
$R^3$ is a $C_{1-6}$ alkyl group (e.g., methyl) optionally substituted by 1 to 3 (preferably 3) halogen atoms (e.g., a fluorine atom);
$R^4$ is a hydrogen atom;
$R^5$ is
(1) an amino group optionally mono- or di-substituted by substituent(s) selected from
(a) a $C_{1-6}$ alkyl group (e.g., methyl), and
(b) a 5- or 6-membered monocyclic non-aromatic heterocyclic group (e.g., tetrahydropyranyl), or
(2) a 3- to 12-membered nitrogen-containing non-aromatic heterocyclic group (e.g., azetidinyl, 3-oxa-8-azabicyclo[3.2.1]octyl, 3-oxa-6-azabicyclo[3.1.1]heptyl) optionally substituted by 1 to 4 halogen atoms (e.g., a fluorine atom); and
Ring A is imidazole,
or a salt thereof.
[Compound D-1]
Compound (I) wherein
$R^1$ is an oxazolyl group (e.g., 1,3-oxazol-5-yl);
$R^2$ is a hydrogen atom;
$R^3$ is a $C_{1-6}$ alkyl group (e.g., methyl) optionally substituted by 1 to 3 (preferably 3) halogen atoms (e.g., a fluorine atom);
$R^4$ is a hydrogen atom;
$R^5$ is
(1) an amino group optionally di-substituted by substituents selected from
(a) a $C_{1-6}$ alkyl group (e.g., methyl), and
(b) a tetrahydropyranyl group (e.g., tetrahydro-2H-pyran-4-yl), or
(2) an azetidinyl group (e.g., azetidin-1-yl) optionally substituted by one halogen atom (e.g., a fluorine atom), a 3-oxa-8-azabicyclo[3.2.1]octyl group (e.g., 3-oxa-8-azabicyclo[3.2.1]oct-8-yl) or a 3-oxa-6-azabicyclo[3.1.1]heptyl group (e.g., 3-oxa-6-azabicyclo[3.1.1]hept-6-yl); and
Ring A is imidazole,
or a salt thereof.
[Compound E]
Compound (I) wherein
$R^1$ is a 5-membered nitrogen-containing aromatic heterocyclic group (e.g., oxazolyl, triazolyl, or pyrazolyl);
$R^2$ is a hydrogen atom;
$R^3$ is
(1) a $C_{1-6}$ alkyl group (e.g., methyl, ethyl) optionally substituted by 1 to 3 halogen atoms (e.g., a fluorine atom),
(2) a halogen atom (e.g., a fluorine atom, a chlorine atom),
(3) a $C_{1-6}$ alkyl-carbonyl group (e.g., acetyl),
(4) a $C_{3-8}$ cycloalkyl group (e.g., cyclopropyl), or
(5) a 5- or 6-membered aromatic heterocyclic group (e.g., oxazolyl);
$R^4$ is a hydrogen atom;
$R^5$ is
(1) a $C_{1-6}$ alkoxy group (e.g., ethoxy),
(2) an amino group optionally mono- or di-substituted by substituent(s) selected from
(a) a $C_{1-6}$ alkyl group (e.g., methyl, ethyl) optionally substituted by a $C_{6-14}$ aryl group (e.g., phenyl),
(b) a $C_{3-8}$ cycloalkyl group (e.g., cyclopropyl),
(c) a 3- to 8-membered monocyclic non-aromatic heterocyclic group (e.g., tetrahydropyranyl), and
(d) a $C_{6-14}$ aryl group (e.g., phenyl),
(3) a $C_{3-8}$ cycloalkyl group (e.g., cyclopropyl), or
(4) a 3- to 12-membered nitrogen-containing non-aromatic heterocyclic group (e.g., azetidinyl, pyrrolidinyl, morpholinyl, 2-oxa-5-azabicyclo[2.2.1]heptyl, 3-oxa-8-azabicyclo[3.2.1]octyl, 3-oxa-6-azabicyclo[3.1.1]heptyl, 2-oxa-6-azaspiro[3.3]heptyl, 3,7-dioxa-9-azabicyclo[3.3.1]nonyl) optionally substituted by 1 to 4 substituents selected from
(a) a $C_{1-6}$ alkoxy group (e.g., methoxy, ethoxy) optionally substituted by 1 to 3 halogen atoms (e.g., a fluorine atom),
(b) a halogen atom (e.g., a fluorine atom),
(c) a hydroxy group, and
(d) a cyano group; and
Ring A is a 5-membered aromatic heterocycle (e.g., imidazole, pyrrole, triazole or pyrazole) optionally further substituted by one $C_{1-6}$ alkyl group (e.g., methyl),
or a salt thereof.
[Compound F]
Compound (I) wherein
$R^1$ is a 5-membered nitrogen-containing aromatic heterocyclic group (e.g., oxazolyl);
$R^2$ is a hydrogen atom;
$R^3$ is a $C_{1-6}$ alkyl group (e.g., methyl, ethyl) optionally substituted by 1 to 3 halogen atoms (e.g., a fluorine atom);
$R^4$ is a hydrogen atom;
$R^5$ is
(1) an amino group optionally mono- or di-substituted by substituent(s) selected from
(a) a $C_{1-6}$ alkyl group (e.g., methyl),
(b) a $C_{3-8}$ cycloalkyl group (e.g., cyclopropyl), and
(c) a 3- to 8-membered monocyclic non-aromatic heterocyclic group (e.g., tetrahydropyranyl), or (2) a 3- to 12-membered nitrogen-containing non-aromatic heterocyclic group (e.g., azetidinyl, pyrrolidinyl, 2-oxa-5-azabicyclo[2.2.1]heptyl, 3-oxa-8-azabicyclo[3.2.1]octyl, 3-oxa-6-azabicyclo[3.1.1]heptyl) optionally substituted by 1 to 4 substituents selected from
    (a) a $C_{1-6}$ alkoxy group (e.g., methoxy, ethoxy) optionally substituted by 1 to 3 halogen atoms (e.g., a fluorine atom), and
    (b) a halogen atom (e.g., a fluorine atom); and
Ring A is a 5-membered aromatic heterocycle (e.g., imidazole, or triazole),
or a salt thereof.

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Of these, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]

The compound of the present invention and the starting compounds can be produced by a method known per se, for example, by method shown in the following scheme and the like. In the following, the "room temperature" generally means 0-40° C. and, unless otherwise specified, each symbol in the chemical formulas described in the schemes is as defined above. In the formulas, each compound includes salts, and examples of such salt include those similar to the salts of the compound of the present invention and the like. The compound obtained in each step can be used directly as the reaction mixture or as a crude product for the next reaction. It can also be isolated from a reaction mixture by a conventional method, and can be easily purified by a separation means such as recrystallization, distillation, chromatography and the like. When the compound in the formula is commercially available, a commercially available product can also be used directly. When each ring in the formula (I) has a substituent, the corresponding precursor also has a similar substituent.

When the starting compound has an amino group, a carboxyl group, a hydroxy group or a heterocyclic group, these groups may be protected by a protecting group generally used in peptide chemistry and the like. By removing the protecting group as necessary after the reaction, the objective compound can be obtained. The protection and deprotection can be performed according to a method known per se, for example, the method described in "Protective Groups in Organic Synthesis, 3rd Ed", John Wiley and Sons, Inc. (1999) (Theodora W. Greene, Peter G. M. Wuts). Preferable examples of the protecting group include a tert-butylcarbamate group, a benzylcarbamate group, a benzyl group, a methyl group, an ethyl group, a tert-butyl and the like.

Examples of the "leaving group" for $LG^1$ to $LG^5$ include a halogen atom (e.g., a chlorine atom, a bromine atom, an iodine atom etc.), $C_{1-6}$ alkylsulfonyloxy (e.g., methanesulfonyloxy, ethanesulfonyloxy, trifluoromethanesulfonyloxy etc.), $C_{1-6}$ alkylsulfonyl (e.g., methanesulfonyl, ethanesulfonyl etc.) and the like. In addition, a substituent capable of converting to a leaving group is encompassed in $LG^1$-$LG^5$, and it can be converted to a leaving group according to a reaction known per se in a desired step. For example, when $LG^1$-$LG^5$ is a methylthio group, it is converted to a methanesulfonyl group by oxidation reaction.

The following each step can be performed without solvent, or by dissolving or suspending starting material compound in a suitable solvent prior to the reaction. In this case, solvent may be used alone, or two or more kinds of these solvents may be mixed in an appropriate ratio and used. Specific examples of the solvent used for the production method of the compound of the present invention include the followings.

alcohols: methanol, ethanol, 1-propanol, 2-propanol, tert-butyl alcohol, tert-amyl alcohol, 2-methoxyethanol etc.

ethers: diethyl ether, diisopropyl ether, diphenyl ether, tetrahydrofuran, 1,4-dioxane, 1,2-dimethoxyethane etc.

aromatic hydrocarbons: benzene, chlorobenzene, toluene, xylene etc.

saturated hydrocarbons: cyclohexane, hexane etc.

amides: N,N-dimethylformamide, N,N-dimethylacetamide, hexamethylphosphoric triamide, N-methylpyrrolidone etc.

halogenated hydrocarbons: dichloromethane, chloroform, carbon tetrachloride, 1,2-dichloroethane etc.

nitriles: acetonitrile, propionitrile etc.

sulfoxides: dimethylsulfoxide etc.

organic bases: triethylamine, pyridine, lutidine etc.

acid anhydrides: acetic anhydride etc.

organic acids: formic acid, acetic acid, propionic acid, trifluoroacetic acid, methanesulfonic acid etc.

inorganic acids: hydrochloric acid, sulfuric acid etc.

esters: methyl acetate, ethyl acetate, butyl acetate etc.

ketones: acetone, methyl ethyl ketone etc.

water

Specific examples of the base or acid scavenger used for the production method of the compound of the present invention include the followings.

inorganic bases: sodium hydroxide, potassium hydroxide, magnesium hydroxide etc.

basic salts: sodium carbonate, potassium carbonate, cesium carbonate, calcium carbonate, sodium hydrogen carbonate etc.

organic bases: triethylamine, N,N-diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole etc.
metal alkoxides: sodium methoxide, sodium ethoxide, potassium tert-butoxide etc.
alkali metal hydrides: sodium hydride, potassium hydride etc.
metal amides: sodium amide, lithiumdiisopropylamide, lithiumhexamethyldisilazide etc.
organic lithium reagents: methyllithium, n-butyllithium, sec-butyllithium, tert-butyllithium etc.

Specific examples of the acid or acid catalyst used for the production method of the compound of the present invention include the followings.
inorganic acids: hydrochloric acid, sulfuric acid, nitric acid, hydrobromic acid, phosphoric acid etc.
organic acids: acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid etc.
Lewis acid: boron trifluoride ether complex, zinc iodide, anhydrous aluminum chloride, anhydrous zinc chloride, anhydrous iron chloride etc.

Compound (I) can be synthesized according to Production Method A explained below.

Unless otherwise specified, each symbol in each general formula in the reaction schemes is as defined above. $R^a$ is a hydrogen atom or an optionally substituted $C_{1-6}$ alkyl group, and in the latter case, two $R^a$ in combination optionally form a ring such as 4,4,5,5-tetramethyl-1,3,2-dioxaborolane and the like. $R^6$ is an optionally substituted hydrocarbon group, an optionally substituted heterocyclic group or a hydrogen atom. $R^7$ and $R^8$ are each an optionally substituted hydrocarbon group, an optionally substituted heterocyclic group or a hydrogen atom, and in this case, $R^7$ and $R^8$ in combination optionally form an optionally substituted heterocyclic group and the like.

Examples of the "optionally substituted $C_{1-6}$ alkyl group" for $R^a$ include those similar to the "optionally substituted $C_{1-6}$ alkyl group" exemplified in $R^1$.

Examples of the "optionally substituted hydrocarbon group" for $R^6$, $R^7$ or $R^8$ include those similar to the "optionally substituted hydrocarbon group" exemplified in $R^2$.

Examples of the "optionally substituted heterocyclic group" for $R^6$, $R^7$ or $R^8$ include those similar to the "optionally substituted heterocyclic group" exemplified in $R^2$.

Examples of the "optionally substituted heterocyclic group" formed by $R^7$ and $R^8$ in combination include those similar to the "optionally substituted heterocyclic group" exemplified in $R^2$.

[Production Method A]

-Scheme 1-
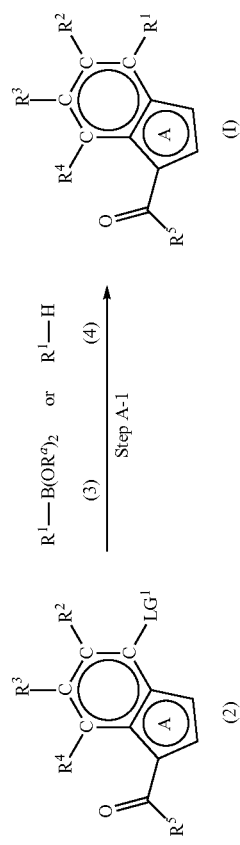
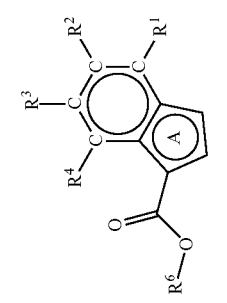
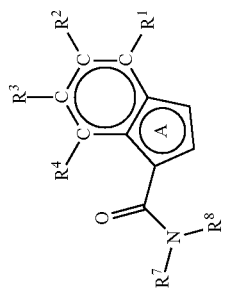

(Step A-1)

Compound (I) of the present invention can be produced by condensing compound (2) with compound (3), or compound (2) with compound (4). The reaction is carried out by reacting compound (2) with compound (3) or with compound (4), in the presence of a metal catalyst. Preferable examples of the metal catalyst include palladium compounds [e.g.: palladium (II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), [1,1-bis(diphenylphosphino)ferrocene]dichloropalladium(II), a complex of palladium(II) acetate and 1,1'-bis(diphenylphosphino)ferrocene, etc.] and copper compounds [e.g.: copper(I) iodide, copper(I) bromide etc.]. The metal catalyst is used in an amount of about 0.000001 to 5 mol per 1 mol of compound (2). The metal catalyst can be used together with a phosphine ligand [e.g.: triphenylphosphine, 4,5-bis(diphenylphosphino)-9,9-dimethylxanthene, tri-tert-butylphosphine, tri-tert-butylphosphine tetrafluoroborate etc.] or an amine ligand [e.g.: 8-methylquinolin-1-ol, 1,10-phenanthroline, 1,2-diaminocyclohexane, N,N'-dimethyl-1,2-ethanediamine etc.]. The phosphine ligand or amine ligand is used in an amount of about 0.01 to 5 mol per 1 mol of compound (2). The reaction is generally carried out in the presence of a base. Examples of the base include inorganic bases, basic salts and the like. Compound (3) or compound (4) is used in an amount of about 0.8 to 10 mol per 1 mol of compound (2). The base is used in an amount of about 1 to 20 mol per 1 mol of compound (2). When a metal catalyst unstable to oxygen is used in this reaction, the reaction is preferably carried out, for example, under an inert gas such as argon gas, nitrogen gas and the like. This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, esters, sulfoxides, water, mixed solvents thereof and the like. While the reaction time varies depending on the kind of the reagent and solvent to be used, it is generally 1 min to 200 hr. The reaction temperature is preferably 0 to 150° C. In addition, microwave may be irradiated to promote the reaction. Compound (2), compound (3) and compound (4) may be a commercially available product, or can also be produced according to a method known per se or a method analogous thereto.

Among compound (I) of the present invention, for example, compound (Ia) can be produced according to Step A-2, and compound (Ib) can be produced according to a sequence reaction step of Step A-2 to Step A-3 or Step A-4 to Step A-5.

(Step A-2)

Compound (Ia) can be produced by condensing compound (2a) with compound (3), or compound (4). The reaction is carried out in the same manner as in the method in Step A-1.

(Step A-3)

Compound (Ib) can be produced by condensing compound (Ia) with compound (5). When $R^6$ is a hydrogen atom in compound (Ia), the condensation reaction is carried out by reacting compound (Ia) or a reactive derivative thereof with compound (5). Examples of the reactive derivative include acid halides such as acid chlorides, acid bromides and the like; acid amides with pyrazole, imidazole, benzotriazole and the like; mixed anhydrides with acetic acid, propionic acid, butyric acid and the like; acid azides; activated esters such as diethoxyphosphate, diphenoxyphosphate, p-nitrophenyl ester, 2,4-dinitrophenyl ester, cyanomethyl ester, pentachlorophenyl ester, an ester with N-hydroxysuccinimide, an ester with N-hydroxyphthalimide, an ester with 1-hydroxybenzotriazole, an ester with 6-chloro-1-hydroxybenzotriazole, an ester with 1-hydroxy-1H-2-pyridone, and the like; activated thioesters such as 2-pyridylthio ester, 2-benzothiazolylthio ester and the like, and the like. Alternatively, instead of use of the reactive derivative, compound (Ia) may be directly reacted with compound (5) in the presence of a suitable condensing agent. Examples of the condensing agent include N,N'-di-substituted carbodiimides such as N,N'-dicyclohexylcarbodiimide, 1-ethyl-3-(3-dimethylaminopropyl)carbodiimide (WSC) hydrochloride and the like; azolides such as N,N'-carbonyldiimidazole and the like; dehydrating agents such as N-ethoxycarbonyl-2-ethoxy-1,2-dihydroquinoline, phosphorus oxychloride, alkoxyacethylene and the like; 2-halogeno pyridinium salts such as 2-chloromethylpyridinium iodide, 2-fluoro-1-methylpyridinium iodide and the like; phosphorylcyanides such as diethylphosphorylcyanide and the like; 2-(7-azabenzotriazol-1-yl)-1,1,3,3-tetramethyluronium hexafluorophosphate (HATU), O-(7-azabenzotriazol-1-yl)-N,N,N',N'-tetramethyluronium tetrafluoroborate (TATU), (1-cyano-2-ethoxy-2-oxoethylidenaminooxy)dimethylamino-morpholino-carbenium hexafluorophosphate (COMU) and the like. The reaction is considered to proceed via a reactive derivative of compound (Ia) by using a condensing agent. Compound (5) is generally used in an amount of about 0.8 to 5 mol per 1 mol of compound (Ia) or a reactive derivative thereof. This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, mixed solvents thereof and the like. In addition, when an acidic substance is generated due to the reaction, the reaction can be carried out in the presence of an acid scavenger to remove the acidic substance from the reaction system. Examples of the acid scavenger include basic salts, organic bases and the like. In addition, for example, basic salts, organic bases and the like can also be used to promote the reaction. While the reaction time varies depending on the kind of the reagent and solvent to be used, it is generally 1 min to 72 hr. The reaction temperature is preferably 0 to 100° C.

When $R^6$ is an optionally substituted hydrocarbon group in compound (Ia), compound (Ib) can be produced by subjecting compound (Ia) to hydrolysis to convert $R^6$ to a hydrogen atom, and subjecting the resulting compound to a condensation reaction with compound (5). The hydrolysis reaction can be carried out using an inorganic base or an inorganic acid, under a reaction condition generically used for a hydrolysis reaction. When $R^6$ is an optionally substituted hydrocarbon group in compound (Ia), the condensation reaction of compound (Ia) with compound (5) can also be carried out in the presence of an organic metal. Preferable examples of the organic metal include aluminium compounds [e.g.: trimethylaluminium etc.] and the like. The organic metal is used in an amount of about 0.8 to 10 mol per 1 mol of compound (Ia). Compound (5) is used in an amount of about 0.8 to 10 mol per 1 mol of compound (Ia). This reaction is preferably carried out, for example, under an inert gas such as argon gas, nitrogen gas and the like. This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, mixed solvents thereof and the like. While the reaction time varies depending on the kind of the reagent and solvent to be used, it is generally 1 min to 50 hr. The reaction temperature is preferably 0 to 100° C. Compound (5) may be a commercially available product, or can also be produced according to a method known per se or a method analogous thereto.

(Step A-4)

Compound (2b) can be produced by condensing compound (2a) with compound (5). The reaction is carried out in the same manner as in the method in Step A-3.

(Step A-5)

Compound (Ib) can be produced by condensing compound (2b) with compound (3) or compound (4). The reaction is carried out in the same manner as in the method in Step A-2.

Compound (2a) may be a commercially available product, or, of compound (2a), compounds (2c), (2d) and (2e) can also be produced, for example, according to Production Method B explained below. $R^9$, $R^{11}$, $R^{12}$ and $R^{13}$ are each an optionally substituted hydrocarbon group, and $R^{10}$ and $R^{14}$ are each a substituent.

Examples of the "optionally substituted hydrocarbon group" for $R^9$, $R^{11}$, $R^{12}$ or $R^{13}$ include those similar to the "optionally substituted hydrocarbon group" exemplified in $R^2$.

Examples of the "substituent" for $R^{10}$ or $R^{14}$ include those similar to the "substituent" for $R^2$.

[Production Method B]

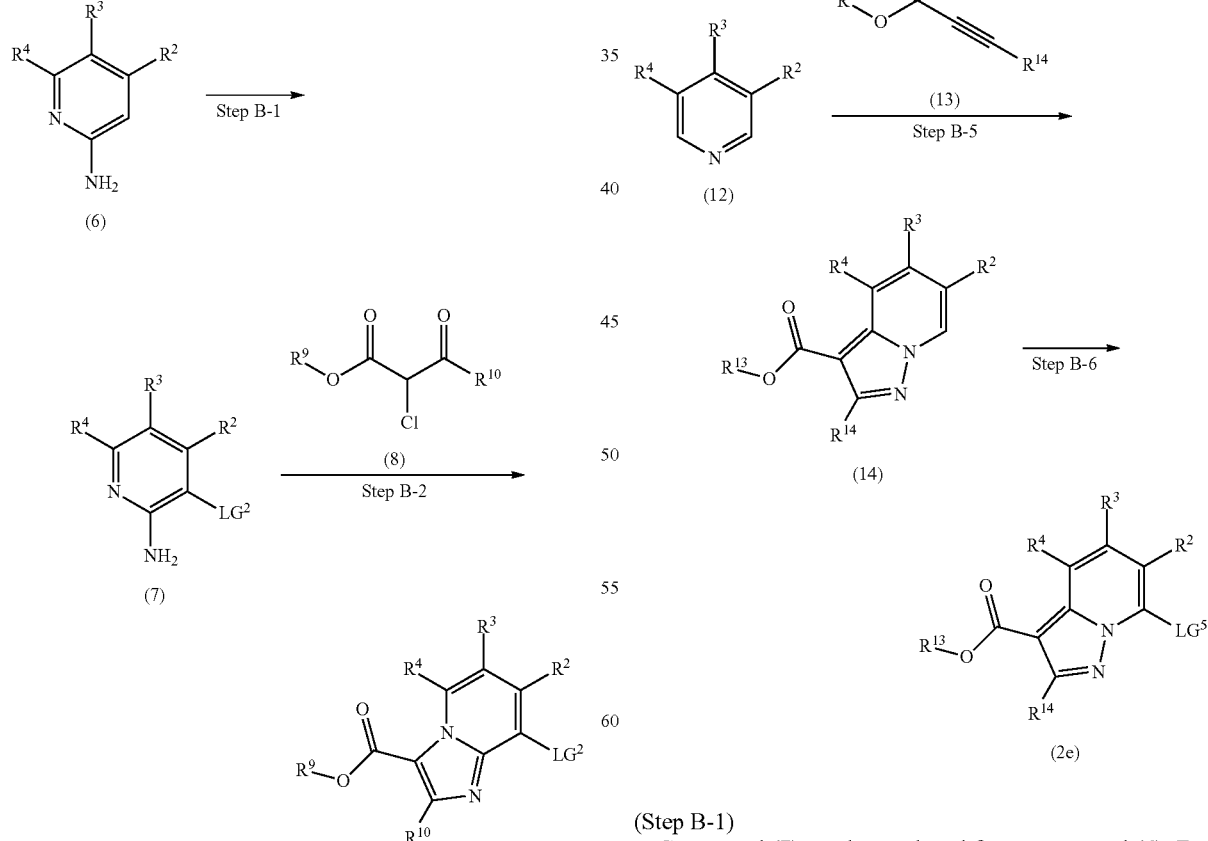

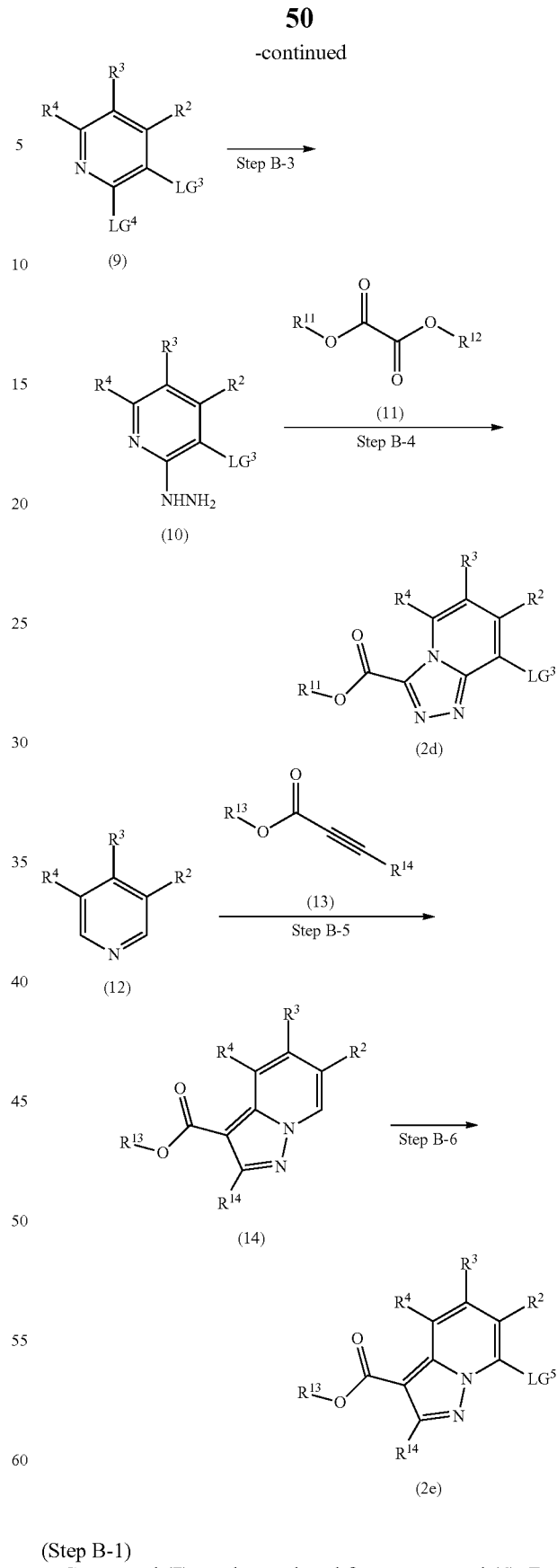

(Step B-1)

Compound (7) can be produced from compound (6). For example, when $LG^2$ is a halogen atom, compound (7) can be produced by reacting compound (6) with a halogen compound. Examples of the halogen compound include chlorine, bromine, iodine, N-chlorosuccinimide, N-bromosuccinimide, N-iodosuccinimide and the like. The halogen compound is used in an amount of about 0.8 to 10 mol per 1 mol of compound (6). This reaction is advantageously carried out in a solvent inert to the reaction. The solvent is not particularly limited as long as the reaction proceeds. Preferable examples thereof include organic acids, ethers, aromatic hydrocarbons, saturated hydrocarbons, amides, halogenated hydrocarbons, nitriles, mixed solvents thereof and the like. While the reaction time varies depending on the kind of the reagent and solvent to be used, it is generally 1 min to 50 hr. The reaction temperature is preferably 0 to 100° C. Compound (6) may be a commercially available product, or can also be produced according to a method known per se or a method analogous thereto.

(Step B-2)

Compound (2c) can be produced by condensing compound (7) with compound (8). The reaction can be carried out in the presence of an inorganic acid, if desired. Preferable examples of the inorganic acid include sulfuric acid and the like. Compound (8) is used in an amount of about 0.8 to 5 mol per 1 mol of compound (7). The acid is used in an amount of about 0.3 to 3 mol per 1 mol of compound (8). This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, esters, sulfoxides, mixed solvents thereof and the like. While the reaction time varies depending on the kind of the reagent and solvent to be used, it is generally 1 to 200 hr. The reaction temperature is preferably 0 to 150° C. In addition, microwave may be irradiated to promote the reaction. Compound (7) and compound (8) may be a commercially available product, or can also be produced according to a method known per se or a method analogous thereto.

(Step B-3)

Compound (10) can be produced by condensing compound (9) with a hydrazine (e.g.: hydrazine, hydrazine hydrate etc.). The hydrazine is used in an amount of about 0.8 to 50 mol per 1 mol of compound (9). This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, sulfoxides, mixed solvents thereof and the like. While the reaction time varies depending on the kind of the reagent and solvent to be used, it is generally 1 to 50 hr. The reaction temperature is preferably 0 to 100° C. Compound (9) may be a commercially available product, or can also be produced according to a method known per se or a method analogous thereto.

(Step B-4)

Compound (2d) can be produced by reacting compound (10) with compound (11). The reaction can be carried out in the presence of an acid, if desired. Preferable examples of the acid include hydrogen chloride and the like. Compound (11) is used in an amount of about 0.8 to 10 mol per 1 mol of compound (10). The acid is used in an amount of about 0.8 to 10 mol per 1 mol of compound (10). This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, sulfoxides, mixed solvents thereof and the like. While the reaction time varies depending on the kind of the reagent and solvent to be used, it is generally 1 to 10 hr. The reaction temperature is preferably 100 to 200° C. Microwave may be irradiated to promote the reaction. Compound (11) may be a commercially available product, or can also be produced according to a method known per se or a method analogous thereto.

(Step B-5)

Compound (14) can be produced, for example, by reacting compound (12) with the reagent prepared from ethyl N-(mesitylsulfonyl)oxyacetoimidate and 60% perchloric acid, and then reacting the resulting compound with compound (13) in the presence of a base. Preferable examples of the base include inorganic bases such as potassium carbonate and the like. The ethyl N-(mesitylsulfonyl)oxyacetoimidate is used in an amount of about 1 to 5 mol per 1 mol of compound (12). The 60% perchloric acid is used in an amount of about 1 to 10 mol per 1 mol of compound (12). Compound (13) is used in an amount of about 1 to 5 mol per 1 mol of compound (12). The base is used in an amount of about 1 to 10 mol per 1 mol of compound (12). This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, mixed solvents thereof and the like. While the reaction time varies depending on the kind of the reagent and solvent to be used, it is generally 12 to 100 hr. The reaction temperature is preferably −10 to 50° C. Compound (12) and compound (13) may be a commercially available product, or can also be produced according to a method known per se or a method analogous thereto.

(Step B-6)

Compound (2e) can be synthesized from compound (14). For example, when $LG^5$ is a halogen atom, compound (2e) can be produced by reacting compound (14) successively with lithium hexadisilazide and a halogen compound. Examples of the halogen compound include chlorine, bromine, iodine, N-chlorosuccinimide, N-bromosuccinimide, N-iodosuccinimide and the like. The lithium hexadisilazide is used in an amount of about 1 to 10 mol per 1 mol of compound (14). The halogen compound is used in an amount of about 1 to 3 mol per 1 mol of compound (14). This reaction is advantageously carried out in a solvent inert to the reaction. The solvent is not particularly limited as long as the reaction proceeds. Preferable examples thereof include ethers, aromatic hydrocarbons, saturated hydrocarbons, amides, mixed solvents thereof and the like. While the reaction time varies depending on the kind of the reagent and solvent to be used, it is generally 1 to 20 hr. The reaction temperature is preferably −10 to 50° C.

The starting compound and/or the production intermediate for the above-mentioned compound (I) may form a salt. While the salt is not particularly limited as long as the reaction can be performed, examples thereof include those similar to the salts optionally formed by the above-mentioned compound (I) and the like, and the like.

As for the configuration isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can be obtained by isomerizing a double bond using heating, an acid catalyst, a transition metal complex, a metal catalyst, a radical catalyst, light irradiation or a strong base catalyst and the like, according to the method described in Jikken Kagaku Kouza (Courses in Experimental Chemistry) 14 (The Chemical Society of Japan ed.), pages 251 to 253, 4th Edition Jikken Kagaku Kouza 19 (The Chemical Society of Japan ed.), pages 273 to 274 or a method analogous thereto.

Compound (I) contains a stereoisomer depending to the kind of a substituent, and each stereoisomer and a mixture thereof are encompassed in the present invention.

Compound (I) may be a hydrate or a non-hydrate.

When desired, compound (I) can be synthesized by performing deprotection reaction, acylation reaction, alkylation reaction, hydrogenation reaction, oxidation reaction, reduction reaction, reaction of carbon chain extension, substituent exchange reaction singly or two or more thereof in combination.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is recemic, d-form and l-form can be isolated according to a conventional optical resolution.

In each of the above-mentioned reactions, when the compound has a functional group such as an amino group, a hydroxy group or a carboxyl group, the reaction can be carried out after a protecting group generally used in peptide chemistry and the like is introduced into these groups. By removing the protecting group as necessary after the reaction, the objective compound can be obtained.

Examples of the protecting group include formyl, $C_{1-6}$ alkyl-carbonyl (e.g., acetyl, propionyl etc.), phenylcarbonyl, $C_{1-6}$ alkoxy-carbonyl (e.g., methoxycarbonyl, ethoxycarbonyl etc.), phenyloxycarbonyl, $C_{7-10}$ aralkyloxy-carbonyl (e.g., benzyloxycarbonyl etc.), trityl, phthaloyl and the like, each of which is optionally substituted. Examples of the substituent include a halogen atom (e.g., fluorine, chlorine, bromine, iodine etc.), $C_{1-6}$ alkyl-carbonyl (e.g., acetyl, propionyl, valeryl etc.), nitro and the like. The number of substituents is, for example, 1 to 3.

The removal method of the protecting group can be carried out according to a method known per se, and for example, a method using acid, base, ultraviolet rays, hydrazine, phenylhydrazine, sodium N-methyldithiocarbamate, tetrabutylammonium fluoride, palladium acetate and the like, a reduction method, and the like can be employed.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

When compound (I) contains a configurational isomer, a diastereomer, a conformer and the like, each can be isolated according to the above-mentioned separation and purification methods, if desired. In addition, when compound (I) is recemic, S-form and R-form can be isolated according to a conventional optical resolution.

When compound (I) contains a stereoisomer, each isomer and a mixture thereof are encompassed in the present invention.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include (1) a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, ethoxycarbonylation, tert-butoxycarbonylation, acetylation, cyclopropylcarbonylation and the like);

(2) a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation and the like);

(3) a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and a prodrug thereof are sometimes collectively abbreviated as "the compound of the present invention".

When compound (I) has isomers such as optical isomer, stereoisomer, positional isomer, rotamer and the like, such isomers and a mixture thereof are also encompassed in compound (I). For example, when compound (I) has optical isomers, an optical isomer resolved from this compound is also encompassed in compound (I). These isomers can be obtained as a single product according to synthesis methods or separation methods known per se (e.g., concentration, solvent extraction, column chromatography, recrystallization, etc.).

Compound (I) may be a crystal, and a single crystal form and a mixture of crystal forms are both encompassed in compound (I). The crystal can be produced by crystallizing according to a crystallization method known per se.

Compound (I) may be a hydrate, a non-hydrate, a solvate or a non-solvate.

Compound (I) may be labeled with an isotope (e.g., $^3$H, $^{11}$C, $^{14}$C, $^{18}$F, $^{35}$S, $^{125}$I etc.) and the like.

Compound (I) also encompasses a deuterium conversion form wherein $^1$H is converted to $^2$H(D).

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Compound (I) may also be used as a PET tracer.

The compound of the present invention has low toxicity, and can be used as it is or in the form of a pharmaceutical composition by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations, or solvent, solubilizing agent, suspending agent, isotonicity agent, buffer and soothing agent for liquid preparations, and the like, and preparation additives such as preservative, antioxidant, colorant, sweetening agent and the like can be added as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthesis aluminum silicate and magnesium alumino metasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agents include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include p-oxybenzoates, chlorobutanol, benzyl alcohol, phenethyl alcohol, dehydroacetic acid and sorbic acid.

Preferable examples of the antioxidant include sulfite and ascorbate.

Preferable examples of the colorant include aqueous water-soluble food tar colors (e.g., food colors such as Food Color Red Nos. 2 and 3, Food Color Yellow Nos. 4 and 5, Food Color Blue Nos. 1 and 2 and the like), water insoluble lake dyes (e.g., aluminum salt of the above-mentioned water-soluble food tar color) and natural dyes (e.g., β-carotene, chlorophyll, ferric oxide red).

Preferable examples of the sweetening agent include saccharin sodium, dipotassium glycyrrhizinate, aspartame and stevia.

Examples of the dosage form of the pharmaceutical composition include oral preparations such as tablet (including sugar-coated tablet, film-coated tablet, sublingual tablet, orally disintegrating tablet), capsules (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion), external preparations (e.g., dermal preparation, ointment), suppository (e.g., rectal suppository, vaginal suppository), pellet, nasal preparation, pulmonary preparation (inhalant), eye drop and the like.

These can be respectively safely administered orally or parenterally (e.g., topically, rectally, intravenously administered).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical formulation, for example, the method described in the Japanese Pharmacopoeia, and the like.

While the content of the compound of the present invention in the pharmaceutical composition varies depending on the dosage form, dose of the compound of the present invention and the like, it is for example, about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the water-soluble film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, cardiotoxicity, carcinogenicity) and a few side effects. Therefore, it can be used as an agent for the prophylaxis or treatment or a diagnostic of various diseases in a mammal (e.g., human, bovine, horse, dog, cat, monkey, mouse, rat).

The compound of the present invention has a superior CH24H inhibitory action and can suppress nerve cell death, Aβ increase, intracerebral inflammation and the like.

Accordingly, the compound of the present invention is useful for the prophylaxis, improvement of symptoms, suppression of progression or treatment of diseases involving enhanced function of CH24H, for example, neurodegenerative disease.

In the present specification, the "neurodegenerative disease" means a disease associated with denaturation of neural tissues.

Specific examples of the neurodegenerative disease include Alzheimer's disease, mild cognitive impairment, Huntington's disease, Parkinson's disease, amyotrophic lateral sclerosis, multiple sclerosis, amyotrophic lateral sclerosis, traumatic brain injury, cerebral infarction, glaucoma and the like.

In addition, the compound of the present invention is useful for the prophylaxis, improvement of symptoms, suppression of progression or treatment of diseases involving enhanced function of CH24H, for example, epilepsy, schizophrenia and the like.

Moreover, the compound of the present invention is useful for the prophylaxis, improvement of symptoms, suppression of progression or treatment of diseases involving enhanced function of CH24H, for example, spasm and the like.

The dose of the compound of the present invention varies depending on the administration subject, route of administration, target disease, symptoms, etc. For example, when it is administered orally to an adult patient (body weight 60 kg), its dose is about 0.01 to 100 mg/kg body weight per dose, preferably 0.05 to 30 mg/kg body weight per dose, more preferably 0.1 to 10 mg/kg body weight per dose and this amount is desirably administered in 1 to 3 portions daily.

When the compound of the present invention is applied to each of the above-mentioned diseases, it can be used in an appropriate combination with a medicament or a treatment method generally employed for the disease.

Examples of the medicament (hereinafter to be abbreviated as "concomitant drug") to be used in combination with the compound of the present invention include acetylcholine esterase inhibitors (e.g., donepezil, rivastigmine, galanthamine, zanapezil etc.), antidementia agents (e.g., memantine), inhibitors of β amyloid protein production, secretion, accumulation, coagulation and/or deposition, β secretase inhibitors (e.g., 6-(4-biphenyl)methoxy-2-[2-(N,N-dimethylamino)ethyl]tetralin, 6-(4-biphenyl)methoxy-2-(N,N-dimethylamino)methyltetralin, 6-(4-biphenyl)methoxy-2-(N,N-dipropylamino)methyltetralin, 2-(N,N-dimethylamino)methyl-6-(4'-methoxybiphenyl-4-yl)methoxytetralin, 6-(4-biphenyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, (3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitory agent, β amyloid protein coagulation inhibitory agent (e.g., PTI-00703, ALZHEMED (NC-531), PPI-368 (JP-A-11-514333), PPI-558 (JP-A-2001-500852), SKF-74652 (Biochem. J. (1999), 340(1), 283-289)), β amyloid vaccine, β amyloid degrading enzyme and the like, cerebral function activators (e.g., aniracetam, nicergoline), other therapeutic drug for Parkinson's disease [(e.g., dopamine receptor agonists (e.g., L-DOPA, bromocriptine, pergolide, talipexole, pramipexole, cabergoline, adamantadine), a monoamine oxidase (MAO) inhibitors (e.g., deprenyl, Selgiline (selegiline), remacemide, riluzole), anticholinergic agents (e.g., trihexyphenidyl, biperiden), COMT inhibitors (e.g., entacapone)], therapeutic drug for amyotropic lateral sclerosis (e.g., riluzole etc., neurotrophic factor), therapeutic drug for abnormal behavior, wandering and the like due to the progress of dementia (e.g., sedative drug, antianxiety drug), apoptosis inhibitors (e.g., CPI-1189, IDN-6556, CEP-1347), neuronal differentiation or regeneration promoters (e.g., leteprinim, xaliproden (SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and optically active forms, salts and hydrates thereof), antidepressants (e.g., desipramine, amitriptyline, imipramine, tramadol), antiepilepsy drug (e.g., lamotrigine), antianxiety drugs (e.g., benzodiazepine), non-steroidal anti-inflammatory drugs (e.g., meloxicam, tenoxicam, indomethacin, ibuprofen, celecoxib, rofecoxib, aspirin, indomethacin), disease-modifying anti-rheumatic drugs (DMARDs), anti-cytokine drugs (e.g., TNF inhibitor, MAP kinase inhibitor), steroidal drugs (e.g., dexamethasone, hexestrol, cortisone acetate), therapeutic agents for incontinence or frequent urination (e.g., flavoxate hydrochloride, oxybutynin hydrochloride, propiverine hydrochloride), phosphodiesterase inhibitors (e.g., sildenafil (citrate)), dopamine agonists (e.g., apomorphine etc.), antiarrhythmics (e.g., mexiletine), sex hormones or derivatives thereof (e.g., progesterone, estradiol, estradiol benzoate), therapeutic agents for osteoporosis (e.g., alfacalcidol, calcitriol, elcatonin, calcitonin salmon, estriol, ipriflavone, disodium pamidronate, sodium alendronate hydrate, disodium incadronate), parathyroid hormone (PTH), calcium receptor antagonists, therapeutic drugs for insomnia (e.g., benzodiazepine medicament, non-benzodiazepine medicament, melatonin agonist), therapeutic drugs for schizophrenia (e.g., typical antipsychotic agents such as haloperidol and the like; atypical antipsychotic agents such as clozapine, olanzapine, risperidone, aripiprazole and the like; medicament acted on metabotropic glutamate receptor or ionic channel-conjugated glutamate receptor; phosphodiesterase inhibitor) and the like.

In addition, a combined use with a transplantation method of neural stem cell or neural precursor cell prepared from embryonic stem cell or nervous tissue, or fetal neural tissue, and a combined use with a pharmaceutical agent such as an immunosuppressant after the transplantation and the like.

Furthermore, the compound of the present invention may be used in combination with the following concomitant drugs.

(1) Therapeutic Agent for Diabetes

For example, insulin preparations (e.g., animal insulin preparation extracted from the pancreas of bovine, swine; human insulin preparation genetically synthesized using *Escherichia coli*, yeast; zinc insulin; protamine zinc insulin; insulin fragment or derivatives (e.g., INS-1), oral insulin preparation), insulin sensitizer (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), α-glucosidase inhibitor (e.g., voglibose, acarbose, miglitol, emiglitate), biguanide (e.g., metformin, buformin or a salt thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof, glucose-dependent insulin secretagogue (e.g., [(3S)-6-({2',6'-dimethyl-4'-[3-(methylsulfonyl)propoxy]biphenyl-3-yl}methoxy)-2,3-dihydro-1-benzofuran-3-yl]acetic acid or a salt thereof)], dipeptidyl peptidase IV inhibitor (e.g., Alogliptin, Vildagliptin, Sitagliptin, Saxagliptin, T-6666, TS-021), β3 agonist (e.g., AJ-9677), GPR40 agonist, GLP-1 receptor agonist [e.g., GLP-1, GLP-1MR agent, NN-2211, AC-2993 (exendin-4), BIM-51077, Aib(8,35)hGLP-1(7,37)NH$_2$, CJC-1131], amylin agonist (e.g., pramlintide), phosphotyrosine phosphatase inhibitors (e.g., sodium vanadate), gluconeogenesis inhibitor (e.g., glycogen phosphorylase inhibitor, glucose-6-phosphatase inhibitors, glucagon antagonists), SGLUT (sodium-glucose cotransporter) inhibitor (e.g., T-1095), 11β-hydroxysteroid dehydrogenase inhibitor (e.g., BVT-3498), adiponectin or an agonist thereof, IKK inhibitor (e.g., AS-2868), leptin resistance improving drugs, somatostatin receptor agonists, glucokinase activators (e.g., Ro-28-1675), GIP (Glucose-dependent insulinotropic peptide) and the like.

(2) Therapeutic Agents for Diabetic Complications

For example, aldose reductase inhibitors (e.g., tolrestat, epalrestat, zenarestat, zopolrestat, minalrestat, fidarestat, CT-112), neurotrophic factor and an increasing agent thereof (e.g., NGF, NT-3, BDNF, neurotrophic factors and increasing drugs described in WO01/14372 (e.g., 4-(4-chlorophenyl)-2-(2-methyl-1-imidazolyl)-5-[3-(2-methylphenoxyl)propyl] oxazole)), nerve regeneration promoting agent (e.g., Y-128), PKC inhibitor (e.g., ruboxistaurin mesylate), AGE inhibitor (e.g., ALT946, pimagedine, pyratoxanthine, N-phenacylthiazolium bromide (ALT766), ALT-711, EXO-226, Pyridorin, pyridoxamine), active oxygen scavengers (e.g., thioctic acid), cerebral vasodilator (e.g., tiapuride, mexiletine), somatostatin receptor agonists (e.g., BIM23190), apoptosis signal regulating kinase-1(ASK-1) inhibitor and the like can be mentioned.

(3) Therapeutic Agent for Hyperlipidemia

For example, statin compound (e.g., pravastatin, simvastatin, lovastatin, atorvastatin, fluvastatin, rosuvastatin, pitavastatin, or a salt thereof (e.g., sodium salt, calcium salt)), squalene synthase inhibitors (e.g., lapaquistat acetate or a salt thereof), fibrate compound (e.g., bezafibrate, clofibrate, simfibrate, clinofibrate), ACAT inhibitor (e.g., Avasimibe, Eflucimibe), anion exchange resin (e.g., colestyramine), probucol, nicotinic acid drug (e.g., nicomol, niceritrol), ethyl icosapentate, phytosterol (e.g., soysterol, gamma oryzanol) and the like.

(4) Antihypertensive Agent

For example, angiotensin converting enzyme inhibitor (e.g., captopril, enalapril, delapril), angiotensin II antagonist (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid, Azilsartan, Azilsartan medoxomil), calcium antagonist (e.g., manidipine, nifedipine, amlodipine, efonidipine, nicardipine), potassium channel opener (e.g., levcromakalim, L-27152, AL 0671, NIP-121), clonidine and the like.

(5) Antiobesity Agent

For example, central-acting antiobesity agent (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonist (e.g., CP-422935); cannabinoid receptor antagonists (e.g., SR-141716, SR-147778); ghrelin antagonist; 11β-hydroxysteroid dehydrogenase inhibitor (e.g., BVT-3498)), pancreatic lipase inhibitors (e.g., orlistat, cetilistat), β3 agonist (e.g., AJ-9677, AZ40140), anorectic peptides (e.g., leptin, CNTF (ciliary neurotrophic factor)), cholecystokinin agonist (e.g., lintitript, FPL-15849), anorexigenic agent (e.g., P-57) and the like.

(6) Diuretic

For example, xanthine derivative (e.g., theobromine sodium salicylate, theobromine calcium salicylate), thiazide preparation (e.g., ethiazide, cyclopenthiazide, trichloromethyazide, hydrochlorothiazide, hydroflumethiazide, benzylhydrochlorothiazide, penflutizide, polythiazide, methyclothiazide), antialdosterone preparation (e.g., spironolactone, triamterene), carbonic anhydrase inhibitors (e.g., acetazolamide), chlorobenzenesulfonamide agent (e.g., chlortalidone, mefruside, indapamide), azosemide, isosorbide, ethacrynic acid, piretanide, bumetanide, furosemide and the like.

(7) Chemotherapeutic Agent

For example, alkylating agents (e.g., cyclophosphamide, ifosfamide), metabolic antagonists (e.g., methotrexate, 5-fluorouracil or derivative thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon and Neo-Furtulon, which are 5-fluorouracil derivatives, and the like are preferable.

(8) Immunotherapeutic Agent

For example, microorganism or bacterial components (e.g., muramyl dipeptide derivative, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.
(9) Antithrombotic Agent For example, heparin (e.g., heparin sodium, heparin calcium, dalteparin sodium), warfarin (e.g., warfarin potassium), anti-thrombin drug (e.g., argatroban), thrombolytic agent (e.g., urokinase, tisokinase, alteplase, nateplase, monteplase, pamiteplase), platelet aggregation inhibitor (e.g., ticlopidine hydrochloride, cilostazol, ethyl icosapentate, beraprost sodium, sarpogrelate hydrochloride) and the like.
(10) Cachexia Improving Medicament For example, cyclooxygenase inhibitors (e.g., indomethacin etc.) [Cancer Research, Vol. 49, pages 5935-5939, 1989], progesterone derivatives (e.g., megestrol acetate) [Journal of Clinical Oncology, Vol. 12, pages 213-225, 1994], glucosteroids (e.g., dexamethasone etc.), metoclopramide agents, tetrahydrocannabinol agents (publications are all as mentioned above), fat metabolism improving agents (e.g., eicosapentanoic acid etc.) [British Journal of Cancer, Vol. 68, pages 314-318, 1993], growth hormones, IGF-1, or antibodies to a cachexia-inducing factor such as TNF-α, LIF, IL-6, oncostatin M and the like.

Two or more kinds of the above-mentioned concomitant drugs may be used in combination at an appropriate ratio.

It is also possible to apply compound of the present invention to each of the above-mentioned diseases in combination with a biologic (e.g., antibody, vaccine preparation etc.), or as a combination therapy in combination with gene therapy method and the like.

Examples of the antibody and vaccine preparation include vaccine preparation to angiotensin II, vaccine preparation to CETP, CETP antibody, TNFα antibody and antibody to other cytokine, amyloid β vaccine preparation, type 1 diabetes vaccine (e.g., DIAPEP-277 manufactured by Peptor Ltd.), anti-HIV antibody, HIV vaccine preparation and the like, antibody or vaccine preparation to cytokine, renin-angiotensin enzyme and a product thereof, antibody or vaccine preparation to enzyme or protein involved in blood lipid metabolism, antibody or vaccine to enzyme or protein involved in blood coagulation or fibrinolytic system, antibody or vaccine preparation to protein involved in saccharometabolism or insulin resistance and the like.

In addition, a combined use with a biological preparation involved in a growth factor such as GH, IGF and the like is possible.

Examples of the gene therapy method include a treatment method using a gene relating to cytokine, renin-angiotensin enzyme and a product thereof, G protein, G protein conjugated receptor and its phosphorylation enzyme, a treatment method using a DNA decoy such as NFκB decoy and the like, a treatment method using an antisense, a treatment method using a gene relating to an enzyme or protein involved in blood lipid metabolism (e.g., gene relating to metabolism, excretion or absorption of cholesterol or triglyceride or HDL-cholesterol or blood phospholipid), a treatment method using a gene relating to an enzyme or protein involved in angiogenesis therapy targeting obstruction of peripheral vessel and the like (e.g., growth factors such as HGF, VEGF etc.), a treatment method using a gene relating to a protein involved in saccharometabolism or insulin resistance, an antisense to cytokine such as TNF and the like, and the like.

In addition, it is possible to use in combination with various organ regeneration methods such as heart regeneration, kidney regeneration, pancreas regeneration, blood vessel regeneration and the like or cell transplantation therapy utilizing bone marrow cell (myelomonocytic cell, myeloid stem cell) or an artificial organ utilizing tissue engineering (e.g., artificial blood vessel and cardiac muscle cell sheet).

The time of administration of the compound of the present invention and that of the concomitant drug are not limited, and they may be administered simultaneously or in a staggered manner to the administration subject. Furthermore, the compound of the present invention and the concomitant drug may be administered as two kinds of preparations containing each active ingredient, or a single preparation containing both active ingredients.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like. When the subject of administration is human, for example, a concomitant drug can be used in 0.01-100 parts by weight relative to 1 part by weight of the compound of the present invention.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

The abbreviations used in the specification mean the following.
THF: tetrahydrofuran
DME: 1,2-dimethoxyethane
DMF: N,N-dimethylformamide
DMA: N,N-dimethylacetamide
DMSO: dimethyl sulfoxide
ESI: electrospray method
APCI: atmospheric chemical ionization
M: mol concentration
N: normal concentration
IPE: diisopropyl ether
WSC: 1-[3-(dimethylamino)propyl]-3-ethylcarbodiimide
HATU: 2-(7-azabenzotriazol-1-yl)-1,1,3,3-tetramethyluronium hexafluorophosphate
HOBt: 1-hydroxybenzotriazole
S-Phos: 2-dicyclohexyl phosphino-2',6'-dimethoxy-1,1'-biphenyl
HPLC: high-performance liquid chromatography
NMP: N-methylpyrrolidone
$^1$H NMR (protone nuclear magnetic resonance spectrum) was measured by Fourier-transform type NMR. For the analysis, ACD/SpecManager (trade name) and the like were used. Peaks with very mild protons such as a hydroxy group, an amino group and the like may not be described.

MS (mass spectrum) was measured by LC/MS (liquid chromatography mass spectrometer). As the ionization method, ESI (Electro Spray Ionization) method, or APCI (Atmospheric Pressure Chemical Ionization) method was used. The data indicates those found. Generally, a molecular ion peak ([M+H]⁺, or, [M−H]⁻) is observed. In the case of a compound having a tert-butoxycarbonyl group (-Boc), a peak after elimination of a tert-butoxycarbonyl group or tert-butyl group may be observed as a fragment ion. In the case of a compound having a hydroxy group (—OH), a peak after elimination of $H_2O$ may be observed as a fragment ion. In the case of a salt, a molecular ion peak or fragment ion peak of free form is generally observed.

The elemental analysis value (Anal.) shows Calculated value (Calcd) and Found value (Found).

Example 1 ethyl 8-(1,3-oxazol-5-yl)-6-(trifluoromethyl)imidazo[1,2-a]pyridine-3-carboxylate A) potassium 2-chloro-3-ethoxy-3-oxoprop-1-en-1-olate To a suspension of potassium tert-butoxide (5.2 g) in IPE (50 mL) were added ethyl 2-chloroacetate (5.6 g) and ethyl formate (3.4 g) under ice-cooling, and the mixture was stirred overnight at room temperature. The precipitate was collected by filtration, and dried to give the title compound (5.8 g). $^1$H NMR (300 MHz, DMSO-$d_6$) δ 1.11 (3H, t, J=7.2 Hz), 3.92 (2H, q, J=7.2 Hz), 8.95 (1H, brs).

B) ethyl 8-bromo-6-(trifluoromethyl)imidazo[1,2-a]pyridine-3-carboxylate

A mixture of 3-bromo-5-(trifluoromethyl)pyridin-2-amine (3.0 g), potassium 2-chloro-3-ethoxy-3-oxoprop-1-en-1-olate (5.4 g), sulfuric acid (0.80 mL) and ethanol (60 mL) was stirred overnight at 90° C. The reaction mixture was diluted with ethyl acetate, and washed with water. The aqueous layer was neutralized with 1N sodium hydroxide, and extracted with ethyl acetate. The organic layers were combined, washed with water and saturated brine, and dried over anhydrous sodium sulfate, and the solvent was evaporated under reduced pressure. The residue was suspended in a mixed solvent of IPE and hexane, and the obtained solid was collected by filtration to give the title compound (2.6 g).

MS (APCI+). found: 337.1, 339.1.

C) 2-(triisopropylsilyl)oxazole

To a solution of oxazole (2.1 g) in THF (90 mL) was added dropwise n-butyllithium hexane solution (1.6M, 19.7 mL) at −78° C. The reaction mixture was stirred at 0° C. for 10 min under nitrogen atmosphere, and triisopropylsilyl triflate (8.5 mL) was added thereto. The reaction mixture was stirred at room temperature for 2 hr, and the solvent was evaporated under reduced pressure. To the residue was added ethyl acetate, and the mixture was washed with water and saturated brine, and dried over anhydrous sodium sulfate, and the solvent was evaporated under reduced pressure to give the title compound (6.7 g).

MS (APCI+): [M+H]⁺ 226.3.

D) 5-(4,4,5,5-tetramethyl-1,3,2-dioxaborolan-2-yl)-2-(triisopropylsilyl)oxazole

To a solution of 2-(triisopropylsilyl)oxazole (6.7 g) in THF (200 mL) was added dropwise n-butyllithium hexane solution (1.6M, 22.3 mL) at −78° C. The reaction mixture was stirred at −78° C. for 1 hr under nitrogen atmosphere, triisopropylborate (8.2 mL) was added thereto, and mixture was stirred at −78° C. for 2 hr. The mixture was allowed to be warmed to room temperature, and stirred overnight. To the reaction mixture was added a solution of 2,3-dimethylbutane-2,3-diol (3.51 g) in THF (20 mL) and acetic acid (2.3 mL), and the mixture was stirred at room temperature for 2 hr. The solvent was evaporated under reduced pressure, water was added thereto, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (8.8 g).

$^1$H NMR (300 MHz, CDCl$_3$) δ 1.14 (18H, d, J=7.2 Hz), 1.35 (12H, s), 1.38-1.52 (3H, m), 7.73 (1H, s).

E) ethyl 8-(1,3-oxazol-5-yl)-6-(trifluoromethyl)imidazo[1,2-a]pyridine-3-carboxylate A mixture of ethyl 8-bromo-6-(trifluoromethyl)imidazo[1,2-a]pyridine-3-carboxylate (500 mg), 5-(4,4,5,5-tetramethyl-1,3,2-dioxaborolan-2-yl)-2-(triisopropylsilyl)oxazole (573 mg), tetrakis(triphenylphosphine)palladium(0) (171 mg), potassium carbonate (410 mg), DME (12 mL) and water (3 mL) was stirred with microwave irradiation at 120° C. for 30 min. The reaction mixture was diluted with water, and extracted with ethyl acetate. The extract was dried over anhydrous magnesium sulfate, and the solvent was evaporated under reduced pressure. The residue was dissolved in THF (6 mL), and 1N hydrochloric acid (2 mL) was added thereto. The mixture was stirred at room temperature for 2 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (0.13 g).

$^1$H NMR (300 MHz, DMSO-$d_6$) δ 1.38 (3H, t, J=7.2 Hz), 4.43 (2H, q, J=7.2 Hz), 8.05 (1H, d, J=1.5 Hz), 8.27 (1H, s), 8.54 (1H, s), 8.72 (1H, s), 9.53-9.60 (1H, m).

Example 2

(8-(1,3-oxazol-5-yl)-6-(trifluoromethyl)imidazo[1,2-a]pyridin-3-yl)(pyrrolidin-1-yl)methanone To a mixture of ethyl 8-(1,3-oxazol-5-yl)-6-(trifluoromethyl)imidazo[1,2-a]pyridine-3-carboxylate (40 mg), THF (2 mL) and ethanol (2 mL) was added 1N aqueous sodium hydroxide solution (0.12 mL), and the mixture was stirred at room temperature for 2 hr. The reaction mixture was acidified with 1N hydrochloric acid, water was added thereto, and the mixture was extracted with ethyl acetate. The extract was dried over anhydrous magnesium sulfate, and the solvent was evaporated under reduced pressure. The residue was dissolved in THF (2 mL), DMF (one drop) was added thereto, and oxalyl chloride (21 µL) was added thereto. The mixture was stirred for 1 hr, and the solvent was evaporated. The residue was dissolved in THF (2 mL), and the obtained solution was added to a mixture of pyrrolidine (21 µL), ethyl acetate (2 mL) and saturated aqueous sodium bicarbonate solution (2 mL). The reaction mixture was stirred for 12 hr, water was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (7 mg). $^1$H NMR (300 MHz, DMSO-d$_6$) δ 1.85-2.03 (4H, m), 3.52-3.66 (2H, m), 3.75-3.92 (2H, m), 7.95 (1H, d, J=1.7 Hz), 8.28 (1H, s), 8.45 (1H, s), 8.70 (1H, s), 9.77 (1H, s).

Example 4 cyclopropyl(4-(1,3-oxazol-5-yl)-6-(trifluoromethyl)-1H-indol-1-yl)methanone

A) 3-bromo-2-iodo-5-(trifluoromethyl)aniline

To a solution of 3-bromo-5-(trifluoromethyl)aniline (5.00 g) in acetic acid (40 mL) was added N-iodosuccinimide (5.16 g) at 0° C., and the mixture was stirred overnight at room temperature under nitrogen atmosphere. The reaction mixture was diluted with ethyl acetate, washed with 10% aqueous sodium thiosulfate solution, saturated aqueous sodium bicarbonate solution and saturated brine, and dried over anhydrous sodium sulfate, and the solvent was evaporated under reduced pressure. The residue was purified by silica gel column chromatography (ethyl acetate/hexane) to give the title compound (5.21 g). $^1$H NMR (300 MHz, CDCl$_3$) δ 4.58 (2H, brs), 6.84 (1H, d, J=1.1 Hz), 7.23 (1H, d, J=1.1 Hz).

B) 3-bromo-5-(trifluoromethyl)-2-((trimethylsilyl)ethynyl)aniline

A mixture of 3-bromo-2-iodo-5-(trifluoromethyl)aniline (5.21 g), ethynyl(trimethyl)silane (2.21 mL), triethylamine (100 mL), dichlorobis(triphenylphosphine)palladium(II) (1.00 g) and copper(I) iodide (0.271 g) was stirred overnight at 80° C. under nitrogen atmosphere. The solvent was evaporated under reduced pressure, to the residue was added saturated aqueous ammonium chloride solution, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (2.70 g).
$^1$H NMR (300 MHz, CDCl$_3$) b 0.30 (9H, s), 4.56 (2H, brs), 6.84 (1H, s), 7.15 (1H, s).

C) 3-bromo-2-ethynyl-5-(trifluoromethyl)aniline

To a solution of 3-bromo-5-(trifluoromethyl)-2-((trimethylsilyl)ethynyl)aniline (2.70 g) in methanol (30 mL) was added potassium carbonate (1.11 g), and the mixture was stirred overnight at room temperature. The solvent was evaporated under reduced pressure, to the residue was added saturated aqueous ammonium chloride solution, and the mixture was extracted with ethyl acetate. The extract was washed with saturated aqueous ammonium chloride solution and saturated brine, and dried over anhydrous sodium sulfate, and the solvent was evaporated under reduced pressure. The residue was purified by silica gel column chromatography (ethyl acetate/hexane) to give the title compound (1.56 g).
$^1$H NMR (300 MHz, CDCl$_3$) δ 3.78 (1H, s), 4.60 (2H, brs), 6.86 (1H, s), 7.16 (1H, s).

D) 4-bromo-6-(trifluoromethyl)-1H-indole

To a solution of potassium tert-butoxide (1.33 g) in NMP (30 mL) was added a solution of 3-bromo-2-ethynyl-5-(trifluoromethyl)aniline (1.56 g) in NMP (5 mL) at 0° C., and the mixture was stirred overnight at room temperature. The reaction mixture was diluted with ethyl acetate, washed with saturated aqueous ammonium chloride solution, water and saturated brine, and dried over anhydrous sodium sulfate, and the solvent was evaporated under reduced pressure. The residue was purified by silica gel column chromatography (NH, ethyl acetate/hexane) to give the title compound (1.08 g).
$^1$H NMR (300 MHz, CDCl$_3$) δ 6.68 (1H, brs), 7.41 (1H, t, J=2.8 Hz), 7.55 (1H, s), 7.64 (1H, s), 8.61 (1H, brs).

E) 5-(6-(trifluoromethyl)-1H-indol-4-yl)oxazole

A mixture of 4-bromo-6-(trifluoromethyl)-1H-indole (300 mg), 5-(4,4,5,5-tetramethyl-1,3,2-dioxaborolan-2-yl)-2-(triisopropylsilyl)oxazole (422 mg), tetrakis(triphenylphosphine)palladium(0) (131 mg) and potassium carbonate (314 mg) in DME/water (3/0.5 mL) was stirred with microwave irradiation at 120° C. for 30 min. The reaction mixture was diluted with saturated aqueous ammonium chloride solution, and extracted with ethyl acetate. The extract was washed with water and saturated brine, and dried over anhydrous sodium sulfate, and the solvent was evaporated under reduced pressure. The residue was dissolved in THF (5 mL), 1N hydrochloric acid (2 mL) was added thereto, and the mixture was stirred overnight at room temperature. To the reaction mixture was added saturated aqueous sodium bicarbonate solution, and the mixture was extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane) to give the title compound (174 mg).
$^1$H NMR (300 MHz, CDCl$_3$) δ 6.96 (1H, brs), 7.49 (1H, t, J=2.8 Hz), 7.58 (1H, s), 7.72 (2H, d, J=8.7 Hz), 8.04 (1H, s), 8.64 (1H, brs).

F) cyclopropyl(4-(1,3-oxazol-5-yl)-6-(trifluoromethyl)-1H-indol-1-yl)methanone

To a solution of 5-(6-(trifluoromethyl)-1H-indol-4-yl)oxazole (50.0 mg) in DMF (1 mL) was added 60% sodium hydride (9.52 mg) at 0° C., and the mixture was stirred for 20 min. To the reaction mixture was added cyclopropanecarbonyl chloride (22 µL) at 0° C., and the mixture was stirred for 3 hr, saturated aqueous ammonium chloride solution was added thereto, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (30.0 mg).
$^1$H NMR (400 MHz, CDCl$_3$) δ 1.14-1.24 (2H, m), 1.36-1.45 (2H, m), 2.33 (1H, tt, J=8.1, 4.2 Hz), 7.13 (1H, d, J=3.7 Hz), 7.57 (1H, s), 7.84 (1H, s), 7.97 (1H, d, J=3.7 Hz), 8.06 (1H, s), 8.82 (1H, s).

Example 16 morpholin-4-yl(8-(1,3-oxazol-5-yl)-6-(trifluoromethyl)imidazo[1,2-a]pyridin-3-yl)methanone To a mixture of ethyl 8-(1,3-oxazol-5-yl)-6-(trifluoromethyl)imidazo[1,2-a]pyridine-3-carboxylate (50 mg), THF (0.5 mL) and ethanol (2 mL) was added 1N aqueous sodium hydroxide solution (1 mL), and the mixture was stirred at room temperature for 2 hr. The reaction mixture was acidified with 1N hydrochloric acid, water was added thereto, and the mixture was extracted with ethyl acetate. The extract was dried over anhydrous magnesium sulfate, and the solvent was evaporated under reduced pressure. The residue was dissolved in DMF (3 mL), and WSC hydrochloride (44 mg), HOBt hydrate (35 mg), morpholine (41 µL) and triethylamine (64 µL) were added thereto. The reaction mixture was stirred at room temperature for 12 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (14 mg).

$^1$H NMR (300 MHz, DMSO-$d_6$) δ 3.63-3.85 (8H, m), 7.93 (1H, d, J 1.5 Hz), 8.20-8.31 (2H, m), 8.71 (1H, s), 9.27 (1H, s).

Example 21

(3,3-difluoroazetidin-1-yl) (8-(1,3-oxazol-5-yl)-6-(trifluoromethyl)imidazo[1,2-a]pyridin-3-yl)methanone To a mixture of ethyl 8-(1,3-oxazol-5-yl)-6-(trifluoromethyl)imidazo[1,2-a]pyridine-3-carboxylate (50 mg), THF (2 mL) and ethanol (6 mL) was added 1N aqueous sodium hydroxide solution (2 mL), and the mixture was stirred at room temperature for 2 hr. The reaction mixture was acidified with 1N hydrochloric acid, water was added thereto, and the mixture was extracted with ethyl acetate. The extract was dried over anhydrous magnesium sulfate, and the solvent was evaporated under reduced pressure. The residue was dissolved in DMF (5 mL), and WSC hydrochloride (59 mg), HOBt hydrate (47 mg), 3,3-difluoroazetidine hydrochloride (40 mg) and triethylamine (129 µL) were added thereto. The reaction mixture was stirred at room temperature for 12 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (9 mg).

$^1$H NMR (300 MHz, DMSO-$d_6$) δ 4.43-5.19 (4H, m), 8.00 (1H, d, J=1.9 Hz), 8.28 (1H, s), 8.43 (1H, s), 8.72 (1H, s), 9.71 (1H, d, J=1.5 Hz).

Example 22

2-oxa-6-azaspiro[3.3]hept-6-yl(8-(1,3-oxazol-5-yl)-6-(trifluoromethyl)imidazo[1,2-a]pyridin-3-yl)methanone To a mixture of ethyl 8-(1,3-oxazol-5-yl)-6-(trifluoromethyl)imidazo[1,2-a]pyridine-3-carboxylate (50 mg), THF (2 mL) and ethanol (6 mL) was added 1N aqueous sodium hydroxide solution (2 mL), and the mixture was stirred at room temperature for 2 hr. The reaction mixture was acidified with 1N hydrochloric acid, water was added thereto, and the mixture was extracted with ethyl acetate. The extract was dried over anhydrous magnesium sulfate, and the solvent was evaporated under reduced pressure. The residue was dissolved in DMF (5 mL), and WSC hydrochloride (59 mg), HOBt hydrate (47 mg), 2-oxa-6-azaspiro[3.3]heptane hemioxalate (44 mg) and triethylamine (129 µL) were added thereto. The reaction mixture was stirred at room temperature for 12 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (8 mg).

$^1$H NMR (300 MHz, DMSO-$d_6$) δ 4.17-4.39 (2H, m), 4.63-4.82 (6H, m), 7.97 (1H, d, J=1.5 Hz), 8.23-8.37 (2H, m), 8.71 (1H, s), 9.75-9.93 (1H, m).

Example 44

8-(1,3-oxazol-5-yl)-N-(tetrahydro-2H-pyran-4-yl)-6-(trifluoromethyl)imidazo[1,2-a]pyridine-3-carboxamide To a mixture of ethyl 8-(1,3-oxazol-5-yl)-6-(trifluoromethyl)imidazo[1,2-a]pyridine-3-carboxylate (100 mg), THF (4 mL) and ethanol (4 mL) was added 1N aqueous sodium hydroxide solution (1 mL), and the mixture was stirred at room temperature for 1 hr. The reaction mixture was acidified with 1N hydrochloric acid, water was added thereto, and the mixture was extracted with ethyl acetate and THF. The extract was dried over anhydrous magnesium sulfate, and the solvent was evaporated under reduced pressure. The residue was dissolved in DMF (3 mL), and HATU (175 mg), tetrahydro-2H-pyran-4-amine hydrochloride (64 mg) and triethylamine (86 µL) were added thereto. The reaction mixture was stirred at room temperature for 12 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (67 mg).

$^1$H NMR (300 MHz, DMSO-$d_6$) δ 1.51-1.71 (2H, m), 1.82-1.85 (2H, m), 3.36-3.49 (2H, m), 3.84-3.97 (2H, m), 4.01-4.16 (1H, m), 7.94 (1H, d, J=1.5 Hz), 8.27 (1H, s), 8.61 (1H, s), 8.65 (2H, s), 9.93 (1H, s).

Example 47

N-methyl-8-(1,3-oxazol-5-yl)-N-(tetrahydro-2H-pyran-4-yl)-6-(trifluoromethyl)imidazo[1,2-a]pyridine-3-carboxamide To a solution of 8-(1,3-oxazol-5-yl)-N-(tetrahydro-2H-pyran-4-yl)-6-(trifluoromethyl)imidazo[1,2-a]pyridine-3-carboxamide (55 mg) and iodomethane (18 µL) in DMF (2 mL) was added 60% sodium hydride (8.7 mg), and the mixture was stirred at room temperature for 1 hr. To the reaction mixture was added saturated aqueous ammonium chloride solution, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (47 mg).

$^1$H NMR (300 MHz, DMSO-$d_6$) δ 1.65-1.77 (2H, m), 1.82-2.00 (2H, m), 3.09 (3H, br. s), 3.41-3.49 (2H, m), 3.85-

4.04 (2H, m), 4.38-4.64 (1H, m), 7.87-7.97 (1H, m), 8.18-8.44 (2H, m), 8.63-8.79 (1H, m), 9.26-9.43 (1H, m).
mp 209-210° C.

Example 58

(1S,4S)-2-oxa-5-azabicyclo[2.2.1]hept-5-yl(8-(1,3-oxazol-5-yl)-6-(trifluoromethyl)[1,2,4]triazolo[4,3-a]pyridin-3-yl)methanone A) 3-chloro-2-hydrazinyl-5-(trifluoromethyl)pyridine To a solution of 2,3-dichloro-5-(trifluoromethyl)pyridine (6.8 g) in ethanol (50 mL) was added hydrazine hydrate (3.15 g) in an ice bath, and the mixture was stirred overnight at 50° C. The mixture was allowed to be cooled to room temperature, and the solvent was evaporated under reduced pressure. The obtained residue was treated with IPE, and the precipitated solid was collected by filtration to give the title compound (7.57 g).
MS (APCI+): [M+H]+ 212.0

B) ethyl 8-chloro-6-(trifluoromethyl)-[1,2,4]triazolo[4,3-a]pyridine-3-carboxylate A mixture of 3-chloro-2-hydrazinyl-5-(trifluoromethyl)pyridine (600 mg), diethyl oxalate (1.15 mL) and 2M hydrogen chloride ethanol solution (9 mL) was heated with microwave irradiation at 140° C. for 2 hr. The reaction mixture was allowed to be cooled to room temperature, and the solvent was evaporated under reduced pressure. The residue was neutralized with saturated aqueous sodium hydrogen carbonate solution, and the mixture was extracted with ethyl acetate. The organic layer was dried over anhydrous magnesium sulfate, and the solvent was evaporated under reduced pressure. The residue was purified by silica gel column chromatography (ethyl acetate/hexane) to give the title compound (290 mg).
MS (APCI+): [M+H]+ 294.0.

C) (1S,4S)-2-oxa-5-azabicyclo[2.2.1]hept-5-yl(8-chloro-6-(trifluoromethyl)-[1,2,4]triazolo[4,3-a]pyridin-3-yl)methanone To a mixture of (1S,4S)-2-oxa-5-azabicyclo[2.2.1]heptane hydrochloride (100 mg) and anhydrous THF (4 mL) was added dropwise trimethylaluminium toluene solution (1.8 M, 0.410 mL) in an ice bath. The reaction solution was stirred at the same temperature for 1 hr under argon gas atmosphere, ethyl 8-chloro-6-(trifluoromethyl)-[1,2,4]triazolo[4,3-a]pyridine-3-carboxylate (180 mg) was added thereto, and the mixture was stirred at room temperature for 2 days. The reaction mixture was slowly added to 1N hydrochloric acid, and the mixture was extracted with ethyl acetate. The organic layer was dried over anhydrous magnesium sulfate, and the solvent was evaporated under reduced pressure. The residue was purified by silica gel column chromatography (ethyl acetate/hexane) to give the title compound (47 mg).
MS (APCI+): [M+H]+ 347.0.

D) (1S,4S)-2-oxa-5-azabicyclo[2.2.1]hept-5-yl(8-(1,3-oxazol-5-yl)-6-(trifluoromethyl) [1,2,4]triazolo[4,3-a]pyridin-3-yl)methanone A mixture of (1S,4S)-2-oxa-5-azabicyclo[2.2.1]hept-5-yl (8-chloro-6-(trifluoromethyl)-[1,2,4]triazolo[4,3-a]pyridin-3-yl)methanone (46 mg), 5-(4,4,5,5-tetramethyl-1,3,2-dioxaborolan-2-yl)-2-(triisopropylsilyl)oxazole (51 mg), [1,1-bis(diphenylphosphino)ferrocene]dichloropalladium(II) (11 mg) and potassium carbonate (37 mg) in DME/water (2/0.5 mL) was stirred with microwave irradiation at 120° C. for 30 min. The reaction mixture was diluted with water, and extracted with ethyl acetate. The extract was dried over anhydrous sodium sulfate, and the solvent was evaporated under reduced pressure. The residue was dissolved in THF (2 mL), and 1N hydrochloric acid (1 mL) was added thereto. The reaction mixture was stirred at room temperature for 1 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (16 mg).
$^1$H NMR (300 MHz, CDCl$_3$) δ 1.95-2.15 (2H, m), 3.67-3.83 (1H, m), 3.92-4.15 (2H, m), 4.28 (1H, s), 4.80 (1H, brs), 5.17-6.27 (1H, m), 7.93 (1H, s), 8.12 (1H, d, J=1.9 Hz), 8.51 (1H, s), 9.72-9.86 (1H, m).

Example 71

(1S,4S)-2-oxa-5-azabicyclo[2.2.1]hept-5-yl(8-(1,3-oxazol-5-yl)-6-(trifluoromethyl)imidazo[1,2-a]pyridin-3-yl)methanone To a mixture of ethyl 8-(1,3-oxazol-5-yl)-6-(trifluoromethyl)imidazo[1,2-a]pyridine-3-carboxylate (150 mg), THF (6 mL) and ethanol (6 mL) was added 1N aqueous sodium hydroxide solution (2 mL), and the mixture was stirred at room temperature for 30 min. The reaction mixture was acidified with 1N hydrochloric acid, water was added thereto, and the mixture was extracted with ethyl acetate and THF. The extract was dried over anhydrous magnesium sulfate, and the solvent was evaporated under reduced pressure. The residue was dissolved in DMF (12 mL), and HATU (263 mg), (1S,4S)-2-oxa-5-azabicyclo[2.2.1]heptane hydrochloride (94 mg) and triethylamine (257 μL) were added thereto. The reaction mixture was stirred at room temperature for 12 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (113 mg).
$^1$H NMR (300 MHz, DMSO-d$_6$) δ 1.83-2.01 (2H, m), 3.37-4.10 (4H, m), 4.73 (1H, br. s), 4.95-5.15 (1H, m), 7.96 (1H, s), 8.21-8.35 (1H, m), 8.35-8.50 (1H, m), 8.65-8.79 (1H, m), 9.41-9.92 (1H, m).

Example 72 optically active (3-hydroxy-3-methylpyrrolidin-1-yl)(8-(1,3-oxazol-5-yl)-6-(trifluoromethyl)imidazo[1,2-a]pyridin-3-yl)methanone Racemic (3-hydroxy-3-methylpyrrolidin-1-yl) (8-(1,3-oxazol-5-yl)-6-(trifluoromethyl)imidazo[1,2-a]pyridin-3-yl) methanone (166 mg) was resolved by HPLC (column: CHIRALPAK AD, 50 mmID×500 mmL, manufactured by Daicel Chemical Industries, mobile phase: ethanol) to give the title compound (66 mg) having a shorter retention time.

Example 73 optically active (3-hydroxy-3-methylpyrrolidin-1-yl) (8-(1,3-oxazol-5-yl)-6-(trifluoromethyl)imidazo[1,2-a]pyridin-3-yl)methanone Racemic (3-hydroxy-3-methylpyrrolidin-1-yl) (8-(1,3-oxazol-5-yl)-6-(trifluoromethyl)imidazo[1,2-a]pyridin-3-yl)methanone (166 mg) was resolved by HPLC (column: CHIRALPAK AD, 50 mmID×500 mmL, manufactured by Daicel Chemical Industries, mobile phase: ethanol) to give the title compound (66 mg) having a longer retention time.

Example 74

8-(1,3-oxazol-5-yl)-N-phenyl-6-(trifluoromethyl)imidazo[1,2-a]pyridine-3-carboxamide A) 8-(1,3-oxazol-5-yl)-6-(trifluoromethyl)imidazo[1,2-a]pyridine-3-carboxylic acid To a mixture of ethyl 8-(1,3-oxazol-5-yl)-6-(trifluoromethyl)imidazo[1,2-a]pyridine-3-carboxylate (2.47 g), THF (75 mL) and EtOH (25 mL) was added 8N aqueous sodium hydroxide solution (1.42 mL), and the mixture was stirred at 50° C. for 4 hr. To the reaction mixture was added 1N hydrochloric acid at 0° C., and the mixture was diluted with water. The insoluble substance was collected by filtration, and washed with cooled IPE to give the title compound (2.21 g).

$^1$H NMR (300 MHz, DMSO-$d_6$) δ 8.00 (1H, d, J=1.1 Hz), 8.27 (1H, s), 8.47 (1H, s), 8.72 (1H, s), 9.64 (1H, s), 13.72 (1H, brs).

B) 8-(1,3-oxazol-5-yl)-N-phenyl-6-(trifluoromethyl)imidazo[1,2-a]pyridine-3-carboxamide To a solution of 8-(1,3-oxazol-5-yl)-6-(trifluoromethyl)imidazo[1,2-a]pyridine-3-carboxylic acid (150 mg) in DMF (2 mL) were added HATU (230 mg) and triethylamine (0.091 mL), and the mixture was stirred at room temperature for 2 min. To the reaction mixture was added aniline (51.7 mg), and the mixture was stirred at room temperature for 1 hr. To the reaction mixture was added aqueous potassium carbonate solution, and the mixture was extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane), and the obtained solid was recrystallized from ethyl acetate/hexane to give the title compound (82 mg).

$^1$H NMR (300 MHz, DMSO-$d_6$) δ 7.15 (1H, t, J=7.4 Hz), 7.40 (2H, t, J=7.9 Hz), 7.77 (2H, d, J=7.6 Hz), 7.99 (1H, d, J=1.3 Hz), 8.31 (1H, s), 8.72 (1H, s), 8.80 (1H, s), 9.90 (1H, s), 10.52 (1H, s).

Example 78

(6-methyl-8-(1,3-oxazol-5-yl)imidazo[1,2-a]pyridin-3-yl)((1S,4S)-2-oxa-5-azabicyclo[2.2.1]hept-5-yl)methanone A) ethyl 8-bromo-6-methylimidazo[1,2-a]pyridine-3-carboxylate A mixture of 3-bromo-5-methylpyridin-2-amine (3 g), potassium 2-chloro-3-ethoxy-3-oxoprop-1-en-1-olate (7.6 g), sulfuric acid (0.86 mL) and 2-propanol (60 mL) was stirred at 90° C. for 24 hr. To the reaction mixture was added saturated aqueous sodium bicarbonate solution, and the mixture was extracted with ethyl acetate. The extract was dried over anhydrous magnesium sulfate, and the solvent was evaporated under reduced pressure. The residue was purified by silica gel column chromatography (ethyl acetate/hexane) to give the title compound (1 g).

$^1$H NMR (300 MHz, DMSO-$d_6$) δ 1.35 (3H, t, J=7.2 Hz), 2.39 (3H, s), 4.37 (2H, q, J=7.2 Hz), 7.85 (1H, d, J=1.1 Hz), 8.28 (1H, s), 9.00-9.07 (1H, m).

B) ethyl 6-methyl-8-(1,3-oxazol-5-yl)imidazo[1,2-a]pyridine-3-carboxylate

A mixture of ethyl 8-bromo-6-methylimidazo[1,2-a]pyridine-3-carboxylate (1478 mg), 5-(4,4,5,5-tetramethyl-1,3,2-dioxaborolan-2-yl)-2-(triisopropylsilyl)oxazole (2018 mg), [1,1-bis(diphenylphosphino)ferrocene]dichloropalladium (II) (426 mg) and potassium carbonate (1443 mg) in DME/water (12/3 mL) was stirred with microwave irradiation at 120° C. for 30 min. The reaction mixture was diluted with water, and extracted with ethyl acetate. The extract was dried over anhydrous sodium sulfate, and the solvent was evaporated under reduced pressure. The residue was dissolved in THF (10 mL), and 1N hydrochloric acid (10 mL) was added thereto. The mixture was stirred at room temperature for 2 hr, saturated aqueous sodium bicarbonate solution was added thereto, and the mixture was extracted with ethyl acetate. The extract was dried over anhydrous sodium sulfate, and the solvent was evaporated under reduced pressure. The residue was purified by silica gel column chromatography (ethyl acetate/hexane), and the obtained solid was recrystallized from ethyl acetate/hexane to give the title compound (1075 mg).

$^1$H NMR (300 MHz, DMSO-$d_6$) δ 1.36 (3H, t, J=7.2 Hz), 2.47 (3H, d, J=0.8 Hz), 4.39 (2H, q, J=7.2 Hz), 7.82 (1H, d, J=1.5 Hz), 8.17 (1H, s), 8.35 (1H, s), 8.64 (1H, s), 9.07 (1H, s).

C) (6-methyl-8-(1,3-oxazol-5-yl)imidazo[1,2-a]pyridin-3-yl)((1S,4S)-2-oxa-5-azabicyclo[2.2.1]hept-5-yl)methanone To a mixture of ethyl 6-methyl-8-(1,3-oxazol-5-yl)imidazo[1,2-a]pyridine-3-carboxylate (200 mg), THF (4 mL) and ethanol (4 mL) was added 1N aqueous sodium hydroxide solution (2 mL), and the mixture was stirred at room temperature for 2 hr. The reaction mixture was acidified with 1N hydrochloric acid, water was added thereto, and the mixture was extracted with ethyl acetate. The extract was dried over anhydrous sodium sulfate, and the solvent was evaporated under reduced pressure. The residue was dissolved in anhydrous DMF (5 mL), and (1S,4S)-2-oxa-5-azabicyclo[2.2.1]heptane hydrochloride (100 mg), HATU (421 mg) and triethylamine (154 μL) were added thereto. The reaction mixture was stirred overnight at room temperature, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (86 mg).

$^1$H NMR (300 MHz, CDCl$_3$) δ 1.93-2.08 (2H, m), 2.45 (3H, d, J=0.8 Hz), 3.81 (2H, brs), 3.96 (1H, d, J=7.2 Hz), 4.09

(1H, d, J=7.6 Hz), 4.77 (1H, s), 5.13 (1H, brs), 7.26 (1H, s), 7.67 (1H, d, J=1.5 Hz), 7.93-8.05 (2H, m), 8.28 (1H, s).

Example 85

3-oxa-8-azabicyclo[3.2.1]oct-8-yl(8-(1,3-oxazol-5-yl)-6-(trifluoromethyl)imidazo[1,2-a]pyridin-3-yl) methanone To a mixture of ethyl 8-(1,3-oxazol-5-yl)-6-(trifluoromethyl)imidazo[1,2-a]pyridine-3-carboxylate (200 mg), THF (6 mL) and ethanol (6 mL) was added 1N aqueous sodium hydroxide solution (2 mL), and the mixture was stirred at room temperature for 30 min. The reaction mixture was acidified with 1N hydrochloric acid, and extracted with ethyl acetate. The extract was dried over anhydrous magnesium sulfate, and the solvent was evaporated under reduced pressure. The residue was dissolved in DMF (12 mL), and HATU (304 mg), 3-oxa-8-azabicyclo[3.2.1]octane hydrochloride (120 mg) and triethylamine (343 μL) were added thereto. The reaction mixture was stirred at room temperature for 12 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (163 mg).
$^1$H NMR (300 MHz, DMSO-$d_6$) δ 1.87-2.03 (4H, m), 3.59-3.72 (2H, m), 3.73-3.84 (2H, m), 4.64 (2H, brs), 7.95 (1H, d, J=1.5 Hz), 8.27 (1H, s), 8.38 (1H, s), 8.71 (1H, s), 9.44-9.52 (1H, m).
mp 262° C.

Example 86

3-oxa-6-azabicyclo[3.1.1]hept-6-yl(8-(1,3-oxazol-5-yl)-6-(trifluoromethyl)imidazo[1,2-a]pyridin-3-yl) methanone To a mixture of ethyl 8-(1,3-oxazol-5-yl)-6-(trifluoromethyl)imidazo[1,2-a]pyridine-3-carboxylate (200 mg), THF (6 mL) and ethanol (6 mL) was added 1N aqueous sodium hydroxide solution (2 mL), and the mixture was stirred at room temperature for 30 min. The reaction mixture was acidified with 1N hydrochloric acid, water was added thereto, and the mixture was extracted with ethyl acetate and THF. The extract was dried over anhydrous magnesium sulfate, and the solvent was evaporated under reduced pressure. The residue was dissolved in DMF (12 mL), and HATU (304 mg), 3-oxa-6-azabicyclo[3.1.1]heptane 2,2,2-trifluoroacetate (170 mg) and triethylamine (343 μL) were added thereto. The reaction mixture was stirred at room temperature for 12 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (169 mg).
$^1$H NMR (300 MHz, DMSO-$d_6$) δ 1.89 (1H, d, J=8.3 Hz), 2.66-2.85 (1H, m), 3.73-3.93 (2H, m), 3.97-4.38 (2H, m), 4.45-4.70 (1H, m), 4.93-5.21 (1H, m), 7.98 (1H, d, J=1.5 Hz), 8.26 (1H, s), 8.47 (1H, s), 8.71 (1H, s), 9.74-9.96 (1H, m).

Example 87

((3S)-3-hydroxypyrrolidin-1-yl)(8-(1,3-oxazol-5-yl)-6-(trifluoromethyl)imidazo[1,2-a]pyridin-3-yl) methanone 8-(1,3-Oxazol-5-yl)-6-(trifluoromethyl)imidazo[1,2-a] pyridine-3-carboxylic acid (1.77 g) was dissolved in DMF (22 mL), and HATU (2.72 g), (S)-pyrrolidin-3-ol (529 μL) and triethylamine (1.08 mL) were added thereto. The reaction mixture was stirred at room temperature for 1 hr, saturated aqueous sodium bicarbonate solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give a solid (1.38 g). The solid (100 mg) was recrystallized from ethyl acetate/hexane to give the title compound (89 mg).
$^1$H NMR (300 MHz, DMSO-$d_6$) δ 1.82-2.07 (2H, m), 3.45-3.73 (2H, m), 3.83-4.04 (2H, m), 4.38 (1H, brs), 5.09 (1H, d, J=3.4 Hz), 7.96 (1H, d, J=1.5 Hz), 8.28 (1H, s), 8.47 (1H, d, J=19.3 Hz), 8.71 (1H, s), 9.78 (1H, s).

Example 90

((3S)-3-(2,2-difluoroethoxy)pyrrolidin-1-yl) (8-(1,3-oxazol-5-yl)-6-(trifluoromethyl)imidazo[1,2-a]pyridin-3-yl)methanone ((3S)-3-Hydroxypyrrolidin-1-yl) (8-(1,3-oxazol-5-yl)-6-(trifluoromethyl)imidazo[1,2-a]pyridin-3-yl)methanone (205 mg) was dissolved in DMF (5 mL), and 60% sodium hydride (26.9 mg) and 2,2-difluoroethyl trifluoromethanesulfonate (91 μL) were added thereto at 0° C. The reaction mixture was stirred at room temperature for 2 hr, saturated aqueous ammonium chloride solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane), and the obtained solid was recrystallized from ethyl acetate/hexane to give the title compound (152 mg).
$^1$H NMR (300 MHz, DMSO-$d_6$) δ 1.95-2.24 (2H, m), 3.52-4.11 (6H, m), 4.33 (1H, d, J=8.3 Hz), 5.90-6.39 (1H, m), 7.95 (1H, d, J=1.5 Hz), 8.28 (1H, s), 8.49 (1H, d, J=3.4 Hz), 8.71 (1H, s), 9.74-9.79 (1H, m).

Example 92

(6-chloro-8-(1,3-oxazol-5-yl)imidazo[1,2-a]pyridin-3-yl)((1S,4S)-2-oxa-5-azabicyclo[2.2.1]hept-5-yl) methanone and Example 93

(6,8-di(1,3-oxazol-5-yl)imidazo[1,2-a]pyridin-3-yl) ((1S,4S)-2-oxa-5-azabicyclo[2.2.1]hept-5-yl)methanone A) 3-bromo-5-chloropyridin-2-amine To a solution of 5-chloropyridin-2-amine (5.0 g) in acetic acid (90 mL) was added dropwise a solution of bromine (12.4 g) in acetic acid (4 mL) at 10° C. The reaction solution was stirred at room temperature for 2 hr, and saturated aqueous sodium thiosulfate solution was added thereto at 0° C. The mixture was stirred for 30 min, the solvent was evaporated under reduced pressure, and the residue was extracted with ethyl acetate. The obtained organic layer was washed successively with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (2.75 g).
$^1$H NMR (300 MHz, CDCl$_3$) δ 4.92 (2H, brs), 7.66 (1H, d, J=2.3 Hz), 7.98 (1H, d, J=2.3 Hz).

B) ethyl 8-bromo-6-chloroimidazo[1,2-a]pyridine-3-carboxylate

A mixture of 3-bromo-5-chloropyridin-2-amine (1.0 g), potassium 2-chloro-3-ethoxy-3-oxoprop-1-en-1-olate (2.27 g), sulfuric acid (0.334 mL) and ethanol (20 mL) was heated with reflux overnight. The solvent was evaporated under reduced pressure, the residue was neutralized with saturated aqueous sodium bicarbonate solution, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (0.84 g).
$^1$H NMR (300 MHz, CDCl$_3$) δ 1.44 (3H, t, J=7.2 Hz), 4.44 (2H, q, J=7.0 Hz), 7.70 (1H, d, J=1.9 Hz), 8.32 (1H, s), 9.41 (1H, d, J=1.9 Hz).

C) (1S,4S)-2-oxa-5-azabicyclo[2.2.1]heptan-5-yl(8-bromo-6-chloroimidazo[1,2-a]pyridin-3-yl)methanone To a mixture of ethyl 8-bromo-6-chloroimidazo[1,2-a]pyridine-3-carboxylate (537 mg), THF (5 mL) and ethanol (5 mL) was added 1N aqueous sodium hydroxide solution (2.95 mL), and the mixture was stirred at room temperature for 2 hr. The reaction mixture was acidified with 1N hydrochloric acid, water was added thereto, and the mixture was extracted with ethyl acetate. The extract was dried over anhydrous sodium sulfate, and the solvent was evaporated under reduced pressure. The residue was dissolved in anhydrous DMF (5 mL), and (1S,4S)-2-oxa-5-azabicyclo[2.2.1]heptane hydrochloride (200 mg), HATU (841 mg) and triethylamine (308 µL) were added thereto. The reaction mixture was stirred overnight at room temperature, water was added thereto, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (548 mg).
MS (APCI+). found: 356.0

D) (6-chloro-8-(1,3-oxazol-5-yl)imidazo[1,2-a]pyridin-3-yl) ((1S,4S)-2-oxa-5-azabicyclo[2.2.1]hept-5-yl)methanone, and, (6,8-di(1,3-oxazol-5-yl)imidazo[1,2-a]pyridin-3-yl) ((1S,4S)-2-oxa-5-azabicyclo[2.2.1]hept-5-yl)methanone A mixture of (1S,4S)-2-oxa-5-azabicyclo[2.2.1]heptan-5-yl(8-bromo-6-chloroimidazo[1,2-a]pyridin-3-yl)methanone (548 mg), 5-(4,4,5,5-tetramethyl-1,3,2-dioxaborolan-2-yl)-2-(triisopropylsilyl)oxazole (594 mg), [1,1-bis(diphenylphosphino)ferrocene]dichloropalladium(II) (125 mg) and potassium carbonate (425 mg) in DME/water (8/2 mL) was stirred with microwave irradiation at 120° C. for 30 min. The reaction mixture was diluted with water, and extracted with ethyl acetate. The extract was dried over anhydrous magnesium sulfate, and the solvent was evaporated under reduced pressure. The residue was dissolved in THF (4 mL), and 1N hydrochloric acid (2 mL) was added thereto. The reaction mixture was stirred at room temperature for 1 hr, saturated aqueous sodium bicarbonate solution was added thereto, and the mixture was extracted with ethyl acetate. The extract was dried over anhydrous sodium sulfate, and the solvent was evaporated under reduced pressure. The residue was purified by silica gel column chromatography (ethyl acetate/hexane), and recrystallized from ethyl acetate/hexane to give (6-chloro-8-(1,3-oxazol-5-yl)imidazo[1,2-a]pyridin-3-yl) ((1S,4S)-2-oxa-5-azabicyclo[2.2.1]hept-5-yl)methanone (64 mg) and (6,8-di(1,3-oxazol-5-yl)imidazo[1,2-a]pyridin-3-yl) ((1S,4S)-2-oxa-5-azabicyclo[2.2.1]hept-5-yl)methanone (19 mg).
$^1$H NMR of (6-chloro-8-(1,3-oxazol-5-yl)imidazo[1,2-a]pyridin-3-yl) ((1S,4S)-2-oxa-5-azabicyclo[2.2.1]hept-5-yl)methanone
$^1$H NMR (300 MHz, CDCl$_3$) δ 1.93-2.08 (2H, m, J=1.9 Hz), 3.82 (2H, brs), 3.91-4.02 (1H, m, J=8.3 Hz), 4.04-4.13 (1H, m), 4.78 (1H, s), 5.15 (1H, brs), 7.79 (1H, d, J=1.9 Hz), 8.05 (2H, s), 8.34 (1H, s), 9.63 (1H, brs).
$^1$H NMR of (6,8-di(1,3-oxazol-5-yl)imidazo[1,2-a]pyridin-3-yl) ((1S,4S)-2-oxa-5-azabicyclo[2.2.1]hept-5-yl)methanone:
$^1$H NMR (300 MHz, CDCl$_3$) δ 1.96-2.09 (2H, m), 3.85 (2H, brs), 3.98 (1H, brs), 4.11 (1H, d, J=7.6 Hz), 4.79 (1H, s), 5.17 (1H, brs), 7.51 (1H, s), 7.99 (1H, s), 8.04 (1H, d, J=1.5 Hz), 8.08 (1H, s), 8.37 (1H, s).

Example 98

N-ethyl-2-methyl-8-(1,3-oxazol-5-yl)-6-(trifluoromethyl)imidazo[1,2-a]pyridine-3-carboxamide

A) ethyl 8-chloro-2-methyl-6-(trifluoromethyl)imidazo[1,2-a]pyridine-3-carboxylate A mixture of 3-chloro-5-(trifluoromethyl)pyridin-2-amine (2 g), ethyl 2-chloro-3-oxobutanoate (1.18 g) and 2-propanol (12 mL) was stirred with heating with microwave irradiation at 150° C. for 7 hr. To the reaction mixture was added saturated aqueous sodium bicarbonate solution, and the mixture was extracted with ethyl acetate. The extract was dried over anhydrous magnesium sulfate, and the solvent was evaporated under reduced pressure. The residue was purified by silica gel column chromatography (ethyl acetate/hexane) to give the title compound (380 mg).
MS (APCI+): [M+H]$^+$ 307.1.

B) ethyl 2-methyl-8-(1,3-oxazol-5-yl)-6-(trifluoromethyl)imidazo[1,2-a]pyridine-3-carboxylate A mixture of ethyl 8-chloro-2-methyl-6-(trifluoromethyl)imidazo[1,2-a]pyridine-3-carboxylate (380 mg), 5-(4,4,5,5-tetramethyl-1,3,2-dioxaborolan-2-yl)-2-(triisopropylsilyl)oxazole (479 mg), tetrakis(triphenylphosphine)palladium(0) (143 mg) and potassium carbonate (343 mg) in DME/water (8/2 mL) was stirred with microwave irradiation at 120° C. for 30 min. The reaction mixture was diluted with water, and extracted with ethyl acetate. The extract was dried over anhydrous magnesium sulfate, and the solvent was evaporated under reduced pressure. The residue was dissolved in THF (12 mL), and 1N hydrochloric acid (4 mL) was added thereto. The reaction mixture was stirred at room temperature for 2 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (78 mg).

MS (APCI+): [M+H]+ 340.1

C) N-ethyl-2-methyl-8-(1,3-oxazol-5-yl)-6-(trifluoromethyl)imidazo[1,2-a]pyridine-3-carboxamide To a mixture of ethyl 2-methyl-8-(1,3-oxazol-5-yl)-6-(trifluoromethyl)imidazo[1,2-a]pyridine-3-carboxylate (50 mg), THF (2 mL) and ethanol (3 mL) was added 1N aqueous sodium hydroxide solution (1 mL), and the mixture was stirred at room temperature for 30 min. The reaction mixture was acidified with 1N hydrochloric acid, water was added thereto, and the mixture was extracted with ethyl acetate and THF. The extract was dried over anhydrous magnesium sulfate, and the solvent was evaporated under reduced pressure. The residue was dissolved in DMF (3 mL), and HATU (84 mg), ethanamine hydrochloride (24 mg) and triethylamine (82 μL) were added thereto. The reaction mixture was stirred at room temperature for 12 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (16 mg).

$^1$H NMR (300 MHz, DMSO-$d_6$) δ 1.19 (3H, t, J=7.2 Hz), 2.68 (3H, s), 3.35-3.46 (2H, m), 7.87 (1H, d, J=1.9 Hz), 8.16 (1H, brs), 8.25 (1H, s), 8.68 (1H, s), 9.42 (1H, s).

Example 125

(8-(1H-imidazol-1-yl)-6-(trifluoromethyl)imidazo[1,2-a]pyridin-3-yl) ((1S,4S)-2-oxa-5-azabicyclo[2.2.1]hept-5-yl)methanone A) (1S,4S)-2-oxa-5-azabicyclo[2.2.1]heptan-5-yl(8-bromo-6-(trifluoromethyl)imidazo[1,2-a]pyridin-3-yl)methanone To a solution of ethyl 8-(1,3-oxazol-5-yl)-6-(trifluoromethyl)imidazo[1,2-a]pyridine-3-carboxylate (0.740 g) in THF/EtOH (15/5 mL) was added 1N aqueous sodium hydroxide solution (2.42 mL), and the mixture was stirred at room temperature for 2 hr. To the reaction mixture was added 1N hydrochloric acid at 0° C., and the solvent was evaporated under reduced pressure. To the residue were added DMF (5 mL), HATU (1.00 g), triethylamine (0.704 mL), and the mixture was stirred for 10 min. (1S,4S)-2-Oxa-5-azabicyclo[2.2.1]heptane hydrochloride (327 mg) was added thereto, and the mixture was stirred overnight at room temperature. To the reaction mixture was added saturated aqueous sodium bicarbonate solution, and the mixture was extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane) to give the title compound (700 mg).

$^1$H NMR (300 MHz, CDCl$_3$) δ 1.91-2.14 (2H, m), 3.82 (2H, brs), 3.88-4.17 (2H, m), 4.79 (1H, s), 5.15 (1H, brs), 7.81 (1H, s), 8.11 (1H, brs), 10.01 (1H, brs).

B) (8-amino-6-(trifluoromethyl)imidazo[1,2-a]pyridin-3-yl)((1S,4S)-2-oxa-5-azabicyclo[2.2.1]hept-5-yl)methanone A mixture of (1S,4S)-2-oxa-5-azabicyclo[2.2.1]heptan-5-yl(8-bromo-6-(trifluoromethyl)imidazo[1,2-a]pyridin-3-yl)methanone (300 mg), 1,1-diphenylmethanimine (209 mg), tris(dibenzylideneacetone)dipalladium(0) (17.6 mg), (9,9-dimethyl-9H-xanthene-4,5-diyl)bis(diphenylphosphine) (44.5 mg) and sodium tert-butoxide (111 mg) in 1,4-dioxane (4.0 mL) was stirred with microwave irradiation at 120° C. for 60 min. The reaction mixture was diluted with saturated aqueous ammonium chloride solution, and extracted with ethyl acetate. The extract was washed with water and saturated brine, and dried over anhydrous sodium sulfate, and the solvent was evaporated under reduced pressure. The residue was diluted with THF, 1N hydrochloric acid was added thereto, and the mixture was stirred at room temperature for 2 hr. The reaction mixture was diluted with aqueous sodium hydrogen carbonate solution, and extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane) to give the title compound (207 mg).

MS (APCI+): [M+H]+ 327.2.

C) (8-(1H-imidazol-1-yl)-6-(trifluoromethyl)imidazo[1,2-a]pyridin-3-yl)((1S,4S)-2-oxa-5-azabicyclo[2.2.1]hept-5-yl)methanone A mixture of (8-amino-6-(trifluoromethyl)imidazo[1,2-a]pyridin-3-yl)((1S,4S)-2-oxa-5-azabicyclo[2.2.1]hept-5-yl)methanone (207 mg) and oxalaldehyde (92.0 mg) in methanol (1.0 mL) was stirred at 70° C. for 5 hr. To the reaction mixture were added methanol (2.0 mL), ammonium chloride (67.9 mg) and formaldehyde (38.1 mg), and the mixture was heated with reflux for 30 min. Phosphoric acid (0.087 mL) was added thereto, and the mixture was heated with reflux overnight. Ice water and 8N aqueous sodium hydroxide solution were added to the reaction mixture at 0° C., and the mixture was extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane), and then HPLC (C18, mobile phase: water/acetonitrile (containing 0.1% TFA)). To the obtained fraction was added saturated aqueous sodium hydrogen carbonate solution, and the mixture was extracted with ethyl acetate. The extract was dried over anhydrous sodium sulfate, and concentrated under reduced pressure, and the obtained solid was recrystallized from ethyl acetate/hexane to give the title compound (12.6 mg).

$^1$H NMR (300 MHz, CDCl$_3$) δ 1.95-2.12 (2H, m), 3.73-4.19 (4H, m), 4.80 (1H, s), 5.17 (1H, brs), 7.31 (1H, s), 7.52 (1H, s), 7.76 (1H, s), 8.12 (1H, brs), 8.62 (1H, s), 10.00 (1H, brs).

Example 126

(5-methyl-7-(1,3-oxazol-5-yl)pyrazolo[1,5-a]pyridin-3-yl) (2-oxa-5-azabicyclo[2.2.1]hept-5-yl)methanone A) ethyl 5-methylpyrazolo[1,5-a]pyridine-3-carboxylate To a solution of ethyl N-(mesitylsulfonyl)oxyacetoimidate (14.7 g) in THF (15 mL) was added 60% perchloric acid (11.2 mL) at 0°, the mixture was stirred for 90 min, and to the reaction mixture was added ice water. The insoluble substance was collected by filtration, washed with water, and dried under stream. The residue was added to a solution of 4-methylpyridine (4.18 mL) in THF (80 mL) at 0° C., and the mixture was stirred overnight at room temperature. The solvent was evaporated under reduced pressure, DMF (80 mL), ethyl propionate (5.21 mL) and potassium carbonate (11.9 g) were added thereto, and the mixture was stirred overnight at room temperature. To the reaction mixture was added water, and the mixture was extracted with ethyl acetate. The extract was washed with 1N hydrochloric acid and saturated brine, and dried over anhydrous sodium sulfate, and the solvent was evaporated under reduced pressure. The residue was purified by silica gel column chromatography (ethyl acetate/hexane) to give the title compound (2.73 g).
$^1$H NMR (300 MHz, CDCl$_3$) δ 1.41 (3H, t, J=7.2 Hz), 2.47 (3H, s), 4.38 (2H, q, J=6.9 Hz), 6.77 (1H, dd, J=7.0, 1.7 Hz), 7.93 (1H, s), 8.34 (1H, s), 8.39 (1H, d, J=7.2 Hz).

B) 5-methylpyrazolo[1,5-a]pyridine-3-carboxylic acid

To a solution of ethyl 5-methylpyrazolo[1,5-a]pyridine-3-carboxylate (2.73 g) in THF/EtOH (30/15 mL) was added 1N aqueous sodium hydroxide solution (20 mL), and the mixture was stirred at 80° C. for 4 hr. To the reaction mixture was added 1N hydrochloric acid at 0° C., and the mixture was extracted with THF/EtOAc. The extract was washed with saturated brine, and dried over anhydrous sodium sulfate, and the solvent was evaporated under reduced pressure. The residue was washed with cooled hexane/IPE to give the title compound (2.11 g).
$^1$H NMR (300 MHz, DMSO-d$_6$) δ 2.44 (3H, s), 6.97 (1H, dd, J=7.0, 1.7 Hz), 7.86 (1H, s), 8.32 (1H, s), 8.72 (1H, d, J=7.2 Hz), 12.34 (1H, brs).

C) 7-iodo-5-methylpyrazolo[1,5-a]pyridine-3-carboxylic acid

To a solution of 5-methylpyrazolo[1,5-a]pyridine-3-carboxylic acid (2.11 g) in THF (40 mL) was added 1M lithiumhexadisilazide THF solution (35.9 mL) at 0° C., the mixture was stirred for 30 min, and iodine (3.65 g) was added thereto. The reaction mixture was stirred overnight at room temperature under nitrogen gas atmosphere, 1N hydrochloric acid was added, and the mixture was extracted with ethyl acetate. The extract was washed with aqueous sodium thiosulfate solution, water and saturated brine, and dried over anhydrous sodium sulfate, and the solvent was evaporated under reduced pressure. The residue was washed with hexane/IPE to give the title compound (3.42 g).
$^1$H NMR (300 MHz, DMSO-d$_6$) δ 2.40 (3H, s), 7.59 (1H, d, J=1.5 Hz), 7.88 (1H, s), 8.41 (1H, s), 12.49 (1H, brs).

D) (1S,4S)-2-oxa-5-azabicyclo[2.2.1]heptan-5-yl(7-iodo-5-methylpyrazolo[1,5-a]pyridin-3-yl)methanone To a solution of 7-iodo-5-methylpyrazolo[1,5-a]pyridine-3-carboxylic acid (500 mg) in DMF (10 mL) were added HATU (755 mg) and triethylamine (0.531 mL), and the mixture was stirred at room temperature for 3 min. To the reaction mixture was added (1S,4S)-2-oxa-5-azabicyclo[2.2.1]heptane hydrochloride (247 mg), and the mixture was stirred at room temperature for 1 hr. To the reaction mixture was added water, and the mixture was extracted with ethyl acetate. The extract was washed with saturated aqueous sodium bicarbonate solution and saturated brine, and dried over anhydrous sodium sulfate, and the solvent was evaporated under reduced pressure. The residue was purified by silica gel column chromatography (NH, ethyl acetate/hexane) to give the title compound (300 mg).
$^1$H NMR (300 MHz, CDCl$_3$) δ 1.96 (2H, brs), 2.41 (3H, s), 3.77 (2H, brs), 3.91 (1H, d, J=7.2 Hz), 4.06 (1H, d, J=7.6 Hz), 4.73 (1H, s), 5.12 (1H, brs), 7.36 (1H, d, J=1.5 Hz), 8.15 (2H, brs).

E) (5-methyl-7-(1,3-oxazol-5-yl)pyrazolo[1,5-a]pyridin-3-yl)((1S,4S)-2-oxa-5-azabicyclo[2.2.1]hept-5-yl)methanone A mixture of (1S,4S)-2-oxa-5-azabicyclo[2.2.1]heptan-5-yl(7-iodo-5-methylpyrazolo[1,5-a]pyridin-3-yl)methanone (300 mg), 5-(4,4,5,5-tetramethyl-1,3,2-dioxaborolan-2-yl)-2-(triisopropylsilyl)oxazole (330 mg), tetrakis(triphenylphosphine)palladium(0) (90 mg) and 3N aqueous potassium carbonate solution (0.522 mL) in DME (3 mL) was stirred with microwave irradiation at 120° C. for 30 min. The reaction mixture was diluted with saturated aqueous ammonium chloride solution, and extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane) to give (5-methyl-7-(2-(triisopropylsilyl)-1,3-oxazol-5-yl)pyrazolo[1,5-a]pyridin-3-yl)((1S,4S)-2-oxa-5-azabicyclo[2.2.1]hept-5-yl)methanone. The obtained (5-methyl-7-(2-(triisopropylsilyl)-1,3-oxazol-5-yl)pyrazolo[1,5-a]pyridin-3-yl)((1S,4S)-2-oxa-5-azabicyclo[2.2.1]hept-5-yl)methanone was dissolved in THF (3 mL), and 1N hydrochloric acid was added thereto. The reaction mixture was stirred at room temperature for 30 min, saturated aqueous ammonium chloride solution was added thereto, and the mixture was extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane), and the obtained solid was recrystallized from ethyl acetate/hexane to give the title compound (83 mg).
$^1$H NMR (400 MHz, CDCl$_3$) δ 1.94-2.02 (2H, m), 2.53 (3H, s), 3.82 (2H, brs), 3.94 (1H, brs), 4.09 (1H, d, J=7.3 Hz), 4.75 (1H, s), 5.15 (1H, brs), 7.39 (1H, d, J=1.2 Hz), 8.07 (1H, s), 8.22 (2H, brs), 8.51 (1H, s).

Example 134

(1S,4S)-2-oxa-5-azabicyclo[2.2.1]hept-5-yl(8-(1H-pyrazol-4-yl)-6-(trifluoromethyl)imidazo[1,2-a]pyridin-3-yl)methanone A mixture of (1S,4S)-2-oxa-5-azacyclo[2.2.1]hept-5-yl(8-bromo-6-(trifluoromethyl)imidazo[1,2-a]pyridin-3-yl)

methanone (100 mg), tert-butyl 4-(4,4,5,5-tetramethyl-1,3,2-dioxaborolan-2-yl)-1H-pyrazole-1-carboxylate (106 mg), tripotassium phosphate (163 mg), S-Phos (21.0 mg), palladium(II) acetate (5.75 mg) and tert-amyl alcohol (2 mL) was stirred with microwave irradiation at 130° C. for 90 min. To the reaction mixture were added palladium acetate (10 mg), S-Phos (50 mg) and tert-butyl 4-(4,4,5,5-tetramethyl-1,3,2-dioxaborolan-2-yl)-1H-pyrazole-1-carboxylate (60 mg), and the mixture was stirred with microwave irradiation at 130° C. for 30 min. The reaction mixture was allowed to be cooled to room temperature, and the insoluble substance was removed by filtration. To the filtrate was added water, and the mixture was extracted with ethyl acetate. The extract was washed with saturated brine, and dried over anhydrous sodium sulfate, and the solvent was evaporated under reduced pressure. The residue was purified by silica gel column chromatography (methanol/ethyl acetate), and then HPLC (C18, mobile phase: water/acetonitrile (containing 0.1% TFA)). To the obtained fraction was added saturated aqueous sodium hydrogen carbonate solution, and the mixture was extracted with ethyl acetate. The extract was dried over anhydrous sodium sulfate, and concentrated under reduced pressure, and the obtained solid was recrystallized from ethyl acetate/hexane to give the title compound (10 mg).

$^1$H NMR (300 MHz, DMSO-$d_6$) δ 1.78-2.03 (2H, m), 3.57-4.09 (4H, m), 4.72 (1H, brs), 5.01 (1H, brs), 8.08 (1H, s), 8.37 (1H, brs), 8.71 (2H, brs), 9.30-9.80 (1H, m), 13.22 (1H, brs).

Example 136 optically active N-methyl-8-(1,3-oxazol-5-yl)-N-(tetrahydrofuran-3-ylmethyl)-6-(trifluoromethyl) imidazo[1,2-a]pyridine-3-carboxamide Racemic N-methyl-8-(1,3-oxazol-5-yl)-N-(tetrahydrofuran-3-ylmethyl)-6-(trifluoromethyl)imidazo[1,2-a]pyridine-3-carboxamide (77 mg) was resolved by HPLC (column: CHIRALPAK AD-H, 20 mmID×250 mmL, manufactured by Daicel Chemical Industries, mobile phase: carbon dioxide/methanol=740/260) to give the title compound (27 mg) having a shorter retention time.

Example 137 optically active N-methyl-8-(1,3-oxazol-5-yl)-N-(tetrahydrofuran-3-ylmethyl)-6-(trifluoromethyl) imidazo[1,2-a]pyridine-3-carboxamide Racemic N-methyl-8-(1,3-oxazol-5-yl)-N-(tetrahydrofuran-3-ylmethyl)-6-(trifluoromethyl)imidazo[1,2-a]pyridine-3-carboxamide (77 mg) was resolved by HPLC (column: CHIRALPAK AD-H, 20 mmID×250 mmL, manufactured by Daicel Chemical Industries, mobile phase: carbon dioxide/methanol=740/260) to give the title compound (29 mg) having a longer retention time.

Example 138

(6-fluoro-8-(1,3-oxazol-5-yl)imidazo[1,2-a]pyridin-3-yl)(3-oxa-8-azabicyclo[3.2.1]oct-8-yl)methanone A) ethyl 8-bromo-6-fluoroimidazo[1,2-a]pyridine-3-carboxylate A mixture of 3-bromo-5-fluoropyridin-2-amine (3.0 g), potassium 2-chloro-3-ethoxy-3-oxoprop-1-en-1-olate (7.4 g), sulfuric acid (0.84 mL) and 2-propanol (60 mL) was heated at 90° C. for 3 days. To the reaction mixture was added saturated aqueous sodium bicarbonate solution, and the mixture was extracted with ethyl acetate. The extract was dried over anhydrous magnesium sulfate, and the solvent was evaporated under reduced pressure. The residue was suspended in ethanol, and the obtained solid was collected by filtration to give the title compound (3.6 g).

$^1$H NMR (300 MHz, DMSO-$d_6$) δ 1.36 (3H, t, J=7.2 Hz), 4.39 (2H, q, J=7.2 Hz), 8.16-8.27 (1H, m), 8.34-8.38 (1H, m), 9.16-9.27 (1H, m).

B) ethyl 6-fluoro-8-(1,3-oxazol-5-yl)imidazo[1,2-a] pyridine-3-carboxylate

A mixture of ethyl 8-bromo-6-fluoroimidazo[1,2-a]pyridine-3-carboxylate (1.0 g), 5-(4,4,5,5-tetramethyl-1,3,2-dioxaborolan-2-yl)-2-(triisopropylsilyl)oxazole (1.2 g), tetrakis(triphenylphosphine)palladium(0) (403 mg) and potassium carbonate (963 mg) in DME/water (15/4 mL) was stirred with microwave irradiation at 120° C. for 40 min. The reaction mixture was diluted with water, and extracted with ethyl acetate. The extract was dried over anhydrous magnesium sulfate, and the solvent was evaporated under reduced pressure. The residue was dissolved in THF (15 mL), and 1N hydrochloric acid (4 mL) was added thereto. The reaction mixture was stirred at room temperature for 2 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (188 mg).

$^1$H NMR (300 MHz, DMSO-$d_6$) δ 1.37 (3H, t, J=7.2 Hz), 4.41 (2H, q, J=7.2 Hz), 8.01 (1H, dd, J=9.0, 2.3 Hz), 8.26 (1H, s), 8.44 (1H, s), 8.71 (1H, s), 9.24 (1H, dd, J=4.3, 2.3 Hz).

C) (6-fluoro-8-(1,3-oxazol-5-yl)imidazo[1,2-a]pyridin-3-yl)(3-oxa-8-azabicyclo[3.2.1]oct-8-yl)methanone To a mixture of ethyl 6-fluoro-8-(1,3-oxazol-5-yl)imidazo [1,2-a]pyridine-3-carboxylate (80 mg), THF (6 mL) and ethanol (6 mL) was added 1N aqueous sodium hydroxide solution (2 mL), and the mixture was stirred at room temperature for 2 hr. The reaction mixture was acidified with 1N hydrochloric acid, water was added thereto, and the mixture was extracted with ethyl acetate and THF. The extract was dried over anhydrous magnesium sulfate, and the solvent was evaporated under reduced pressure. The residue was dissolved in DMF (6 mL), and HATU (144 mg), 3-oxa-8-azabicyclo[3.2.1]octane hydrochloride (56.5 mg) and triethylamine (162 µL) were added thereto. The reaction mixture was stirred at room temperature for 12 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (50 mg).

$^1$H NMR (300 MHz, DMSO-$d_6$) δ 1.85-2.02 (4H, m), 3.57-3.84 (4H, m), 4.63 (2H, brs), 7.91 (1H, dd, J=8.9, 2.5 Hz), 8.26-8.28 (2H, m), 8.69 (1H, s), 9.14 (1H, dd, J=4.9, 2.5 Hz).

Example 139 optically active N-methyl-8-(1,3-oxazol-5-yl)-N-(tetrahydrofuran-2-ylmethyl)-6-(trifluoromethyl)imidazo[1,2-a]pyridine-3-carboxamide Racemic N-methyl-8-(1,3-oxazol-5-yl)-N-(tetrahydrofuran-2-ylmethyl)-6-(trifluoromethyl)imidazo[1,2-a]pyridine-3-carboxamide (55 mg) was resolved by HPLC (column: CHIRALPAK AD-H, 20 mmID×250 mmL, manufactured by Daicel Chemical Industries, mobile phase: carbon dioxide/methanol=770/230) to give the title compound (22 mg) having a shorter retention time.

Example 140 optically active N-methyl-8-(1,3-oxazol-5-yl)-N-(tetrahydrofuran-2-ylmethyl)-6-(trifluoromethyl)imidazo[1,2-a]pyridine-3-carboxamide Racemic N-methyl-8-(1,3-oxazol-5-yl)-N-(tetrahydrofuran-2-ylmethyl)-6-(trifluoromethyl)imidazo[1,2-a]pyridine-3-carboxamide (55 mg) was resolved by HPLC (column: CHIRALPAK AD-H, 20 mmID×250 mmL, manufactured by Daicel Chemical Industries, mobile phase: carbon dioxide/methanol=770/230) to give the title compound (19 mg) having a longer retention time.

Example 141

(8-(1-methyl-1H-pyrazol-4-yl)-6-(trifluoromethyl)imidazo[1,2-a]pyridin-3-yl)((1S,4S)-2-oxa-5-azabicyclo[2.2.1]hept-5-yl)methanone A mixture of (8-bromo-6-(trifluoromethyl)imidazo[1,2-a]pyridin-3-yl)((1S,4S)-2-oxa-5-azabicyclo[2.2.1]hept-5-yl)methanone (50.0 mg), 1-methyl-4-(4,4,5,5-tetramethyl-1,3,2-dioxaborolan-2-yl)-1H-pyrazole (40.0 mg), [1,1'-bis(diphenylphosphino)ferrocene]palladium(II) dichloride dichloromethane adduct (10.5 mg) and cesium carbonate (125 mg) in DME (2.5 mL) was stirred with microwave irradiation at 120° C. for 30 min. To the reaction mixture was added 0.1N hydrochloric acid, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (15.6 mg).
$^1$H NMR (300 MHz, CDCl$_3$) δ 1.93-2.11 (2H, m), 3.83 (2H, brs), 3.91-4.18 (5H, m), 4.78 (1H, s), 5.15 (1H, brs), 7.67 (1H, s), 8.08 (1H, brs), 8.14 (1H, s), 8.60 (1H, s), 9.86 (1H, brs).

Example 142

3-oxa-8-azabicyclo[3.2.1]oct-8-yl(8-(1H-1,2,4-triazol-1-yl)-6-(trifluoromethyl)imidazo[1,2-a]pyridin-3-yl)methanone A) 8-bromo-6-(trifluoromethyl)imidazo[1,2-a]pyridine-3-carboxylic acid To a mixture of ethyl 8-bromo-6-(trifluoromethyl)imidazo[1,2-a]pyridine-3-carboxylate (490 mg) in a mixed solvent of THF (9 mL) and ethanol (3 mL) was added 8N aqueous sodium hydroxide solution (273 μL), and the mixture was stirred at room temperature for 1.5 hr, and then at 50° C. for 1 hr. The reaction solution was neutralized with 6N hydrochloric acid under ice-cooling, and the obtained solid was collected by filtration, and washed with water and IPE to give the title compound (380 mg).

MS (APCI+). found: 308.9, 311.0

B) 3-oxa-8-azabicyclo[3.2.1]octan-8-yl(8-bromo-6-(trifluoromethyl)imidazo[1,2-a]pyridin-3-yl)methanone To a solution of 8-bromo-6-(trifluoromethyl)imidazo[1,2-a]pyridine-3-carboxylic acid (300 mg) in DMF (6 mL) were added HATU (443 mg) and triethylamine (0.311 mL), and the mixture was stirred at room temperature for 10 min. To the reaction mixture was added 3-oxa-8-azabicyclo[3.2.1]octane hydrochloride (160 mg), and the mixture was stirred at room temperature for 30 min. To the reaction mixture was added saturated aqueous sodium bicarbonate solution, and the mixture was extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane) to give the title compound (315 mg).
$^1$H NMR (300 MHz, CDCl$_3$) δ 1.95-2.22 (4H, m), 3.72-3.93 (4H, m), 4.68 (2H, brs), 7.79 (1H, d, J=1.5 Hz), 7.98 (1H, s), 9.58 (1H, s).

C) 3-oxa-8-azabicyclo[3.2.1]oct-8-yl(8-(1H-1,2,4-triazol-1-yl)-6-(trifluoromethyl)imidazo[1,2-a]pyridin-3-yl)methanone A mixture of 3-oxa-8-azabicyclo[3.2.1]octan-8-yl(8-bromo-6-(trifluoromethyl)imidazo[1,2-a]pyridin-3-yl)methanone (315 mg), 1H-1,2,4-triazole (108 mg), copper(I) iodide (44.5 mg), 8-quinolinol (33.9 mg) and potassium carbonate (215 mg) in DMSO (3.0 mL) was stirred with microwave irradiation at 170° C. for 30 min. To the reaction mixture was added 0.1N hydrochloric acid, and the mixture was extracted with ethyl acetate. The extract was washed with saturated aqueous ammonium chloride solution and saturated brine, and dried over anhydrous sodium sulfate, and the solvent was evaporated under reduced pressure. The residue was purified by silica gel column chromatography (ethyl acetate/hexane), and the obtained solid was recrystallized from ethyl acetate/hexane to give the title compound (22.0 mg).
$^1$H NMR (300 MHz, CDCl$_3$) δ 1.96-2.24 (4H, m), 3.73-3.97 (4H, m), 4.71 (2H, brs), 8.02 (1H, s), 8.20 (1H, s), 8.28 (1H, d, J=1.5 Hz), 9.57 (1H, s), 10.11 (1H, s).

Example 143

(6-cyclopropyl-8-(1,3-oxazol-5-yl)imidazo[1,2-a]pyridin-3-yl)(3-oxa-8-azabicyclo[3.2.1]oct-8-yl)methanone A) 6-cyclopropyl-8-(1,3-oxazol-5-yl)imidazo[1,2-a]pyridine-3-carboxylic acid To a mixture of ethyl 6-cyclopropyl-8-(1,3-oxazol-5-yl)imidazo[1,2-a]pyridine-3-carboxylate (150 mg) in a mixed solvent of THF (3 mL) and ethanol (1.2 mL) was added 8N aqueous sodium hydroxide solution (95 μL), and the mixture was stirred at 70° C. for 50 min. The reaction mixture was neutralized with 6N hydrochloric acid in an ice bath, and extracted with ethyl acetate. The extract was washed with saturated brine, and dried over anhydrous sodium sulfate, and the solvent was evaporated under reduced pressure to give the title Compound (140 mg).

$^1$H NMR (300 MHz, DMSO-d$_6$) δ 0.76-0.85 (2H, m), 0.97-1.13 (2H, m), 2.13-2.25 (1H, m), 7.58 (1H, d, J=1.5 Hz), 8.17 (1H, s), 8.28 (1H, s), 8.62 (1H, s), 9.12 (1H, d, J=1.5 Hz), 13.22 (1H, s).

B) (6-cyclopropyl-8-(1,3-oxazol-5-yl)imidazo[1,2-a]pyridin-3-yl)(3-oxa-8-azabicyclo[3.2.1]oct-8-yl)methanone 6-Cyclopropyl-8-(1,3-oxazol-5-yl)imidazo[1,2-a]pyridine-3-carboxylic acid (135 mg) was dissolved in DMF (4 mL), and HATU (229 mg), 3-oxa-8-azabicyclo[3.2.1]octane hydrochloride (113 mg) and triethylamine (91 μL) were added thereto. The reaction mixture was stirred at room temperature for 1 hr, saturated aqueous sodium bicarbonate solution was added thereto, and the mixture was extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane), and the obtained solid was recrystallized from ethyl acetate/hexane to give the title compound (43 mg).

$^1$H NMR (300 MHz, DMSO-d$_6$) δ 0.78 (2H, dd, J=4.9, 1.9 Hz), 0.96-1.07 (2H, m), 1.93 (4H, s), 2.09-2.22 (1H, m), 3.58-3.82 (4H, m), 4.62 (2H, brs), 7.51 (1H, d, J=1.9 Hz), 8.16 (1H, s) 8.17 (1H, s), 8.61 (1H, s), 8.89 (1H, d, J=1.1 Hz).

Example 146 ethyl 6-cyclopropyl-8-(1,3-oxazol-5-yl)imidazo[1,2-a]pyridine-3-carboxylate

A) 5-cyclopropylpyridin-2-amine

To a mixture of 5-bromopyridin-2-amine (5.0 g) in a mixed solvent of toluene (100 mL) and water (5 mL) were added cyclopropylboronic acid (4.59 g), tricyclohexyl phosphine (1.62 g), palladium(II) acetate (0.649 g) and tripotassium phosphate (21.5 g) at room temperature. The mixture was stirred overnight at 80° C. under argon atmosphere. The reaction mixture was allowed to be cooled to room temperature, and the insoluble substance was removed by filtration. To the filtrate was added ethyl acetate, and the mixture was extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane) to give the title compound (1.33 g).

$^1$H NMR (300 MHz, DMSO-d$_6$) δ 0.44-0.55 (2H, m), 0.72-0.86 (2H, m), 1.73 (1H, tt, J=8.4, 5.2 Hz), 5.62 (2H, s), 6.35 (1H, d, J=9.1 Hz), 7.03 (1H, dd, J=8.5, 2.5 Hz), 7.73 (1H, d, J=2.7 Hz).

B) 3-bromo-5-cyclopropylpyridin-2-amine

To a solution of 5-cyclopropylpyridin-2-amine (1.33 g) in acetic acid (15 mL) was added bromine (762 μL) at 0° C., and the mixture was stirred at room temperature for 2 hr. The reaction mixture was basified with 1N aqueous sodium hydroxide solution at 0° C., and extracted with ethyl acetate. The extract was dried over anhydrous magnesium sulfate, and the solvent was evaporated under reduced pressure. The residue was purified by silica gel column chromatography (NH, ethyl acetate/hexane) to give the title compound (1.11 g).

$^1$H NMR (300 MHz, DMSO-d$_6$) δ 0.53-0.63 (2H, m), 0.77-0.88 (2H, m), 1.78 (1H, tt, J=8.4, 5.3 Hz), 5.92 (2H, s), 7.40 (1H, d, J=1.9 Hz), 7.79 (1H, d, J=2.3 Hz).

C) ethyl 8-bromo-6-cyclopropylimidazo[1,2-a]pyridine-3-carboxylate

A mixture of 3-bromo-5-cyclopropylpyridin-2-amine (0.753 g), potassium 2-chloro-3-ethoxy-3-oxoprop-1-en-1-olate (1.30 g), sulfuric acid (0.208 mL) and ethanol (15 mL) was heated with reflux overnight. The reaction mixture was neutralized with 1N sodium hydroxide at 0° C., and extracted with ethyl acetate. The organic layer was washed with saturated aqueous sodium bicarbonate solution and saturated brine, and dried over anhydrous sodium sulfate, and the solvent was evaporated under reduced pressure. The residue was purified by silica gel column chromatography (ethyl acetate/hexane) to give the title compound (565 mg).

$^1$H NMR (300 MHz, DMSO-d$_6$) δ 0.75-0.83 (2H, m), 0.96-1.06 (2H, m), 1.35 (3H, t, J=7.2 Hz), 2.05-2.19 (1H, m), 4.37 (2H, q, J=7.2 Hz), 7.66 (1H, d, J=1.5 Hz), 8.27 (1H, s), 9.04 (1H, d, J=1.1 Hz).

D) ethyl 6-cyclopropyl-8-(2-(triisopropylsilyl)oxazol-5-yl) imidazo[1,2-a]pyridine-3-carboxylate A mixture of ethyl 8-bromo-6-cyclopropylimidazo[1,2-a]pyridine-3-carboxylate (240 mg), 5-(4,4,5,5-tetramethyl-1,3,2-dioxaborolan-2-yl)-2-(triisopropylsilyl)oxazole (300 mg), tetrakis(triphenylphosphine)palladium(0) (90 mg) and potassium carbonate (215 mg) in DME/water (4/1 mL) was stirred with microwave irradiation at 120° C. for 30 min. The reaction mixture was diluted with water, and extracted with ethyl acetate. The extract was dried over anhydrous sodium sulfate, and the solvent was evaporated under reduced pressure. The residue was purified by silica gel column chromatography (ethyl acetate/hexane), and the obtained solid was recrystallized from ethyl acetate/hexane to give the title compound (225 mg).

$^1$H NMR (300 MHz, DMSO-d$_6$) δ 0.73-0.79 (2H, m), 1.03-1.11 (2H, m), 1.16 (18H, d, J=7.2 Hz), 1.32-1.40 (3H, m), 1.40-1.50 (3H, m), 2.14-2.30 (1H, m), 4.39 (2H, q, J=7.2 Hz), 7.59 (1H, d, J=1.5 Hz), 8.23 (1H, s), 8.35 (1H, s), 9.01 (1H, d, J=1.5 Hz).

E) ethyl 6-cyclopropyl-8-(1,3-oxazol-5-yl)imidazo[1,2-a]pyridine-3-carboxylate

Ethyl 6-cyclopropyl-8-(2-(triisopropylsilyl)oxazol-5-yl)imidazo[1,2-a]pyridine-3-carboxylate (220 mg) was dissolved in THF (4.8 mL), and 1N hydrochloric acid (2.5 mL) was added thereto. The reaction mixture was stirred overnight at room temperature, 1N aqueous sodium hydroxide solution was added thereto, and the mixture was extracted with ethyl acetate. The extract was dried over anhydrous sodium sulfate, and the solvent was evaporated under reduced pressure to give a solid (226 mg). The obtained solid (100 mg) was recrystallized from ethyl acetate/hexane to give the title compound (34 mg).

$^1$H NMR (300 MHz, DMSO-d$_6$) δ 0.77-0.86 (2H, m), 1.01-1.10 (2H, m), 1.37 (3H, t, J=7.2 Hz), 2.15-2.29 (1H, m), 4.39 (2H, q, J=6.9 Hz), 7.61 (1H, d, J=1.9 Hz), 8.17 (1H, s), 8.34 (1H, s), 8.64 (1H, s), 9.04 (1H, d, J=1.5 Hz).

Example 155

1-(3-((1S,4S)-2-oxa-5-azabicyclo[2.2.1]hept-5-ylcarbonyl)-8-(1,3-oxazol-5-yl)imidazo[1,2-a]pyridin-6-yl)ethanone A) 6-amino-5-bromonicotinonitrile To a solution of 6-aminonicotinonitrile (5.0 g) in acetic acid (50 mL) was added bromine (4.3 mL) under ice-cooling. The reaction mixture was stirred at room temperature for 3 days, and the precipitate was collected by filtration. The obtained solid was suspended in ethyl acetate and IPE, and collected by filtration to give the title compound (8.2 g).
$^1$H NMR (300 MHz, DMSO-$d_6$) δ 7.31 (2H, brs), 8.19 (1H, d, J 1.9 Hz), 8.36 (1H, d, J=1.9 Hz).

B) ethyl 8-bromo-6-cyanoimidazo[1,2-a]pyridine-3-carboxylate

A mixture of 6-amino-5-bromonicotinonitrile (6.3 g), potassium 2-chloro-3-ethoxy-3-oxoprop-1-en-1-olate (15 g), sulfuric acid (2.2 mL) and ethanol (160 mL) was heated with reflux for 30 hr. To the reaction mixture was added saturated aqueous sodium bicarbonate solution, and the mixture was extracted with ethyl acetate. The extract was dried over anhydrous magnesium sulfate, and the solvent was evaporated under reduced pressure. The residue was purified by silica gel column chromatography (ethyl acetate/hexane) to give the title compound (4.3 g).
$^1$H NMR (300 MHz, DMSO-$d_6$) δ 1.37 (3H, t, J=7.0 Hz), 4.42 (2H, q, J=7.2 Hz), 8.34 (1H, d, J=1.5 Hz), 8.48 (1H, s), 9.69 (1H, d, J=1.5 Hz).

C) ethyl 3-((1S,4S)-2-oxa-5-azabicyclo[2.2.1]heptane-5-carbonyl)-8-bromoimidazo[1,2-a]pyridine-6-carboxylate To a mixture of ethyl 8-bromo-6-cyanoimidazo[1,2-a]pyridine-3-carboxylate (2.0 g), THF (20 mL) and ethanol (20 mL) was added 1N aqueous sodium hydroxide solution (13 mL), and the mixture was stirred at room temperature for 1 hr. The reaction mixture was acidified with 1N hydrochloric acid, water was added thereto, and the mixture was extracted with THF. The extract was dried over anhydrous magnesium sulfate, and the solvent was evaporated under reduced pressure. The residue was dissolved in DMF (20 mL), and HATU (2.6 g), (1S,4S)-2-oxa-5-azabicyclo[2.2.1]heptane hydrochloride (0.92 g) and triethylamine (2.8 mL) were added thereto. The reaction mixture was stirred at room temperature for 12 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane) to give the title compound (1.2 g).
MS (APCI+). found: 394.0, 396.1

D) 3-((1S,4S)-2-oxa-5-azabicyclo[2.2.1]heptane-5-carbonyl)-8-bromo-N-methoxy-N-methylimidazo[1,2-a]pyridine-6-carboxamide To a mixture of ethyl 3-((1S,4S)-2-oxa-5-azabicyclo[2.2.1]heptane-5-carbonyl)-8-bromoimidazo[1,2-a]pyridine-6-carboxylate (390 mg), THF (10 mL) and ethanol (10 mL) was added 1N aqueous sodium hydroxide solution (3 mL), and the mixture was stirred at room temperature for 2 hr. The reaction mixture was acidified with 1N hydrochloric acid, water was added thereto, and the mixture was extracted with ethyl acetate. The extract was dried over anhydrous magnesium sulfate, and the solvent was evaporated under reduced pressure. The residue was dissolved in DMF (6 mL), and HATU (489 mg), N,O-dimethylhydroxylamine hydrochloride (125 mg) and triethylamine (552 µL) were added thereto. The reaction mixture was stirred at room temperature for 12 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane) to give the title compound (286 mg).
MS (APCI+). found: 409.0, 411.1

E) 1-(3-((1S,4S)-2-oxa-5-azabicyclo[2.2.1]heptane-5-carbonyl)-8-bromoimidazo[1,2-a]pyridin-6-yl)ethanone To a solution of 3-((1S,4S)-2-oxa-5-azabicyclo[2.2.1]heptane-5-carbonyl)-8-bromo-N-methoxy-N-methylimidazo[1,2-a]pyridine-6-carboxamide (286 mg) in THF (10 mL) was added dropwise 1M methylmagnesium bromide THF solution (2.1 mL) under ice-cooling. The reaction mixture was stirred at 0° C. for 20 min, 1N hydrochloric acid was added thereto, and the mixture was extracted with ethyl acetate. The extract was dried over anhydrous magnesium sulfate, and the solvent was evaporated under reduced pressure to give the title compound as a crude product.
MS (APCI+). found: 364.0, 366.1

F) 1-(3-((1S,4S)-2-oxa-5-azabicyclo[2.2.1]hept-5-ylcarbonyl)-8-(1,3-oxazol-5-yl)imidazo[1,2-a]pyridin-6-yl)ethanone A mixture of the obtained 1-(3-((1S,4S)-2-oxa-5-azabicyclo[2.2.1]heptane-5-carbonyl)-8-bromoimidazo[1,2-a]pyridin-6-yl)ethanone obtained in Step E of Example 155, 5-(4,4,5,5-tetramethyl-1,3,2-dioxaborolan-2-yl)-2-(triisopropylsilyl)oxazole (80 mg), tetrakis(triphenylphosphine)palladium(0) (25 mg) and potassium carbonate (61 mg) in DME/water (2/0.5 mL) was stirred with microwave irradiation at 120° C. for 30 min. The reaction mixture was diluted with water, and extracted with ethyl acetate. The extract was dried over anhydrous magnesium sulfate, and the solvent was evaporated under reduced pressure. The residue was dissolved in THF (3 mL), and 1N hydrochloric acid (1 mL) was added thereto. The reaction mixture was stirred at room temperature for 2 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (13 mg).
$^1$H NMR (300 MHz, DMSO-$d_6$) δ 1.82-1.97 (2H, m), 2.68 (3H, s), 3.57-3.97 (4H, m), 4.73 (1H, s), 5.04 (1H, brs), 8.15-8.25 (2H, m), 8.30-8.47 (1H, m), 8.67 (1H, s), 9.69-10.14 (1H, m).

Example 156

3-oxa-6-azabicyclo[3.1.1]hept-6-yl(8-(1H-1,2,4-triazol-1-yl)-6-(trifluoromethyl)imidazo[1,2-a]pyridin-3-yl)methanone

A) 3-iodo-5-(trifluoromethyl)pyridin-2-amine

To a mixture of 5-(trifluoromethyl)pyridin-2-amine (12.0 g), silver(I) sulfate (23.1 g) and ethanol (400 mL) was added iodine (37.6 g) in several parts at room temperature, and the reaction mixture was stirred overnight at room temperature. To the reaction solution was added saturated aqueous sodium thiosulfate solution, and the mixture was stirred for 30 min, and neutralize with 1N aqueous sodium hydroxide solution. The insoluble substance was removed by filtration, the filtrate was extracted with ethyl acetate, and the solvent was evaporated under reduced pressure. The residue was purified by silica gel column chromatography (NH, ethyl acetate/hexane) to give the title compound (14.3 g).
MS (APCI+): [M+H]$^+$ 289.0

B) 3-(1H-1,2,4-triazol-1-yl)-5-(trifluoromethyl)pyridin-2-amine

A mixture of 3-iodo-5-(trifluoromethyl)pyridin-2-amine (5.0 g), 1,2,4-triazole (1.44 g), copper(I) iodide (0.496 g), 8-quinolinol (0.378 g), potassium carbonate (2.88 g) and DMSO (50 mL) was stirred at 120° C. for 7 hr under nitrogen gas atmosphere. The reaction solution was allowed to be cooled to room temperature, diluted with ethyl acetate, and filtered through basic silica gel column (ethyl acetate). The filtrate was washed successively with water and saturated brine, and dried over anhydrous sodium sulfate, and the solvent was evaporated under reduced pressure. The residue was purified successively by silica gel column chromatography (ethyl acetate/hexane) and silica gel column chromatography (NH, ethyl acetate/hexane) to give the title compound (2.4 g).
$^1$H NMR (300 MHz, DMSO-d$_6$) δ 6.02 (2H, brs), 7.71 (1H, d, J=2.3 Hz), 8.22 (1H, s), 8.43 (1H, d, J=1.1 Hz), 8.49 (1H, s).

C) ethyl 8-(1H-1,2,4-triazol-1-yl)-6-(trifluoromethyl)imidazo[1,2-a]pyridine-3-carboxylate A mixture of 3-(1H-1,2,4-triazol-1-yl)-5-(trifluoromethyl)pyridin-2-amine (2.4 g), potassium 2-chloro-3-ethoxy-3-oxoprop-1-en-1-olate (4.54 g), sulfuric acid (0.670 mL) and ethanol (100 mL) was heated with reflux for 3 days. The reaction mixture was concentrated under reduced pressure, ethyl acetate was added thereto, and the mixture was washed with water. The aqueous layer was neutralize with saturated aqueous sodium bicarbonate solution, and extracted with ethyl acetate. The organic layers were combined, washed with water and saturated brine, and dried over anhydrous sodium sulfate, and the solvent was evaporated under reduced pressure. The residue was purified by silica gel column chromatography (ethyl acetate/hexane), and the obtained solid was recrystallized from ethyl acetate/hexane to give the title compound (2.22 g).
MS (APCI+): [M+H]$^+$ 326.0

D) 8-(1H-1,2,4-triazol-1-yl)-6-(trifluoromethyl)imidazo[1,2-a]pyridine-3-carboxylic acid To a mixture of ethyl 8-(1H-1,2,4-triazol-1-yl)-6-(trifluoromethyl)imidazo[1,2-a]pyridine-3-carboxylate (320 mg), THF (4 mL) and ethanol (4 mL) was added 2N aqueous sodium hydroxide solution (0.98 mL), and the mixture was stirred at room temperature 3 hr. The reaction mixture was acidified with 1N hydrochloric acid, water was added thereto, and the mixture was extracted with ethyl acetate. The extract was washed successively with water and saturated brine, and dried over anhydrous magnesium sulfate, and the solvent was evaporated under reduced pressure. The residue was recrystallized from THF/hexane to give the title compound (270 mg).
MS (APCI+): [M+H]$^+$ 298.1

E) 3-oxa-6-azabicyclo[3.1.1]hept-6-yl(8-(1H-1,2,4-triazol-1-yl)-6-(trifluoromethyl)imidazo[1,2-a]pyridin-3-yl)methanone A mixture of 8-(1H-1,2,4-triazol-1-yl)-6-(trifluoromethyl)imidazo[1,2-a]pyridine-3-carboxylic acid (80 mg), 3-oxa-6-azabicyclo[3.1.1]heptane 2,2,2-trifluoroacetate (75 mg), HATU (133 mg), triethylamine (150 μL) and anhydrous DMF (3 mL) was stirred at room temperature for 12 hr, saturated aqueous sodium bicarbonate solution was added thereto, and the mixture was extracted with ethyl acetate. The extract was dried over anhydrous magnesium sulfate, and the solvent was evaporated under reduced pressure. The residue was purified by silica gel column chromatography (ethyl acetate/hexane), and the obtained solid was recrystallized from ethyl acetate/hexane to give the title compound (59 mg).
$^1$H NMR (300 MHz, DMSO-d$_6$) δ 1.90 (1H, d, J=8.3 Hz), 2.49-2.59 (4H, m), 2.69-2.87 (1H, m), 3.80-3.94 (2H, m), 8.16 (1H, d, J=1.5 Hz), 8.46 (1H, s), 8.51 (1H, s), 9.88-9.95 (2H, m).

Example 85-1

3-oxa-8-azabicyclo[3.2.1]oct-8-yl(8-(1,3-oxazol-5-yl)-6-(trifluoromethyl)imidazo[1,2-a]pyridin-3-yl)methanone To a mixture of 8-(1,3-oxazol-5-yl)-6-(trifluoromethyl)imidazo[1,2-a]pyridine-3-carboxylic acid (80 g), triethylamine (113 mL) and DMF (2000 mL) were added (1-cyano-2-ethoxy-2-oxoethylideneaminooxy)dimethylamino-morpholino-carbenium hexafluorophosphate (127 g) and 3-oxa-8-azabicyclo[3.2.1]octane hydrochloride (42.3 g) at 0° C., and the mixture was stirred at room temperature for 1 hr. To the reaction mixture was added saturated aqueous sodium bicarbonate solution at 0° C. The obtained solid was collected by filtration, and washed with saturated aqueous sodium bicarbonate solution, water, ethanol and methyl tert-butyl ether to give the title compound (104 g).
$^1$H NMR (300 MHz, DMSO-d$_6$) δ 1.94 (4H, s), 3.56-3.85 (4H, m), 4.64 (2H, brs), 7.93 (1H, d, J=1.9 Hz), 8.26 (1H, s), 8.37 (1H, s), 8.71 (1H, s), 9.40-9.50 (1H, m).

Example 177

(3-fluoroazetidin-1-yl)(8-(1,3-oxazol-5-yl)-6-(trifluoromethyl)imidazo[1,2-a]pyridin-3-yl)methanone A mixture of 8-(1,3-oxazol-5-yl)-6-(trifluoromethyl)imidazo[1,2-a]pyridine-3-carboxylic acid (100 mg), HATU (154 mg), 3-fluoroazetidine hydrochloride (45.0 mg), N,N-diisopropylethylamine (0.147 mL) and DMF (2 mL) was stirred at room temperature for 5 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane), and recrystallized from ethyl acetate/hexane to give the title compound (110 mg).

$^1$H NMR (300 MHz, CDCl$_3$) δ 4.37-4.81 (4H, m), 5.34-5.63 (1H, m), 7.95 (1H, d, J=1.9 Hz), 8.03 (1H, s), 8.07 (1H, s), 8.38 (1H, s), 9.94-9.98 (1H, m).

The compounds of Examples produced according to the methods described in the above-mentioned Production Methods and Examples, or a method analogous thereto are shown in the following tables. MS in the tables means actual measured value.

TABLE 1

| Example | IUPAC Name | Structure | MS |
|---------|------------|-----------|-----|
| 1 | ethyl 8-(1,3-oxazol-5-yl)-6-(trifluoromethyl)imidazo[1,2-a]pyridine-3-carboxylate | 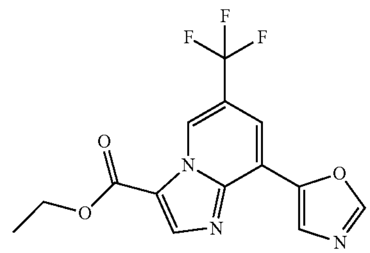 [SMILES: CCOC(=O)c1cnc2c(-c3cnco3)cc(C(F)(F)F)cn12] | 326.1 |
| 2 | (8-(1,3-oxazol-5-yl)-6-(trifluoromethyl)imidazo[1,2-a]pyridin-3-yl)(pyrrolidin-1-yl)methanone | 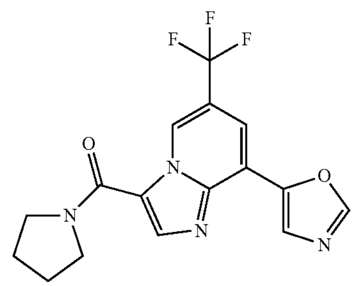 [SMILES: O=C(c1cnc2c(-c3cnco3)cc(C(F)(F)F)cn12)N1CCCC1] | 351.0 |
| 3 | N-ethyl-8-(1,3-oxazol-5-yl)-6-(trifluoromethyl)imidazo[1,2-a]pyridine-3-carboxamide | 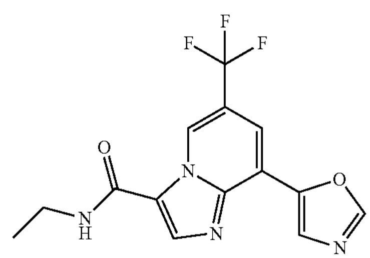 [SMILES: CCNC(=O)c1cnc2c(-c3cnco3)cc(C(F)(F)F)cn12] | 322.9 |
| 4 | cyclopropyl(4-(1,3-oxazol-5-yl)-6-(trifluoromethyl)-1H-indol-1-yl)methanone | 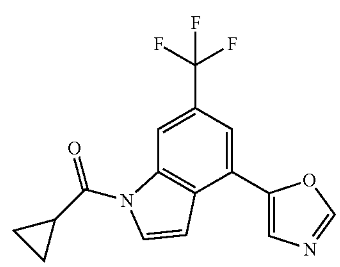 [SMILES: O=C(C1CC1)n1ccc2c(-c3cnco3)cc(C(F)(F)F)cc21] | 321.1 |
| 5 | azetidin-1-yl(8-(1,3-oxazol-5-yl)-6-(trifluoromethyl)imidazo[1,2-a]pyridin-3-yl)methanone | 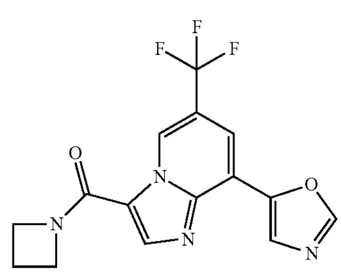 [SMILES: O=C(c1cnc2c(-c3cnco3)cc(C(F)(F)F)cn12)N1CCC1] | 337.1 |

TABLE 1-continued

| Example | IUPAC Name | Structure | MS |
|---|---|---|---|
| 6 | N,N-dimethyl-8-(1,3-oxazol-5-yl)-6-(trifluoromethyl)imidazo[1,2-a]pyridine-3-carboxamide | 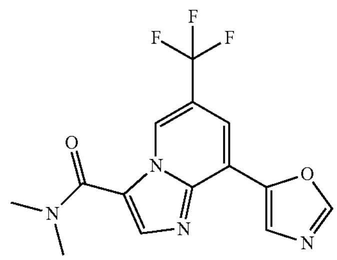 [SMILES: CN(C)C(=O)c1cnc2c(-c3cnco3)cc(C(F)(F)F)cn12] | 325.1 |
| 7 | N-cyclopropyl-8-(1,3-oxazol-5-yl)-6-(trifluoromethyl)imidazo[1,2-a]pyridine-3-carboxamide | 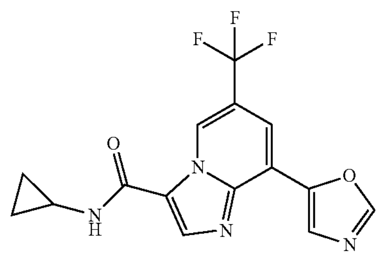 [SMILES: O=C(NC1CC1)c1cnc2c(-c3cnco3)cc(C(F)(F)F)cn12] | 335.0 |
| 8 | ethyl 6-methyl-8-(1,3-oxazol-5-yl)imidazo[1,2-a]pyridine-3-carboxylate | 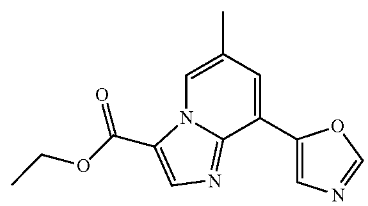 [SMILES: CCOC(=O)c1cnc2c(-c3cnco3)cc(C)cn12] | 272.0 |

TABLE 2

| Example | IUPAC Name | Structure | MS |
|---|---|---|---|
| 9 | N-ethyl-6-methyl-8-(1,3-oxazol-5-yl)imidazo[1,2-a]pyridine-3-carboxamide | 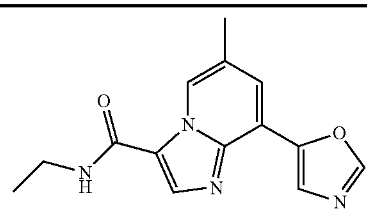 | 271.0 |
| 10 | (6-methyl-8-(1,3-oxazol-5-yl)imidazo[1,2-a]pyridin-3-yl)(pyrrolidin-1-yl)methanone | 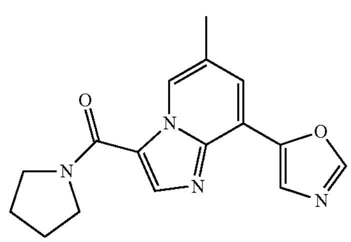 [SMILES: Cc1cc(-c2cnco2)c2ncc(C(=O)N3CCCC3)n2c1] | 297.1 |
| 11 | N-(2-methoxyethyl)-8-(1,3-oxazol-5-yl)-6-(trifluoromethyl)imidazo[1,2-a]pyridine-3-carboxamide | 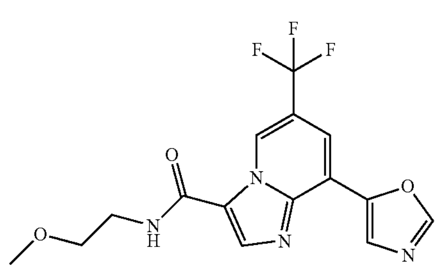 [SMILES: COCCNC(=O)c1cnc2c(-c3cnco3)cc(C(F)(F)F)cn12] | 353.0 |

TABLE 2-continued

| | | | |
|---|---|---|---|
| 12 | (3-methoxyazetidin-1-yl)(8-(1,3-oxazol-5-yl)-6-(trifluoromethyl)imidazo[1,2-a]pyridin-3-yl)methanone | 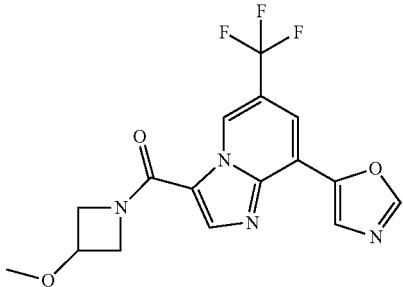 [SMILES: COC1CN(C(=O)c2cnc3c(-c4cnco4)cc(C(F)(F)F)cn23)C1] | 367.0 |
| 13 | ethyl 6-fluoro-8-(1,3-oxazol-5-yl)imidazo[1,2-a]pyridine-3-carboxylate | 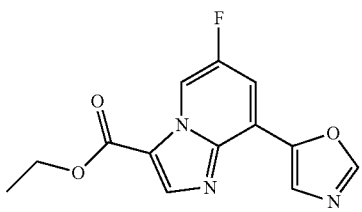 [SMILES: CCOC(=O)c1cnc2c(-c3cnco3)cc(F)cn12] | 276.0 |
| 14 | (6-fluoro-8-(1,3-oxazol-5-yl)imidazo[1,2-a]pyridin-3-yl)(pyrrolidin-1-yl)methanone | 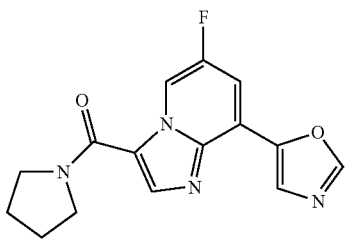 [SMILES: O=C(c1cnc2c(-c3cnco3)cc(F)cn12)N1CCCC1] | 301.1 |
| 15 | N-ethyl-6-fluoro-8-(1,3-oxazol-5-yl)imidazo[1,2-a]pyridine-3-carboxamide | 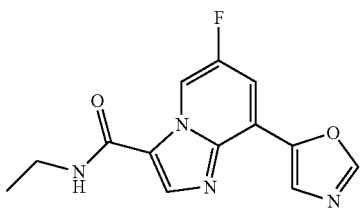 [SMILES: CCNC(=O)c1cnc2c(-c3cnco3)cc(F)cn12] | 272.9 |
| 16 | morpholin-4-yl(8-(1,3-oxazol-5-yl)-6-(trifluoromethyl)imidazo[1,2-a]pyridin-3-yl)methanone | 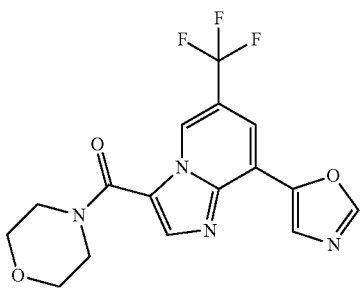 | 367.0 |

TABLE 3

| | | | |
|---|---|---|---|
| 17 | N-ethyl-N-methyl-8-(1,3-oxazol-5-yl)-6-(trifluoromethyl)imidazo[1,2-a]pyridine-3-carboxamide | 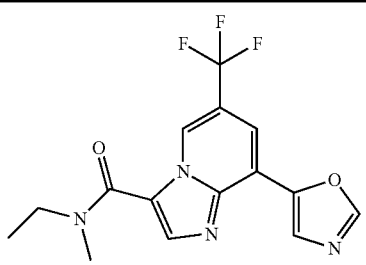 | 339.1 |

TABLE 3-continued

| | | | |
|---|---|---|---|
| 18 | (8-(1,3-oxazol-5-yl)-6-(trifluoromethyl)[1,2,4]triazolo[4,3-a]pyridin-3-yl)(pyrrolidin-1-yl)methanone | 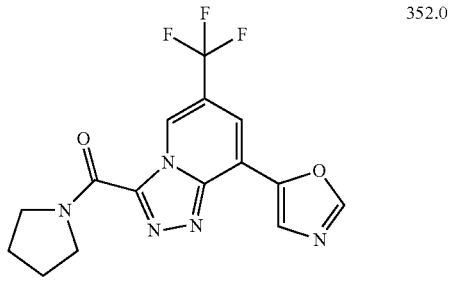 | 352.0 |
| 19 | N-ethyl-8-(1,3-oxazol-5-yl)-6-(trifluoromethyl)[1,2,4]triazolo[4,3-a]pyridine-3-carboxamide | 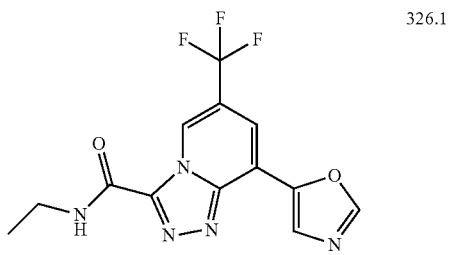 | 326.1 |
| 20 | (6-fluoro-8-(1,3-oxazol-5-yl)imidazo[1,2-a]pyridin-3-yl)(morpholin-4-yl)methanone | 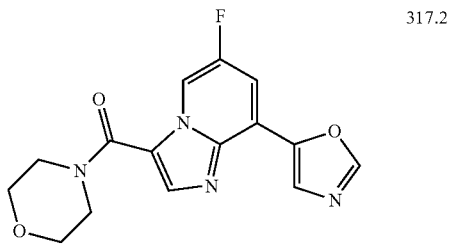 | 317.2 |
| 21 | (3,3-difluoroazetidin-1-yl)(8-(1,3-oxazol-5-yl)-6-(trifluoromethyl)imidazo[1,2-a]pyridin-3-yl)methanone | 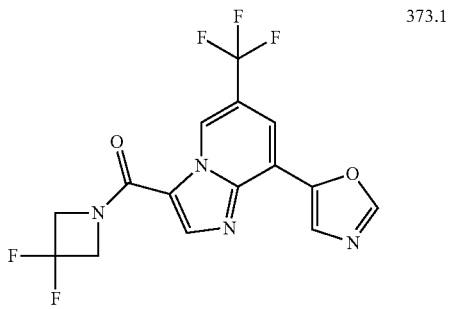 | 373.1 |
| 22 | 2-oxa-6-azaspiro[3.3]hept-6-yl(8-(1,3-oxazol-5-yl)-6-(trifluoromethyl)imidazo[1,2-a]pyridin-3-yl)methanone | 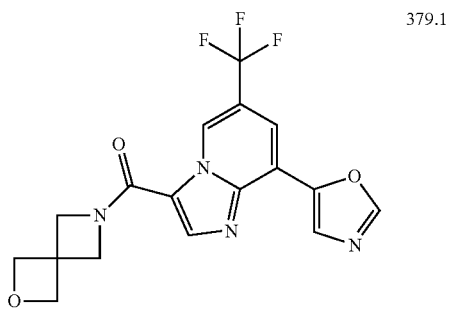 | 379.1 |

TABLE 3-continued

| | | | |
|---|---|---|---|
| 23 | (3-hydroxypyrrolidin-1-yl)(8-(1,3-oxazol-5-yl)-6-(trifluoromethyl)imidazo[1,2-a]pyridin-3-yl)methanone | 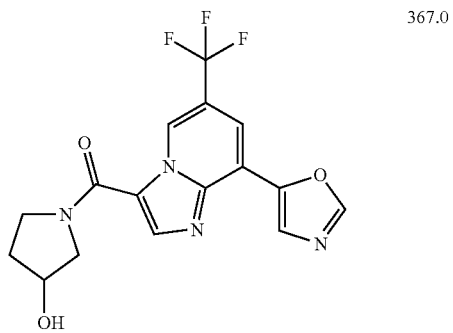 | 367.0 |
| 24 | N,N-diethyl-8-(1,3-oxazol-5-yl)-6-(trifluoromethyl)imidazo[1,2-a]pyridine-3-carboxamide | 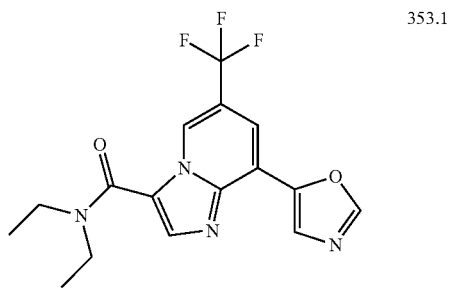 | 353.1 |

TABLE 4

| | | | |
|---|---|---|---|
| 25 | N-(cyclopropylmethyl)-8-(1,3-oxazol-5-yl)-6-(trifluoromethyl)imidazo[1,2-a]pyridine-3-carboxamide | 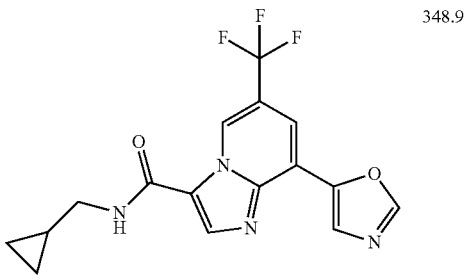 | 348.9 |
| 26 | 8-oxa-3-azabicyclo[3.2.1]oct-3-yl(8-(1,3-oxazol-5-yl)-6-(trifluoromethyl)imidazo[1,2-a]pyridin-3-yl)methanone | 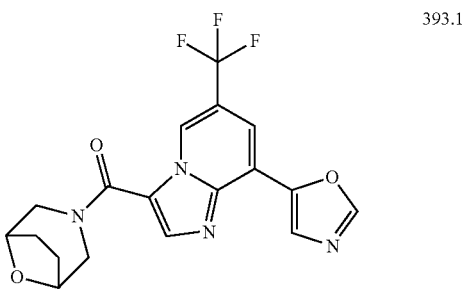 | 393.1 |
| 27 | (8-(1,3-oxazol-5-yl)-6-(trifluoromethyl)imidazo[1,2-a]pyridin-3-yl)(2,2,6,6-tetrafluoromorpholin-4-yl)methanone | 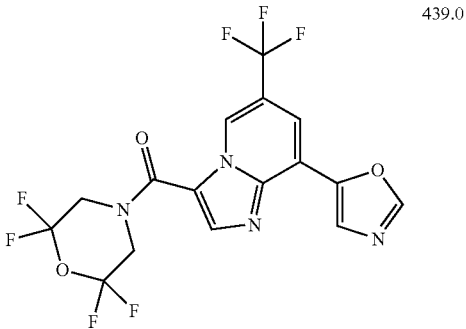 | 439.0 |

TABLE 4-continued

| | | | |
|---|---|---|---|
| 28 | (3-hydroxy-3-methylpyrrolidin-1-yl)(8-(1,3-oxazol-5-yl)-6-(trifluoromethyl)imidazo[1,2-a]pyridin-3-yl)methanone | 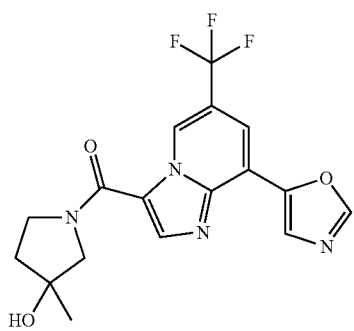 [SMILES: CC1(O)CCN(C(=O)c2cnc3c(-c4cnco4)cc(C(F)(F)F)cn23)C1] | 381.1 |
| 29 | (3,3-difluoroazetidin-1-yl)(6-fluoro-8-(1,3-oxazol-5-yl)imidazo[1,2-a]pyridin-3-yl)methanone | 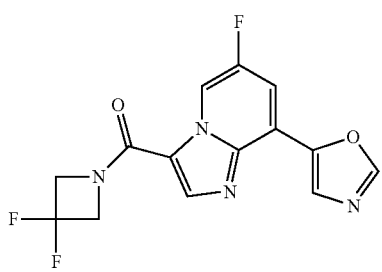 [SMILES: O=C(c1cnc2c(-c3cnco3)cc(F)cn12)N1CC(F)(F)C1] | 323.1 |
| 30 | ((2R,6S)-2,6-dimethylmorpholin-4-yl)(8-(1,3-oxazol-5-yl)-6-(trifluoromethyl)imidazo[1,2-a]pyridin-3-yl)methanone | 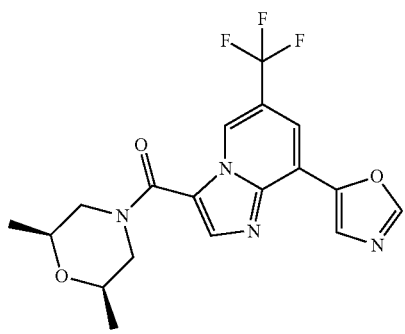 [SMILES: C[C@@H]1CN(C(=O)c2cnc3c(-c4cnco4)cc(C(F)(F)F)cn23)C[C@H](C)O1] | 395.2 |
| 31 | N-(2,2-difluoroethyl)-8-(1,3-oxazol-5-yl)-6-(trifluoromethyl)imidazo[1,2-a]pyridine-3-carboxamide | 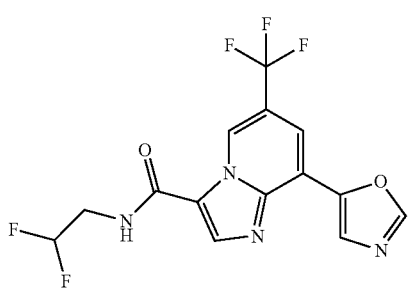 | 358.9 |
| 32 | 8-(1,3-oxazol-5-yl)-6-(trifluoromethyl)imidazo[1,2-a]pyridine-3-carboxylic acid | 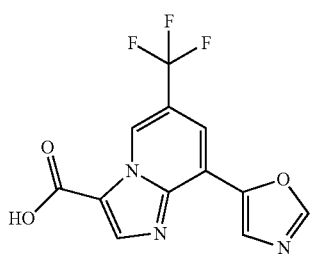 [SMILES: O=C(O)c1cnc2c(-c3cnco3)cc(C(F)(F)F)cn12] | 295.9 |

TABLE 5

| | | | |
|---|---|---|---|
| 33 | 8-(1,3-oxazol-5-yl)-N-(oxetan-3-yl)-6-(trifluoromethyl)imidazo[1,2-a]pyridine-3-carboxamide | 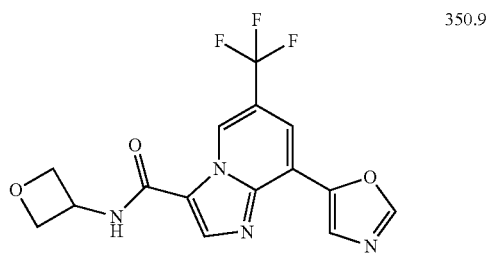 | 350.9 |
| 34 | 8-(1,3-oxazol-5-yl)-N-(oxetan-3-ylmethyl)-6-(trifluoromethyl)imidazo[1,2-a]pyridine-3-carboxamide | 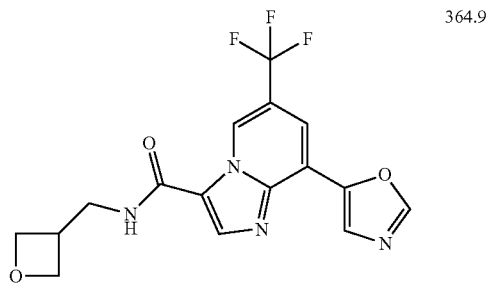 | 364.9 |
| 35 | N-isopropyl-N-methyl-8-(1,3-oxazol-5-yl)-6-(trifluoromethyl)imidazo[1,2-a]pyridine-3-carboxamide | 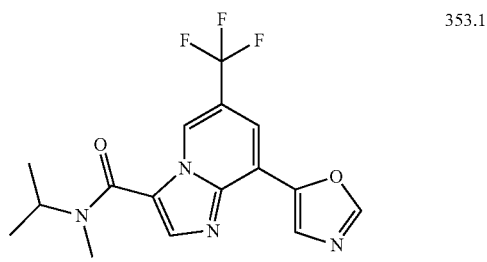 | 353.1 |
| 36 | N-(2,2-difluoroethyl)-N-methyl-8-(1,3-oxazol-5-yl)-6-(trifluoromethyl)imidazo[1,2-a]pyridine-3-carboxamide | 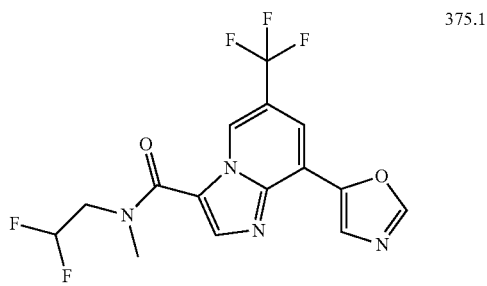 | 375.1 |
| 37 | N-methyl-8-(1,3-oxazol-5-yl)-N-(oxetan-3-yl)-6-(trifluoromethyl)imidazo[1,2-a]pyridine-3-carboxamide | 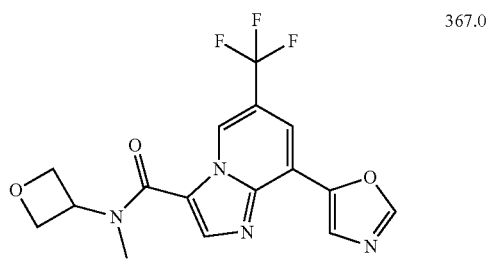 | 367.0 |
| 38 | N-methyl-8-(1,3-oxazol-5-yl)-N-(oxetan-3-ylmethyl)-6-(trifluoromethyl)imidazo[1,2-a]pyridine-3-carboxamide | 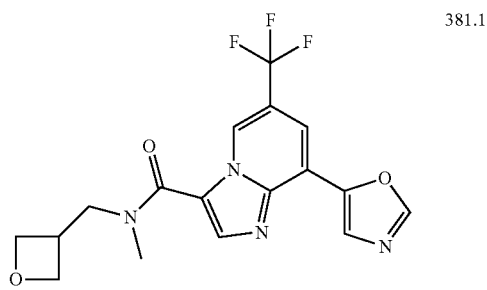 | 381.1 |

TABLE 5-continued
| | | | |
|---|---|---|---|
| 39 | 3-azabicyclo[3.1.0]hex-3-yl(8-(1,3-oxazol-5-yl)-6-(trifluoromethyl)imidazo[1,2-a]pyridin-3-yl)methanone | 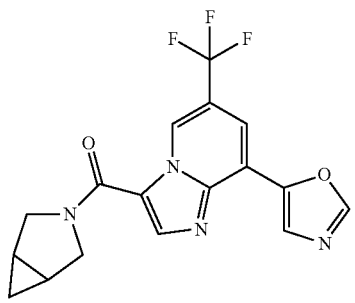 [SMILES: O=C(c1cnc2c(-c3cnco3)cc(C(F)(F)F)cn12)N1CC2CC2C1] | 363.2 |
| 40 | 2-oxa-6-azaspiro[3.5]non-6-yl(8-(1,3-oxazol-5-yl)-6-(trifluoromethyl)imidazo[1,2-a]pyridin-3-yl)methanone | 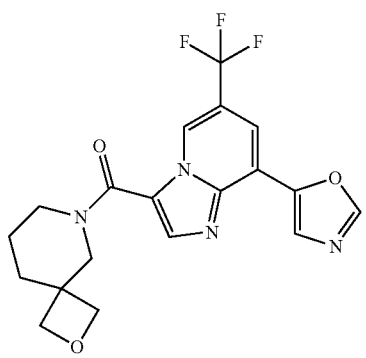 [SMILES: O=C(c1cnc2c(-c3cnco3)cc(C(F)(F)F)cn12)N1CCCC2(COC2)C1] | 407.1 |
TABLE 6
| | | | |
|---|---|---|---|
| 41 | (4-methylpiperazin-1-yl)(8-(1,3-oxazol-5-yl)-6-(trifluoromethyl)imidazo[1,2-a]pyridin-3-yl)methanone | 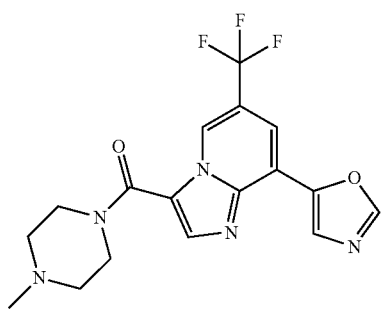 [SMILES: CN1CCN(C(=O)c2cnc3c(-c4cnco4)cc(C(F)(F)F)cn23)CC1] | 380.2 |
| 42 | (3-hydroxypiperidin-1-yl)(8-(1,3-oxazol-5-yl)-6-(trifluoromethyl)imidazo[1,2-a]pyridin-3-yl)methanone | 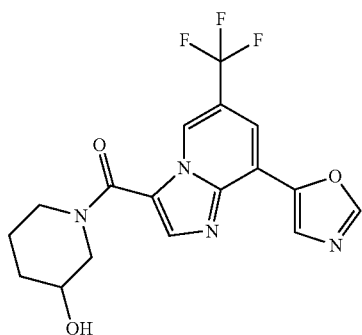 [SMILES: O=C(c1cnc2c(-c3cnco3)cc(C(F)(F)F)cn12)N1CCCC(O)C1] | 381.1 |

TABLE 6-continued

| 43 | (4-hydroxypiperidin-1-yl)(8-(1,3-oxazol-5-yl)-6-(trifluoromethyl)imidazo[1,2-a]pyridin-3-yl)methanone | 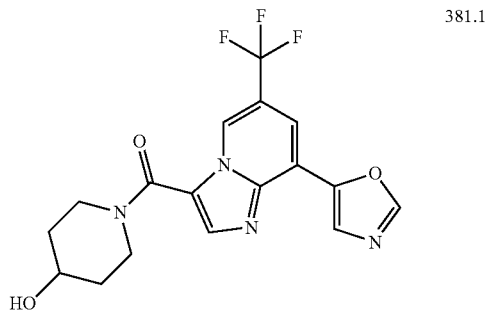 | 381.1 |
| 44 | 8-(1,3-oxazol-5-yl)-N-(tetrahydro-2H-pyran-4-yl)-6-(trifluoromethyl)imidazo[1,2-a]pyridine-3-carboxamide | 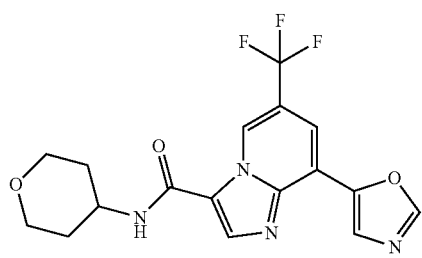 | 379.0 |
| 45 | 8-(1,3-oxazol-5-yl)-N-(tetrahydro-2H-pyran-3-yl)-6-(trifluoromethyl)imidazo[1,2-a]pyridine-3-carboxamide | 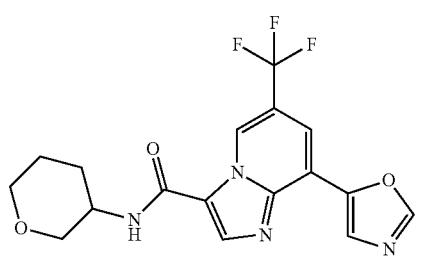 [SMILES: O=C(NC1CCCOC1)c1cnc2c(-c3cnco3)cc(C(F)(F)F)cn12] | 379.0 |
| 46 | N-(cyclopropylmethyl)-N-methyl-8-(1,3-oxazol-5-yl)-6-(trifluoromethyl)imidazo[1,2-a]pyridine-3-carboxamide | 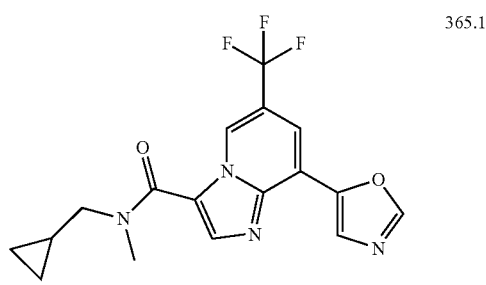 | 365.1 |
| 47 | N-methyl-8-(1,3-oxazol-5-yl)-N-(tetrahydro-2H-pyran-4-yl)-6-(trifluoromethyl)imidazo[1,2-a]pyridine-3-carboxamide | 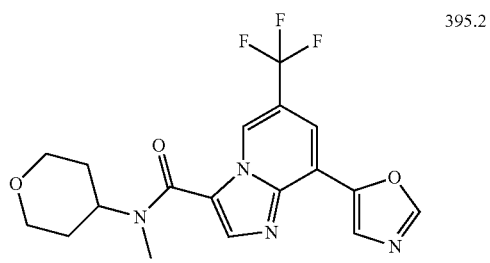 | 395.2 |
| 48 | N-methyl-8-(1,3-oxazol-5-yl)-N-(tetrahydro-2H-pyran-3-yl)-6-(trifluoromethyl)imidazo[1,2-a]pyridine-3-carboxamide | 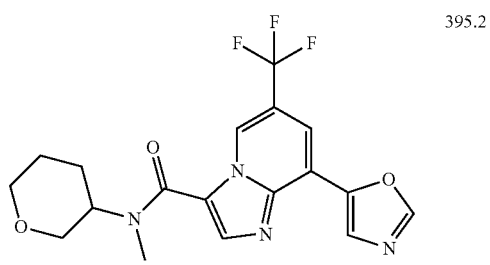 | 395.2 |

TABLE 7

| 49 | 1-oxa-7-azaspiro[4.4]non-7-yl(8-(1,3-oxazol-5-yl)-6-(trifluoromethyl)imidazo[1,2-a]pyridin-3-yl)methanone | 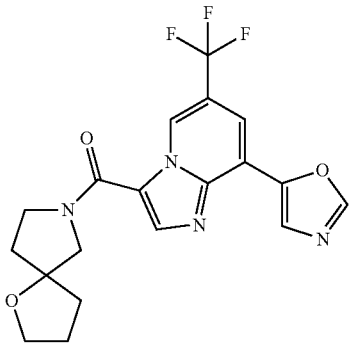 [SMILES: O=C(c1cnc2c(-c3cnco3)cc(C(F)(F)F)cn12)N1CCC2(CCCO2)C1] | 407.1 |
| 50 | 2-oxa-7-azaspiro[4.4]non-7-yl(8-(1,3-oxazol-5-yl)-6-(trifluoromethyl)imidazo[1,2-a]pyridin-3-yl)methanone | 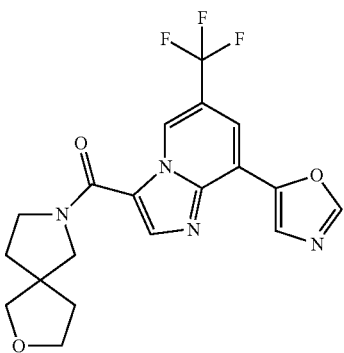 [SMILES: O=C(c1cnc2c(-c3cnco3)cc(C(F)(F)F)cn12)N1CCC2(CCOC2)C1] | 407.1 |
| 51 | N-methyl-8-(1,3-oxazol-5-yl)-6-(trifluoromethyl)imidazo[1,2-a]pyridine-3-carboxamide | 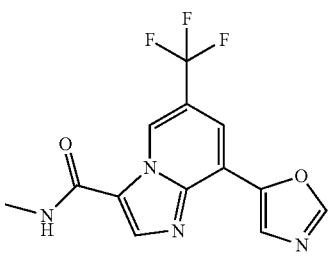 [SMILES: CNC(=O)c1cnc2c(-c3cnco3)cc(C(F)(F)F)cn12] | 308.8 |
| 52 | (3,3-difluoropyrrolidin-1-yl)(8-(1,3-oxazol-5-yl)-6-(trifluoromethyl)imidazo[1,2-a]pyridin-3-yl)methanone | 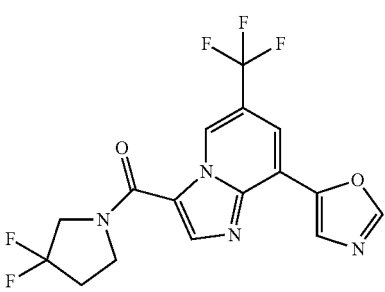 [SMILES: O=C(c1cnc2c(-c3cnco3)cc(C(F)(F)F)cn12)N1CCC(F)(F)C1] | 387.1 |
| 53 | (3-methylpyrrolidin-1-yl)(8-(1,3-oxazol-5-yl)-6-(trifluoromethyl)imidazo[1,2-a]pyridin-3-yl)methanone | 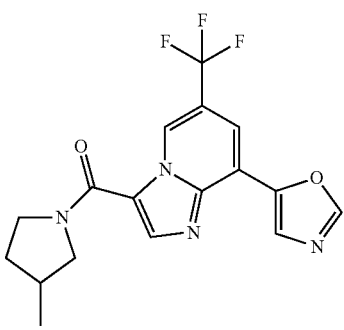 [SMILES: CC1CCN(C(=O)c2cnc3c(-c4cnco4)cc(C(F)(F)F)cn23)C1] | 365.1 |

TABLE 7-continued

| 54 | (3,3-difluoroazetidin-1-yl)(6-methyl-8-(1,3-oxazol-5-yl)imidazo[1,2-a]pyridin-3-yl)methanone | 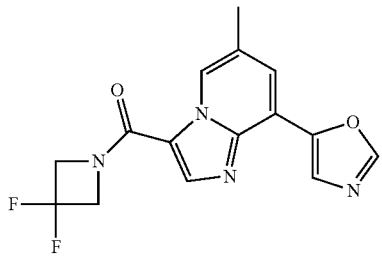 [SMILES: Cc1cc(-c2cnco2)c2ncc(C(=O)N3CC(F)(F)C3)n2c1] | 319.1 |
| 55 | (2-methylmorpholin-4-yl)(8-(1,3-oxazol-5-yl)-6-(trifluoromethyl)imidazo[1,2-a]pyridin-3-yl)methanone | 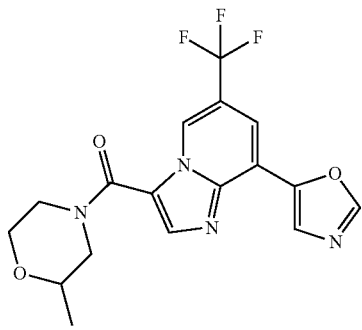 [SMILES: CC1CN(C(=O)c2cnc3c(-c4cnco4)cc(C(F)(F)F)cn23)CCO1] | 381.1 |
| 56 | (3-methylmorpholin-4-yl)(8-(1,3-oxazol-5-yl)-6-(trifluoromethyl)imidazo[1,2-a]pyridin-3-yl)methanone | 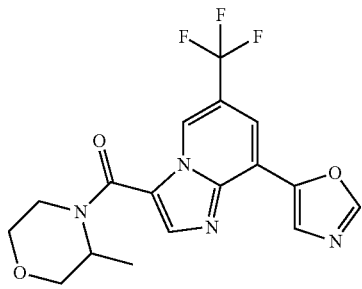 [SMILES: CC1COCCN1C(=O)c1cnc2c(-c3cnco3)cc(C(F)(F)F)cn12] | 381.1 |

TABLE 8

| 57 | N-cyclopropyl-N-ethyl-8-(1,3-oxazol-5-yl)-6-(trifluoromethyl)imidazo[1,2-a]pyridine-3-carboxamide | 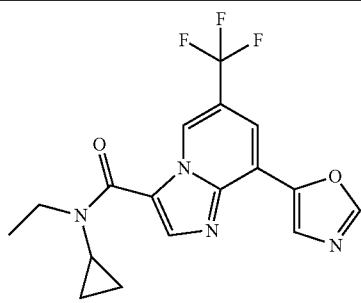 | 365.1 |
| 58 | (1S,4S)-2-oxa-5-azabicyclo[2.2.1]hept-5-yl(8-(1,3-oxazol-5-yl)-6-(trifluoromethyl)[1,2,4]triazolo[4,3-a]pyridin-3-yl)methanone | 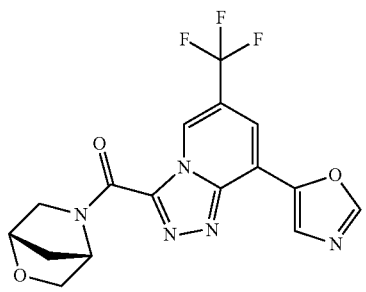 [SMILES: O=C(c1nnc2c(-c3cnco3)cc(C(F)(F)F)cn12)N1C[C@@H]2C[C@H]1CO2] | 380.1 |

TABLE 8-continued

| | | | |
|---|---|---|---|
| 59 | (3-methoxypyrrolidin-1-yl)(8-(1,3-oxazol-5-yl)-6-(trifluoromethyl)imidazo[1,2-a]pyridin-3-yl)methanone | 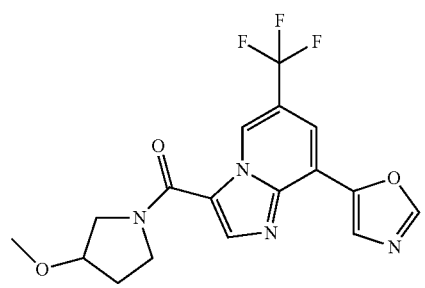 [SMILES: COC1CCN(C(=O)c2cnc3c(-c4cnco4)cc(C(F)(F)F)cn23)C1] | 381.1 |
| 60 | 2-oxa-6-azaspiro[3.4]oct-6-yl(8-(1,3-oxazol-5-yl)-6-(trifluoromethyl)imidazo[1,2-a]pyridin-3-yl)methanone | 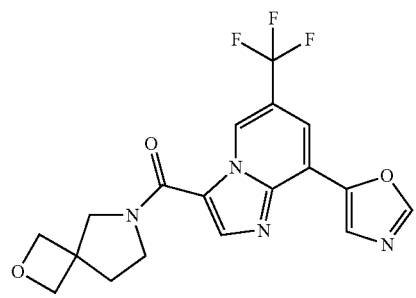 [SMILES: O=C(c1cnc2c(-c3cnco3)cc(C(F)(F)F)cn12)N1CCC2(COC2)C1] | 393.1 |
| 61 | (3,5-dimethylmorpholin-4-yl)(8-(1,3-oxazol-5-yl)-6-(trifluoromethyl)imidazo[1,2-a]pyridin-3-yl)methanone | 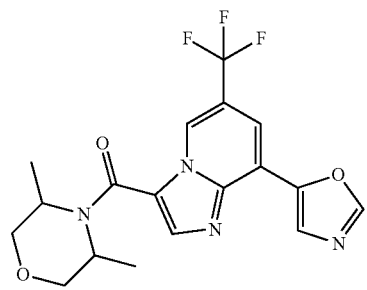 [SMILES: CC1COCC(C)N1C(=O)c1cnc2c(-c3cnco3)cc(C(F)(F)F)cn12] | 395.2 |
| 62 | 1,4-oxazepan-4-yl(8-(1,3-oxazol-5-yl)-6-(trifluoromethyl)imidazo[1,2-a]pyridin-3-yl)methanone | 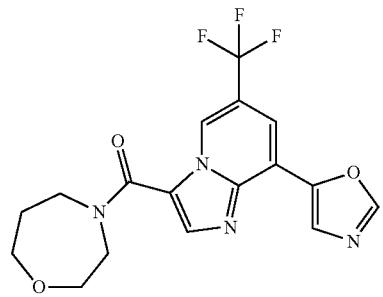 [SMILES: O=C(c1cnc2c(-c3cnco3)cc(C(F)(F)F)cn12)N1CCCOCC1] | 381.1 |
| 63 | N-cyclopropyl-N-methyl-8-(1,3-oxazol-5-yl)-6-(trifluoromethyl)imidazo[1,2-a]pyridine-3-carboxamide | 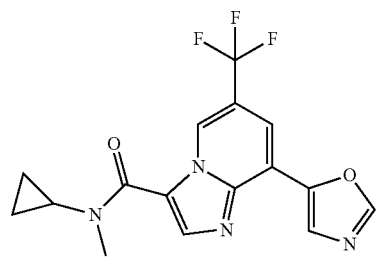 [SMILES: CN(C(=O)c1cnc2c(-c3cnco3)cc(C(F)(F)F)cn12)C1CC1] | 351.1 |

TABLE 8-continued

| | | | |
|---|---|---|---|
| 64 | N-((3-methyloxetan-3-yl)methyl)-8-(1,3-oxazol-5-yl)-6-(trifluoromethyl)imidazo[1,2-a]pyridine-3-carboxamide | 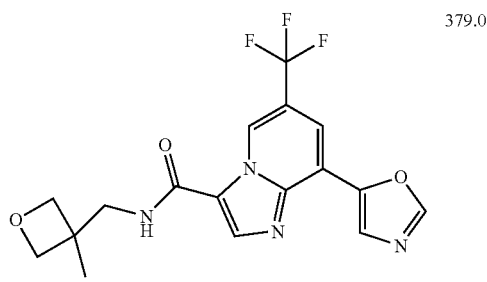 | 379.0 |

TABLE 9

| | | | |
|---|---|---|---|
| 65 | N-methyl-N-((3-methyloxetan-3-yl)methyl)-8-(1,3-oxazol-5-yl)-6-(trifluoromethyl)imidazo[1,2-a]pyridine-3-carboxamide | 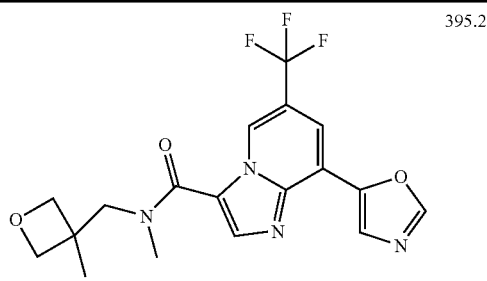 | 395.2 |
| 66 | (3,3-difluoroazetidin-1-yl)(8-(1,3-oxazol-5-yl)-6-(trifluoromethyl)[1,2,4]triazolo[4,3-a]pyridin-3-yl)methanone | 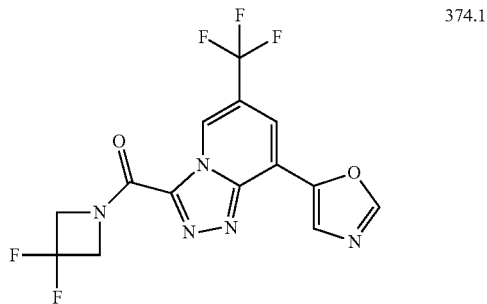 | 374.1 |
| 67 | N-benzyl-8-(1,3-oxazol-5-yl)-6-(trifluoromethyl)imidazo[1,2-a]pyridine-3-carboxamide | 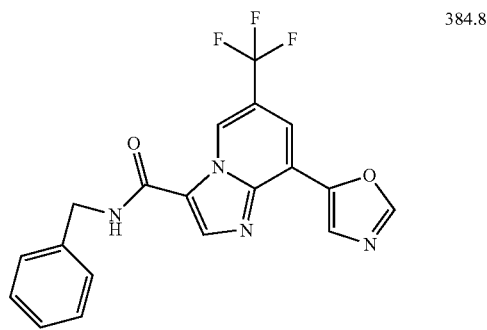 | 384.8 |
| 68 | N-benzyl-N-methyl-8-(1,3-oxazol-5-yl)-6-(trifluoromethyl)imidazo[1,2-a]pyridine-3-carboxamide | 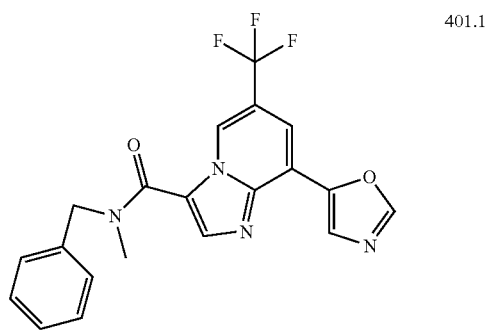 | 401.1 |

TABLE 9-continued

| | | | |
|---|---|---|---|
| 69 | (3-methylazetidin-1-yl)(8-(1,3-oxazol-5-yl)-6-(trifluoromethyl)imidazo[1,2-a]pyridin-3-yl)methanone | 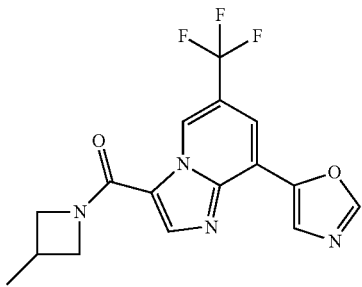 [SMILES: CC1CN(C(=O)c2cnc3c(-c4cnco4)cc(C(F)(F)F)cn23)C1] | 351.1 |
| 70 | (2-methylazetidin-1-yl)(8-(1,3-oxazol-5-yl)-6-(trifluoromethyl)imidazo[1,2-a]pyridin-3-yl)methanone | 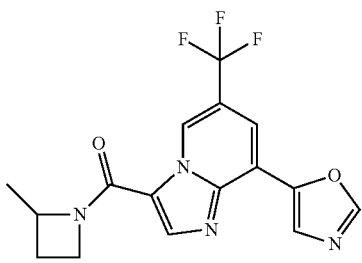 [SMILES: CC1CCN1C(=O)c1cnc2c(-c3cnco3)cc(C(F)(F)F)cn12] | 351.1 |
| 71 | (1S,4S)-2-oxa-5-azabicyclo[2.2.1]hept-5-yl(8-(1,3-oxazol-5-yl)-6-(trifluoromethyl)imidazo[1,2-a]pyridin-3-yl)methanone | 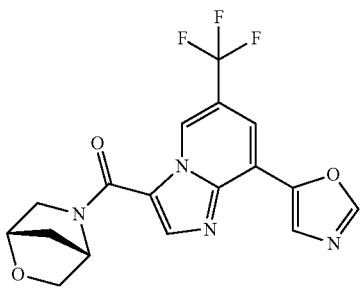 [SMILES: O=C(c1cnc2c(-c3cnco3)cc(C(F)(F)F)cn12)N1C[C@@H]2C[C@H]1CO2] | 379.1 |
| 72 | optically active (3-hydroxy-3-methylpyrrolidin-1-yl)(8-(1,3-oxazol-5-yl)-6-(trifluoromethyl)imidazo[1,2-a]pyridin-3-yl)methanone | 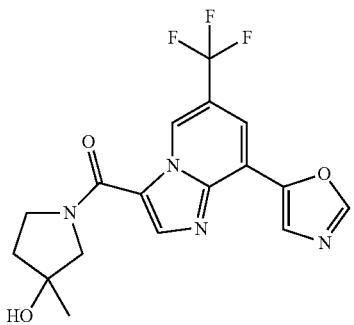 [SMILES: CC1(O)CCN(C(=O)c2cnc3c(-c4cnco4)cc(C(F)(F)F)cn23)C1] | 381.1 |

TABLE 10

| | | | |
|---|---|---|---|
| 73 | optically active (3-hydroxy-3-methylpyrrolidin-1-yl)(8-(1,3-oxazol-5-yl)-6-(trifluoromethyl)imidazo[1,2-a]pyridin-3-yl)methanone | 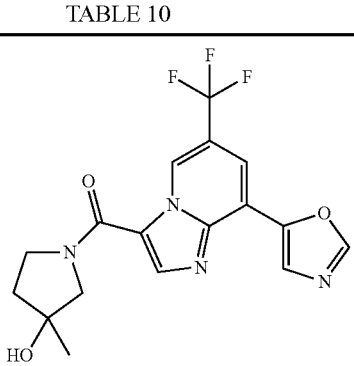 | 381.1 |

TABLE 10-continued

| | | | |
|---|---|---|---|
| 74 | 8-(1,3-oxazol-5-yl)-N-phenyl-6-(trifluoromethyl)imidazo[1,2-a]pyridine-3-carboxamide | 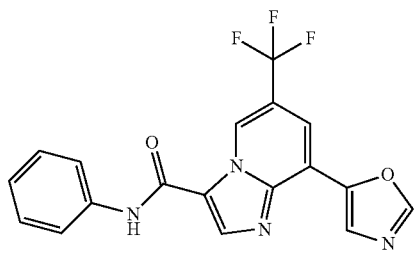 [SMILES: O=C(Nc1ccccc1)c1cnc2c(-c3cnco3)cc(C(F)(F)F)cn12] | 370.9 |
| 75 | (3-ethoxypyrrolidin-1-yl)(8-(1,3-oxazol-5-yl)-6-(trifluoromethyl)imidazo[1,2-a]pyridin-3-yl)methanone | 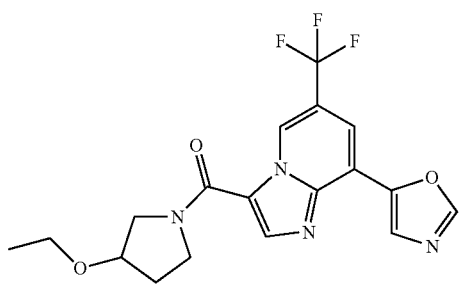 [SMILES: CCOC1CCN(C(=O)c2cnc3c(-c4cnco4)cc(C(F)(F)F)cn23)C1] | 395.2 |
| 76 | (3-(2,2-difluoroethoxy)pyrrolidin-1-yl)(8-(1,3-oxazol-5-yl)-6-(trifluoromethyl)imidazo[1,2-a]pyridin-3-yl)methanone | 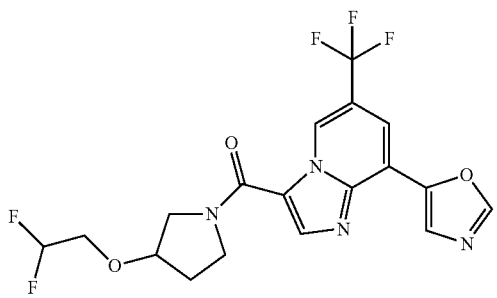 [SMILES: O=C(c1cnc2c(-c3cnco3)cc(C(F)(F)F)cn12)N1CCC(OCC(F)F)C1] | 431.1 |
| 77 | (3-(difluoromethoxy)pyrrolidin-1-yl)(8-(1,3-oxazol-5-yl)-6-(trifluoromethyl)imidazo[1,2-a]pyridin-3-yl)methanone | 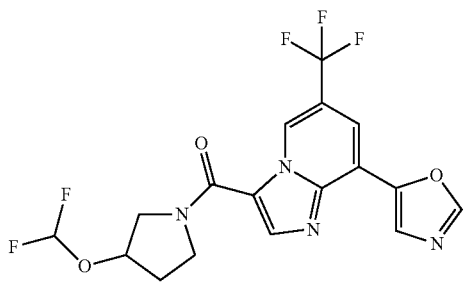 [SMILES: O=C(c1cnc2c(-c3cnco3)cc(C(F)(F)F)cn12)N1CCC(OC(F)F)C1] | 417.1 |
| 78 | (6-methyl-8-(1,3-oxazol-5-yl)imidazo[1,2-a]pyridin-3-yl)((1S,4S)-2-oxa-5-azabicyclo[2.2.1]hept-5-yl)methanone | 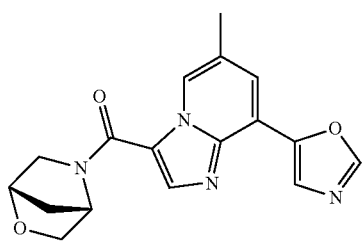 [SMILES: Cc1cc(-c2cnco2)c2ncc(C(=O)N3C[C@@H]4C[C@H]3CO4)n2c1] | 325.1 |

TABLE 10-continued

| | | | |
|---|---|---|---|
| 79 | ((3R)-3-(difluoromethoxy)pyrrolidin-1-yl)(8-(1,3-oxazol-5-yl)-6-(trifluoromethyl)imidazo[1,2-a]pyridin-3-yl)methanone | 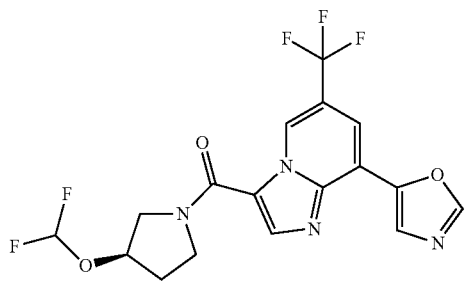 [SMILES: O=C(c1cnc2c(-c3cnco3)cc(C(F)(F)F)cn12)N1CC[C@@H](OC(F)F)C1] | 417.1 |
| 80 | ((3R)-3-methoxypyrrolidin-1-yl)(8-(1,3-oxazol-5-yl)-6-(trifluoromethyl)imidazo[1,2-a]pyridin-3-yl)methanone | 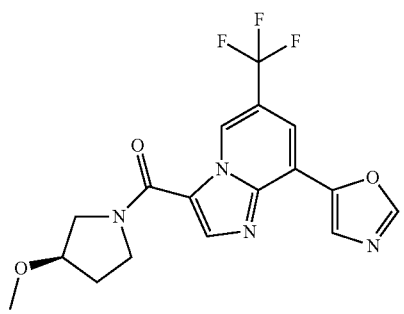 [SMILES: CO[C@@H]1CCN(C(=O)c2cnc3c(-c4cnco4)cc(C(F)(F)F)cn23)C1] | 381.1 |

TABLE 11

| | | | |
|---|---|---|---|
| 81 | ((3R)-3-(2,2-difluoroethoxy)pyrrolidin-1-yl)(8-(1,3-oxazol-5-yl)-6-(trifluoromethyl)imidazo[1,2-a]pyridin-3-yl)methanone | 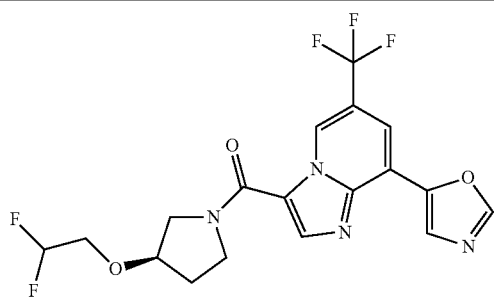 | 431.1 |
| 82 | ((3S)-3-methoxypyrrrolidin-1-yl)(8-(1,3-oxazol-5-yl)-6-(trifluoromethyl)imidazo[1,2-a]pyridin-3-yl)methanone | 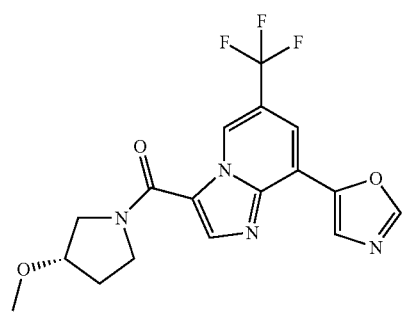 [SMILES: CO[C@H]1CCN(C(=O)c2cnc3c(-c4cnco4)cc(C(F)(F)F)cn23)C1] | 381.1 |
| 83 | ((3R)-3-hydroxypyrrolidin-1-yl)(8-(1,3-oxazol-5-yl)-6-(trifluoromethyl)imidazo[1,2-a]pyridin-3-yl)methanone | 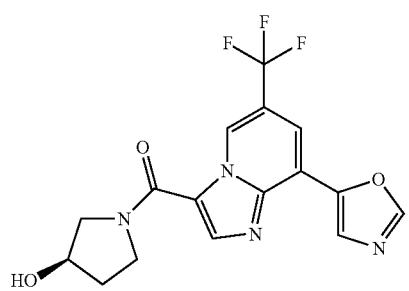 [SMILES: O=C(c1cnc2c(-c3cnco3)cc(C(F)(F)F)cn12)N1CC[C@@H](O)C1] | 367.1 |

TABLE 11-continued

| | | | |
|---|---|---|---|
| 84 | (3,3-difluoropyrrolidin-1-yl)(8-(1,3-oxazol-5-yl)-6-(trifluoromethyl)[1,2,4]triazolo[4,3-a]pyridin-3-yl)methanone | | 388.1 |
| 85 | 3-oxa-8-azabicyclo[3.2.1]oct-8-yl(8-(1,3-oxazol-5-yl)-6-(trifluoromethyl)imidazo[1,2-a]pyridin-3-yl)methanone | | 393.2 |
| 86 | 3-oxa-6-azabicyclo[3.1.1]hept-6-yl(8-(1,3-oxazol-5-yl)-6-(trifluoromethyl)imidazo[1,2-a]pyridin-3-yl)methanone | | 379.1 |
| 87 | ((3S)-3-hydroxypyrrolidin-1-yl)(8-(1,3-oxazol-5-yl)-6-(trifluoromethyl)imidazo[1,2-a]pyridin-3-yl)methanone | | 367.1 |
| 88 | (8-(1,3-oxazol-5-yl)-6-(trifluoromethyl)imidazo[1,2-a]pyridin-3-yl)(piperidin-1-yl)methanone | | 365.0 |

TABLE 12

| 89 | ((3S)-3-(difluoromethoxy)pyrrolidin-1-yl)(8-(1,3-oxazol-5-yl)-6-(trifluoromethyl)imidazo[1,2-a]pyridin-3-yl)methanone | | 417.0 |
|---|---|---|---|
| 90 | ((3S)-3-(2,2-difluoroethoxy)pyrrolidin-1-yl)(8-(1,3-oxazol-5-yl)-6-(trifluoromethyl)imidazo[1,2-a]pyridin-3-yl)methanone | | 431.0 |
| 91 | (3-methoxypyrrolidin-1-yl)(8-(1,3-oxazol-5-yl)-6-(trifluoromethyl)[1,2,4]triazolo[4,3-a]pyridin-3-yl)methanone | | 382.1 |
| 92 | (6-chloro-8-(1,3-oxazole-5-yl)imidazo[1,2-a]pyridin-3-yl)((1S,4S)-2-oxa-5-azabicyclo[2.2.1]hept-5-yl)methanone | | 345.1 |
| 93 | (6,8-di(1,3-oxazol-5-yl)imidazo[1,2-a]pyridin-3-yl)((1S,4S)-2-oxa-5-azabicyclo[2.2.1]hept-5-yl)methanone | | 378.1 |

TABLE 12-continued

| | | | |
|---|---|---|---|
| 94 | 1-((8-(1,3-oxazol-5-yl)-6-(trifluoromethyl)imidazo[1,2-a]pyridin-3-yl)carbonyl)piperidin-4-one | 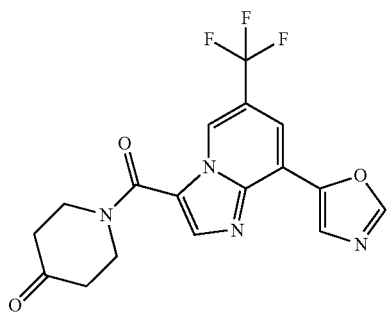 [SMILES: O=C1CCN(C(=O)c2cnc3c(-c4cnco4)cc(C(F)(F)F)cn23)CC1] | 379.1 |
| 95 | ethyl 2,6-dimethyl-8-(1,3-oxazol-5-yl)imidazo[1,2-a]pyridine-3-carboxylate | 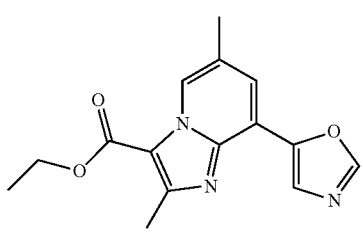 [SMILES: CCOC(=O)c1c(C)nc2c(-c3cnco3)cc(C)cn12] | 286.1 |
| 96 | ethyl 2-methyl-8-(1,3-oxazol-5-yl)-6-(trifluoromethyl)imidazo[1,2-a]pyridine-3-carboxylate | 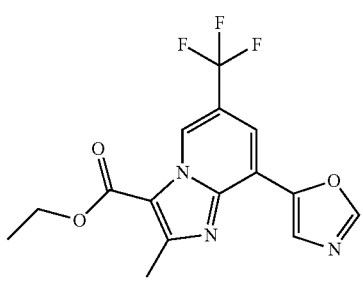 [SMILES: CCOC(=O)c1c(C)nc2c(-c3cnco3)cc(C(F)(F)F)cn12] | 340.2 |

TABLE 13

| | | | |
|---|---|---|---|
| 97 | ethyl 6-fluoro-2-methyl-8-(1,3-oxazol-5-yl)imidazo[1,2-a]pyridine-3-carboxylate | 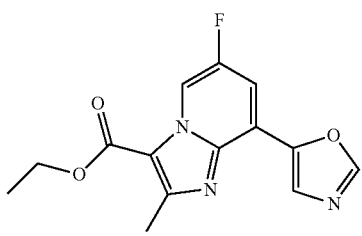 [SMILES: CCOC(=O)c1c(C)nc2c(-c3cnco3)cc(F)cn12] | 290.0 |
| 98 | N-ethyl-2-methyl-8-(1,3-oxazol-5-yl)-6-(trifluoromethyl)imidazo[1,2-a]pyridine-3-carboxamide | 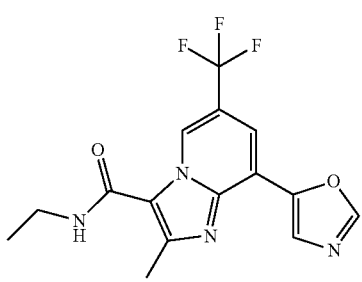 [SMILES: CCNC(=O)c1c(C)nc2c(-c3cnco3)cc(C(F)(F)F)cn12] | 336.9 |

TABLE 13-continued

| # | Name | Structure | Mass |
|---|------|-----------|------|
| 99 | N-ethyl-6-fluoro-2-methyl-8-(1,3-oxazol-5-yl)imidazo[1,2-a]pyridine-3-carboxamide | 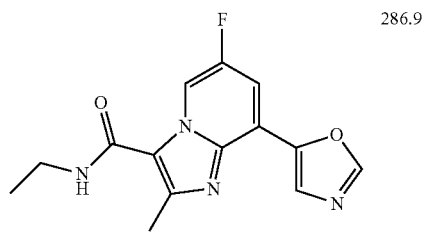 | 286.9 |
| 100 | N-ethyl-6-fluoro-N,2-dimethyl-8-(1,3-oxazol-5-yl)imidazo[1,2-a]pyridine-3-carboxamide | 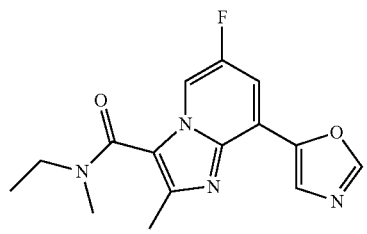 [SMILES: CCN(C)C(=O)c1c(C)nc2c(-c3cnco3)cc(F)cn12] | 303.2 |
| 101 | N-ethyl-2,6-dimethyl-8-(1,3-oxazol-5-yl)imidazo[1,2-a]pyridine-3-carboxamide | 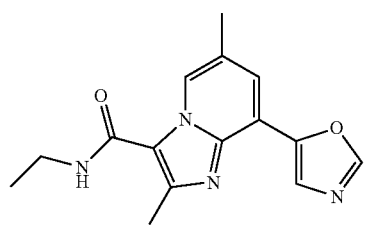 [SMILES: CCNC(=O)c1c(C)nc2c(-c3cnco3)cc(C)cn12] | 285.1 |
| 102 | N-ethyl-N,2,6-trimethyl-8-(1,3-oxazol-5-yl)imidazo[1,2-a]pyridine-3-carboxamide | 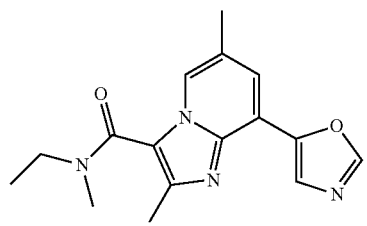 [SMILES: CCN(C)C(=O)c1c(C)nc2c(-c3cnco3)cc(C)cn12] | 299.2 |
| 103 | N-ethyl-N,2-dimethyl-8-(1,3-oxazol-5-yl)-6-(trifluoromethyl)imidazo[1,2-a]pyridine-3-carboxamide | 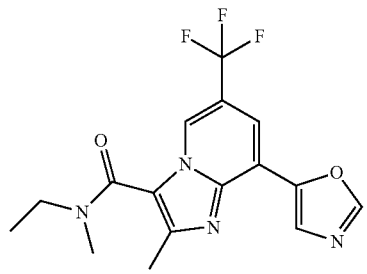 [SMILES: CCN(C)C(=O)c1c(C)nc2c(-c3cnco3)cc(C(F)(F)F)cn12] | 353.1 |
| 104 | (6-fluoro-8-(1,3-oxazol-5-yl)imidazo[1,2-a]pyridin-3-yl)((1S,4S)-2-oxa-5-azabicyclo[2.2.1]hept-5-yl)methanone | 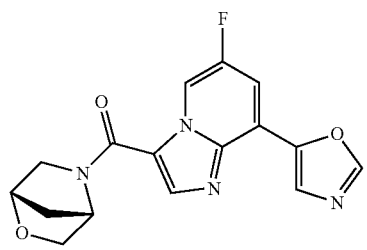 [SMILES: O=C(c1cnc2c(-c3cnco3)cc(F)cn12)N1C[C@@H]2C[C@H]1CO2] | 329.2 |

TABLE 14

| | | | |
|---|---|---|---|
| 105 | (3,3-difluoropyrrolidin-1-yl)(6-fluoro-8-(1,3-oxazol-5-yl)imidazo[1,2-a]pyridin-3-yl)methanone | | 337.0 |
| 106 | N-(cyclopropyl-6-fluoro-N-methyl-8-(1,3-oxazol-5-yl)imidazo[1,2-a]pyridine-3-carboxamide | | 301.1 |
| 107 | N-benzyl-8-(1,3-oxazol-5-yl)-6-(trifluoromethyl)[1,2,4]triazolo[4,3-a]pyridine-3-carboxamide | | 388.1 |
| 108 | 8-(1,3-oxazol-5-yl)-N-(tetrahydrofuran-2-ylmethyl)-6-(trifluoromethyl)[1,2,4]triazolo[4,3-a]pyridine-3-carboxamide | | 382.1 |
| 109 | N-benzyl-N-methyl-8-(1,3-oxazol-5-yl)-6-(trifluoromethyl)[1,2,4]triazolo[4,3-a]pyridine-3-carboxamide | | 402.1 |

TABLE 14-continued

| | | | |
|---|---|---|---|
| 110 | N-methyl-8-(1,3-oxazol-5-yl)-N-(tetrahydrofuran-2-ylmethyl)-6-(trifluoromethyl)[1,2,4]triazolo[4,3-a]pyridine-3-carboxamide | 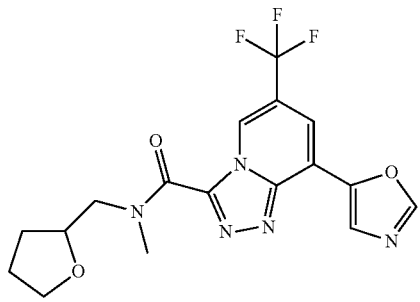 | 396.2 |
| 111 | 8-(1,3-oxazol-5-yl)-N-(tetrahydro-2H-pyran-4-yl)-6-(trifluoromethyl)[1,2,4]triazolo[4,3-a]pyridine-3-carboxamide | 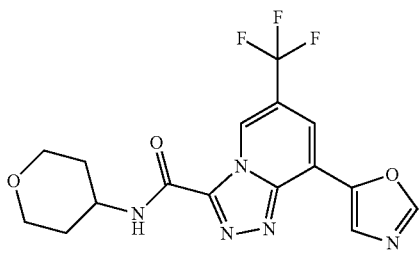 [SMILES: O=C(NC1CCOCC1)c1nnc2c(-c3cnco3)cc(C(F)(F)F)cn12] | 382.1 |
| 112 | N-methyl-8-(1,3-oxazol-5-yl)-N-(tetrahydro-2H-pyran-4-yl)-6-(trifluoromethyl)[1,2,4]triazolo[4,3-a]pyridine-3-carboxamide | 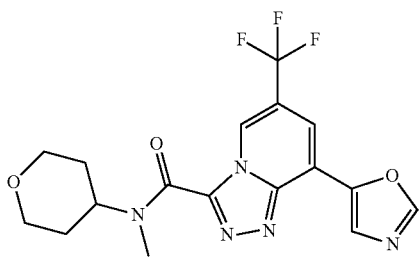 [SMILES: CN(C(=O)c1nnc2c(-c3cnco3)cc(C(F)(F)F)cn12)C1CCOCC1] | 396.2 |

TABLE 15

| | | | |
|---|---|---|---|
| 113 | N-(cyclopropylmethyl)-8-(1,3-oxazol-5-yl)-6-(trifluoromethyl)[1,2,4]triazolo[4,3-a]pyridine-3-carboxamide | 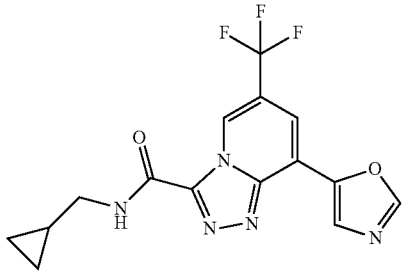 [SMILES: O=C(NCC1CC1)c1nnc2c(-c3cnco3)cc(C(F)(F)F)cn12] | 352.0 |
| 114 | N,N-dimethyl-8-(1,3-oxazol-5-yl)-6-(trifluoromethyl)[1,2,4]triazolo[4,3-a]pyridine-3-carboxamide | 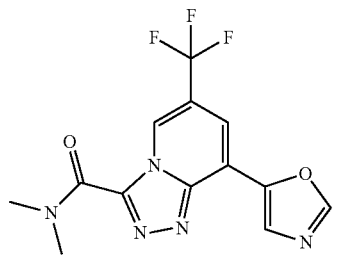 [SMILES: CN(C)C(=O)c1nnc2c(-c3cnco3)cc(C(F)(F)F)cn12] | 326.2 |

TABLE 15-continued

| | | | |
|---|---|---|---|
| 115 | (4,4-difluoropiperidin-1-yl)(8-(1,3-oxazol-5-yl)-6-(trifluoromethyl)imidazo[1,2-a]pyridin-3-yl)methanone | 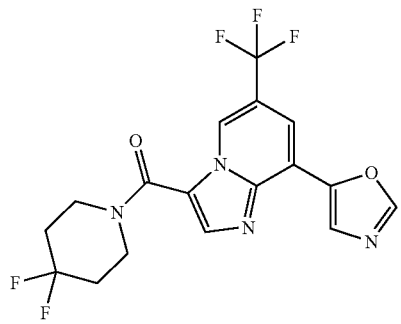 [SMILES: O=C(c1cnc2c(-c3cnco3)cc(C(F)(F)F)cn12)N1CCC(F)(F)CC1] | 401.1 |
| 116 | (6-cyclopropyl-8-(1,3-oxazol-5-yl)imidazo[1,2-a]pyridin-3-yl)((1S,4S)-2-oxa-5-azabicyclo[2.2.1]hept-5-yl)methanone | 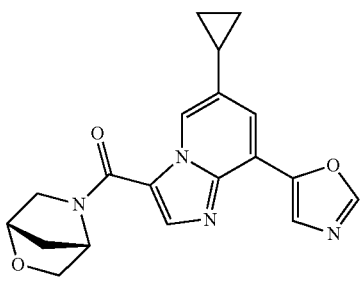 [SMILES: O=C(c1cnc2c(-c3cnco3)cc(C3CC3)cn12)N1C[C@@H]2C[C@H]1CO2] | 351.2 |
| 117 | 8-(1,3-oxazol-5-yl)-N-((3R)-tetrahydrofuran-3-yl)-6-(trifluoromethyl)imidazo[1,2-a]pyridine-4-carboxamide | 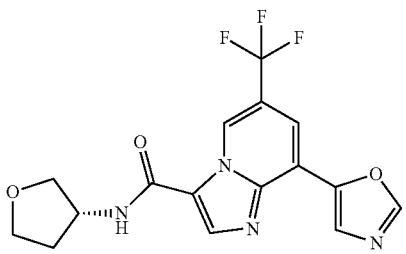 [SMILES: O=C(N[C@@H]1CCOC1)c1cnc2c(-c3cnco3)cc(C(F)(F)F)cn12] | 364.9 |
| 118 | N-methyl-8-(1,3-oxazol-5-yl)-N-((3R)-tetrahydrofuran-3-yl)-6-(trifluoromethyl)imidazo[1,2-a]pyridine-3-carboxamide | 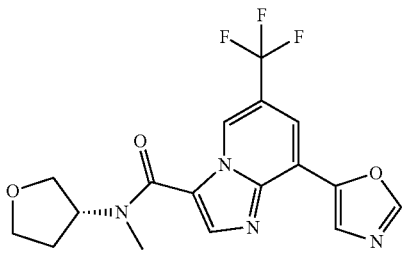 [SMILES: CN(C(=O)c1cnc2c(-c3cnco3)cc(C(F)(F)F)cn12)[C@@H]1CCOC1] | 381.1 |
| 119 | 8-(1,3-oxazol-5-yl)-N-(tetrahydrofuran-2-ylmethyl)-6-(trifluoromethyl)imidazo[1,2-a]pyridine-3-carboxamide | 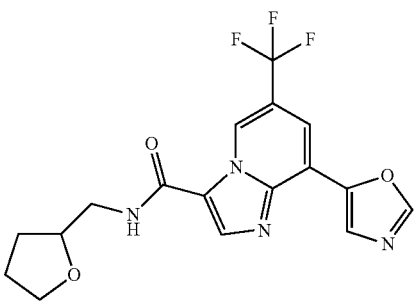 [SMILES: O=C(NCC1CCCO1)c1cnc2c(-c3cnco3)cc(C(F)(F)F)cn12] | 378.9 |

TABLE 15-continued

| 120 | morpholin-4-yl(8-(1,3-oxazol-5-yl)-6-(trifluoromethyl)[1,2,4]triazolo[4,3-a]pyridin-3-yl)methanone | 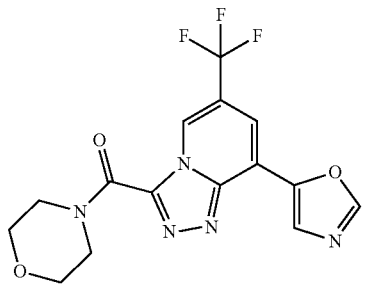 [SMILES: O=C(c1nnc2c(-c3cnco3)cc(C(F)(F)F)cn12)N1CCOCC1] | 368.0 |

TABLE 16

| 121 | 8-(1,3-oxazol-5-yl)-N-((3S)-tetrahydrofuran-3-yl)-6-(trifluoromethyl)imidazo[1,2-a]pyridine-3-carboxamide | 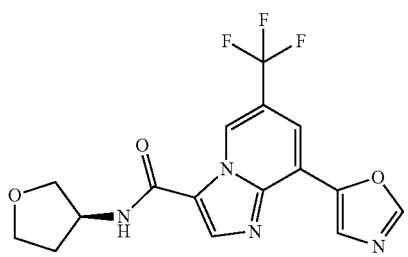 [SMILES: O=C(N[C@H]1CCOC1)c1cnc2c(-c3cnco3)cc(C(F)(F)F)cn12] | 364.9 |
| 122 | N-methyl-8-(1,3-oxazol-5-yl)-N-(tetrahydrofuran-2-ylmethyl)-6-(trifluoromethyl)imidazo[1,2-a]pyridine-3-carboxamide | 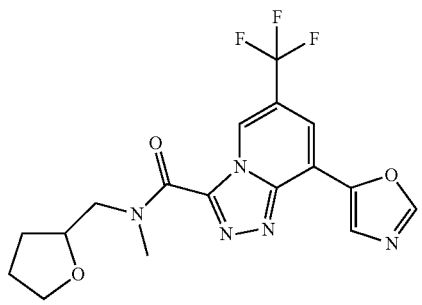 [SMILES: CN(CC1CCCO1)C(=O)c1nnc2c(-c3cnco3)cc(C(F)(F)F)cn12] | 395.2 |
| 123 | N-methyl-8-(1,3-oxazol-5-yl)-N-((3S)-tetrahydrofuran-3-yl)-6-(trifluoromethyl)imidazo[1,2-a]pyridine-3-carboxamide | 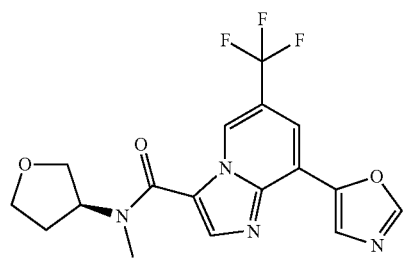 [SMILES: CN(C(=O)c1cnc2c(-c3cnco3)cc(C(F)(F)F)cn12)[C@H]1CCOC1] | 381.1 |
| 124 | N-(cyclopropylmethyl)-N-methyl-8-(1,3-oxazol-5-yl)-6-(trifluoromethyl)[1,2,4]triazolo[4,3-a]pyridine-3-carboxamide | 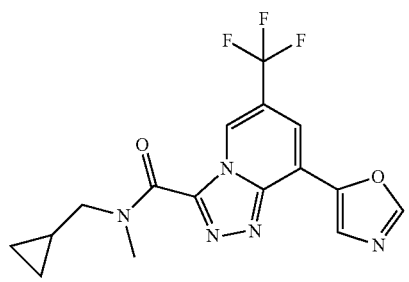 [SMILES: CN(CC1CC1)C(=O)c1nnc2c(-c3cnco3)cc(C(F)(F)F)cn12] | 366.1 |

TABLE 16-continued

| | | | |
|---|---|---|---|
| 125 | (8-(1H-imidazol-1-yl)-6-(trifluoromethyl)imidazo[1,2-a]pyridin-3-yl)((1S,4S)-2-oxa-5-azabicyclo[2.2.1]hept-5-yl)methanone | 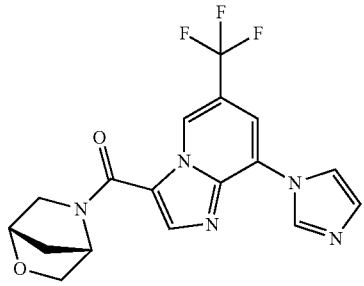 [SMILES: O=C(c1cnc2c(-n3ccnc3)cc(C(F)(F)F)cn12)N1C[C@@H]2C[C@H]1CO2] | 378.1 |
| 126 | (5-methyl-7-(1,3-oxazol-5-yl)pyrazolo[1,5-a]pyridin-3-yl)((1S,4S)-2-oxa-5-azabicyclo[2.2.1]hept-5-yl)methanone | 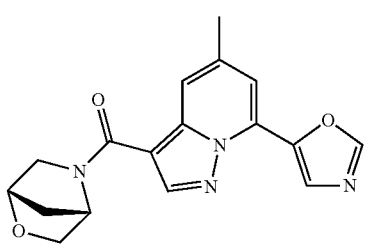 [SMILES: Cc1cc(-c2cnco2)n2ncc(C(=O)N3C[C@@H]4C[C@H]3CO4)c2c1] | 325.1 |
| 127 | N-(2,2-difluoromethyl)-8-(1,3-oxazol-5-yl)-6-(trifluoromethyl)[1,2,4]triazolo[4,3-a]pyridine-3-carboxamide | 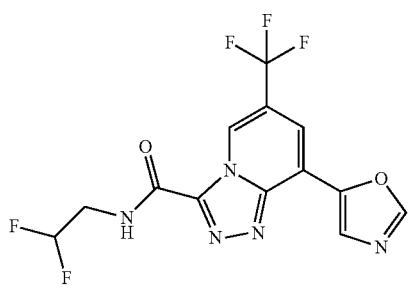 [SMILES: O=C(NCC(F)F)c1nnc2c(-c3cnco3)cc(C(F)(F)F)cn12] | 359.8 |
| 128 | (1S,4S)-2-oxa-5-azabicyclo[2.2.1]hept-5-yl(8-(1H-1,2,4-triazol-1-yl)-6-(trifluoromethyl)imidazo[1,2-a]pyridin-3-yl)methanone | 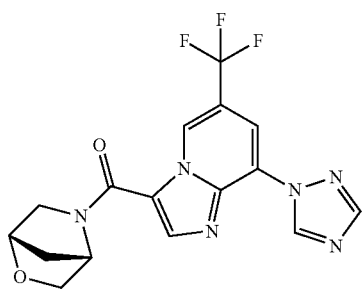 | 379.1 |

TABLE 17

| | | | |
|---|---|---|---|
| 129 | (1S,4S)-2-oxa-5-azabicyclo[2.2.1]hept-5-yl(8-(1H-pyrazol-5-yl)-6-(trifluoromethyl)imidazo[1,2-a]pyridin-3-yl)methanone | 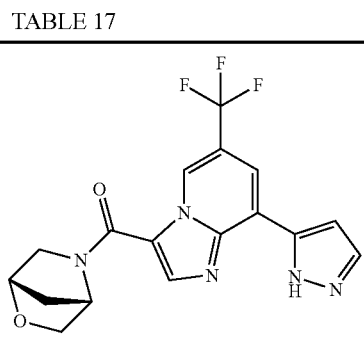 | 378.1 |

TABLE 17-continued

| | | | |
|---|---|---|---|
| 130 | 8-(1,3-oxazol-5-yl)-N-(tetrahydrofuran-3-ylmethyl)-6-(trifluoromethyl)imidazo[1,2-a]pyridine-3-carboxamide | 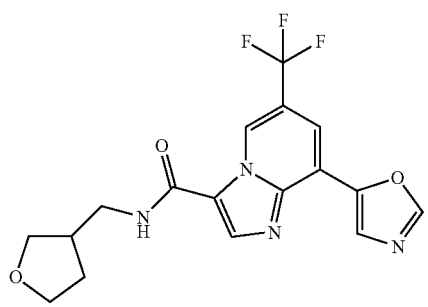 [SMILES: O=C(NCC1CCOC1)c1cnc2c(-c3cnco3)cc(C(F)(F)F)cn12] | 379.0 |
| 131 | N-methyl-8-(1,3-oxazol-5-yl)-N-(tetrahydrofuran-3-ylmethyl)-6-(trifluoromethyl)imidazo[1,2-a]pyridine-3-carboxamide | 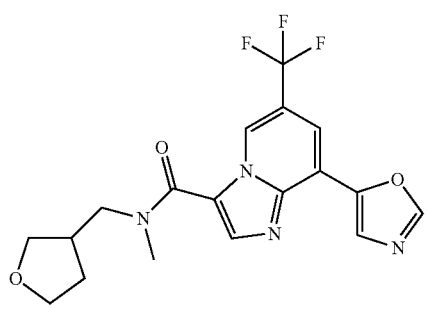 [SMILES: CN(CC1CCOC1)C(=O)c1cnc2c(-c3cnco3)cc(C(F)(F)F)cn12] | 395.2 |
| 132 | (6-methyl-8-(1,3-oxazol-5-yl)imidazo[1,2-a]pyridin-3-yl)(3-oxa-8-azabicyclo[3.2.1]oct-8-yl)methanone | 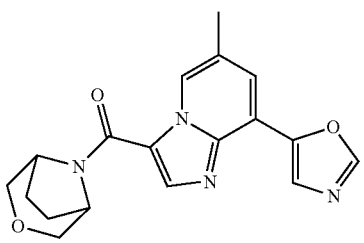 [SMILES: Cc1cc(-c2cnco2)c2ncc(C(=O)N3C4CCC3COC4)n2c1] | 339.2 |
| 133 | (6-methyl-8-(1,3-oxazol-5-yl)imidazo[1,2-a]pyridin-3-yl)(3-oxa-6-azabicyclo[3.1.1]hept-6-yl)methanone | 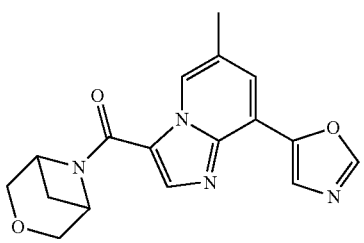 [SMILES: Cc1cc(-c2cnco2)c2ncc(C(=O)N3C4COCC3C4)n2c1] | 325.1 |
| 134 | (1S,4S)-2-oxa-5-azabicyclo[2.2.1]hept-5-yl(8-(1H-pyrazol-4-yl)-6-(trifluoromethyl)imidazo[1,2-a]pyridin-3-yl)methanone | 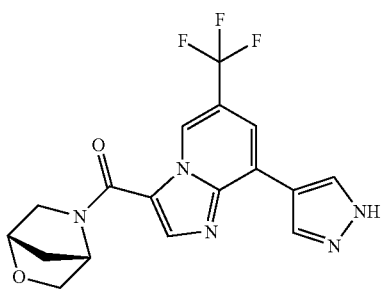 [SMILES: O=C(c1cnc2c(-c3cn[nH]c3)cc(C(F)(F)F)cn12)N1C[C@@H]2C[C@H]1CO2] | 378.1 |

TABLE 17-continued

| | | | |
|---|---|---|---|
| 135 | (1R,4R)-2-oxa-5-azabicyclo[2.2.1]hept-5-yl(8-(1,3-oxazol-5-yl)-6-(trifluoromethyl)imidazo[1,2-a]pyridin-3-yl)methanone | 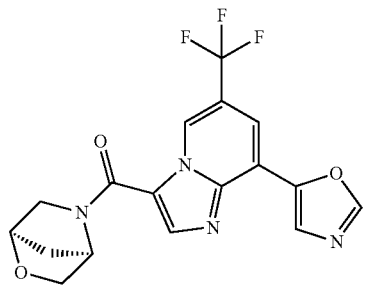 [SMILES: O=C(c1cnc2c(-c3cnco3)cc(C(F)(F)F)cn12)N1C[C@H]2C[C@@H]1CO2] | 379.1 |
| 136 | optically active N-methyl-8-(1,3-oxazol-5-yl)-N-(tetrahydrofuran-3-ylmethyl)-6-(trifluoromethyl)imidazo[1,2-a]pyridine-3-carboxamide | 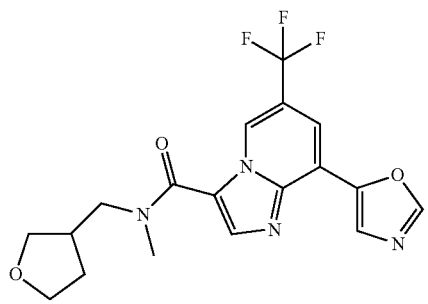 [SMILES: CN(CC1CCOC1)C(=O)c1cnc2c(-c3cnco3)cc(C(F)(F)F)cn12] | 395.2 |

TABLE 18

| | | | |
|---|---|---|---|
| 137 | optically active N-methyl-8-(1,3-oxazol-5-yl)-N-(tetrahydrofuran-3-ylmethyl)-6-(trifluoromethyl)imidazo[1,2-a]pyridine-3-carboxamide | 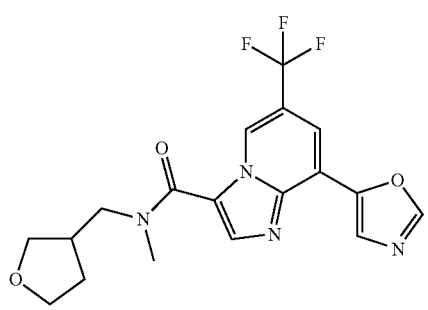 [SMILES: CN(CC1CCOC1)C(=O)c1cnc2c(-c3cnco3)cc(C(F)(F)F)cn12] | 395.2 |
| 138 | (6-fluoro-8-(1,3-oxazol-5-yl)imidazo[1,2-a]pyridin-3-yl)(3-oxa-8-azabicyclo[3.2.1]oct-8-yl)methanone | 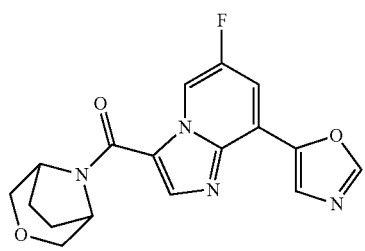 [SMILES: O=C(c1cnc2c(-c3cnco3)cc(F)cn12)N1C2CCC1COC2] | 343.0 |
| 139 | optically active N-methyl-8-(1,3-oxazol-5-yl)-N-(tetrahydrofuran-2-ylmethyl)-6-(trifluoromethyl)imidazo[1,2-a]pyridine-3-carboxamide | 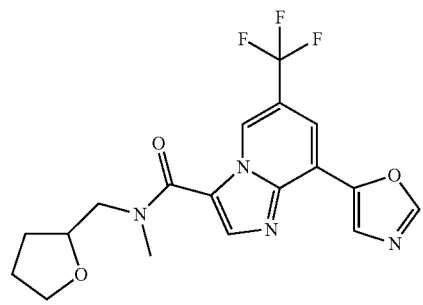 [SMILES: CN(CC1CCCO1)C(=O)c1cnc2c(-c3cnco3)cc(C(F)(F)F)cn12] | 395.2 |

TABLE 18-continued

| | | | |
|---|---|---|---|
| 140 | optically active N-methyl-8-(1,3-oxazol-5-yl)-N-(tetrahydrofuran-2-ylmethyl)-6-(trifluoromethyl)imidazo[1,2-a]pyridine-3-carboxamide | 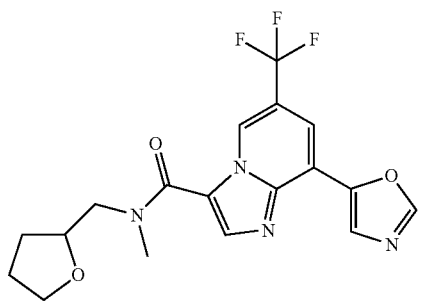 [SMILES: CN(CC1CCCO1)C(=O)c1cnc2c(-c3cnco3)cc(C(F)(F)F)cn12] | 395.2 |
| 141 | (8-(1-methyl-1H-pyrazol-4-yl)-6-(trifluoromethyl)imidazo[1,2-a]pyridin-3-yl)((1S,4S)-2-oxa-5-azabicyclo[2.2.1]hept-5-yl)methanone | 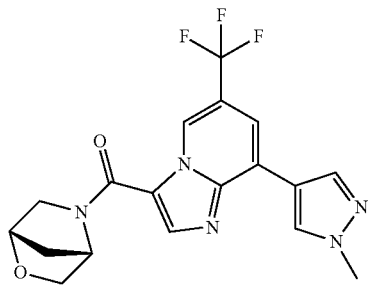 [SMILES: Cn1cc(-c2cc(C(F)(F)F)cn3c(C(=O)N4C[C@@H]5C[C@H]4CO5)cnc23)cn1] | 392.1 |
| 142 | 3-oxa-8-azabicyclo[3.2.1]oct-8-yl(8-(1H-1,2,4-triazol-1-yl)-6-(trifluoromethyl)imidazo[1,2-a]pyridin-3-yl)methanone | 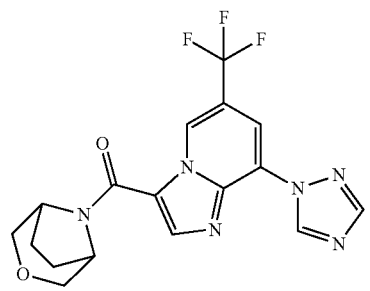 [SMILES: O=C(c1cnc2c(-n3cncn3)cc(C(F)(F)F)cn12)N1C2CCC1COC2] | 393.2 |
| 143 | (6-cyclopropyl-8-(1,3-oxazol-5-yl)imidazo[1,2-a]pyridin-3-yl)(3-oxa-8-azabicyclo[3.2.1]oct-8-yl)methanone | 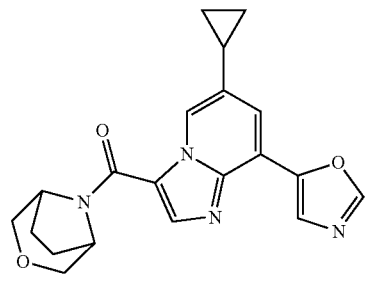 [SMILES: O=C(c1cnc2c(-c3cnco3)cc(C3CC3)cn12)N1C2CCC1COC2] | 365.1 |
| 144 | (3,3-difluoroazetidin-1-yl)(8-(1H-1,2,4-triazol-1-yl)-6-(trifluoromethyl)imidazo[1,2-a]pyridin-3-yl)methanone | 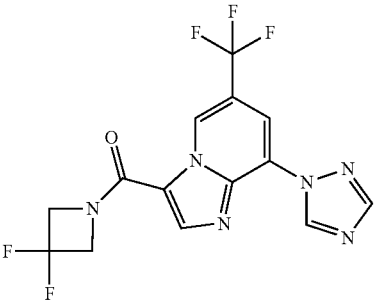 [SMILES: O=C(c1cnc2c(-n3cncn3)cc(C(F)(F)F)cn12)N1CC(F)(F)C1] | 373.1 |

TABLE 19

| | | | |
|---|---|---|---|
| 145 | N-methyl-N-(tetrahydro-2H-pyran-4-yl)-8-(1H-1,2,4-triazol-1-yl)-6-(trifluoromethyl)imidazo[1,2-a]pyridine-3-carboxamide | 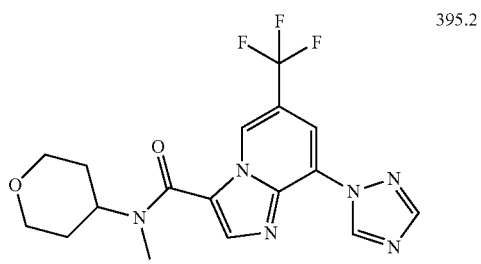 | 395.2 |
| 146 | ethyl 6-cyclopropyl-8-(1,3-oxazol-5-yl)imidazo[1,2-a]pyridine-3-carboxylate | 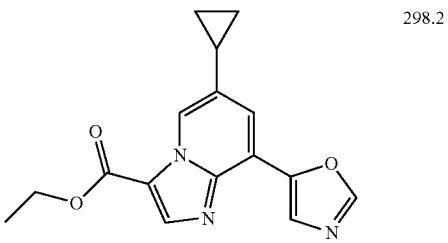 | 298.2 |
| 147 | (3,3-difluoroazetidin-1-yl)(6-ethyl-8-(1,3-oxazol-5-yl)imidazo[1,2-a]pyridin-3-yl)methanone | 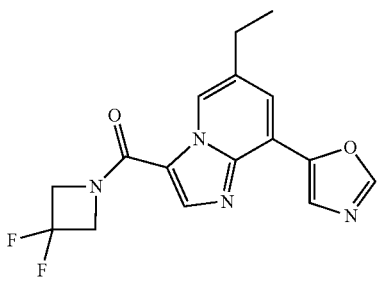 [SMILES: CCc1cc(-c2cnco2)c2ncc(C(=O)N3CC(F)(F)C3)n2c1] | 333.2 |
| 148 | (6-ethyl-8-(1,3-oxazol-5-yl)imidazo[1,2-a]pyridin-3-yl)((1S,4S)-2-oxa-5-azabicyclo[2.2.1]hept-5-yl)methanone | 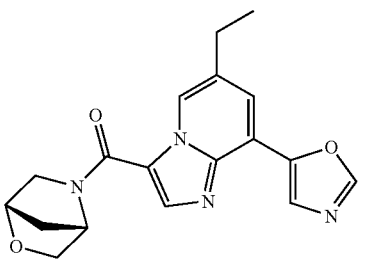 [SMILES: CCc1cc(-c2cnco2)c2ncc(C(=O)N3C[C@@H]4C[C@H]3CO4)n2c1] | 339.2 |
| 149 | (6-ethyl-8-(1,3-oxazol-5-yl)imidazo[1,2-a]pyridin-3-yl)(3-oxa-8-azabicyclo[3.2.1]oct-8-yl)methanone | 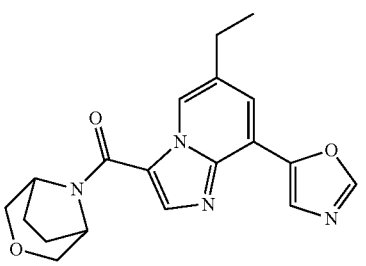 [SMILES: CCc1cc(-c2cnco2)c2ncc(C(=O)N3C4CCC3COC4)n2c1] | 353.1 |
| 150 | ethyl 6-ethyl-8-(1,3-oxazol-5-yl)imidazo[1,2-a]pyridine-3-carboxylate | 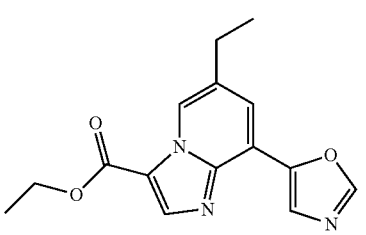 [SMILES: CCOC(=O)c1cnc2c(-c3cnco3)cc(CC)cn12] | 286.1 |

TABLE 19-continued

| | | | |
|---|---|---|---|
| 151 | 6-oxa-3-azabicyclo[3.1.1]hept-3-yl(8-(1,3-oxazol-5-yl)-6-(trifluoromethyl)imidazo[1,2-a]pyridin-3-yl)methanone | 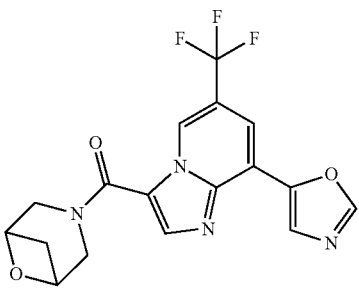 [SMILES: O=C(c1cnc2c(-c3cnco3)cc(C(F)(F)F)cn12)N1CC2CC(C1)O2] | 379.1 |
| 152 | ethyl 6-cyano-8-(1,3-oxazol-5-yl)imidazo[1,2-a]pyridine-3-carboxylate | 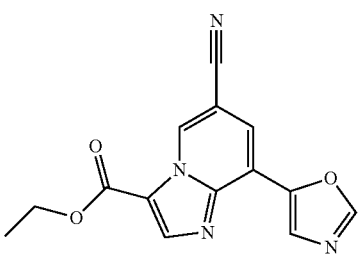 [SMILES: CCOC(=O)c1cnc2c(-c3cnco3)cc(C#N)cn12] | 283.2 |

TABLE 20

| | | | |
|---|---|---|---|
| 153 | 3-(3-oxa-8-azabicyclo[3.2.1]oct-8-yl)carbonyl)-8-(1,3-oxazol-5-yl)imidazo[1,2-a]pyridine-6-carbonitrile | 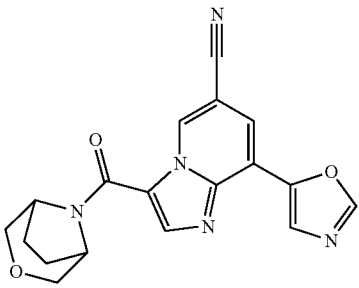 [SMILES: N#Cc1cc(-c2cnco2)c2ncc(C(=O)N3C4CCC3COC4)n2c1] | 350.1 |
| 154 | (3,3-difluoropyridin-1-yl)(8-(1H-1,2,4-triazol-1-yl)-6-(trifluoromethyl)imidazo[1,2-a]pyridin-3-yl)methanone | 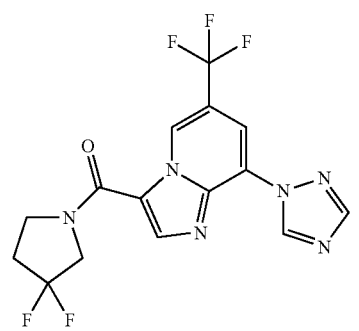 [SMILES: O=C(c1cnc2c(-n3cncn3)cc(C(F)(F)F)cn12)N1CCC(F)(F)C1] | 387.1 |
| 155 | 1-(3-(((1S,4S)-2-oxa-5-azabicyclo[2.2.1]hept-5-ylcarbonyl)-8-(1,3-oxazol-5-yl)imidazo[1,2-a]pyridin-6-yl)ethanone | 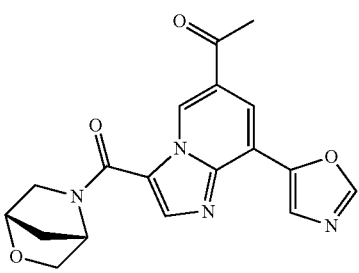 [SMILES: CC(=O)c1cc(-c2cnco2)c2ncc(C(=O)N3C[C@@H]4C[C@H]3CO4)n2c1] | 353.1 |

TABLE 20-continued

| 156 | 3-oxa-6-azabicyclo[3.1.1]hept-6-yl(8-(1H-1,2,4-triazol-1-yl)-6-(trifluoromethyl)imidazo[1,2-a]pyridin-3-yl)methanone | 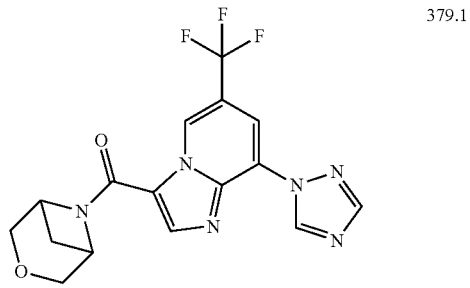 | 379.1 |
| 157 | ((3S)-3-hydroxypyrrolidin-1-yl)(8-(1H-1,2,4-triazol-1-yl)-6-(trifluoromethyl)imidazo[1,2-a]pyridin-3-yl)methanone | 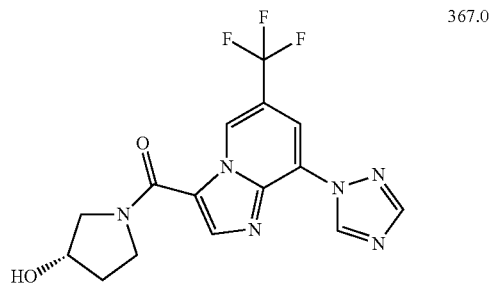 | 367.0 |
| 158 | 2-oxa-6-azaspiro[3.4]oct-6-yl(8-(1H-1,2,4-triazol-1-yl)-6-(trifluoromethyl)imidazo[1,2-a]pyridin-3-yl)methanone | 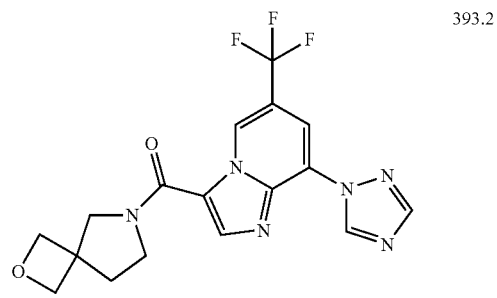 | 393.2 |
| 159 | ((3S)-3-(difluoromethoxy)pyrrolidin-1-yl)(8-(1H-1,2,4-triazol-1-yl)-6-(trifluoromethyl)imidazo[1,2-a]pyridin-3-yl)methanone | 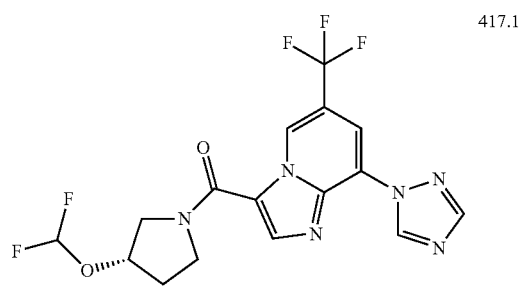 | 417.1 |
| 160 | (6-(difluoromethyl)-8-(1H-1,2,4-triazol-1-yl)imidazo[1,2-a]pyridin-3-yl)(3-oxa-8-azabicyclo[3.2.1]oct-8-yl)methanone | 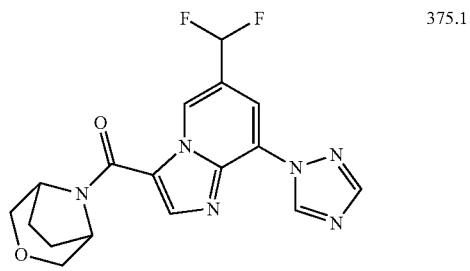 | 375.1 |

TABLE 21

| # | Name | Structure | Mass |
|---|---|---|---|
| 161 | (3,3-difluoroazetidin-1-yl)(6-(difluoromethyl)-8-(1H-1,2,4-triazol-1-yl)imidazo[1,2-a]pyridin-3-yl)methanone | 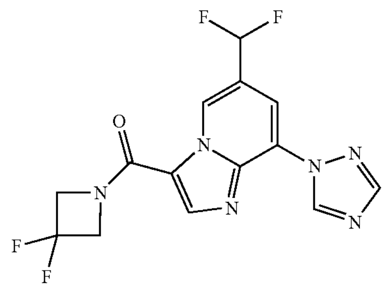 [SMILES: O=C(c1cnc2c(-n3cncn3)cc(C(F)F)cn12)N1CC(F)(F)C1] | 355.1 |
| 162 | ethyl 6-(difluoromethyl)-8-(1H-1,2,4-triazol-1-yl)imidazo[1,2-a]pyridine-3-carboxylate | 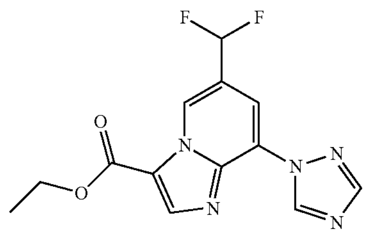 [SMILES: CCOC(=O)c1cnc2c(-n3cncn3)cc(C(F)F)cn12] | 308.2 |
| 163 | (6-methyl-8-(1H-1,2,4-triazol-1-yl)imidazo[1,2-a]pyridin-3-yl)(3-oxa-8-azabicyclo[3.2.1]oct-8-yl)methanone | 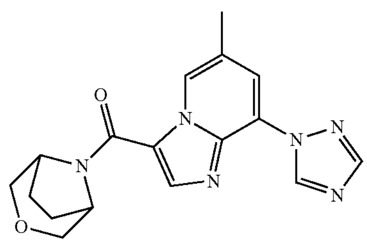 [SMILES: Cc1cc(-n2cncn2)c2ncc(C(=O)N3C4CCC3COC4)n2c1] | 339.2 |
| 164 | (3,3-difluoroazetidin-1-yl)(6-methyl-8-(1H-1,2,4-triazol-1-yl)imidazo[1,2-a]pyridin-3-yl)methanone | 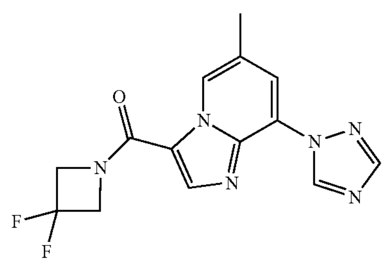 [SMILES: Cc1cc(-n2cncn2)c2ncc(C(=O)N3CC(F)(F)C3)n2c1] | 319.1 |
| 165 | ethyl 6-methyl-8-(1H-1,2,4-triazol-1-yl)imidazo[1,2-a]pyridine-3-carboxylate | 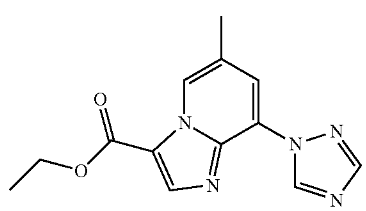 [SMILES: CCOC(=O)c1cnc2c(-n3cncn3)cc(C)cn12] | 272.1 |
| 166 | ethyl 6-(ethoxymethyl)-8-(1H-1,2,4-triazol-1-yl)imidazo[1,2-a]pyridine-3-carboxylate | 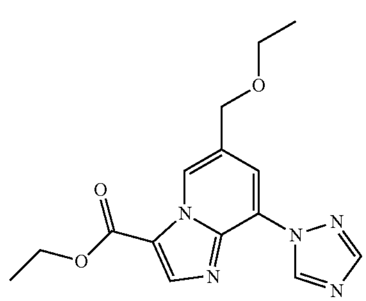 [SMILES: CCOCc1cc(-n2cncn2)c2ncc(C(=O)OCC)n2c1] | 316.2 |

TABLE 21-continued

| | | | |
|---|---|---|---|
| 167 | ethyl 6-cyclopropyl-8-(1H-1,2,4-triazol-1-yl)imidazo[1,2-a]pyridine-3-carboxylate | 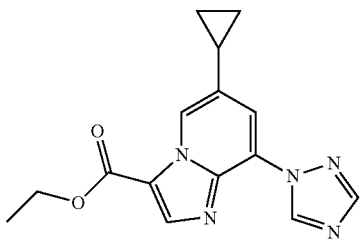 [SMILES: CCOC(=O)c1cnc2c(-n3cncn3)cc(C3CC3)cn12] | 298.1 |
| 168 | ethyl 6-(1,1-difluoroethyl)-8-(1,3-oxazol-5-yl)imidazo[1,2-a]pyridine-3-carboxylate | 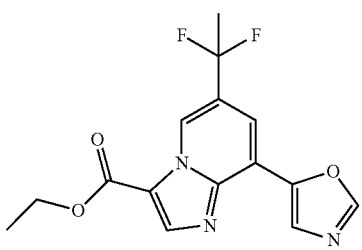 [SMILES: CCOC(=O)c1cnc2c(-c3cnco3)cc(C(C)(F)F)cn12] | 322.1 |

TABLE 22

| | | | |
|---|---|---|---|
| 169 | (6-(1,1-difluoroethyl)-8-(1,3-oxazol-5-yl)imidazo[1,2-a]pyridin-3-yl)(3-oxa-8-azabicyclo[3.2.1]oct-8-yl)methanone | 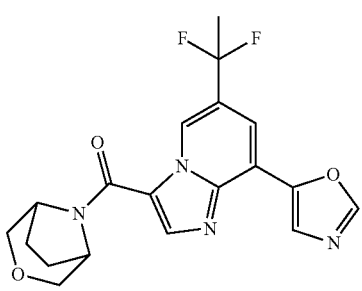 [SMILES: CC(F)(F)c1cc(-c2cnco2)c2ncc(C(=O)N3C4CCC3COC4)n2c1] | 389.1 |
| 170 | (6-(1,1-difluoroethyl)-8-(1,3-oxazol-5-yl)imidazo[1,2-a]pyridin-3-yl)((1S,4S)-2-oxa-5-azabicyclo[2.2.1]hept-5-yl)methanone | 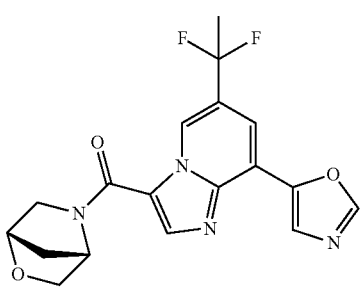 [SMILES: CC(F)(F)c1cc(-c2cnco2)c2ncc(C(=O)N3C[C@@H]4C[C@H]3CO4)n2c1] | 375.1 |
| 171 | (6-(difluoromethyl)-8-(1,3-oxazol-5-yl)imidazo[1,2-a]pyridin-3-yl)((1S,4S)-2-oxa-5-azabicyclo[2.2.1]hept-5-yl)methanone | 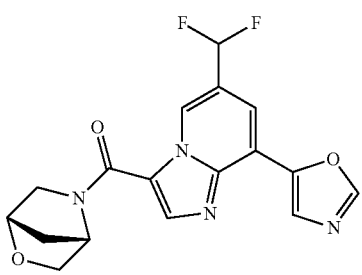 [SMILES: O=C(c1cnc2c(-c3cnco3)cc(C(F)F)cn12)N1C[C@@H]2C[C@H]1CO2] | 361.1 |

TABLE 22-continued

| | | | |
|---|---|---|---|
| 172 | (6-(difluoromethyl)-8-(1,3-oxazol-5-yl)imidazo[1,2-a]pyridin-3-yl)(3-oxa-8-azabicyclo[3.2.1]oct-8-yl)methanone | 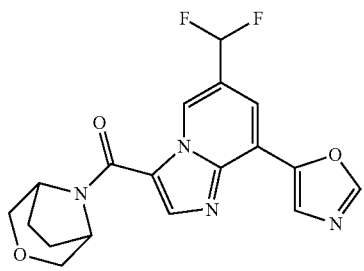 [SMILES: O=C(c1cnc2c(-c3cnco3)cc(C(F)F)cn12)N1C2CCC1COC2] | 375.1 |
| 173 | (3,3-difluoroazetidin-1-yl)(6-(difluoromethyl)-8-(1,3-oxazol-5-yl)imidazo[1,2-a]pyridin-3-yl)methanone | 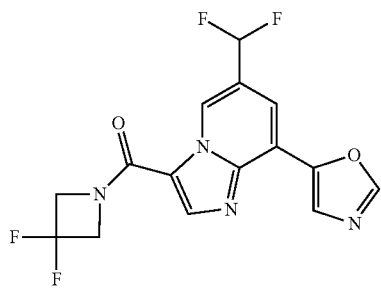 [SMILES: O=C(c1cnc2c(-c3cnco3)cc(C(F)F)cn12)N1CC(F)(F)C1] | 355.0 |

TABLE 23

| Example | IUPAC Name | Structure | MS |
|---|---|---|---|
| 174 | (1,1-dioxidothiomorpholin-4-yl)(8-(1,3-oxazol-5-yl)-6-(trifluoromethyl)imidazo[1,2-a]pyridin-3-yl)methanone | 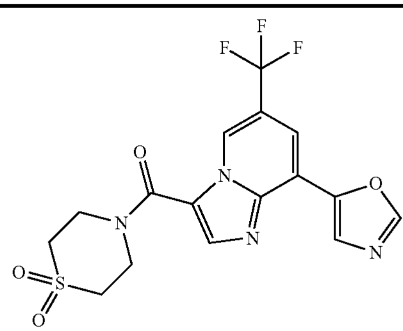 | 413.1 |
| 175 | (2R)-1-((8-(1,3-oxazol-5-yl)-6-(trifluoromethyl)imidazo[1,2-a]pyridin-3-yl)carbonyl)pyrrolidine-2-carbonitrile | 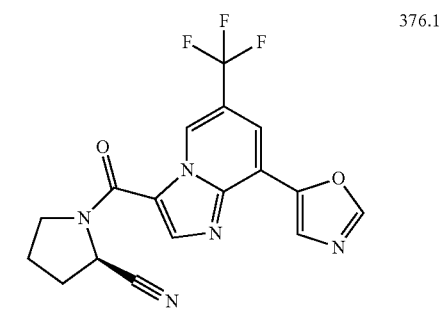 | 376.1 |
| 176 | 3,7-dioxa-9-azabicyclo[3.3.1]non-9-yl(8-(1,3-oxazol-5-yl)-6-(trifluoromethyl)imidazo[1,2-a]pyridin-3-yl)methanone | 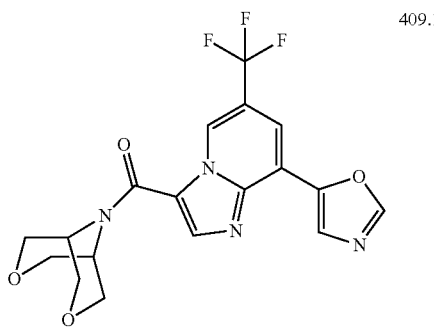 | 409.1 |

TABLE 23-continued

| Example | IUPAC Name | Structure | MS |
|---|---|---|---|
| 177 | (3-fluoroazetidin-1-yl)(8-(1,3-oxazol-5-yl)-6-(trifluoromethyl)imidazo[1,2-a]pyridin-3-yl)methanone | 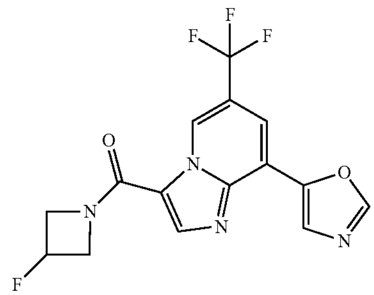 [SMILES: O=C(c1cnc2c(-c3cnco3)cc(C(F)(F)F)cn12)N1CC(F)C1] | 355.0 |

Formulation Example 1 (production of capsule)

| | |
|---|---|
| 1) compound of Example 1 | 30 mg |
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin capsule.

Formulation Example 2 (production of tablet)

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

Experimental Example 1

Construction of Human CH24H (CYP46) Expression Vector

A plasmid DNA for expressing human CH24H in a FreeStyle 293 cell was produced as follows. Using Full-Length Mammalian Gene Collection No. 4819975 (Invitrogen) as a template, and the following two kinds of synthesized DNAs:

```
                                      (SEQ ID NO: 1)
5'-GCCCCGGAGCCATGAGCCCCGGGCTG-3'
and (SEQ ID NO: 2)
5'-GTCCTGCCTGGAGGCCCCCTCAGCAG-3',
```

PCR was performed to amplify 91-1625 by region of human CH24H (BC022539). The obtained fragment was cloned using TOPO TA Cloning Kit (Invitrogen). The obtained fragment was subcloned to pcDNA3.1(+) digested with BamHI and XhoI to give a plasmid DNA for human CH24H expression (pcDNA3.1(+)/hCH24H).

Experimental Example 2

Expression of Human CH24H and Preparation of Human CH24H Lysate

The expression of human CH24H was performed using FreeStyle 293 Expression System (Invitrogen). According to the manual attached to FreeStyle 293 Expression System and using the plasmid DNA for human CH24H expression (pcDNA3.1(+)/hCH24H) constructed in Experimental Example 1, a transient expression using FreeStyle 293-F cell was performed. After transfection, the cells were cultured at 37° C., 8% $CO_2$ with shaking at 125 rpm for 2 days. The cells were collected by centrifugation, and suspended in a suspension buffer (100 mM potassium phosphate (pH 7.4), 0.1 mM EDTA, 1 mM DTT, 20% Glycerol). The suspended product was disrupted by a polytron homogenizer (manufactured by Kinematica), and centrifuged at 9000×g for 10 min, and the supernatant was collected. The collected supernatant was cryopreserved (−80° C.) as a human CH24H lysate standard product.

Experimental Example 3

Measurement of CH24H Inhibitory Activity

For the measurement of CH24H inhibitory activity, using the human CH24H lysate prepared in Experimental Example 2, the amount of 24-HC produced from cholesterol by catalytic activity of CH24H was measured in the presence of a test compound, and compared with that measured in the absence of the test compound. That is, a test compound solution at various concentrations was mixed with a reaction buffer (50 mM potassium phosphate containing 0.1% BSA and Complete, EDTA-free, pH 7.4) and human CH24H lysate. Then, [$^{14}$C] cholesterol (53 mCi/mmol specific activity, 15 μM) was added, and CH24H reaction was performed at 37° C. for 5 hr. After completion of the reaction, a quenching solution consisting of chloroform/methanol/distilled water (2:2:1 v/v) was added, and the resulting 24-HC was extracted by shaking. The extract was applied to silica gel thin layer chromatography (ethyl acetate:toluene=4:6), and the obtained $^{14}$C-24HC fraction was measured with BAS2500 (Fujifilm Corporation).

The inhibitory rate (%) was calculated from the ratio of radioactivity in the presence of a test compound relative to the radioactivity in the absence of the test compound. The results are shown in the following Tables 24 and 25.

TABLE 24

| Test Compound | Inhibitory Rate (%) in 1 μM |
| --- | --- |
| Example 1 | 86 |
| Example 2 | 89 |
| Example 4 | 88 |
| Example 16 | 87 |
| Example 21 | 99 |
| Example 22 | 93 |
| Example 44 | 93 |
| Example 47 | 92 |
| Example 58 | 80 |
| Example 71 | 88 |
| Example 74 | 96 |
| Example 78 | 94 |
| Example 85 | 88 |
| Example 86 | 95 |
| Example 87 | 94 |
| Example 90 | 91 |
| Example 92 | 86 |
| Example 93 | 68 |
| Example 98 | 69 |
| Example 107 | 89 |
| Example 116 | 90 |
| Example 126 | 93 |
| Example 128 | 86 |
| Example 134 | 71 |
| Example 138 | 82 |
| Example 142 | 87 |
| Example 143 | 91 |
| Example 155 | 84 |
| Example 156 | 94 |
| Example 171 | 91 |

TABLE 25

| Test Compound | Inhibitory Rate (%) in 1 μM |
| --- | --- |
| Example 175 | 80 |
| Example 176 | 94 |
| Example 177 | 86 |

Experimental Example 4

Quantification Test of 24-HC

Animals used were 6-week-old female C57BL/6N mice (3 mice/group). A test compound was suspended in a 0.5% aqueous methylcellulose [133-14255 WAKO] solution (1 mg/mL). The body weight of the mice was measured, and the solution was forcibly administered orally and repeatedly once a day for 3 days. At 16 hours after the third administration, half of the brain was harvested, and the amount of 24-HC was measured.

The wet weight of the brain was measured, and the brain was homogenized with about 4-fold amount (0.5 mL) of saline. This solution was used as a brain extract. The 24-HC in the brain extract was extracted with an acetonitrile solution (98% acetonitrile, 1.98% methanol, 0.02% formic acid), and quantified by HPLC. The average value of 24-HC amount was calculated and the results are shown in relative values with the control group as 100%. The results are shown in the following Table 26.

TABLE 26

| Test Compound | Decreasing Rate (%) in 30 mg/kg |
| --- | --- |
| Example 21 | 56 |
| Example 47 | 67 |
| Example 52 | 52 |
| Example 63 | 57 |
| Example 66 | 67 |
| Example 71 | 79 |
| Example 77 | 53 |
| Example 85 | 71 |
| Example 86 | 67 |
| Example 90 | 70 |
| Example 147 | 79 |

Experimental Example 5

Novel Object Recognition Test Using an APP Transgenic Mouse (Tg2576)

Animals used were 6-week-old Tg2576 mice and their wild-type mice (10 mice/group). A test compound was suspended in a 0.5% aqueous methyl cellulose [133-14255 WAKO] solution (3 mg/mL). The body weight of the mice was measured, and the solution was forcibly administered orally and repeatedly at 10 mL/kg once a day for 6 weeks. Then, a novel object recognition test was performed as follows. On the day before acquisition trial, the mice kept in the same cage were put in an observation box in which the illuminance was set to 300 lx, and habituated for 30 min. After the habituation, a compound was orally administered. On the next day, the mice were put, as an acquisition trial, in an observation box in which two same objects were placed, and the number and duration of contacts to the objects were measured for 5 min under 300 lx. A compound was orally administered after the measurement. The day after the acquisition trial, the one object was replaced with a novel object, and the number and duration of contacts to each of the object were measured for 5 min. A metal cylinder and ceramic triangular pyramid were used in this test. A control group (test compound-untreated group) and a control group in wild-type mice were used for comparison. The results are shown as the rate (%) of the number and duration of contacts to the novel object relative to the total number and duration of contacts to the objects. The results are shown in the following Table 27.

TABLE 27

| | | wild-type mice control group | APP transgenic mouse | |
| --- | --- | --- | --- | --- |
| | | | control group | Example 85 |
| exploration Rate (%) of Novel Object | number of contacts | 61.2 | 50.0 | 54.4 |
| | duration of contacts | 69.7 | 52.1 | 61.8 |

INDUSTRIAL APPLICABILITY

The compound of the present invention has a superior CH24H inhibitory action, which is useful as an agent for the prophylaxis or treatment of neurodegenerative disease (e.g., Alzheimer's disease, mild cognitive impairment, Huntington's disease, Parkinson's disease, amyotrophic lateral sclerosis, traumatic brain injury, cerebral infarction, glaucoma, multiple sclerosis etc.), epilepsy, schizophrenia or the like.

This application is based on patent application No. 2012-229227 filed in Japan, the contents of which are encompassed in full herein.

The invention claimed is:

1. A compound represented by the formula (I):

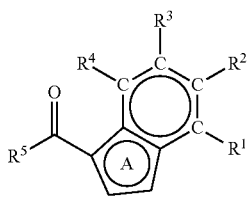

wherein
$R^1$ is a 5-membered nitrogen-containing aromatic heterocyclic group optionally substituted by 1 to 3 substituents selected from (1) an optionally substituted $C_{1-6}$ alkyl group, (2) a halogen atom, (3) an optionally substituted hydroxy group, (4) an optionally substituted sulfanyl group, and (5) an optionally substituted amino group;
$R^2$ is a hydrogen atom or a substituent;
$R^3$ is an optionally substituted $C_{1-6}$ alkyl group, a halogen atom, a cyano group, an acyl group, an optionally substituted hydroxy group, an optionally substituted sulfanyl group, an optionally substituted amino group, an optionally substituted carbocyclic group, or an optionally substituted heterocyclic group;
$R^4$ is a hydrogen atom or a substituent;
$R^5$ is an optionally substituted $C_{1-6}$ alkyl group, an optionally substituted hydroxy group, an optionally substituted amino group, an optionally substituted carbocyclic group, or an optionally substituted heterocyclic group; and
Ring A is an optionally further substituted 5-membered aromatic heterocycle,
or a salt thereof.

2. The compound or salt of claim 1, wherein $R^1$ is a 5-membered nitrogen-containing aromatic heterocyclic group optionally substituted by 1 to 3 optionally substituted $C_{1-6}$ alkyl group(s).

3. The compound or salt of claim 1, wherein $R^2$ is a hydrogen atom.

4. The compound or salt of claim 1, wherein $R^3$ is an optionally substituted $C_{1-6}$ alkyl group, a halogen atom, a cyano group, an acyl group, an optionally substituted $C_{3-8}$ cycloalkyl group, or an optionally substituted 5- or 6-membered aromatic heterocyclic group.

5. The compound or salt of claim 1, wherein $R^4$ is a hydrogen atom.

6. The compound or salt of claim 1, wherein $R^5$ is an optionally substituted $C_{1-6}$ alkyl group, an optionally substituted hydroxy group, an optionally substituted amino group, an optionally substituted $C_{3-8}$ cycloalkyl group, or an optionally substituted 3- to 12-membered non-aromatic heterocyclic group.

7. The compound or salt of claim 1, wherein Ring A is an optionally further substituted 5-membered nitrogen-containing aromatic heterocycle.

8. The compound or salt of claim 1, wherein
$R^1$ is
(1) an oxazolyl group,
(2) an imidazolyl group,
(3) a triazolyl group, or
(4) a pyrazolyl group,
each of which is optionally substituted by one $C_{1-6}$ alkyl group;
$R^2$ is a hydrogen atom;
$R^3$ is
(1) a $C_{1-6}$ alkyl group optionally substituted by 1 to 3 substituents selected from
   (a) a halogen atom, and
   (b) a $C_{1-6}$ alkoxy group,
(2) a halogen atom,
(3) a cyano group,
(4) a $C_{1-6}$ alkyl-carbonyl group,
(5) a $C_{3-8}$ cycloalkyl group, or
(6) an oxazolyl group;
$R^4$ is a hydrogen atom;
$R^5$ is
(1) a hydroxy group,
(2) a $C_{1-6}$ alkoxy group,
(3) an amino group optionally mono- or di-substituted by substituent(s) selected from (a) a $C_{1-6}$ alkyl group optionally substituted by 1 to 3 substituents selected from
  (i) a $C_{1-6}$ alkoxy group,
  (ii) a $C_{3-6}$ cycloalkyl group,
  (iii) a halogen atom,
  (iv) an oxetanyl group and a tetrahydrofuranyl group, each of which is optionally substituted by one $C_{1-6}$ alkyl group, and
  (v) a $C_{6-14}$ aryl group,
(b) a $C_{3-8}$ cycloalkyl group,
(c) an oxetanyl group, a tetrahydropyranyl group and a tetrahydrofuranyl group, and
(d) a $C_{6-14}$ aryl group,
(4) a $C_{3-8}$ cycloalkyl group, or
(5) an azetidinyl group, a pyrrolidinyl group, a morpholinyl group, a piperazinyl group, a piperidyl group, an oxazepanyl group, an 8-oxa-3-azabicyclo[3.2.1]octyl group, a 3-azabicyclo[3.1.0]hexyl group, a 2-oxa-5-azabicyclo[2.2.1]heptyl group, a 3-oxa-8-azabicyclo[3.2.1]octyl group, a 3-oxa-6-azabicyclo[3.1.1]heptyl group, a 6-oxa-3-azabicyclo[3.1.1]heptyl group, a 2-oxa-6-azaspiro[3.3]heptyl group, a 2-oxa-6-azaspiro[3.5]nonyl group, a 1-oxa-7-azaspiro[4.4]nonyl group, a 2-oxa-7-azaspiro[4.4]nonyl group, a 2-oxa-6-azaspiro[3.4]octyl group, a dioxidothiomorpholinyl group or a 3,7-dioxa-9-azabicyclo[3.3.1]nonyl group, each of which is optionally substituted by 1 to 4 substituents selected from
  (a) a $C_{1-6}$ alkoxy group optionally substituted by 1 to 3 halogen atoms,
  (b) a halogen atom,
  (c) a hydroxy group,
  (d) a $C_{1-6}$ alkyl group,
  (e) an oxo group, and
  (f) a cyano group; and
Ring A is
(1) imidazole,
(2) pyrrole,
(3) triazole, or
(4) pyrazole,
each of which is optionally further substituted by one $C_{1-6}$ alkyl group.

9. The compound or salt of claim 1, wherein
$R_1$ is
(1) an oxazolyl group, or
(2) a triazolyl group;
$R^2$ is a hydrogen atom;
$R^3$ is a $C_{1-6}$ alkyl group optionally substituted by 1 to 3 halogen atoms;
$R^4$ is a hydrogen atom;
$R^5$ is
(1) an amino group optionally di-substituted by substituents selected from
  (a) a $C_{1-6}$ alkyl group, and
  (b) a tetrahydropyranyl group, or
(2) an azetidinyl group, a pyrrolidinyl group, a 2-oxa-5-azabicyclo[2.2.1]heptyl group, a 3-oxa-8-azabicyclo[3.2.1]octyl group or a 3-oxa-6-azabicyclo[3.1.1]heptyl group, each of which is optionally substituted by 1 to 4 substituents selected from
  (a) a $C_{1-6}$ alkoxy group optionally substituted by 1 to 3 halogen atoms, and
  (b) a halogen atom; and
Ring A is imidazole.

10. 3-Oxa-8-azabicyclo[3.2.1]oct-8-yl(8-(1,3-oxazol-5-yl)-6-(trifluoromethyl)imidazo[1,2-a]pyridin-3-yl)methanone or a salt thereof.

11. 3-Oxa-6-azabicyclo[3.1.1]hept-6-yl(8-(1,3-oxazol-5-yl)-6-(trifluoromethyl)imidazo[1,2-a]pyridin-3-yl)methanone or a salt thereof.

12. N-Methyl-8-(1,3-oxazol-5-yl)-N-(tetrahydro-2H-pyran-4-yl)-6-(trifluoromethyl)imidazo[1,2-a]pyridine-3-carboxamide or a salt thereof.

13. A pharmaceutical composition comprising the compound or salt of claim 1.

\* \* \* \* \*